United States Patent
Matlock et al.

(10) Patent No.: US 11,027,105 B2
(45) Date of Patent: Jun. 8, 2021

(54) ADJUSTABLE INSTRUMENT FOR DILATION OF ANATOMICAL PASSAGEWAY

(71) Applicants: Acclarent, Inc., Irvine, CA (US); Biosense Webster (Israel) Ltd., Yokneam (IL)

(72) Inventors: George L. Matlock, Pleasanton, CA (US); Yehuda Algawi, Binyamina (IL); Ilya Sitnitsky, Nahariya (IL); Andres C. Altmann, Haifa (IL); Ygal Zucker, Haifa (IL); Don Q. Ngo-Chu, Irvine, CA (US); Vadim Gliner, Haifa (IL); Christopher T. Beeckler, Brea, CA (US); John H. Thinnes, Jr., Mission Viejo, CA (US); Assaf Govari, Haifa (IL)

(73) Assignees: Biosense Webster (Israel) Ltd., Yokneam (IL); Acclarent, Inc., Irvine, CA (US)

( * ) Notice: Subject to any disclaimer, the term of this patent is extended or adjusted under 35 U.S.C. 154(b) by 113 days.

(21) Appl. No.: 16/032,489

(22) Filed: Jul. 11, 2018

(65) Prior Publication Data
US 2019/0015646 A1   Jan. 17, 2019

Related U.S. Application Data

(60) Provisional application No. 62/531,977, filed on Jul. 13, 2017, provisional application No. 62/555,841, filed on Sep. 8, 2017.

(51) Int. Cl.
*A61M 29/02* (2006.01)
*A61B 17/34* (2006.01)
(Continued)

(52) U.S. Cl.
CPC ............. *A61M 29/02* (2013.01); *A61B 1/07* (2013.01); *A61B 1/233* (2013.01); *A61B 17/24* (2013.01);
(Continued)

(58) Field of Classification Search
CPC ..... A61B 2017/2905; A61B 2017/2908; A61F 2/958; A61F 2002/9623; A61F 2/962;
(Continued)

(56) References Cited

U.S. PATENT DOCUMENTS

| | | | |
|---|---|---|---|
| 4,551,292 A | 11/1985 | Fletcher et al. | |
| 5,325,868 A | * 7/1994 | Kimmelstiel | A61B 17/22 600/585 |

(Continued)

FOREIGN PATENT DOCUMENTS

| | | |
|---|---|---|
| CN | 107233656 A | 10/2017 |
| EP | 2018205 A1 | 1/2009 |

(Continued)

OTHER PUBLICATIONS

Dictionary.com defintion for "dilator" as accessed Aug. 14, 2020; https://www.dictionary.com/browse/dilator?s=t.*

(Continued)

*Primary Examiner* — Wade Miles
(74) *Attorney, Agent, or Firm* — Frost Brown Todd LLC

(57) ABSTRACT

An apparatus includes an instrument body, a shaft assembly, a dilation catheter, a guidewire, and a proximal deflection actuation assembly. The dilation catheter includes an expandable dilator and is slidable relative to the shaft assembly to thereby position the dilator distally relative to the distal end of the shaft assembly. The proximal deflection actuation assembly is positioned at the proximal end of the shaft assembly and is operable to selectively deflect the length of the shaft assembly relative to the longitudinal axis (Continued)

of the instrument body to thereby deflect the longitudinal axis of the shaft assembly away from the longitudinal axis of the instrument body.

20 Claims, 81 Drawing Sheets

(51) Int. Cl.
| | |
|---|---|
| *A61M 25/01* | (2006.01) |
| *A61M 25/09* | (2006.01) |
| *A61B 17/24* | (2006.01) |
| *A61M 25/10* | (2013.01) |
| *A61B 17/00* | (2006.01) |
| *A61M 25/00* | (2006.01) |
| *A61B 1/07* | (2006.01) |
| *A61B 1/233* | (2006.01) |
| *A61B 1/00* | (2006.01) |
| *A61B 1/005* | (2006.01) |

(52) U.S. Cl.
CPC ..... *A61B 17/3421* (2013.01); *A61M 25/0113* (2013.01); *A61M 25/0136* (2013.01); *A61M 25/0147* (2013.01); *A61M 25/09* (2013.01); *A61M 25/09041* (2013.01); *A61B 1/0052* (2013.01); *A61B 1/00183* (2013.01); *A61B 2017/00309* (2013.01); *A61B 2017/00323* (2013.01); *A61B 2217/005* (2013.01); *A61M 25/0041* (2013.01); *A61M 25/10* (2013.01); *A61M 25/10188* (2013.11); *A61M 2025/09125* (2013.01); *A61M 2025/1093* (2013.01); *A61M 2029/025* (2013.01); *A61M 2210/0618* (2013.01); *A61M 2210/0681* (2013.01)

(58) Field of Classification Search
CPC ...... A61F 2/966; A61F 2/9661; A61F 2/9662; A61F 2002/9665; A61F 2002/9583; A61F 2002/9586; A61M 2025/09116; A61M 2025/09125; A61M 2025/0161; A61M 25/0054; A61M 25/0097; A61M 25/25; A61M 25/1011; A61M 29/00; A61M 29/02; A61M 2029/025; A61M 25/0147; A61M 2025/015; A61M 25/10
See application file for complete search history.

(56) References Cited

U.S. PATENT DOCUMENTS

| | | | | |
|---|---|---|---|---|
| 5,358,478 | A * | 10/1994 | Thompson | A61M 25/0136 604/528 |
| 5,472,017 | A * | 12/1995 | Kovalcheck | A61B 1/0052 138/103 |
| 5,549,637 | A * | 8/1996 | Crainich | A61B 17/29 606/170 |
| 5,743,456 | A * | 4/1998 | Jones | A61B 17/0684 227/176.1 |
| 5,755,702 | A * | 5/1998 | Hillstead | A61M 25/0662 604/167.03 |
| 6,066,102 | A * | 5/2000 | Townsend | A61B 10/06 600/104 |
| 7,720,521 | B2 | 5/2010 | Chang et al. | |
| 8,100,824 | B2 * | 1/2012 | Hegeman | A61B 17/29 600/141 |
| 8,123,722 | B2 | 2/2012 | Chang et al. | |
| 8,190,389 | B2 | 5/2012 | Kim et al. | |
| 8,320,711 | B2 | 11/2012 | Altmann et al. | |
| 8,409,244 | B2 * | 4/2013 | Hinman | A61B 17/00 606/205 |
| 8,702,626 | B1 | 4/2014 | Kim et al. | |
| 9,095,646 | B2 | 8/2015 | Chow et al. | |
| 9,127,786 | B1 * | 9/2015 | Arratia | A61M 25/09 |
| 9,155,492 | B2 | 10/2015 | Jenkins et al. | |
| 9,167,961 | B2 | 10/2015 | Makower et al. | |
| 9,198,736 | B2 | 12/2015 | Kim et al. | |
| 9,220,559 | B2 * | 12/2015 | Worrell | A61B 18/1447 |
| 9,561,045 | B2 * | 2/2017 | Hinman | A61B 17/29 |
| 9,566,121 | B2 * | 2/2017 | Staunton | F16D 15/00 |
| 9,700,334 | B2 * | 7/2017 | Hinman | A61B 17/00 |
| 9,962,530 | B2 | 5/2018 | Johnson et al. | |
| 10,188,280 | B1 * | 1/2019 | Wall, Jr. | A61B 18/0218 |
| 2004/0236316 | A1 * | 11/2004 | Danitz | A61B 34/70 606/1 |
| 2005/0033357 | A1 * | 2/2005 | Braun | A61B 17/29 606/207 |
| 2005/0273084 | A1 * | 12/2005 | Hinman | A61B 17/00 606/1 |
| 2006/0020287 | A1 * | 1/2006 | Lee | A61B 17/29 606/205 |
| 2007/0161969 | A1 * | 7/2007 | Andersen | A61M 25/09041 604/533 |
| 2007/0208252 | A1 | 9/2007 | Makower | |
| 2007/0270755 | A1 * | 11/2007 | Von Oepen | B25B 9/00 604/164.13 |
| 2008/0009829 | A1 * | 1/2008 | Ta | A61F 2/915 604/509 |
| 2008/0159825 | A1 * | 7/2008 | Tegg | A61M 25/01 411/262 |
| 2008/0183128 | A1 | 7/2008 | Morriss et al. | |
| 2009/0005738 | A1 * | 1/2009 | Franer | A61B 17/3462 604/164.01 |
| 2009/0177119 | A1 * | 7/2009 | Heidner | A61M 25/09 600/585 |
| 2010/0030031 | A1 | 2/2010 | Goldfarb et al. | |
| 2010/0082012 | A1 * | 4/2010 | Hattangadi | A61M 25/007 604/509 |
| 2010/0130823 | A1 * | 5/2010 | Ando | A61B 1/00078 600/141 |
| 2010/0130996 | A1 * | 5/2010 | Doud | A61M 5/34 606/159 |
| 2010/0228191 | A1 * | 9/2010 | Alvarez | A61M 25/0105 604/95.01 |
| 2010/0274188 | A1 | 10/2010 | Chang et al. | |
| 2011/0004057 | A1 | 1/2011 | Goldfarb et al. | |
| 2011/0054446 | A1 * | 3/2011 | Schultz | A61B 5/283 604/528 |
| 2011/0060214 | A1 | 3/2011 | Makower | |
| 2011/0077621 | A1 * | 3/2011 | Graham | A61M 25/01 604/528 |
| 2012/0071857 | A1 * | 3/2012 | Goldfarb | A61M 25/09041 604/514 |
| 2012/0078096 | A1 * | 3/2012 | Krolik | A61B 17/320725 600/435 |
| 2012/0259215 | A1 * | 10/2012 | Gerrans | A61M 25/1011 600/435 |
| 2013/0030519 | A1 * | 1/2013 | Tran | A61F 2/2433 623/2.11 |
| 2013/0060316 | A1 * | 3/2013 | Sanati | A61F 2/954 623/1.11 |
| 2013/0274715 | A1 | 10/2013 | Chan et al. | |
| 2014/0100552 | A1 * | 4/2014 | Gallacher | A61M 25/09041 604/528 |
| 2014/0200444 | A1 | 7/2014 | Kim et al. | |
| 2014/0364725 | A1 | 12/2014 | Makower | |
| 2015/0112134 | A1 | 4/2015 | Suehara et al. | |
| 2015/0157829 | A1 * | 6/2015 | Bunch | A61M 25/02 604/174 |
| 2015/0174372 | A1 * | 6/2015 | Kaiser | A61F 2/0045 604/174 |
| 2015/0306358 | A1 * | 10/2015 | Duffy | A61F 2/966 623/1.11 |
| 2015/0313732 | A1 * | 11/2015 | Fulton, III | A61B 17/22 623/1.11 |
| 2016/0008083 | A1 | 1/2016 | Kesten et al. | |
| 2016/0015250 | A1 | 1/2016 | Suehara et al. | |
| 2016/0058985 | A1 | 3/2016 | Lam et al. | |
| 2016/0082233 | A1 * | 3/2016 | Ha | A61M 29/02 606/199 |

(56) References Cited

U.S. PATENT DOCUMENTS

| | | | |
|---|---|---|---|
| 2016/0310042 A1 | 10/2016 | Kesten et al. | |
| 2017/0055818 A1* | 3/2017 | Kermani | A61B 17/24 |
| 2017/0056632 A1 | 3/2017 | Jenkins et al. | |
| 2017/0143944 A1* | 5/2017 | Harpaz | A61M 25/1011 |
| 2017/0238822 A1* | 8/2017 | Young | A61B 5/02154 |
| 2017/0259048 A1* | 9/2017 | Matlock | A61M 29/02 |
| 2017/0266413 A1* | 9/2017 | Khuu | A61F 2/2427 |
| 2018/0085174 A1* | 3/2018 | Radtke | A61B 34/20 |
| 2018/0104461 A1* | 4/2018 | Matlock | A61M 29/02 |
| 2018/0200488 A1* | 7/2018 | Drake | A61M 25/01 |
| 2018/0279994 A1* | 10/2018 | Schaer | A61B 8/42 |
| 2018/0303505 A1 | 10/2018 | Algawi et al. | |
| 2018/0333560 A1* | 11/2018 | Milner | A61M 25/0136 |
| 2019/0015645 A1 | 1/2019 | Matlock et al. | |
| 2019/0015646 A1* | 1/2019 | Matlock | A61M 25/09 |
| 2019/0038301 A1 | 2/2019 | Algawi et al. | |
| 2019/0192176 A1* | 6/2019 | Palushi | A61M 25/0097 |

FOREIGN PATENT DOCUMENTS

| | | |
|---|---|---|
| EP | 2397108 A2 | 12/2011 |
| EP | 2976025 B1 | 12/2016 |

OTHER PUBLICATIONS

U.S. Appl. No. 16/032,471.
U.S. Appl. No. 62/640,598, entitled "Fluid Fitting for Dilation Instrument," filed Mar. 9, 2018.
U.S. Appl. No. 15/852,530, entitled "Reusable Navigation Guidewire," filed Dec. 22, 2017.
U.S. Appl. No. 15/861,959, entitled "Navigation Guidewire with Interlocked Coils," filed Jan. 4, 2018.
U.S. Appl. No. 15/933,737, entitled "Apparatus to Secure Field Generating Device to Chair," filed Mar. 23, 2018.
U.S. Appl. No. 15/955,232, entitled "Deflectable Guide for Medical Instrument," filed Apr. 17, 2018.
U.S. Appl. No. 16/032,471, entitled "Adjustable Instrument for Dilation of Anatomical Passageway," filed Jul. 11, 2018.
Merriam Webster definition for "about" as accessed May 4, 2020; https://www.merriam-webster.com/dictionary/about.
International Search Report and Written Opinion dated Nov. 21, 2018 for International Application No. PCT/US2018/042021, 19 pages.

* cited by examiner

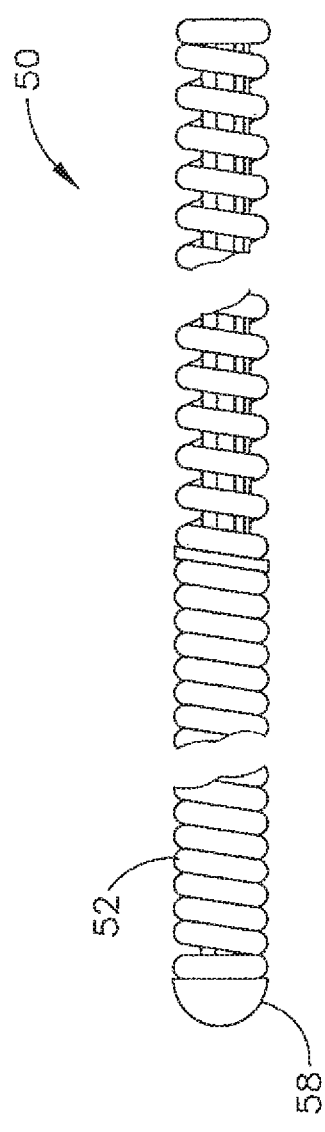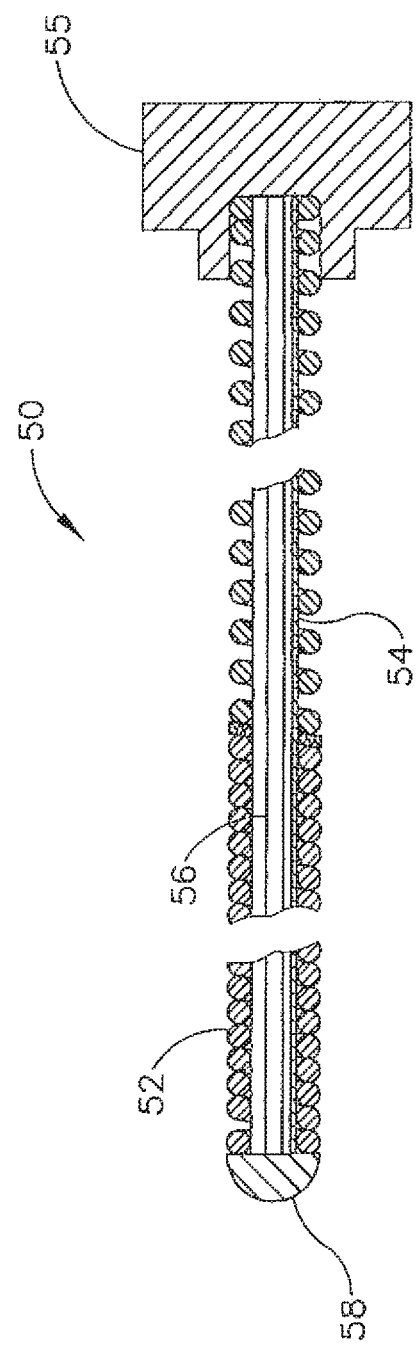
Fig. 3
Fig. 4

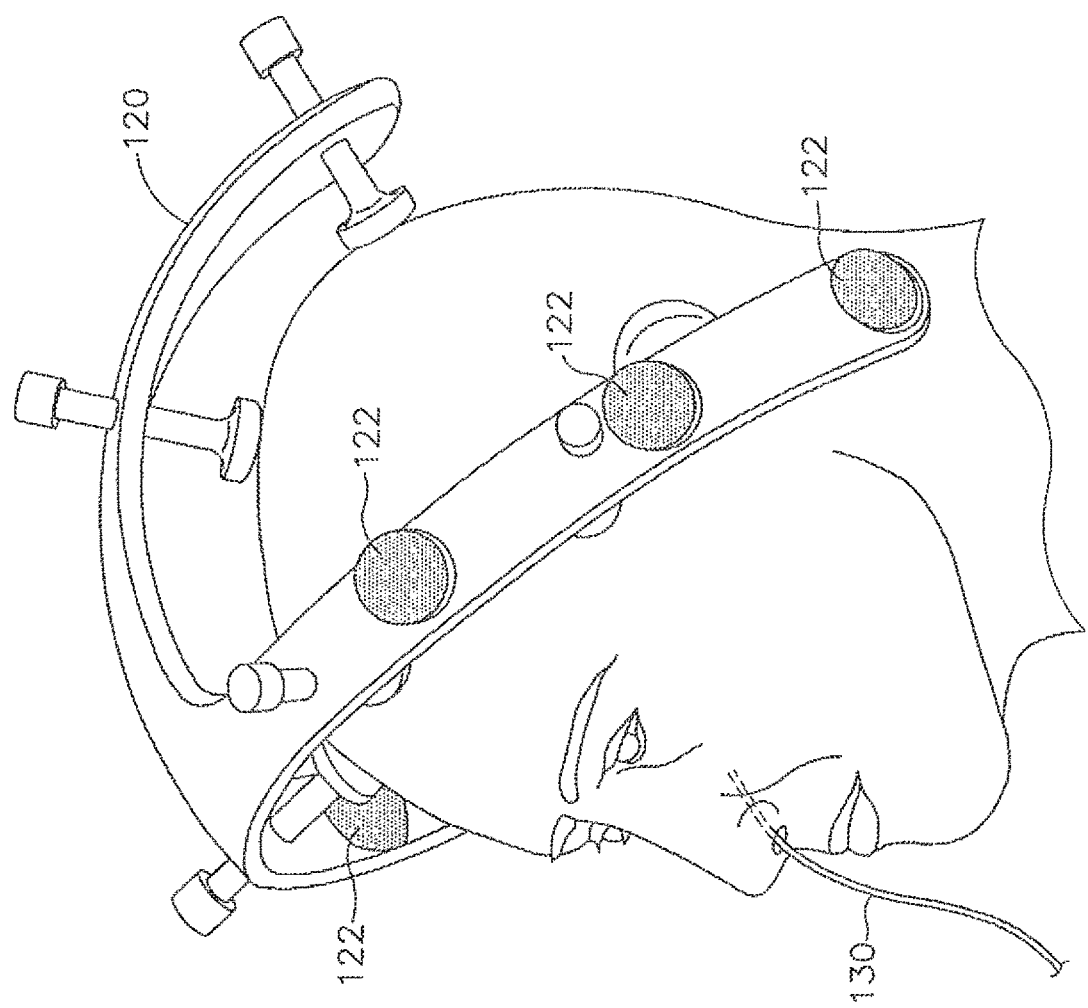

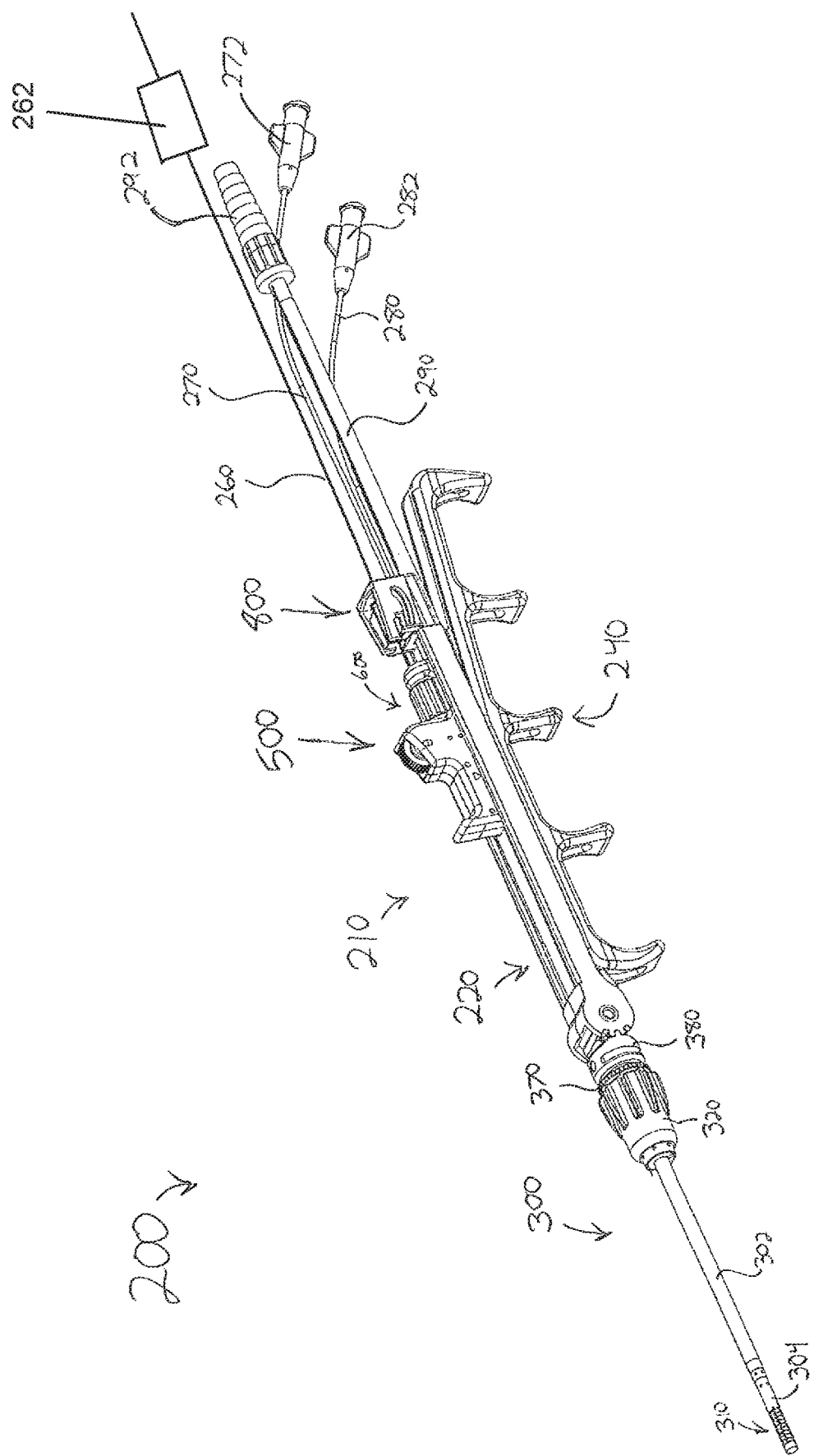

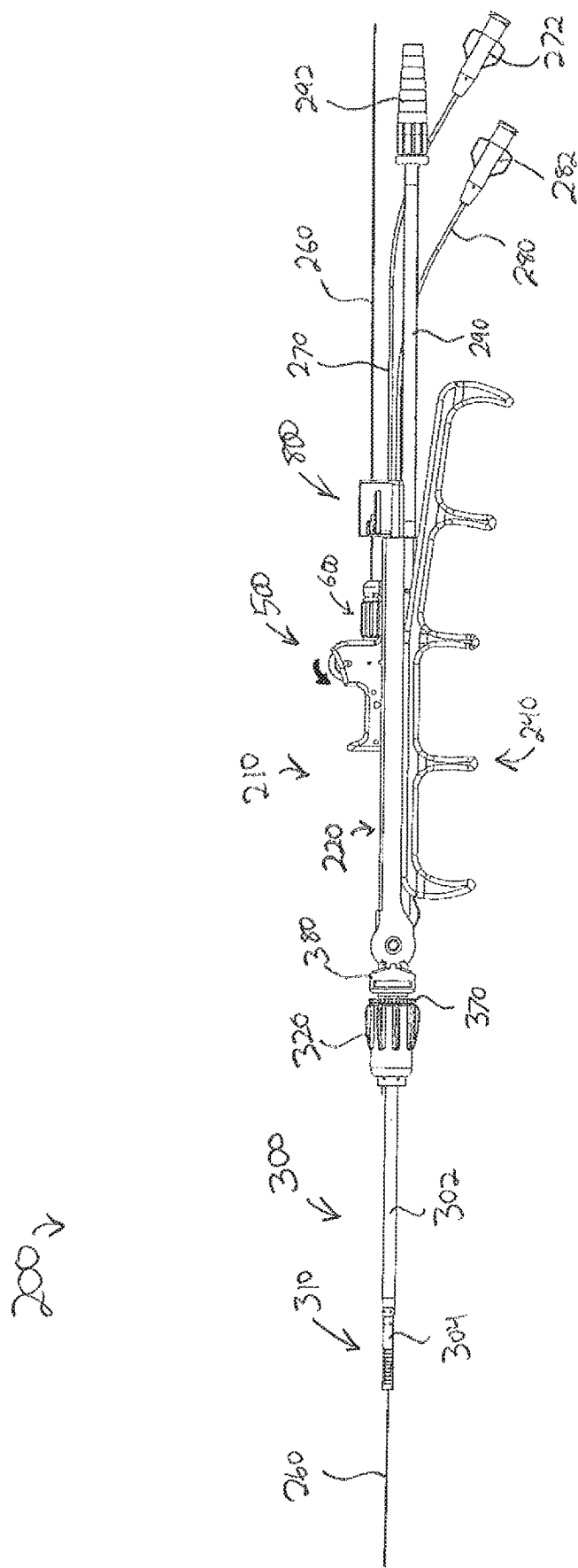

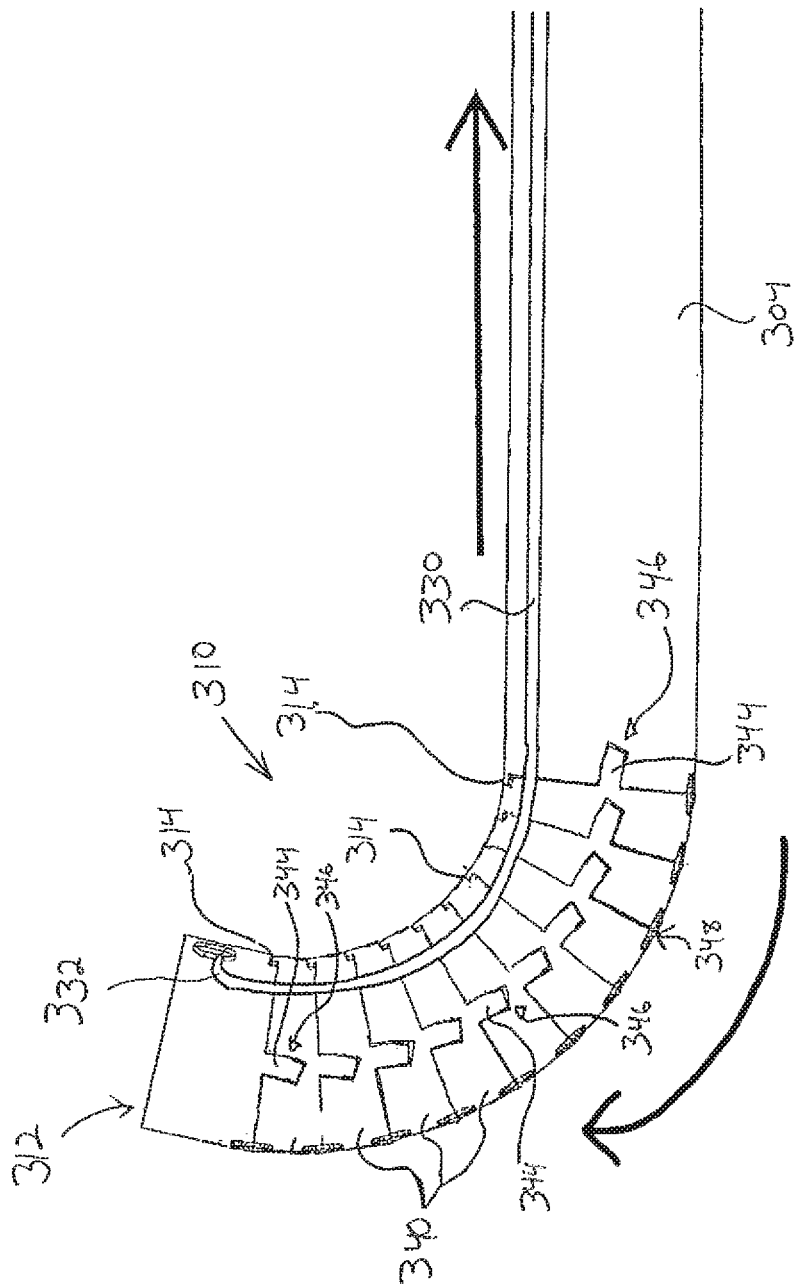

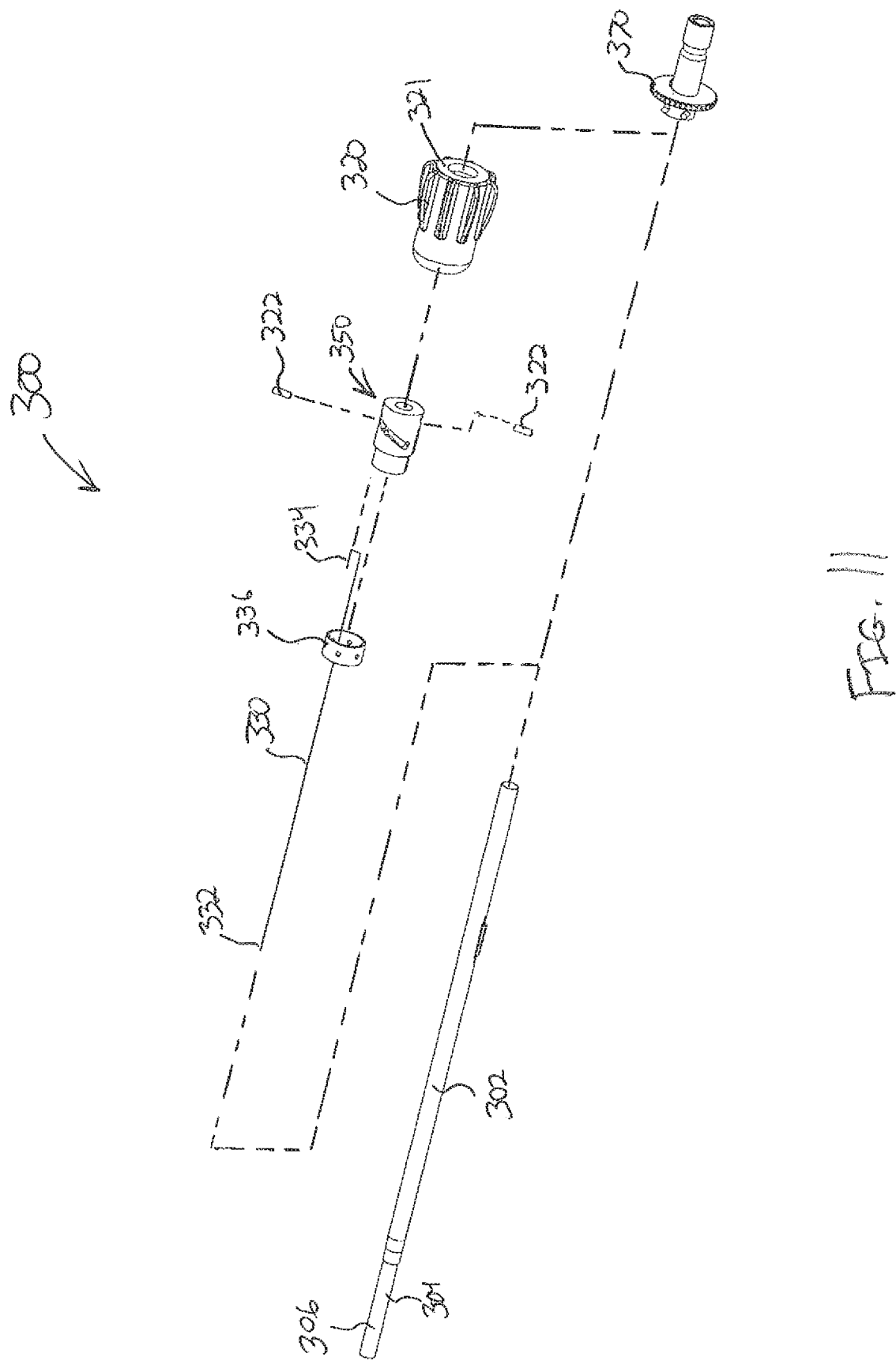

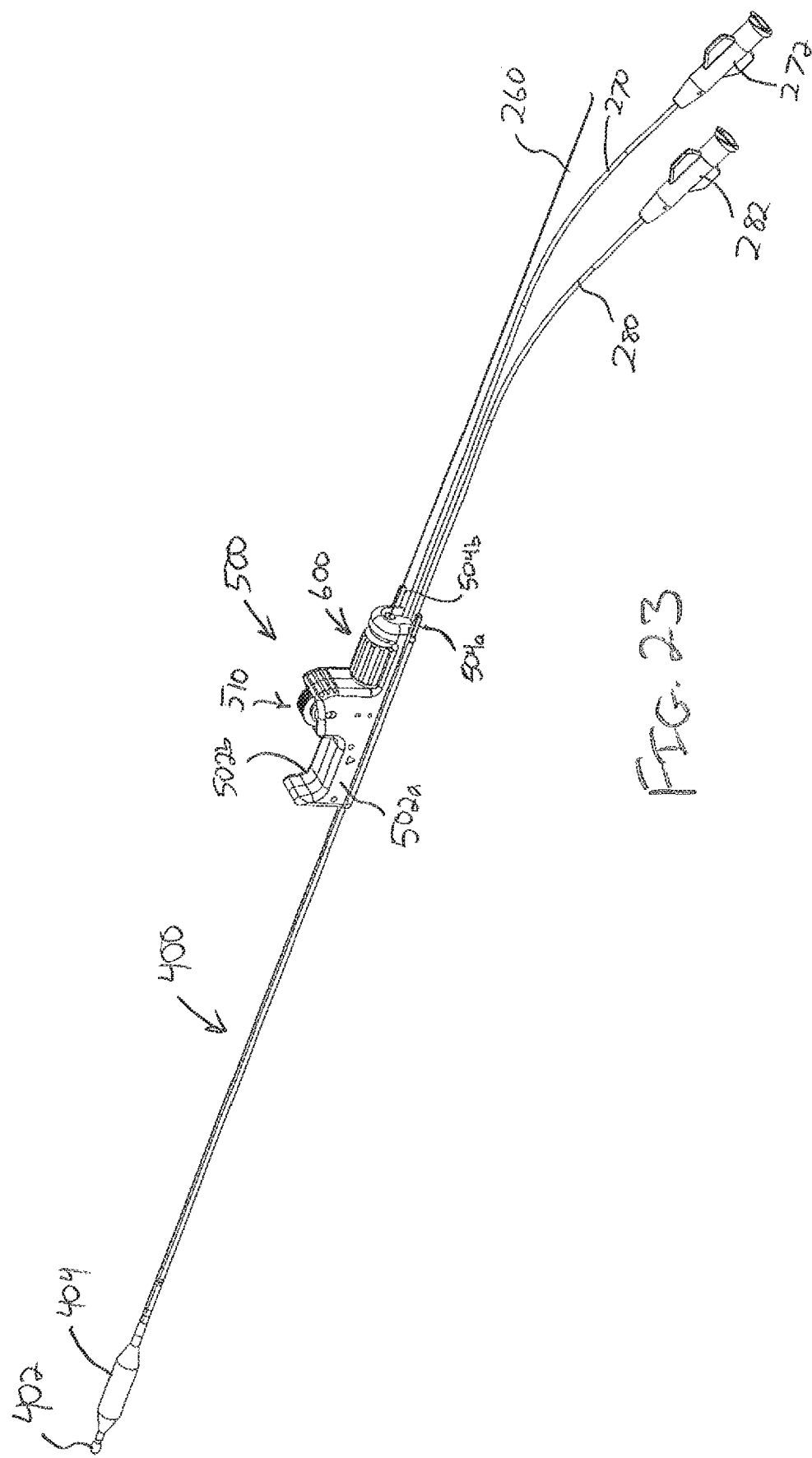

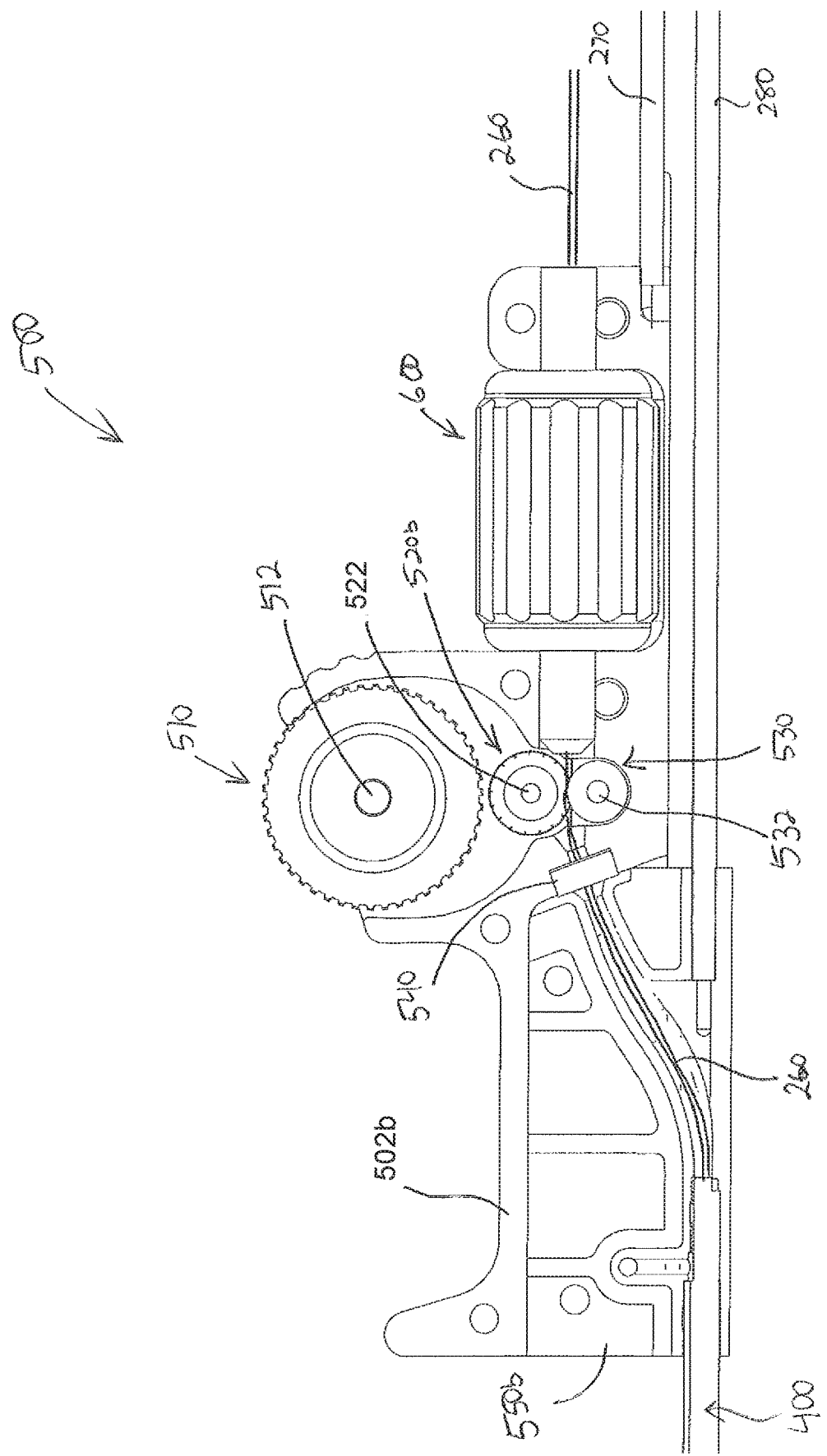

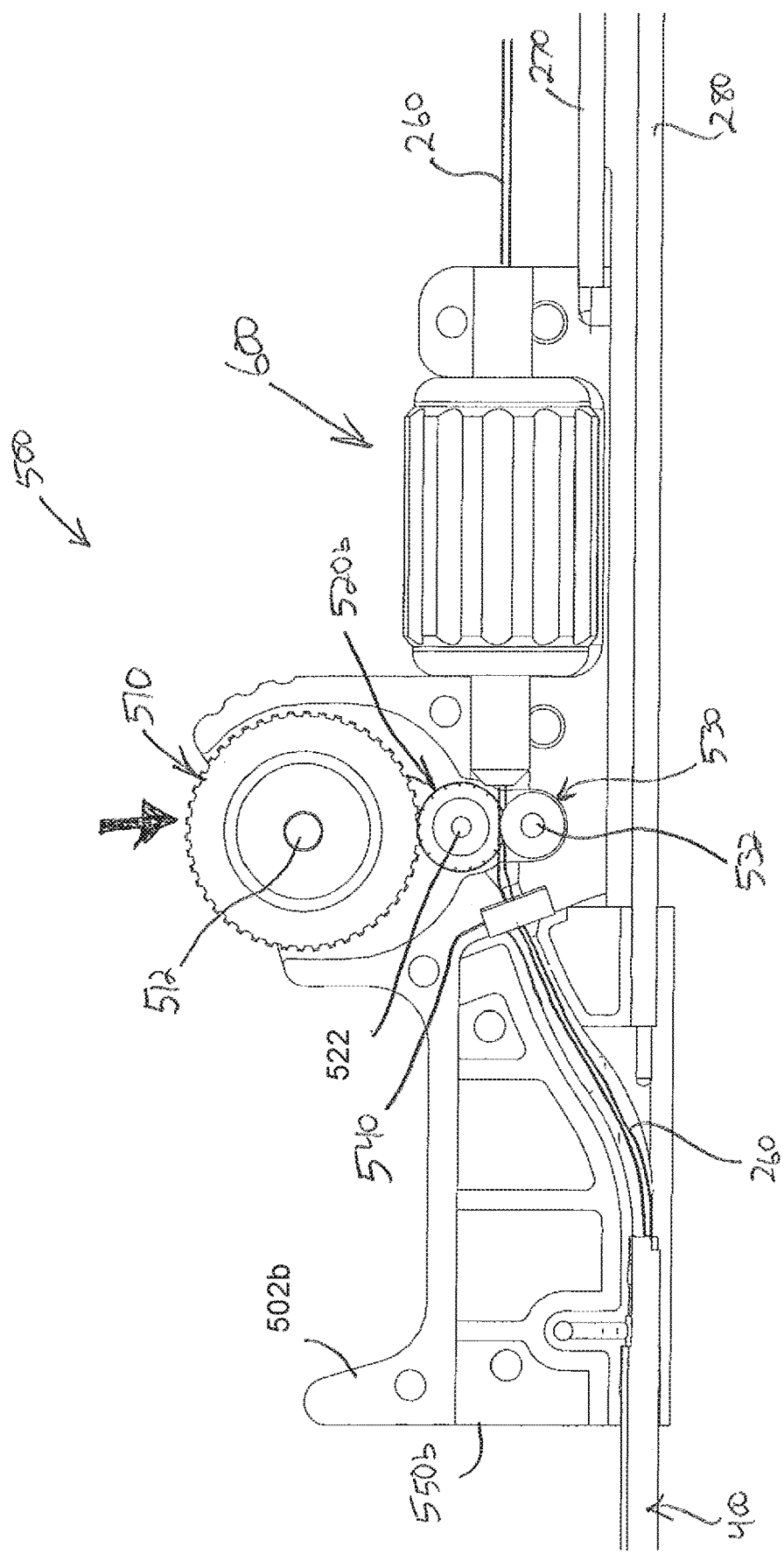

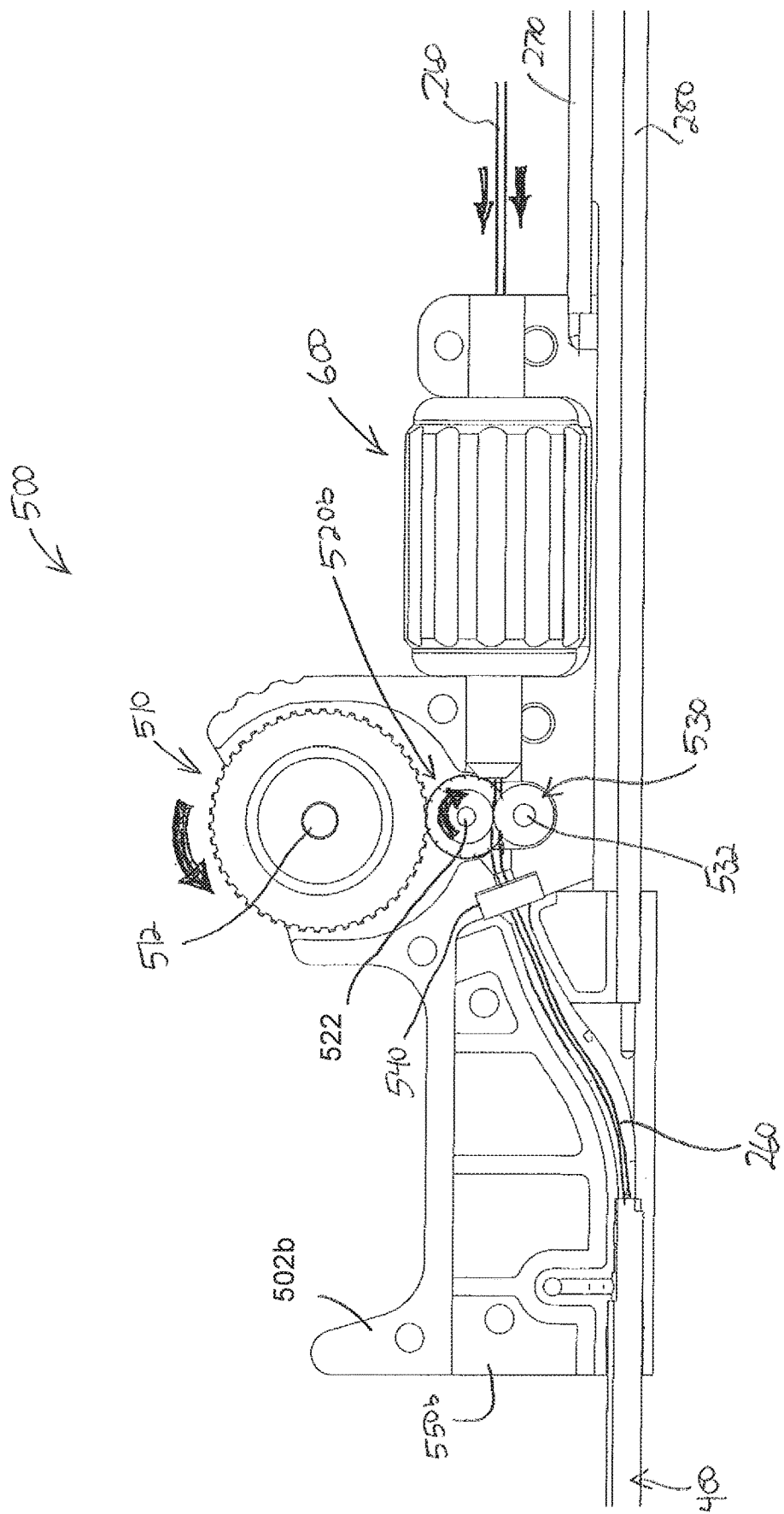

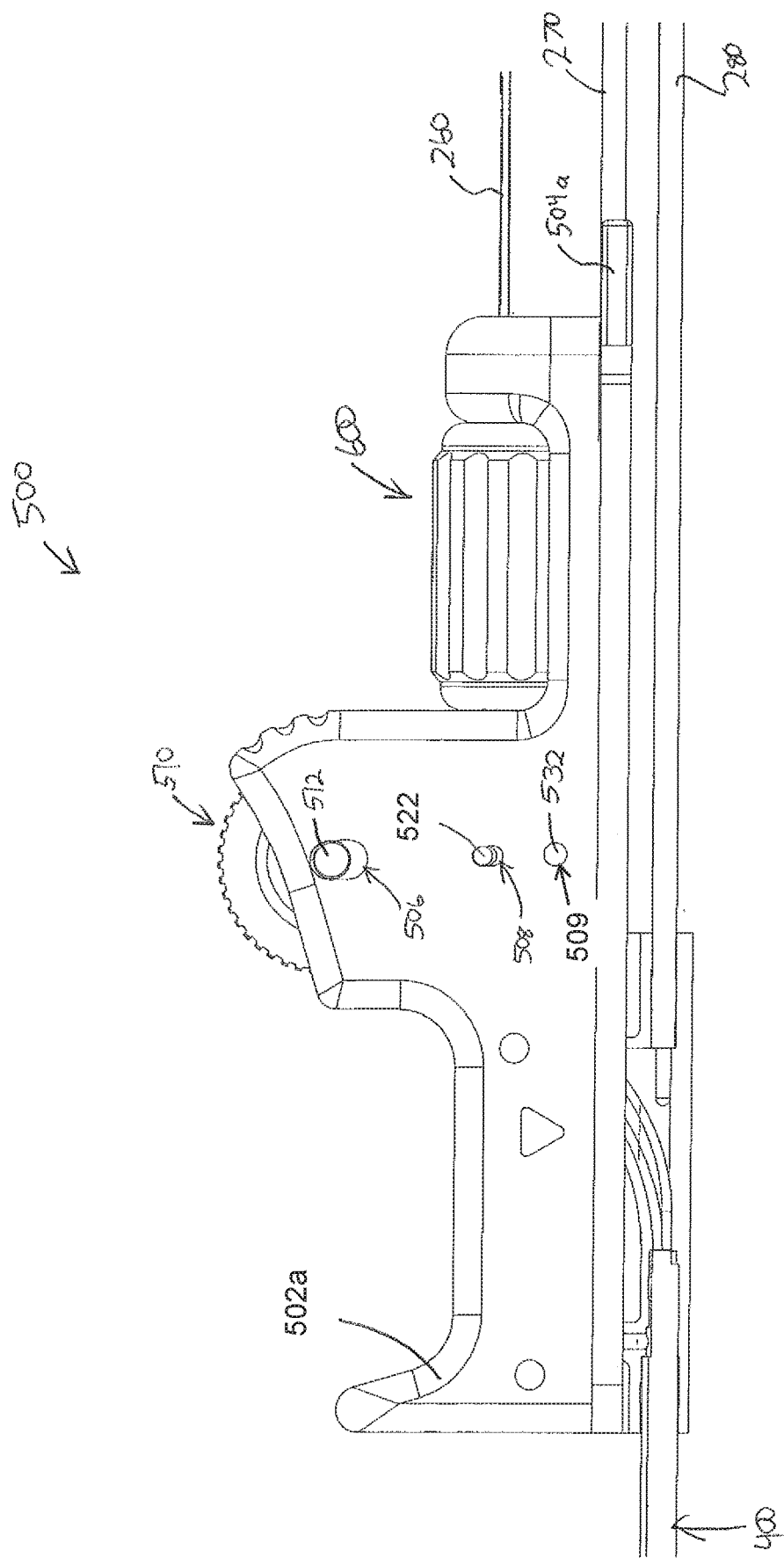

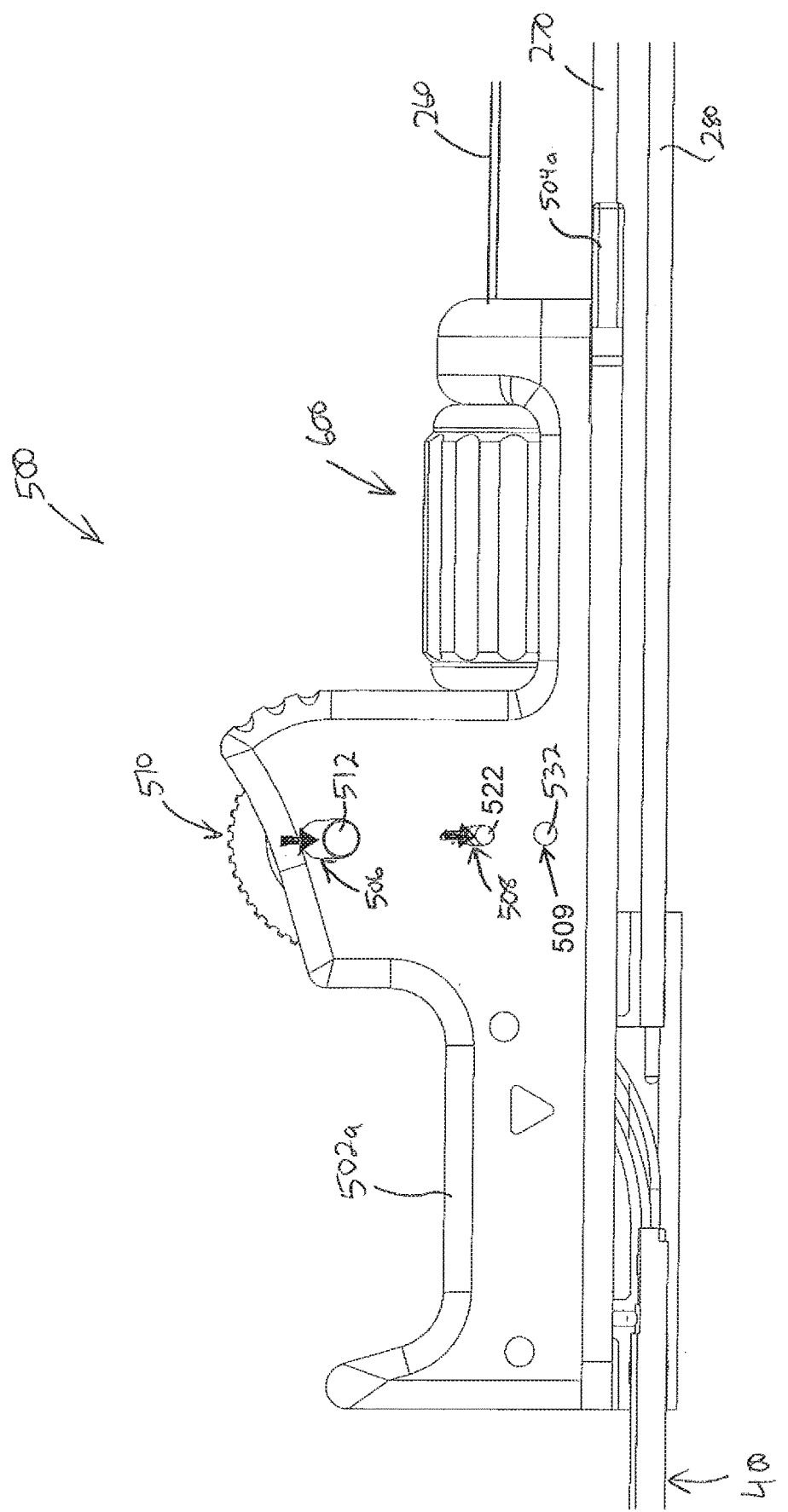

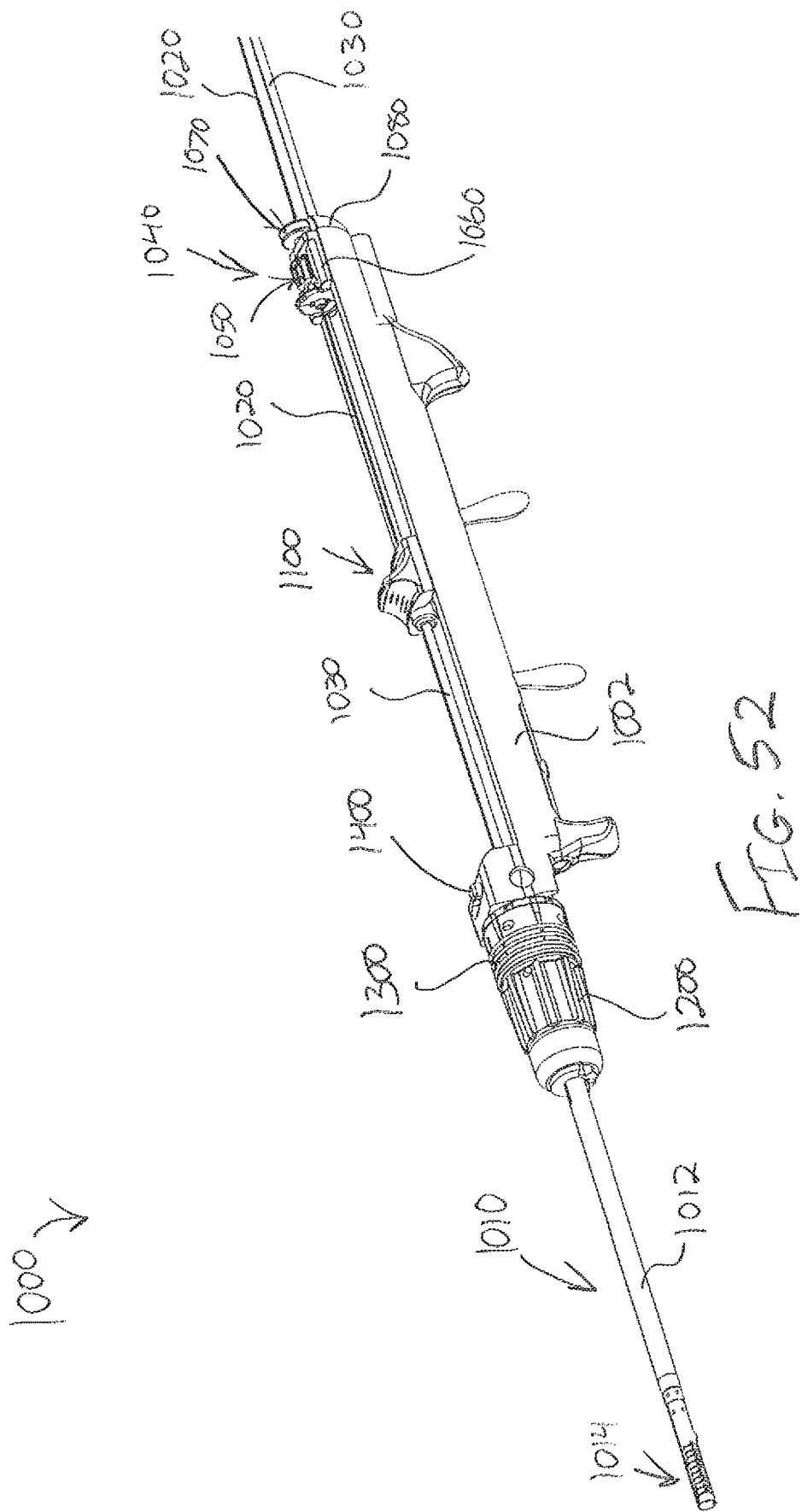

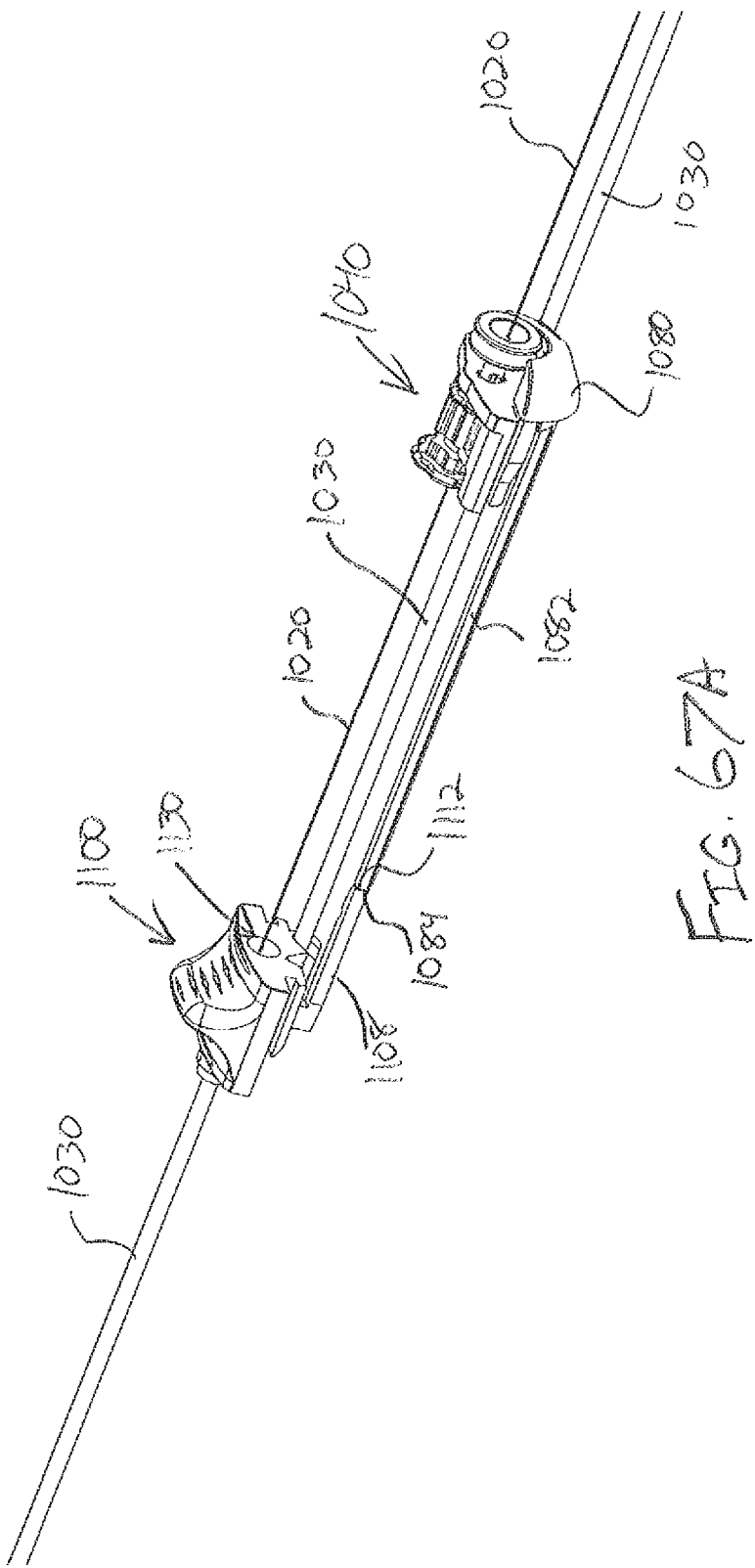

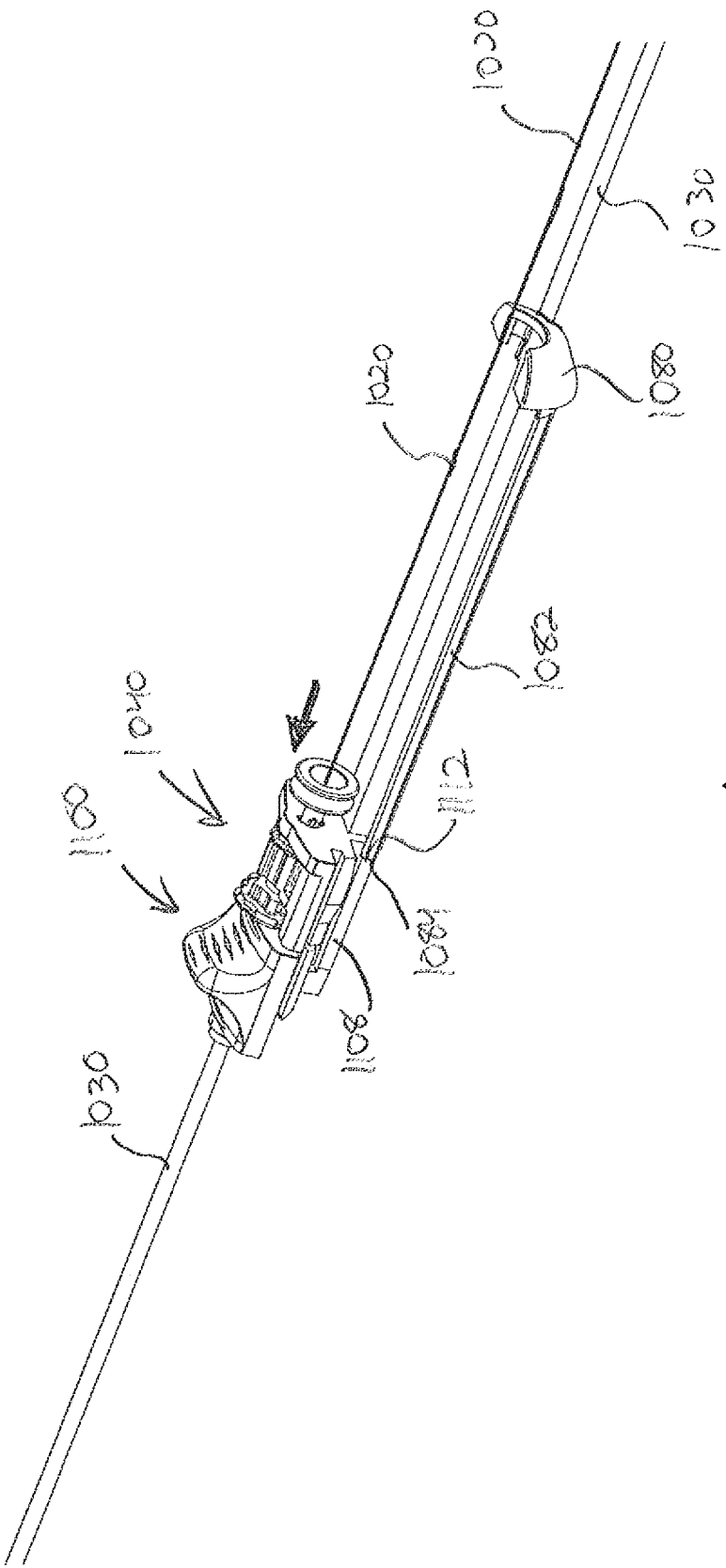

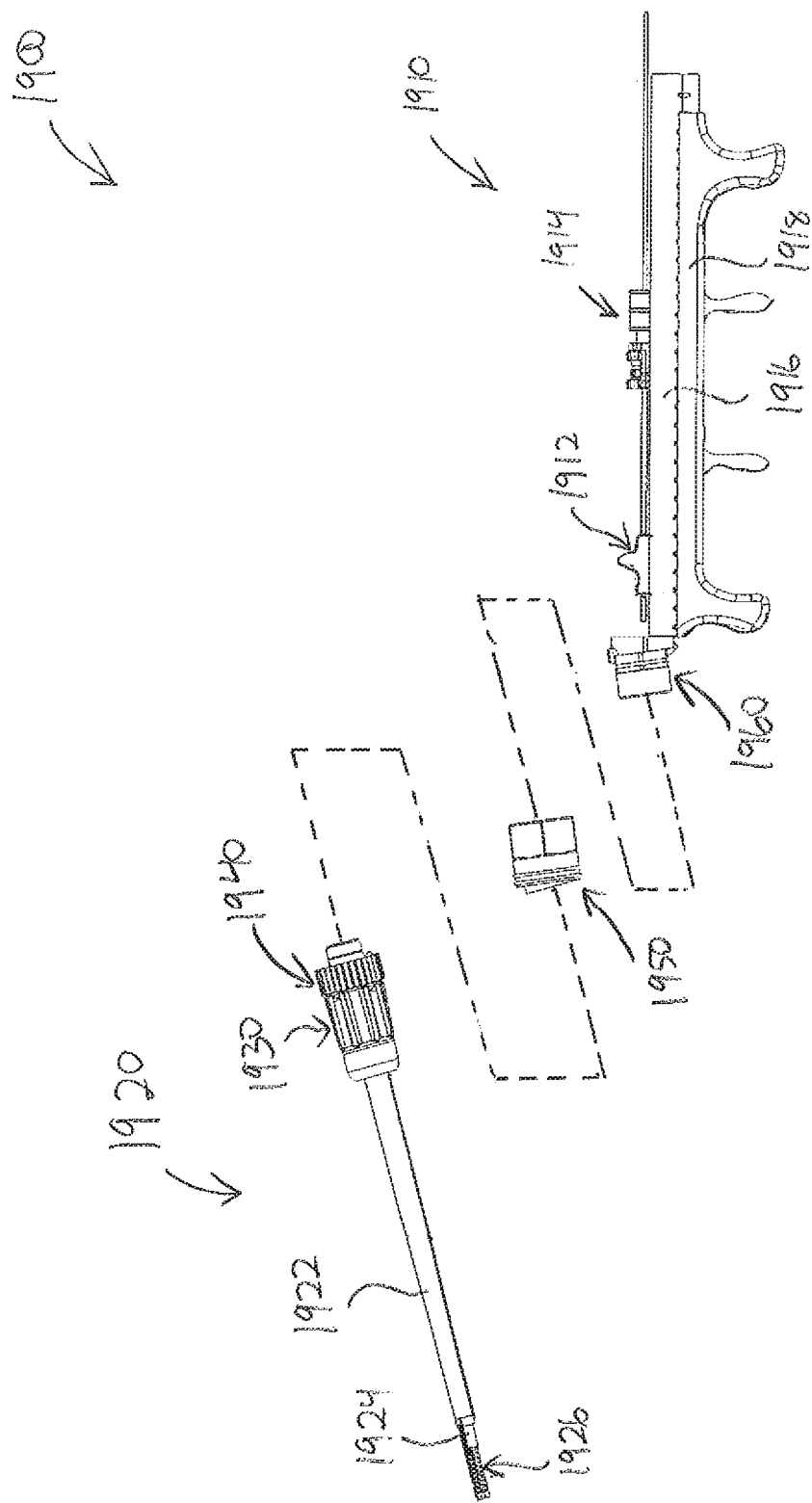

ADJUSTABLE INSTRUMENT FOR DILATION OF ANATOMICAL PASSAGEWAY

PRIORITY

This application claims priority to U.S. Provisional Pat. App. No. 62/531,977, entitled "Adjustable Instrument for Dilation of Anatomical Passageway," filed Jul. 13, 2017, the disclosure of which is incorporated by reference herein.

This application also claims priority to U.S. Provisional Pat. App. No. 62/555,841, entitled "Adjustable Instrument for Dilation of Anatomical Passageway," filed Sep. 8, 2017, the disclosure of which is incorporated by reference herein.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and guide catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, the disclosure of which is incorporated by reference herein. An example of such a system is the Relieva® Spin Balloon Sinuplasty™ System by Acclarent, Inc. of Irvine, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, the disclosure of which is incorporated by reference herein.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pat. No. 9,155,492, entitled "Sinus Illumination Lightwire Device," issued Oct. 13, 2015, the disclosure of which is incorporated by reference herein. An example of such an illuminating guidewire is the Relieva Luma Sentry® Sinus Illumination System by Acclarent, Inc. of Irvine, Calif.

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.) so as to superimpose the current location of the instrument on the preoperatively obtained images. In some IGS procedures, a digital tomographic scan (e.g., CT or MRI, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or coils that are responsive to externally generated electromagnetic fields) mounted thereon are used to perform the procedure while the sensors send data to the computer indicating the current position of each surgical instrument. The computer correlates the data it receives from the instrument-mounted sensors with the digital map that was created from the preoperative tomographic scan. The tomographic scan images are displayed on a video monitor along with an indicator (e.g., cross hairs or an illuminated dot, etc.) showing the real-time position of each surgical instrument relative to the anatomical structures shown in the scan images. In this manner, the surgeon is able to know the precise position of each sensor-equipped instrument by viewing the video monitor even if the surgeon is unable to directly visualize the instrument itself at its current location within the body.

An example of an electromagnetic IGS systems that may be used in ENT and sinus surgery is the CARTO® 3 System by Biosense-Webster, Inc., of Irvine, Calif. When applied to functional endoscopic sinus surgery (FESS), balloon sinuplasty, and/or other ENT procedures, the use of IGS systems allows the surgeon to achieve more precise movement and positioning of the surgical instruments than can be achieved by viewing through an endoscope alone. As a result. IGS systems may be particularly useful during performance of FESS, balloon sinuplasty, and/or other ENT procedures where anatomical landmarks are not present or are difficult to visualize endoscopically. Examples of use of an IGS system in an ENT procedure are described in U.S. Pat. Pub. No. 2014/0364725, entitled "Systems and Methods for Performing Image Guided Procedures within the Ear, Nose, Throat and Paranasal Sinuses," published Dec. 11, 2014, the disclosure of which is incorporated by reference herein; and U.S. patent application Ser. No. 15/933,737, entitled "Apparatus to Secure Field Generating Device to Chair," filed Mar. 23, 2018, the disclosure of which is incorporated by reference herein.

It may be desirable to provide easily controlled placement of a balloon in dilation procedures, including procedures that will be performed only by a single operator. While several systems and methods have been made and used to inflate an inflatable member such as a dilation balloon, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 3 depicts a detailed side elevational view of the illuminating guide wire of FIG. 2A;

FIG. 4 depicts a detailed side cross-sectional view of the illuminating guidewire of FIG. 2A;

FIG. 7 depicts a perspective view of the head of a patient, with components of the navigation system of FIG. 6;

FIG. 8 depicts a perspective view of an exemplary alternative dilation catheter instrument;

FIG. 9B depicts a side elevational view of the instrument of FIG. 8, with the guidewire in a distal position and the dilation catheter in the proximal position;

FIG. 10B depicts a cross-sectional side view of the flexible shaft member of FIG. 10A in a bent configuration;

FIG. 11 depicts an exploded perspective view of a shaft assembly of the instrument of FIG. 8;

FIG. 23 depicts a perspective view of an actuator, the dilation catheter, and other components of the instrument of FIG. 8;

FIG. 32A depicts a side elevational view of the actuator of FIG. 23, with a housing half omitted, with the first drive wheel in a first vertical position, and with the second drive wheel in a first vertical position;

FIG. 32B depicts a side elevational view of the actuator of FIG. 23, with a housing half omitted, with the first drive wheel in a second vertical position, and with the second drive wheel in the first vertical position;

FIG. 32D depicts a side elevational view of the actuator of FIG. 23, with a housing half omitted, with the first drive wheel in the third vertical position, with the second drive wheel in the second vertical position, and with the drive wheels being rotated to advance the guidewire;

FIG. 33A depicts a side elevational view of the actuator of FIG. 23, with the first drive wheel in the first vertical position, and with the second drive wheel in the first vertical position;

FIG. 33B depicts a side elevational view of the actuator of FIG. 23, with the first drive wheel in the second vertical position, and with the second drive wheel in the second vertical position;

FIG. 52 depicts a perspective view of another exemplary alternative dilation catheter instrument;

FIG. 53C' depicts a side elevational view of the instrument of FIG. 52 with the guidewire in a third distal position and the dilation catheter in the second distal position;

FIG. 67A depicts a perspective view of dilation catheter and guidewire actuation components of the instrument of FIG. 52, with the guidewire and dilation catheter both in the respective proximal positions of FIG. 53A;

FIG. 67B depicts a perspective view of the dilation catheter and guidewire actuation components of FIG. 67A, with the guidewire in the first distal position and the dilation catheter in the proximal position of FIG. 53B;

FIG. 79B depicts a perspective view of the instrument of FIG. 79A, with the shaft assembly oriented obliquely relative to the longitudinal axis of a handle assembly;

FIG. 80A depicts a side elevational view of the instrument of FIG. 79A, with the shaft assembly oriented parallel to the longitudinal axis of a handle assembly FIG. 80B depicts a side elevational view of the instrument of FIG. 79A, with the shaft assembly oriented obliquely relative to the longitudinal axis of a handle assembly;

FIG. 81 depicts a partially exploded side elevational view of the instrument of FIG. 79A, with the shaft assembly in a partially disassembled state;

FIG. 82 depicts a perspective view of a distal portion of the handle assembly of the instrument of FIG. 79A;

FIG. 83 depicts a side elevational view of the distal portion of FIG. 82;

FIG. 84 depicts a perspective view of a deflection adjustment knob of the shaft assembly of the instrument of FIG. 79A;

FIG. 85 depicts another perspective view of the adjustment knob of FIG. 84;

FIG. 86 depicts a side elevational view of the adjustment knob of FIG. 84; and

FIG. 87 depicts a perspective view of the proximal end of the shaft assembly of the instrument of FIG. 79A.

Figure 1:
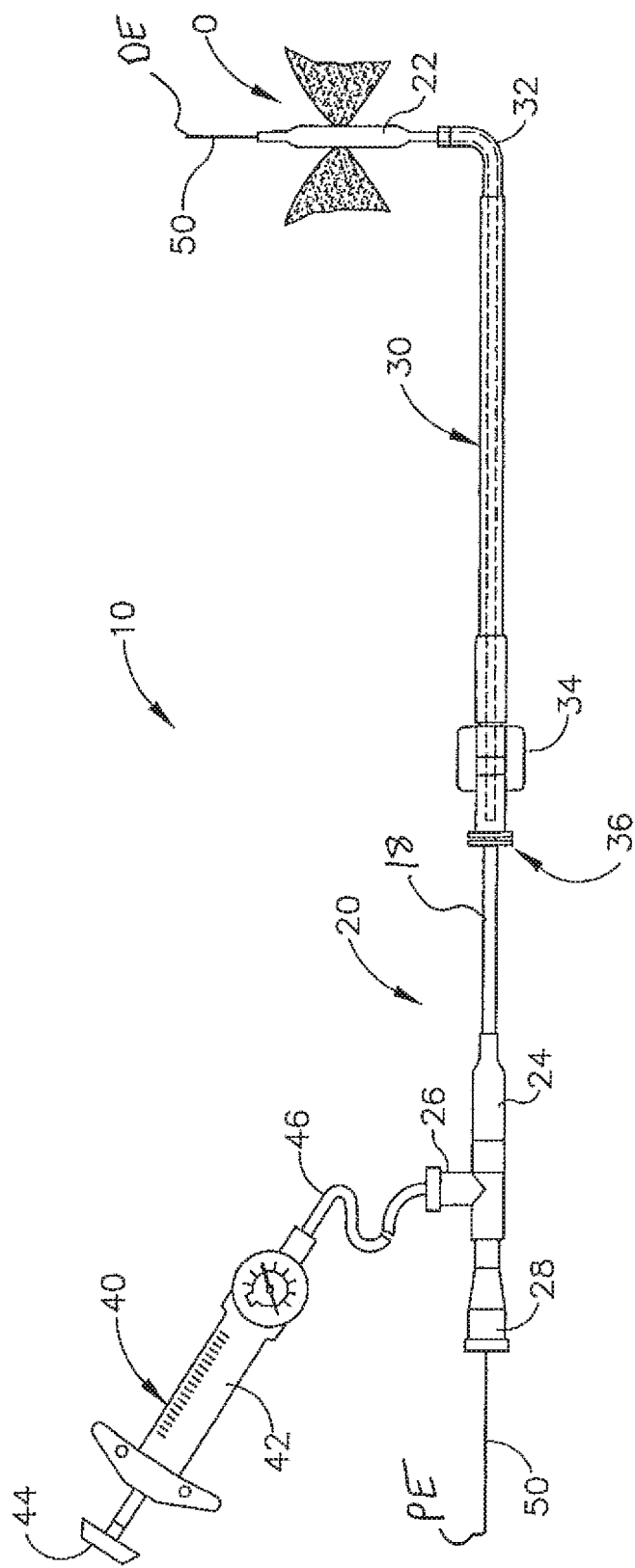
FIG. 1 depicts a side elevational view of an exemplary dilation catheter system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIG. 1 shows an exemplary dilation catheter system (10) that may be used to dilate the ostium of a paranasal sinus; or to dilate some other anatomical passageway (e.g., within the ear, nose, or throat, etc.). Dilation catheter system (10) of this example comprises a dilation catheter (20), a guide catheter (30), an inflator (40), and a guidewire (50). By way of example only, dilation catheter system (10) may be configured in accordance with at least some of the teachings of U.S. Patent Pub. No. 2011/0004057, the disclosure of which is incorporated by reference herein. In some versions, at least part of dilation catheter system (10) is configured similar to the Relieva® Spin Balloon Sinuplasty System by Acclarent, Inc. of Irvine, Calif.

Figure 2A:
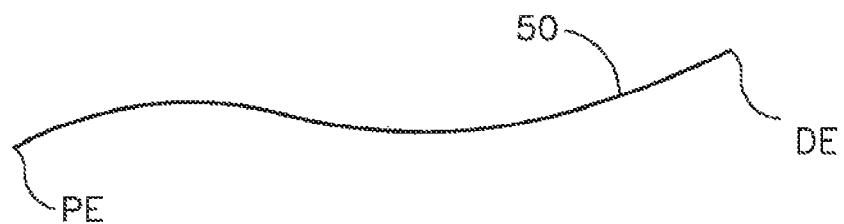
FIG. 2A depicts a side elevational view of an exemplary illuminating guidewire of the dilation catheter system of FIG. 1.
Figure 2B:
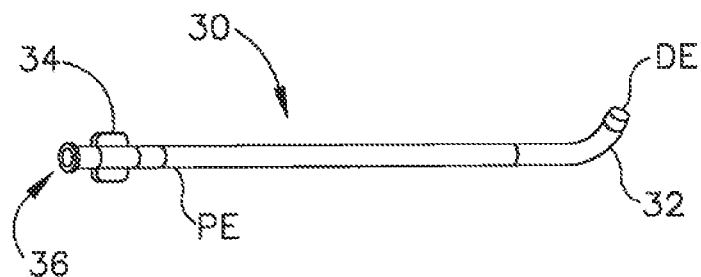
FIG. 2B depicts a side elevational view of an exemplary guide catheter of the dilation catheter system of FIG. 1.
Figure 2C:
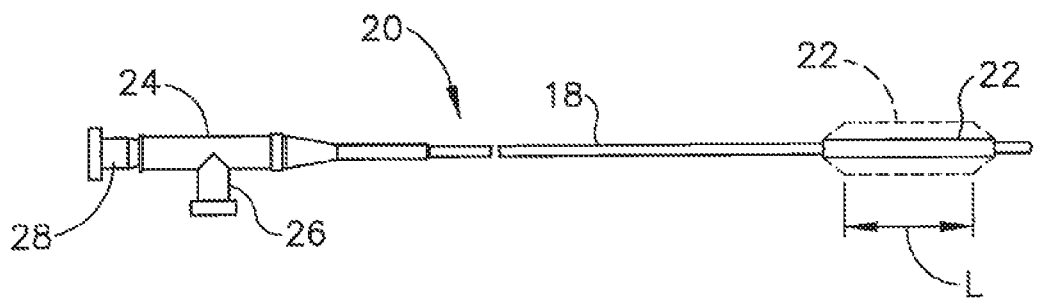
FIG. 2C depicts a side elevational view of an exemplary dilation catheter of the dilation catheter system of FIG. 1.

As best seen in FIG. 2C, the distal end (DE) of dilation catheter (20) includes an inflatable dilator (22). The proximal end (PE) of dilation catheter (20) includes a grip (24), which has a lateral port (26) and an open proximal end (28). A hollow-elongate shaft (18) extends distally from grip. Dilation catheter (20) includes a first lumen (not shown) formed within shaft (18) that provides fluid communication between lateral port (26) and the interior of dilator (22). Dilator catheter (20) also includes a second lumen (not shown) formed within shaft (18) that extends from open proximal end (28) to an open distal end that is distal to dilator (22). This second lumen is configured to slidably receive guidewire (50). The first and second lumens of dilator catheter (20) are fluidly isolated from each other. Thus, dilator (22) may be selectively inflated and deflated by communicating fluid along the first lumen via lateral port (26) while guidewire (50) is positioned within the second lumen. In some versions, dilator catheter (20) is configured similar to the Relieva Ultirra® Sinus Balloon Catheter by Acclarent, Inc. of Irvine, Calif.

As best seen in FIG. 2B, guide catheter (30) of the present example includes a bent distal portion (32) at its distal end (DE) and a grip (34) at its proximal end (PE). Grip (34) has an open proximal end (36). Guide catheter (30) defines a lumen that is configured to slidably receive dilation catheter (20), such that guide catheter (30) may guide dilator (22) out through bent distal end (32). In some versions, guide catheter (30) is configured similar to the Relieva Flex®, Sinus Guide Catheter by Acclarent, Inc. of Irvine, Calif. Other suitable forms that guide catheter (30) may take will be apparent to those of ordinary skill in the art in view of the teachings herein.

Referring back to FIG. 1, inflator (40) of the present example comprises a barrel (42) that is configured to hold fluid and a plunger (44) that is configured to reciprocate relative to barrel (42) to selectively discharge fluid from (or draw fluid into) barrel (42). Barrel (42) is fluidly coupled with lateral port (26) via a flexible tube (46). Thus, inflator (40) is operable to add fluid to dilator (22) or withdraw fluid from dilator (22) by translating plunger (44) relative to barrel (42). In the present example, the fluid communicated by inflator (40) comprises saline, though it should be understood that any other suitable fluid may be used. There are various ways in which inflator (40) may be filled with fluid (e.g., saline, etc.). By way of example only, before flexible tube (46) is coupled with lateral port (26), the distal end of flexible tube (46) may be placed in a reservoir containing the fluid. Plunger (44) may then be retracted from a distal position to a proximal position to draw the fluid into barrel (42). Inflator (40) may then be held in an upright position, with the distal end of barrel (42) pointing upwardly, and plunger (44) may then be advanced to an intermediate or slightly distal position to purge any air from barrel (42). The distal end of flexible tube (46) may then be coupled with lateral port (26). In some versions, inflator (40) is constructed and operable in accordance with at least some of the teachings of U.S. Pat. No. 9,962,530, entitled "Inflator for Dilation of Anatomical Passageway," issued May 8, 2018, the disclosure of which is incorporated by reference herein.

As shown in FIGS. 2A, 3, and 4, guidewire (50) of the present example comprises a coil (52) positioned about a core wire (54). An illumination fiber (56) extends along the interior of core wire (54) and terminates in an atraumatic lens (58). A connector (55) at the proximal end of guidewire (50) enables optical coupling between illumination fiber (56) and a light source (not shown). Illumination fiber (56) may comprise one or more optical fibers. Lens (58) is configured to project light when illumination fiber (56) is illuminated by the light source, such that illumination fiber (56) transmits light from the light source to the lens (58). In some versions, the distal end of guidewire (50) is more flexible than the proximal end of guidewire (50). Guidewire (50) has a length enabling the distal end of guidewire (50) to be positioned distal to dilator (22) while the proximal end of guidewire (50) is positioned proximal to grip (24). Guidewire (50) may include indicia along at least part of its length (e.g., the proximal portion) to provide the operator with visual feedback indicating the depth of insertion of guidewire (50) relative to dilation catheter (20). By way of example only, guidewire (50) may be configured in accordance with at least some of the teachings of U.S. Pat. No. 9,155,492, entitled "Sinus Illumination Lightwire Device," issued Oct. 13, 2015, the disclosure of which is incorporated by reference herein. In some versions, guidewire (50) is configured similar to the Relieva Luma Sentry® Sinus Illumination System by Acclarent, Inc. of Irvine, Calif. Other suitable forms that guidewire (50) may take will be apparent to those of ordinary skill in the art in view of the teachings herein.

II. Exemplary Method for Dilating the Ostium of a Maxillary Sinus

FIGS. 5A-5E show an exemplary method for using dilation catheter system (10) discussed above to dilate a sinus ostium (O) of a maxillary sinus (MS) of a patient. While the present example is being provided in the context of dilating a sinus ostium (O) of a maxillary sinus (MS), it should be understood that dilation catheter system (10) may be used in various other procedures. By way of example only, dilation catheter system (10) and variations thereof may be used to dilate a Eustachian tube, a larynx, a choana, a sphenoid sinus ostium, one or more openings associated with one or more ethmoid sinus air cells, the frontal recess, and/or other passageways associated with paranasal sinuses. Other suitable ways in which dilation catheter system (10) may be used will be apparent to those of ordinary skill in the art in view of the teachings herein.

Figure 5A:
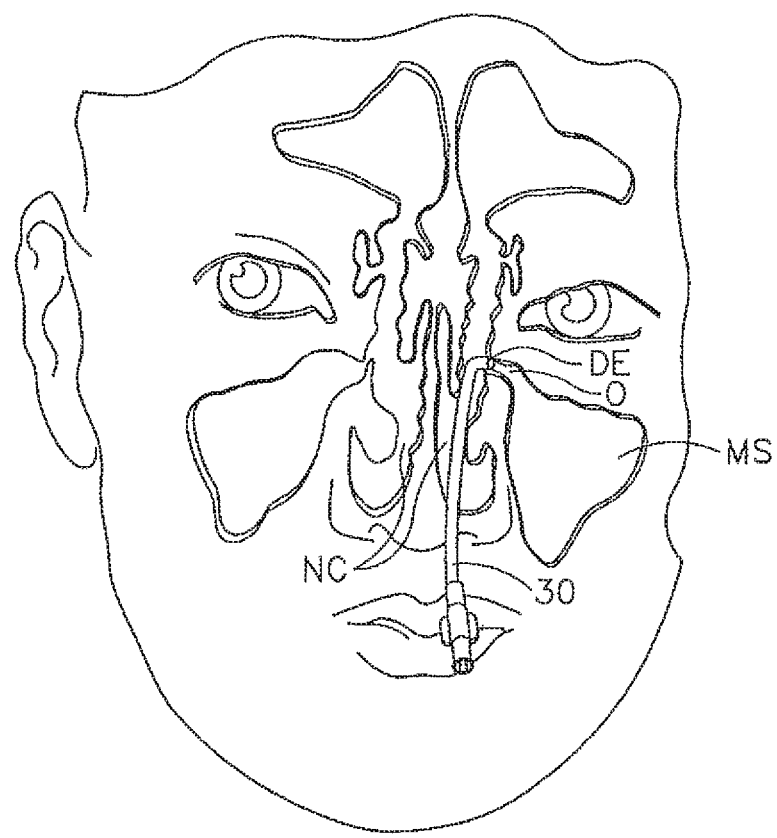
FIG. 5A depicts a front view of the guide catheter of FIG. 2B positioned adjacent an ostium of the maxillary sinus.
Figure 5C:
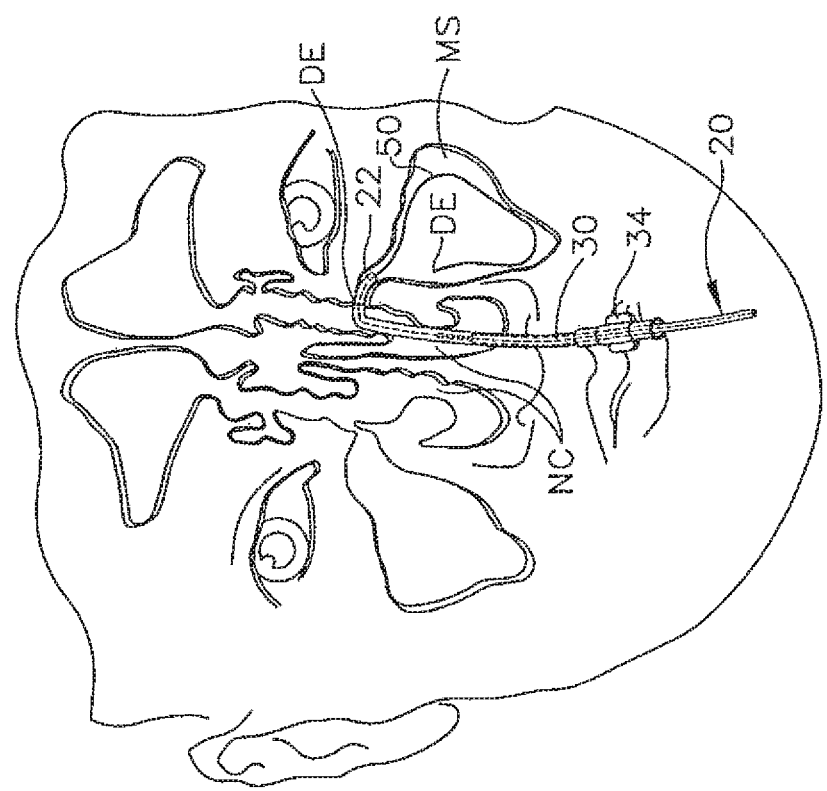
FIG. 5C depicts a front view of the guide catheter of FIG. 2B positioned adjacent an ostium of the maxillary sinus, with the illuminating guidewire of FIG. 2A translated further distally relative to the guide catheter and into the maxillary sinus.
Figure 5B:
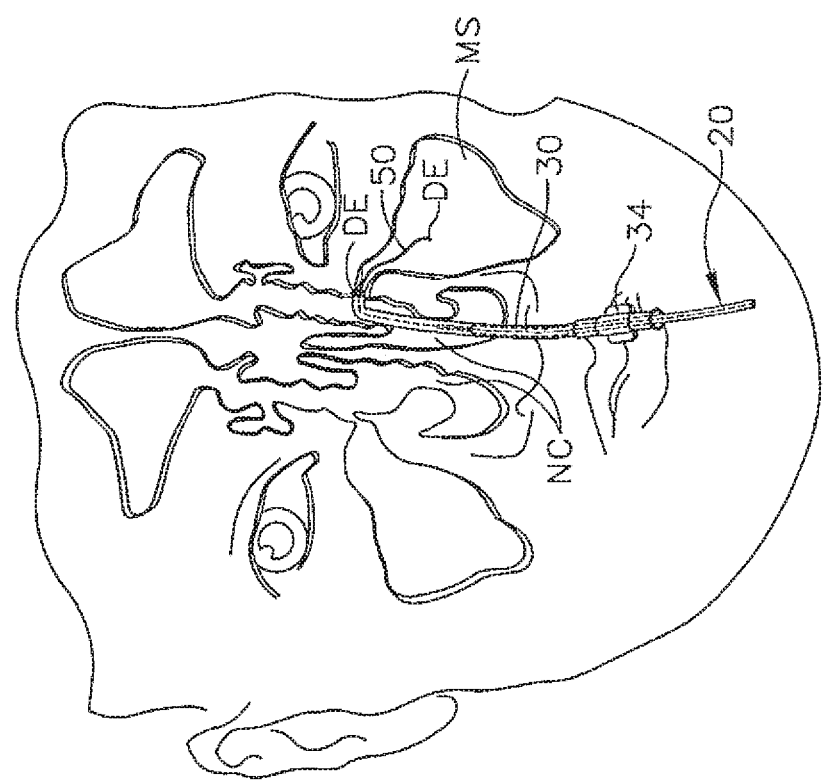
FIG. 5B depicts a front view of the guide catheter of FIG. 2B positioned adjacent an ostium of the maxillary sinus, with the dilation catheter of FIG. 2C and the illuminating guidewire of FIG. 2A positioned in the guide catheter and a distal portion of the guidewire positioned in the maxillary sinus.

In the procedure of the present example, guide catheter (30) may be inserted transnasally and advanced through the nasal cavity (NC) to a position within or near the targeted anatomical passageway to be dilated, the sinus ostium (O), as shown in FIG. 5A. Inflatable dilator (22) and the distal end of guidewire (50) may be positioned within or proximal to bent distal end (32) of guide catheter (30) at this stage. This positioning of guide catheter (30) may be verified endoscopically with an endoscope and/or by direct visualization, radiography, and/or by any other suitable method. After guide catheter (30) has been positioned, the operator may advance guidewire (50) distally through guide catheter (30) such that a distal portion of the guidewire (50) passes through the ostium (O) of the maxillary sinus (MS) and into the cavity of the maxillary sinus (MS) as shown in FIGS. 5B and 5C. The operator may illuminate illumination fiber (56) and lens (58), which may provide transcutaneous illumination through the patient's face to enable the operator to visually confirm positioning of the distal end of guidewire (50) in the maxillary sinus (MS) with relative ease.

Figure 5E:
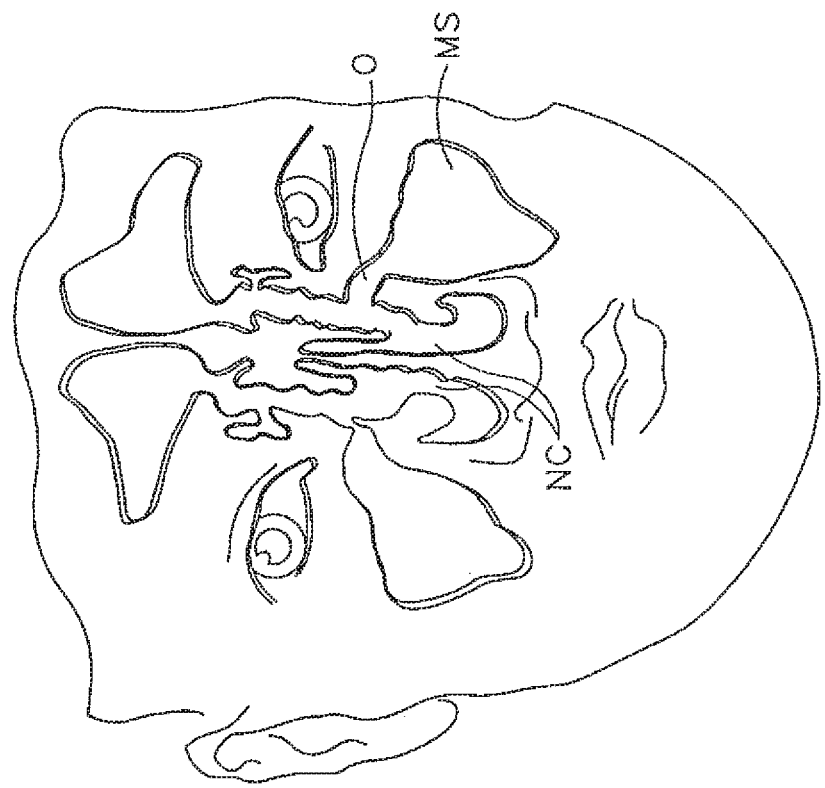
FIG. 5E depicts a front view of an ostium of the maxillary sinus, with the ostium having been enlarged by inflation of the balloon of FIG. 5D.
Figure 5D:
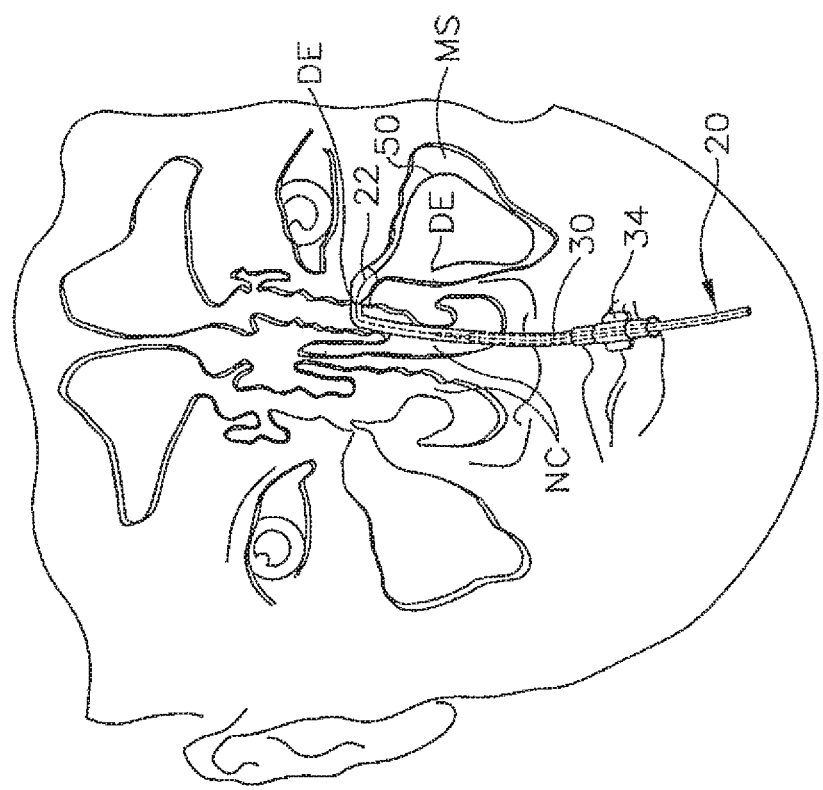
FIG. 5D depicts a front view of the guide catheter of FIG. 2B positioned adjacent an ostium of the maxillary sinus, with the dilation catheter of FIG. 2C translated distally relative to the guide catheter along the illuminating guidewire of FIG. 2A so as to position a balloon of the dilation catheter within the ostium.

As shown in FIG. 5C, with guide catheter (30) and guidewire (50) suitably positioned, dilation catheter (20) is advanced along guidewire (50) and through bent distal end (32) of guide catheter (30), with dilator (22) in a non-dilated state until dilator (22) is positioned within the ostium (O) of the maxillary sinus (MS) (or some other targeted anatomical passageway). After dilator (22) has been positioned within the ostium (O), dilator (22) may be inflated, thereby dilating the ostium (O), as shown in FIG. 5D. To inflate dilator (22), plunger (44) may be actuated to push saline from barrel (42) of inflator (40) through dilation catheter (20) into dilator (22). The transfer of fluid expands dilator (22) to an expanded state to open or dilate the ostium (O), such as by remodeling the bone, etc., forming ostium (O). By way of example only, dilator (22) may be inflated to a volume sized to achieve about 10 to about 12 atmospheres. Dilator (22) may be held at this volume for a few seconds to sufficiently open the ostium (O) (or other targeted anatomical passageway). Dilator (22) may then be returned to a non-expanded state by reversing plunger (44) of inflator (40) to bring the saline back to inflator (40). Dilator (22) may be repeatedly inflated and deflated in different ostia and/or other targeted anatomical passageways. Thereafter, dilation catheter (20), guidewire (50), and guide catheter (30) may be removed from the patient as shown in FIG. 5E.

In some instances, it may be desirable to irrigate the sinus and paranasal cavity after dilation catheter (20) has been used to dilate the ostium (O). Such irrigation may be performed to flush out blood, etc. that may be present after the dilation procedure. For example, in some cases, guide catheter (30) may be allowed to remain in place after removal of guidewire (50) and dilation catheter (20) and a lavage fluid, other substance, or one or more other devices (e.g., lavage catheters, balloon catheters, cutting balloons, cutters, chompers, rotating cutters, rotating drills, rotating blades, sequential dilators, tapered dilators, punches, dissectors, burs, non-inflating mechanically expandable members, high frequency mechanical vibrators, dilating stents and radiofrequency ablation devices, microwave ablation devices, laser devices, snares, biopsy tools, scopes, and devices that deliver diagnostic or therapeutic agents) may be passed through guide catheter (30) for further treatment of the condition. By way of example only, irrigation may be carried out in accordance with at least some of the teachings of U.S. Pub. No. 2008/0183128, entitled "Methods, Devices and Systems for Treatment and/or Diagnosis of Disorders of the Ear, Nose and Throat," published Jul. 31, 2008, the disclosure of which is incorporated by reference herein. An example of an irrigation catheter that may be fed through guide catheter (30) to reach the irrigation site after removal of dilation catheter (20) is the Relieva Vortex® Sinus Irrigation Catheter by Acclarent, Inc. of Irvine, Calif. Another example of an irrigation catheter that may be fed through guide catheter (30) to reach the irrigation site after removal of dilation catheter (20) is the Relieva Ultirra® Sinus Irrigation Catheter by Acclarent, Inc. of Irvine, Calif. Of course, irrigation may be provided in the absence of a dilation procedure; and a dilation procedure may be completed without also including irrigation.

III. Exemplary Image Guided Surgery Navigation System

Figure 6:
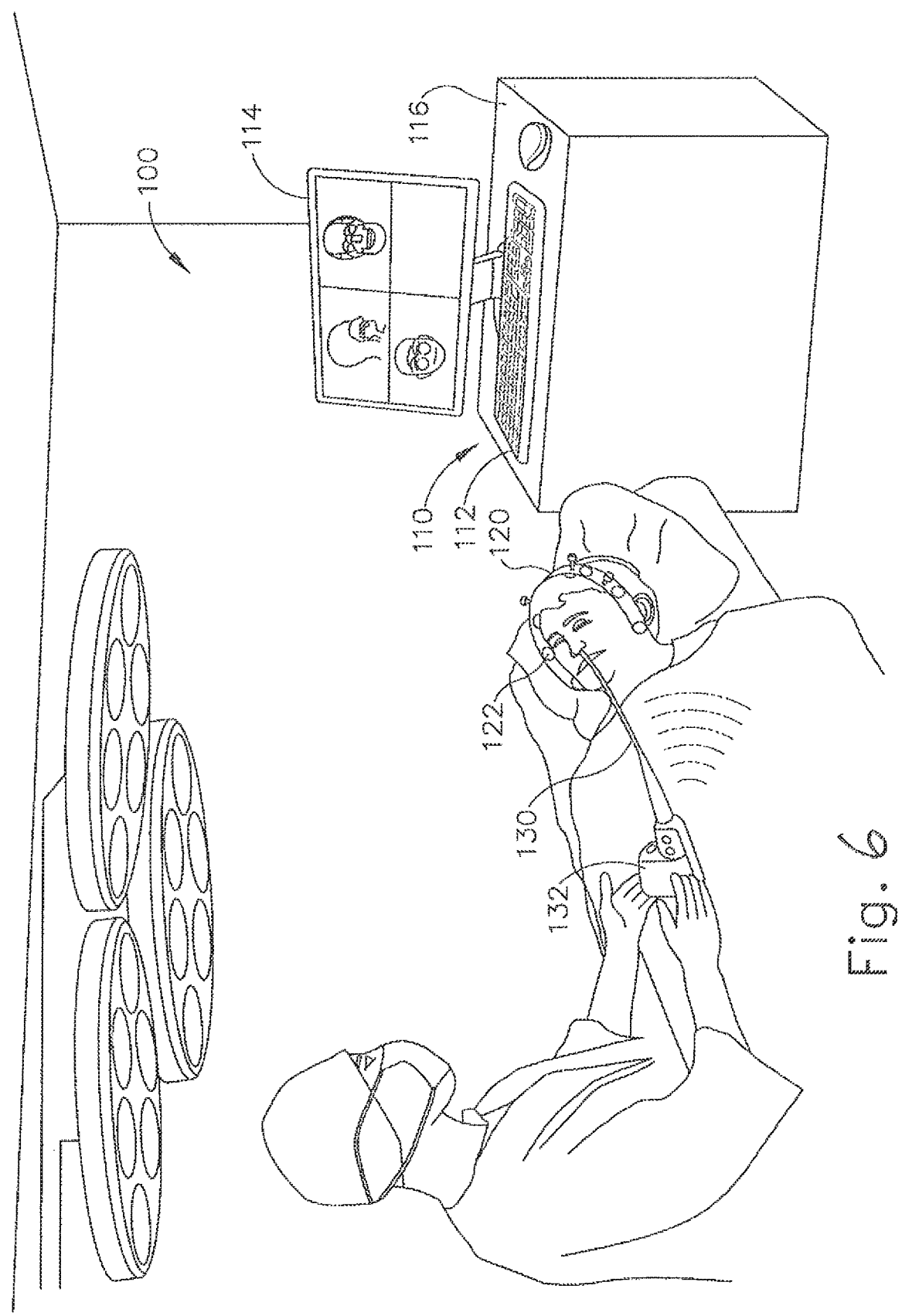
FIG. 6 depicts a schematic view of an exemplary sinus surgery navigation system.

FIG. 6 shows an exemplary IGS navigation system (100) whereby an ENT procedure may be performed using IGS. In some instances, IGS navigation system (100) is used during a procedure where dilation catheter assembly (10) that may be used to dilate the ostium of a paranasal sinus; or to dilate some other anatomical passageway (e.g., within the ear, nose, or throat, etc.). However, it should be understood that IGS navigation system (100) may be readily used in various other kinds of procedures.

In addition to or in lieu of having the components and operability described herein IGS navigation system (100) may be constructed and operable in accordance with at least some of the teachings of U.S. Pat. No. 8,702,626, entitled "Guidewires for Performing Image Guided Procedures," issued Apr. 22, 2014, the disclosure of which is incorporated by reference herein; U.S. Pat. No. 8,320,711, entitled "Anatomical Modeling from a 3-D Image and a Surface Mapping," issued Nov. 27, 2012, the disclosure of which is incorporated by reference herein; U.S. Pat. No. 8,190,389, entitled "Adapter for Attaching Electromagnetic Image Guidance Components to a Medical Device," issued May 29, 2012, the disclosure of which is incorporated by reference herein; U.S. Pat. No. 8,123,722, entitled "Devices, Systems and Methods for Treating Disorders of the Ear, Nose and Throat," issued Feb. 28, 2012, the disclosure of which is incorporated by reference herein; and U.S. Pat. No. 7,720,521, entitled "Methods and Devices for Performing Procedures within the Ear, Nose, Throat and Paranasal Sinuses," issued May 18, 2010, the disclosure of which is incorporated by reference herein.

Similarly, in addition to or in lieu of having the components and operability described herein, IGS navigation system (100) may be constructed and operable in accordance with at least some of the teachings of U.S. Pat. Pub. No. 2014/0364725, entitled "Systems and Methods for Performing Image Guided Procedures within the Ear, Nose, Throat and Paranasal Sinuses," published Dec. 11, 2014, the disclosure of which is incorporated by reference herein; U.S. Pat. Pub. No. 2014/0200444, entitled "Guidewires for Performing Image Guided Procedures," published Jul. 17, 2014, the disclosure of which is incorporated by reference herein; U.S. Pat. No. 9,198,736, entitled "Adapter for Attaching Electromagnetic Image Guidance Components to a Medical Device," issued Dec. 1, 2015, the disclosure of which is incorporated by reference herein; U.S. Pat. Pub. No. 2011/0060214, entitled "Systems and Methods for Performing Image Guided Procedures within the Ear, Nose, Throat and Paranasal Sinuses," published Mar. 10, 2011, the disclosure of which is incorporated by reference herein; U.S. Pat. No. 9,167,961, entitled "Methods and Apparatus for Treating Disorders of the Ear Nose and Throat," issued Oct. 27, 2015, the disclosure of which is incorporated by reference herein; and U.S. Pat. Pub. No. 2007/0208252, entitled "Systems and Methods for Performing Image Guided Procedures within the Ear, Nose, Throat and Paranasal Sinuses," published Sep. 6, 2007, the disclosure of which is incorporated by reference herein.

IGS navigation system (100) of the present example comprises a set of magnetic field generators (122). Before a surgical procedure begins, field generators (122) are fixed to the head of the patient. As best seen in FIG. 3, field generators (122) are incorporated into a frame (120), which is clamped to the head of the patient. While field generators (122) are secured to the head of the patient in this example, it should be understood that field generators (122) may instead be positioned at various other suitable locations and on various other suitable structures. By way of example only, field generators (122) may be mounted on an independent structure that is fixed to a table or chair on which the patient is positioned, on a floor-mounted stand that has been locked in position relative to the head of the patient, and/or at any other suitable location(s) and/or on any other suitable structure(s).

Field generators (122) are operable to generate an electromagnetic field around the head of the patient. In particular, field generators (122) are operated so as to transmit alternating magnetic fields of different frequencies into a region in proximity to frame (120). Field generators (122) thereby enable tracking of the position of a navigation guidewire (130) that is inserted into a nasal sinus of the patient and in other locations within the patient's head. Various suitable components that may be used to form and drive field generators (122) will be apparent to those of ordinary skill in the art in view of the teachings herein.

Navigation guidewire (130) may be used as a substitute for guidewire (30) described above, and may include a sensor (not shown) that is responsive to movement within the fields generated by field generators (122). In particular, signals generated by the sensor of navigation guidewire (130) may be processed by processor (110) to determine the three-dimensional location of navigation guidewire (130) within the patient. Various suitable forms that the sensor may take will be apparent to those of ordinary skill in the art in view of the teachings herein, particularly in view of several of the references that are cited herein in the context of IGS navigation system (100). It should be understood that, when used as a substitute for guidewire (30) in dilation catheter system (10), navigation guidewire (130) may facilitate navigation of instrumentation of dilation catheter system (10) within the patient during performance of a procedure to dilate the ostium of a paranasal sinus; or to dilate some other anatomical passageway (e.g., within the ear, nose, or throat, etc.). It should also be understood that other components of dilation catheter system (10) may incorporate a sensor like the sensor of navigation guidewire (130).

IGS navigation system (100) of the present example further comprises a processor (110), which controls field generators (122) and other elements of IGS navigation system (100). Processor (110) comprises a processing unit communicating with one or more memories. Processor (110) of the present example is mounted in a console (116), which comprises operating controls (112) that include a keypad and/or a pointing device such as a mouse or trackball. A physician uses operating controls (112) to interact with processor (110) while performing the surgical procedure.

Console (116) also connects to other elements of system (100). For instance, as shown in FIG. 2 a coupling unit (132) is secured to the proximal end of navigation guidewire (130). Coupling unit (132) of this example is configured to provide wireless communication of data and other signals between console (116) and navigation guidewire (130). In some versions, coupling unit (132) simply communicates data or other signals from navigation guidewire (130) to console (116) uni-directionally, without also communicating data or other signals from console (116). In some other versions, coupling unit (132) provides bidirectional communication of data or other signals between navigation guidewire (130) to console (116). While coupling unit (132) of the present example couples with console (116) wirelessly, some other versions may provide wired coupling between coupling unit (132) and console (116). Various other suitable features and functionality that may be incorporated into coupling unit (132) will be apparent to those of ordinary skill in the art in view of the teachings herein.

Processor (110) uses software stored in a memory of processor (110) to calibrate and operate system (100). Such operation includes driving field generators (122), processing data from navigational guidewire (130), processing data from operating controls (112), and driving display screen (114). The software may be downloaded to processor (110) in electronic form, over a network, for example, or it may, alternatively or additionally, be provided and/or stored on non-transitory tangible media, such as magnetic, optical, or electronic memory.

Processor (110) is further operable to provide video in real time via display screen (114), showing the position of the distal end of navigational guidewire (130) in relation to a video camera image of the patient's head, a CT scan image of the patient's head, and/or a computer generated three-dimensional model of the anatomy within and adjacent to the patient's nasal cavity. Display screen (114) may display such images simultaneously and/or superimposed on each other. Moreover, display screen (114) may display such images during the surgical procedure. Such displayed images may also include graphical representations of instruments that are inserted in the patient's head, such as navigational guidewire (130), such that the operator may view the virtual rendering of the instrument at its actual location in real time. Such graphical representations may actually look like the instrument or may be a much simpler representation such as a dot, crosshairs, etc. By way of example only, display screen (114) may provide images in accordance with at least some of the teachings of U.S. Pub. No. 2016/0008083, entitled "Guidewire Navigation for Sinuplasty," published Jan. 14, 2016, the disclosure of which is incorporated by reference herein. In the event that the operator is also using an endoscope, the endoscopic image may also be provided on display screen (114). The images provided through display screen (114) may help guide the operator in maneuvering and otherwise manipulating instruments within the patient's head.

In the present example, navigational guidewire (130) includes one or more coils at the distal end of navigational guidewire (130). Such a coil serves as a sensor as referred to above. When such a coil is positioned within an electromagnetic field generated by field generators (122), movement of the coil within that magnetic field may generate electrical current in the coil, and this electrical current may be communicated along the electrical conduit(s) in navigational guidewire (130) and further to processor (110) via coupling unit (132). This phenomenon may enable IGS navigation system (00) to determine the location of the distal end of navigational guidewire (130) within a three-dimensional space as will be described in greater detail below. In particular, processor (110) executes an algorithm to calculate location coordinates of the distal end of navigational guidewire (130) from the position related signals of the coil(s) in navigational guidewire (130).

In some instances, navigational guidewire (130) is used to generate a three-dimensional model of the anatomy within and adjacent to the patient's nasal cavity; in addition to being used to provide navigation for dilation catheter system (100) within the patient's nasal cavity. Alternatively, any other suitable device may be used to generate a three-dimensional model of the anatomy within and adjacent to the patient's nasal cavity before navigational guidewire (130) is used to provide navigation for dilation catheter system (100) within the patient's nasal cavity. By way of example only, a model of this anatomy may be generated in accordance with at least some of the teachings of U.S. Pub. No. 2016/0310042, entitled "System and Method to Map Structures of Nasal Cavity," published Oct. 27, 2016, the disclosure of which is incorporated by reference herein. Still other suitable ways in which a three-dimensional model of the anatomy within and adjacent to the patient's nasal cavity may be generated will be apparent to those of ordinary skill in the art in view of the teachings herein. It should also be understood that, regardless of how or where the three-dimensional model of the anatomy within and adjacent to the patient's nasal cavity is generated, the model may be stored on console (116). Console (116) may thus render images of at least a portion of the model via display screen (114) and further render real-time video images of the position of navigational guidewire (130) in relation to the model via display screen (114).

IV. First Exemplary Alternative Dilation Catheter Instrument

A. Overview

It may be desirable to provide a variation of dilation catheter system (10) that enables the operator to adjust various features to facilitate uses in different scenarios, without requiring the operator to switch between different instruments. For instance, it may be desirable to enable use of a single dilation instrument that may be used to dilate various different anatomical passageways (e.g., frontal sinus ostium, frontal recess, maxillary sinus ostium, sphenoid sinus ostium, ethmoid sinus ostium, Eustachian tube, etc.) by making simple adjustments to structural features of the instrument. Similarly, it may me desirable to facilitate use of a single dilation instrument to perform procedures on a patient regardless of whether the patient is in a sitting position or supine position. In addition, it may be desirable to provide an instrument with actuation features that enable translation of a dilation catheter, translation of a guidewire, and spinning of a guidewire, all with a single hand. The instrument (200) described below includes examples of features that provide all the foregoing functionality, among other functionalities.

Figure 9A:
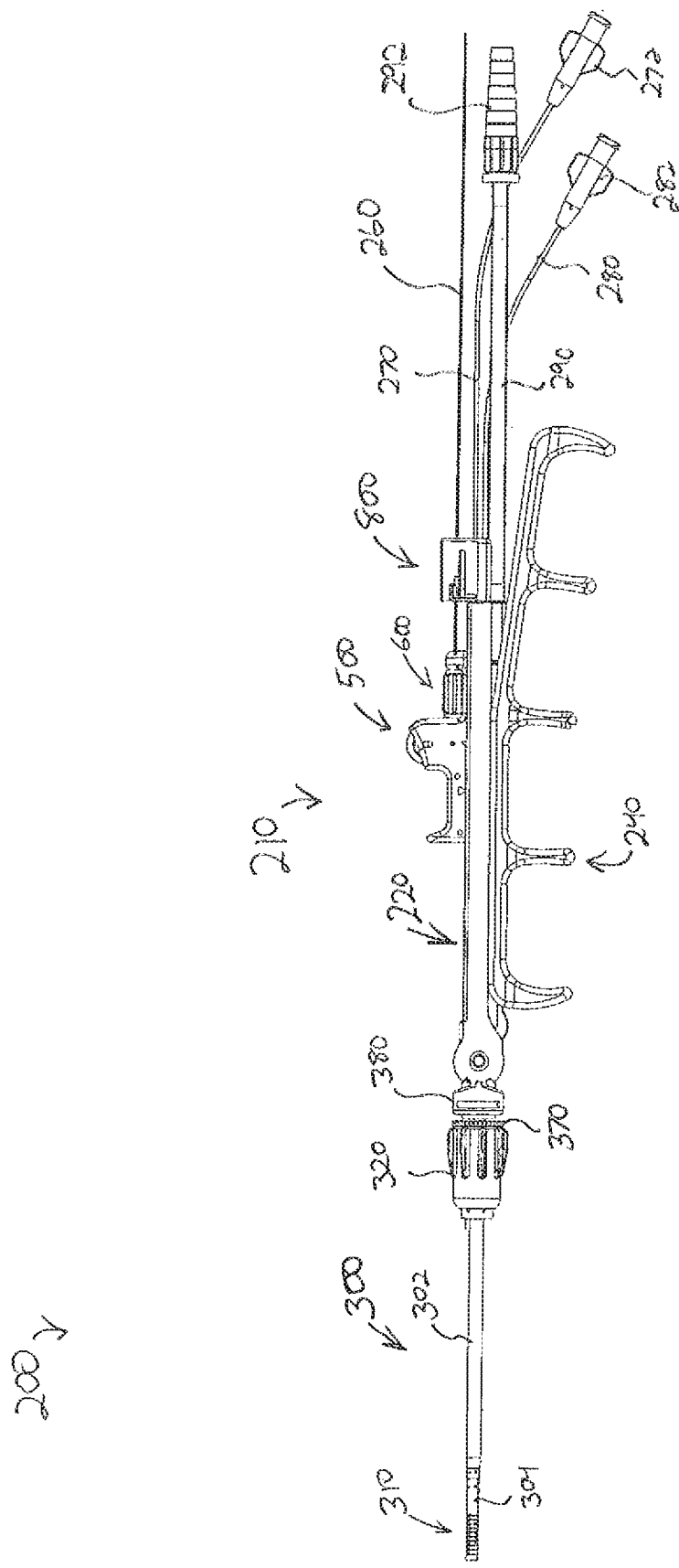
FIG. 9A depicts a side elevational view of the instrument of FIG. 8, with a guidewire in a proximal position and a dilation catheter in a proximal position.
Figure 9C:
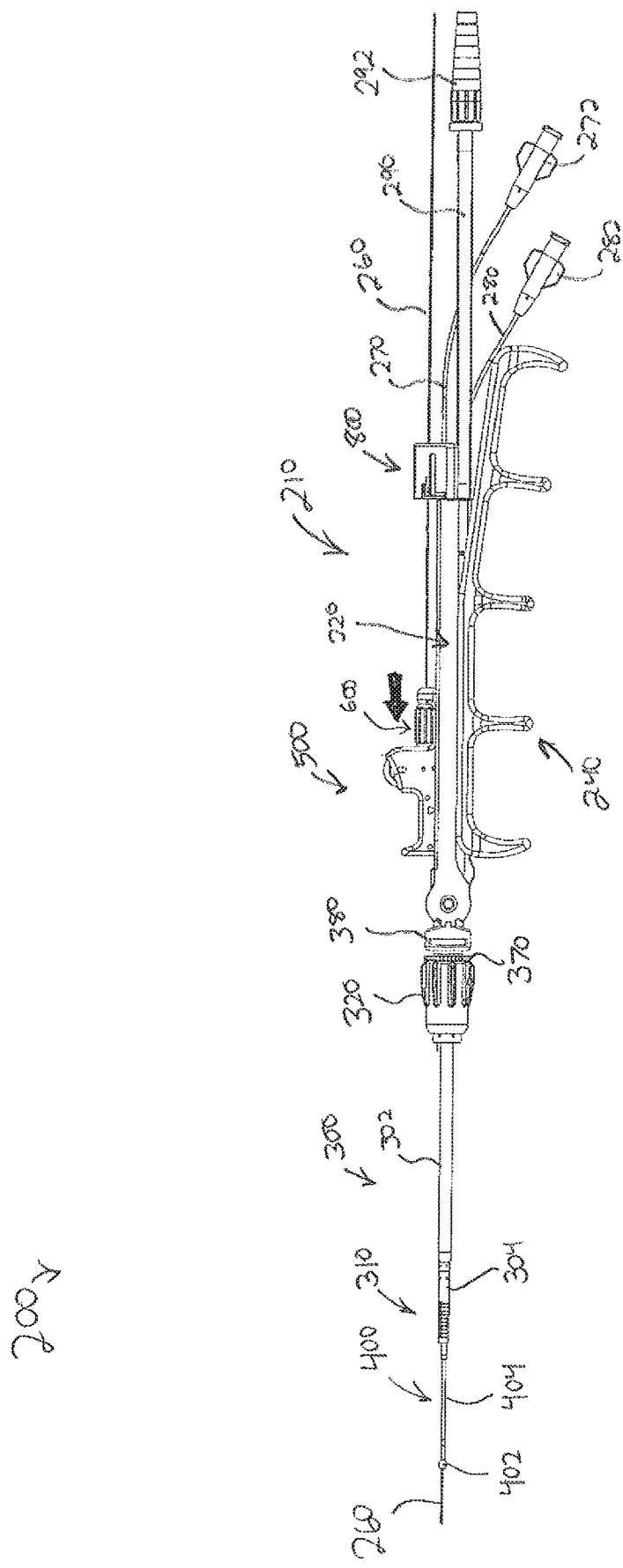
FIG. 9C depicts a side elevational view of the instrument of FIG. 8, with the guidewire in the distal position and the dilation catheter in a distal position, and with a dilator of the dilation catheter in a non-expanded state.
Figure 9D:
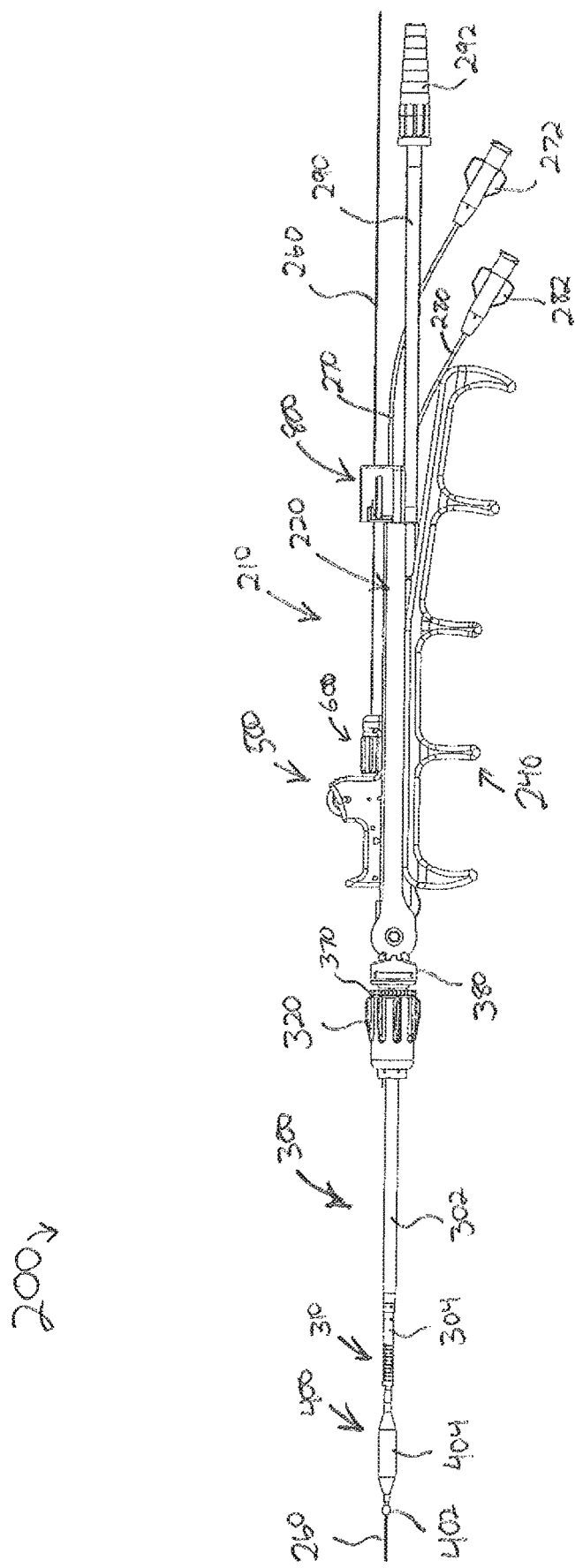
FIG. 9D depicts a side elevational view of the instrument of FIG. 8, with the guidewire in the distal position and the dilation catheter in a distal position, and with the dilator in an expanded state.

As shown in FIGS. 8-9D, instrument (200) of the present example comprises a handle assembly (210), a shaft assembly (300), an actuator (500), and a guidewire locking assembly (800). All these components and their associated features will be described in greater detail below. Instrument (200) further includes a guidewire (260), a irrigation conduit (280), an inflation conduit (270), and a suction conduit (290). In some versions, guidewire (260) is operable to emit light like guidewire (50), such that the proximal end of guidewire (260) is coupled with a light source. In some other versions, guidewire (260) is operable to provide position tracking like guidewire (130), such that the proximal end of guidewire (260) is coupled with an IGS navigation system like IGS navigation system (100). Other suitable forms that guidewire (260) may take will be apparent to those of ordinary skill in the art in view of the teachings herein.

In the present example, as shown in FIG. 8, guidewire (260) includes a slip coupling (262). Slip coupling (262) secures a proximal portion (263) of guidewire (260) with a distal portion (261) of guidewire (260) and provides tensile strain relief in guidewire (260). Slip coupling (262) also allows the distal portion (261) of guidewire (260) to rotate relative to the proximal portion of guidewire (260) through at least 360 degrees of rotation; while still providing simultaneous longitudinal translation of the distal and proximal portions (261, 263) of guidewire (260). Thus, when guidewire (260) is rotated about the longitudinal axis of guidewire (260) as described in greater detail below, slip coupling (262) prevents the build-up of torsion along the proximal portion (263) of guidewire (260); while allowing the distal portion (261) of guidewire (260) to rotate freely. In versions where guidewire (260) includes one or more optical fibers like guidewire (50), slip coupling (262) includes features allowing light to pass freely through slip coupling (262), such that slip coupling (262) maintains optical continuity between the distal and proximal portions (261, 263) of guidewire (260). In versions where guidewire (260) includes one or more sensors like guidewire (130), slip coupling (262) includes features that provide electrical continuity between the distal and proximal portions of guidewire (260).

Figure 50:
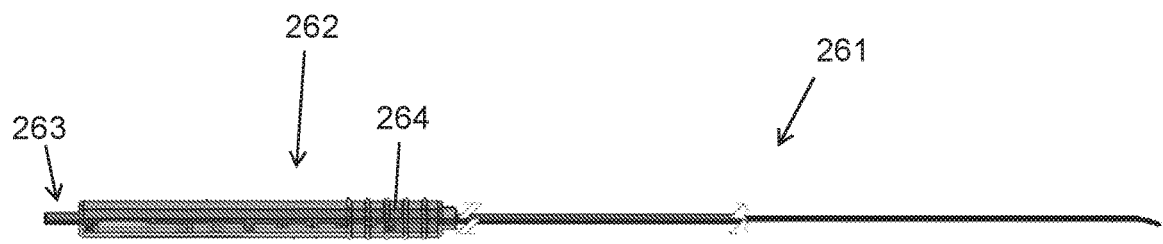
FIG. 50 depicts a side elevational view of a slip coupling coupled with the guidewire of FIG. 9A.
Figure 51:
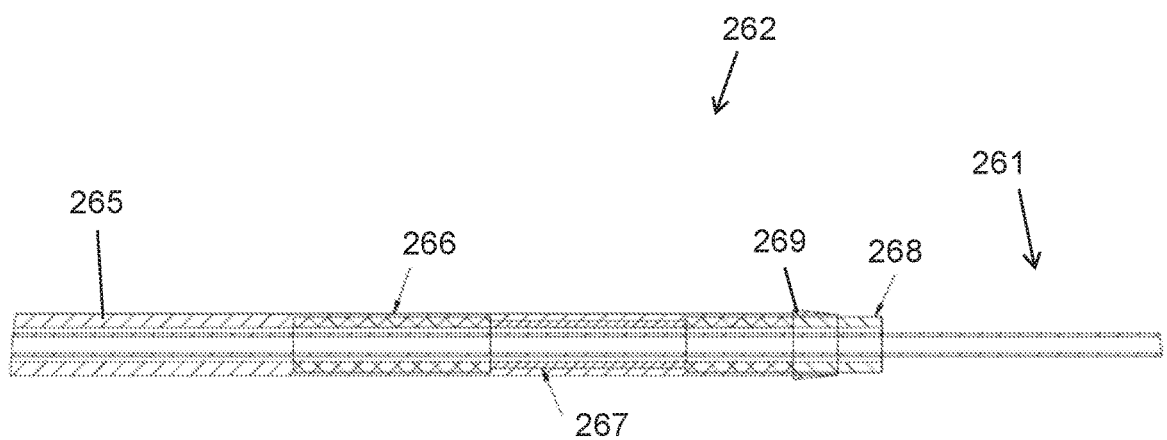
FIG. 51 depicts a cross-sectional side view of a portion of the slip coupling of FIG. 50.

FIGS. 50-51 show slip coupling (262) of the present example in greater detail. As shown in FIG. 50, slip coupling (262) includes a housing assembly (264), which may be formed by a pair of mating halves or any other suitable components. Proximal portion (263) of guidewire (260) is fixedly secured relative to housing assembly (264); while distal portion (261) of guidewire (260) is configured to rotate relative to housing assembly (264), about the longitudinal axis of guidewire (260). FIG. 51 shows components that are contained within housing assembly (264). In particular, FIG. 51 shows an outer sleeve (265), a proximal tube member (266), an intermediate tube member (267), a distal tube member (268), and a ferrule (269). Outer sleeve (265), tube members (266, 267, 268), and ferrule (269) are all coaxially aligned with each other. Intermediate tube member (267) is longitudinally interposed between proximal and distal tube members (266, 268). All tube members (266, 267, 268) are positioned within the interior of outer sleeve (265). In some versions, distal tube member (268) includes a heat shrink and/or a distal fillet.

Outer sleeve (265) is fixedly secured relative to housing assembly (264) via ferrule (269). Outer sleeve (265) is also fixedly secured relative to proximal portion (263) of guidewire (260). The interface between ferrule (269) and housing assembly (264) may be further sealed by an adhesive and/or any other suitable means. Proximal and distal tube members (266, 268) are fixedly secured to outer sleeve (265) (e.g., via an adhesive or other means), such that proximal and distal tube members (266, 268) are also fixedly secured relative to housing assembly (264). Intermediate tube member (267) is fixedly secured to distal portion (261) of guidewire (260). However, intermediate tube member (267) is not fixedly secured to outer sleeve (265). Moreover, distal portion (261) of guidewire (260) is not fixedly secured to distal tube member (268) or outer sleeve (265). Intermediate tube member (267) is free to rotate within outer sleeve (265). Thus, outer sleeve (265) and tube members (266, 268) cooperate to longitudinally constrain intermediate tube member (267) and distal portion (261) of guidewire (260) relative to housing assembly (264); while permitting intermediate tube member (267) and distal portion (261) of guidewire (260) to rotate relative to housing assembly (264).

By way of further example only, components of slip coupling (262) may be formed of metal, plastic, composite, ceramic, and/or various other kinds of materials. In addition, components of slip coupling (262) that are fixedly secured to each other may be fixedly secured using welding, soldering, adhesive bonding, mechanical crimping, and/or other kinds of techniques. Other suitable forms that slip coupling (262) may take will be apparent to those of ordinary skill in the art in view of the teachings herein.

The proximal end of inflation conduit (270) also includes a fitting (272), which may be coupled with a source of inflation fluid (e.g., saline, etc.). By way of example only, fitting (272) may be coupled with an inflator like inflator (40) described above. The proximal end of irrigation conduit (280) includes a fitting (282), which may be coupled with a source of irrigation fluid (e.g., saline, etc.). The proximal end of suction conduit (290) also includes a fitting (292), which may be coupled with a source of suction (e.g., vacuum pump).

As shown in FIGS. 9A-9D, instrument (200) is operable to transition among various states during use in a dilation procedure. FIG. 9A shows instrument (200) in a state where guidewire (260) and a dilation catheter (400) are both in proximal positions. During a dilation procedure, this operational state of instrument (200) may correspond with a procedure state like the one shown in FIG. 5A. FIG. 9B shows instrument (200) in a state where actuator (500) has been actuated to drive guidewire (260) distally, while dilation catheter (400) remains in a proximal position. During a dilation procedure, this operational state of instrument (200) may correspond with a procedure state like the one shown in FIG. 5B. FIG. 9C shows instrument (200) in a state where actuator (500) has been actuated to drive dilation catheter (400) distally, while guidewire (260) remains in the distal position. During a dilation procedure, this operational state of instrument (200) may correspond with a procedure state like the one shown in FIG. 5C. FIG. 9D shows instrument (200) in a state where a dilator (404) of dilation catheter (400) has been expanded. During a dilation procedure, this operational state of instrument (200) may correspond with a procedure state like the one shown in FIG. 5D.

B. Exemplary Guide Distal End Deflection Assembly

As noted above, it may be desirable to enable use of a single dilation instrument that may be used to dilate various different anatomical passageways (e.g., frontal sinus ostium, frontal recess, maxillary sinus ostium, sphenoid sinus ostium, ethmoid sinus ostium, Eustachian tube, etc.) by making simple adjustments to structural features of the instrument. Shaft assembly (300) of the present example is configured to enable such adjustment. Shaft assembly (300) includes a rigid shaft member (302) and a flexible shaft member (304). In some versions, both shaft members (302, 304) are formed of a metallic material. By way of example only, one or both of shaft members (302, 304) may be formed of stainless steel and/or nitinol. In some such versions, shaft members (302, 304) (and at least some other portions of instrument (200)) may be reusable, with such reusable components being subject to cleaning and sterilization between uses on different patients. In some other versions, one or both of shaft members (302, 304) may be formed of a polymeric material. In some such versions, shaft members (302, 304) may be treated as single-use-only components.

Figure 10A:
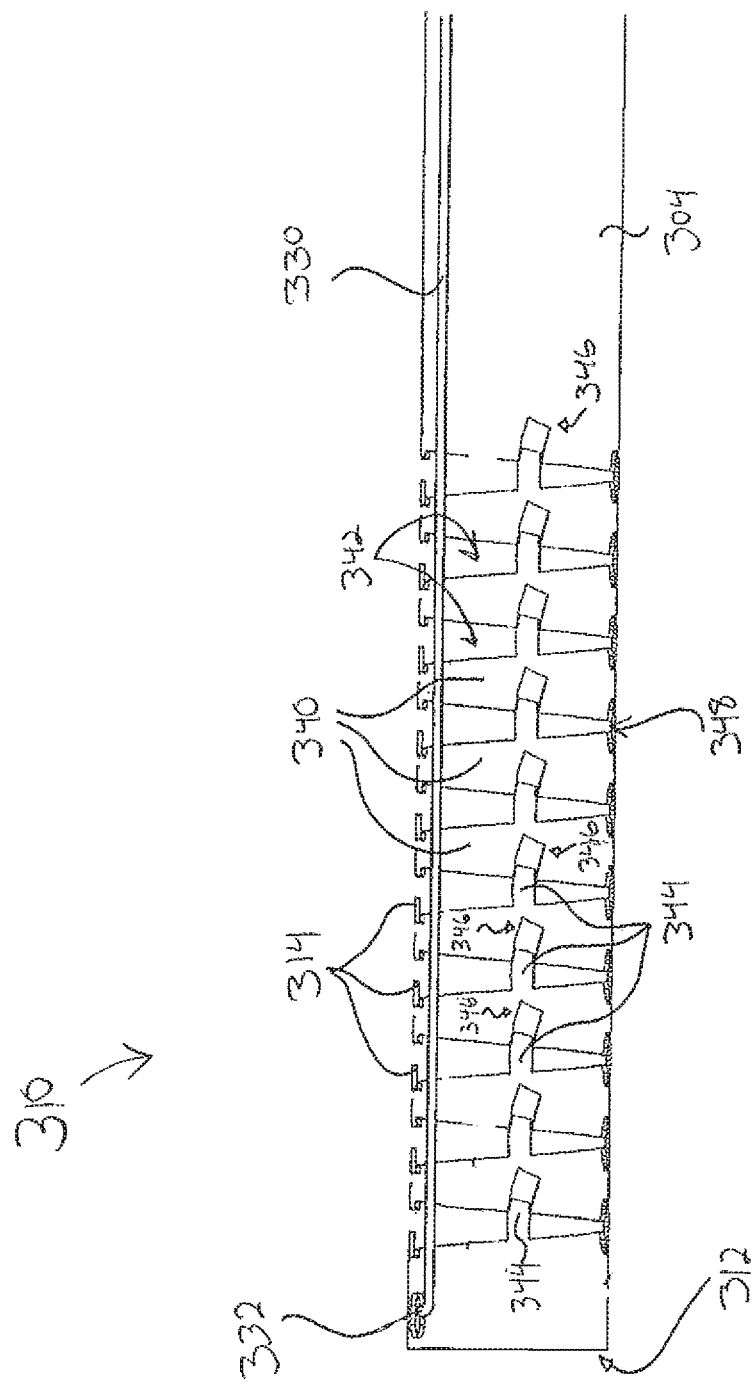
FIG. 10A depicts a cross-sectional side view of a distal portion of a flexible shaft member of the instrument of FIG. 8, with the distal portion in a straight configuration.

Flexible shaft member (304) is secured to rigid shaft member (302), is coaxially aligned with rigid shaft member (302), and is positioned distally in relation to rigid shaft member (302). As best seen in FIGS. 10A-10B, flexible shaft member (304) includes a flex section (310) that is formed by a series of ribs (340), which are separated by a series of notches (342). Notches (342) are generally V-shaped, with a circular opening at the vertex of each "V." Notches (342) also include tab portions (344) that fit in corresponding sub-notches (346). The top of each "V" includes a set of stop features (314).

As shown in FIG. 10A, when flex section (310) is in a straight configuration, tab portions (344) are disposed in corresponding sub-notches (346) but are not fully seated in sub-notches (346). As also shown in FIG. 10A, when flex section (310) is in a straight configuration, stop features (314) are separated from each other. FIG. 10B shows flex section (310) in a fully bent configuration. In this state, tab portions (344) are fully seated in sub-notches (346) and stop features (314) are engaged with each other. During the transition between the states shown in FIGS. 10A-10B, tab portions (344) and sub-notches (346) may cooperate to ensure that flex section (310) bends in a consistent fashion, with sufficient lateral stability; and that flex section (310) provides a consistent and stable bent or straight state.

By way of example only, flex section (310) may be formed through laser cutting or any other suitable manufacturing process. Also in the present example, as shown in FIG. 11, flex section (310) is covered with a flexible wrap (306). Flexible wrap (306) prevents tissue and other structures from getting snagged or pinched in notches (342), without compromising the flexibility of flex section (310). Flexible wrap (306) may also ensure that suction provided through shaft assembly (300) is focused at distal end (312). Various suitable forms that flex section (310) may take will be apparent to those of ordinary skill in the art in view of the teachings herein. By way of further example only, flex section (310) may be constructed and operable in accordance with at least some of the teachings of U.S. patent application Ser. No. 15/955,232, entitled "Deflectable Guide for Medical Instrument," filed Apr. 17, 2018, the disclosure of which is incorporated by reference herein.

Figure 16:
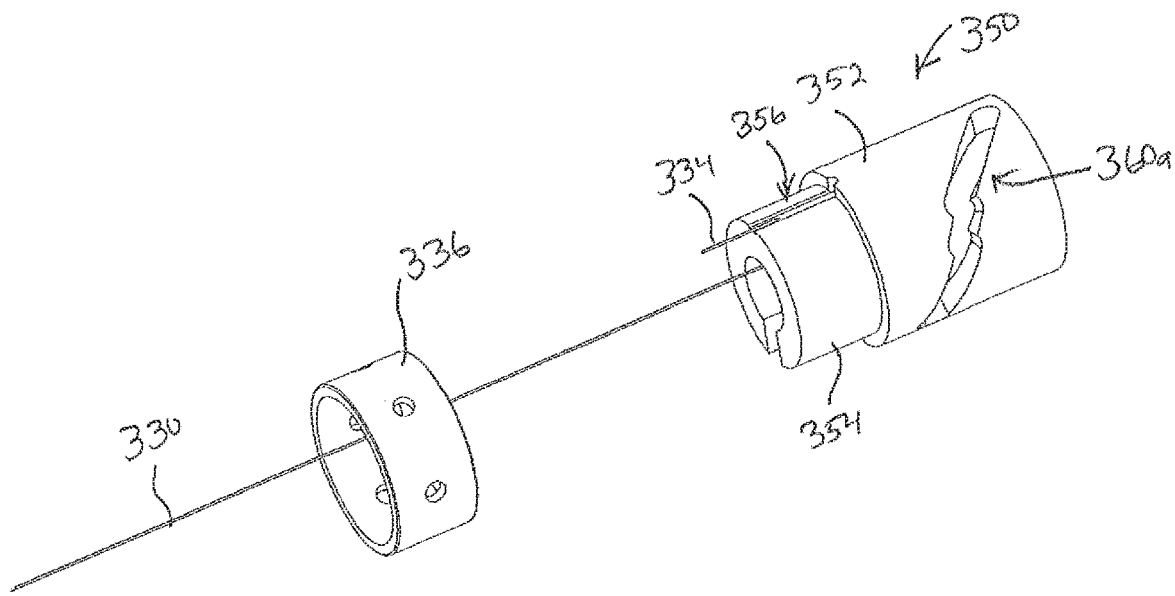
FIG. 16 depicts an exploded perspective view of components of the shaft assembly of FIG. 11.

In order to provide controlled bending of flex section (310), a push-pull wire (330) is disposed within shaft members (302, 304). As shown in FIGS. 10A-10B, a distal end (332) of push-pull wire (330) is secured to the distal end (312) of flexible shaft member (304), distal to flex section (310). Push-pull wire (330) is disposed near the tops of the "V"s of notches (342). Thus, when push-pull wire (330) is pulled proximally, flex section (310) will bend to a deflected configuration. When push-pull wire (330) is pushed distally, flex section (310) will bend toward a straight configuration. As shown in FIGS. 11 and 16, a proximal end (334) of push-pull wire (330) is secured to a cam barrel (350) by a collar (336). In particular, proximal end (334) is disposed in a bore of cam barrel (350) passes transversely through cam barrel (350), then extends distally along a trough (356) formed in cam barrel (350). Collar (336) is secured to a necked-down region (354) of cam barrel (350), thereby securing proximal end (334) in trough (356). As will be described in greater detail below, translation of cam barrel (350) will cause translation of push-pull wire (330), which will thereby cause straightening or bending of flex section (310).

As best seen in FIG. 11, cam barrel (350) is disposed within a deflection control knob (320), both of which are coaxially disposed about the proximal end of rigid shaft member (302), with a rotary control knob (370) being positioned proximal to deflection control knob (320). A pair of pins (322) are rigidly secured within the interior of deflection control knob (320) such that pins (322) rotate unitarily with deflection control knob (320) about the longitudinal axis of shaft assembly (300). Pins (322) are angularly offset from each other by 180° in this example.

Figure 12:
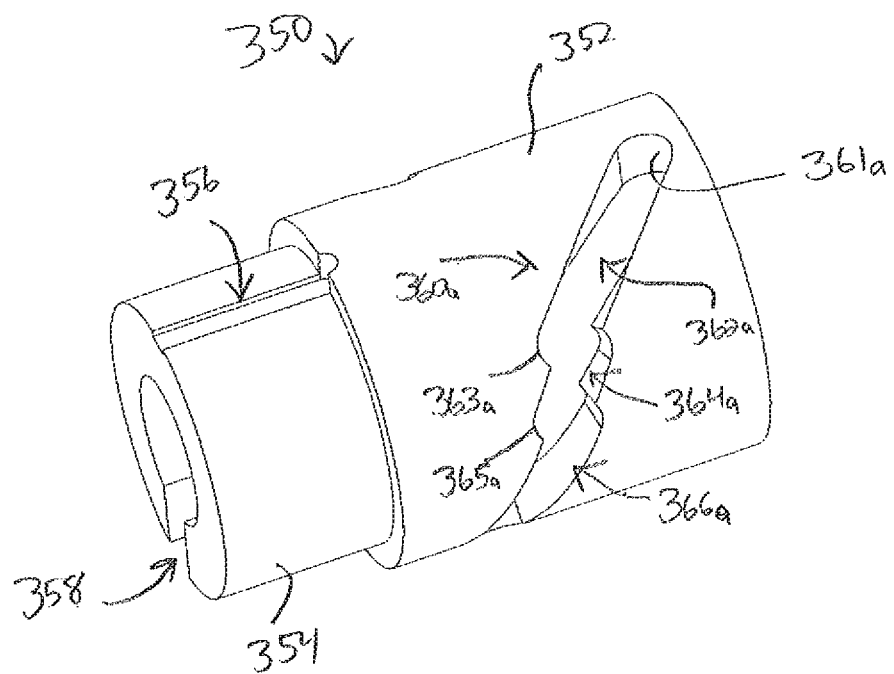
FIG. 12 depicts a perspective view of a cam barrel of the shaft assembly of FIG. 11.
Figure 13:
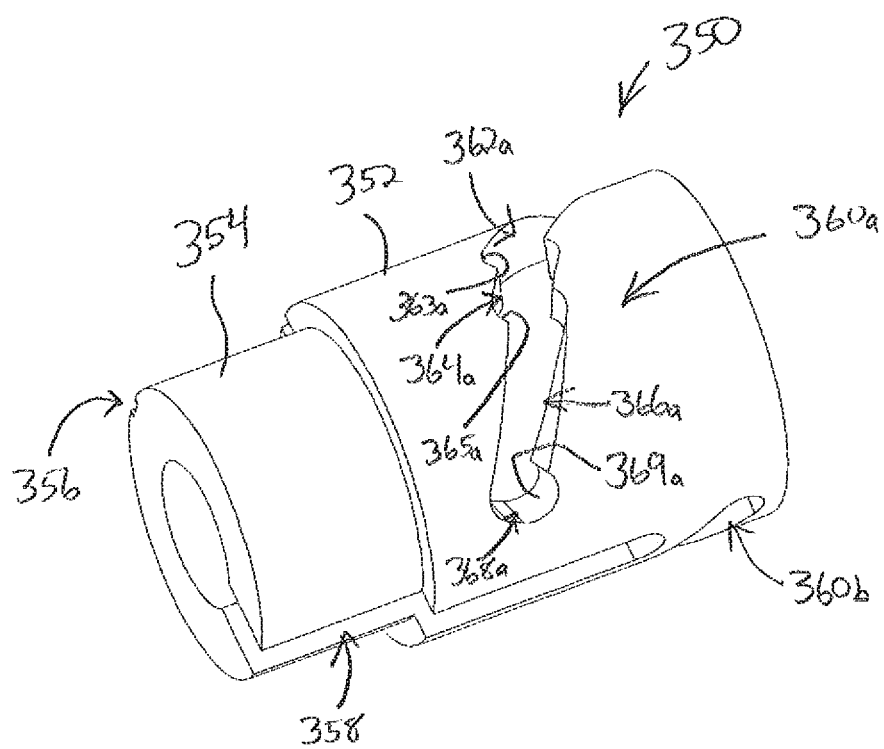
FIG. 13 depicts another perspective view of the cam barrel of FIG. 12.

As best seen in FIGS. 12-15, cam barrel (350) includes a pair of opposing cam slots (360a, 360b), which are located in a proximal region (352) of cam barrel (350). Cam barrel (350) also includes a lateral channel (358), which extends through necked-down region (354) and a portion of proximal region (352). Cam slots (360a, 360b) extend along generally helical paths, with features providing slight deviation from purely helical configurations. In particular, cam slot (360a) includes a first section (362a), a second section (364a), and a third section (366a). As shown in FIG. 12, first section (362a) extends from an end (361a) to an end (363a). End (363a) provides a step to transition from first section (362a) to second section (364a). When pin (322) encounters end (363a) as will be described in greater detail below, the step provided by end (363a) will provide a slight resistance to further motion of pin (322), thereby providing tactile feedback to the operator and helping to maintain the position of pin (322) at end (363a). Second section (364a) further terminates in another end (365a). Again, end (365a) provides a step to transition from second section (364a) to third section (366a). As shown in FIG. 13, third section (366a) further terminates in an end (368a), which has an associated notch (369a).

Figure 14:
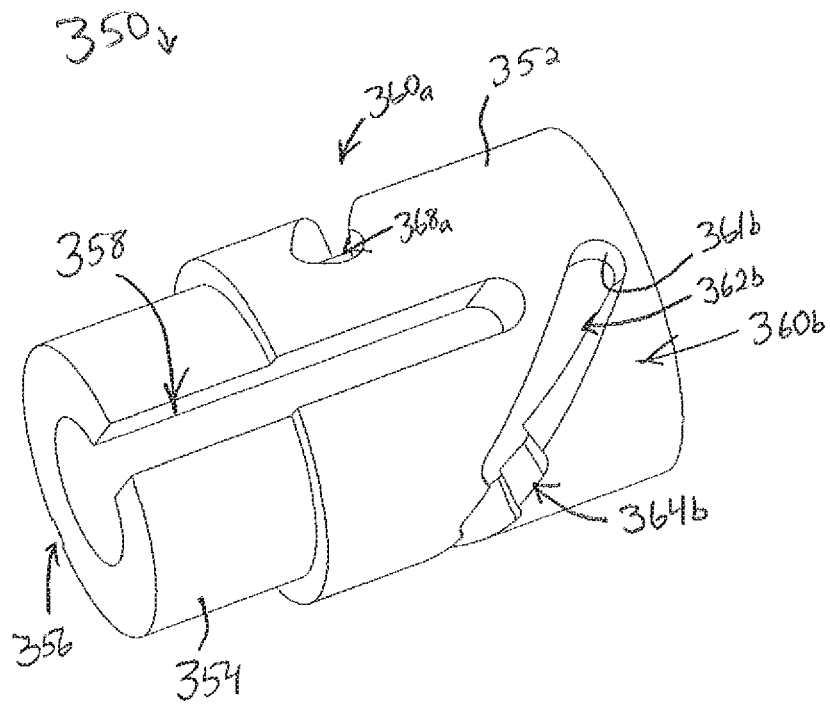
FIG. 14 depicts another perspective view of the cam barrel of FIG. 12.
Figure 15:
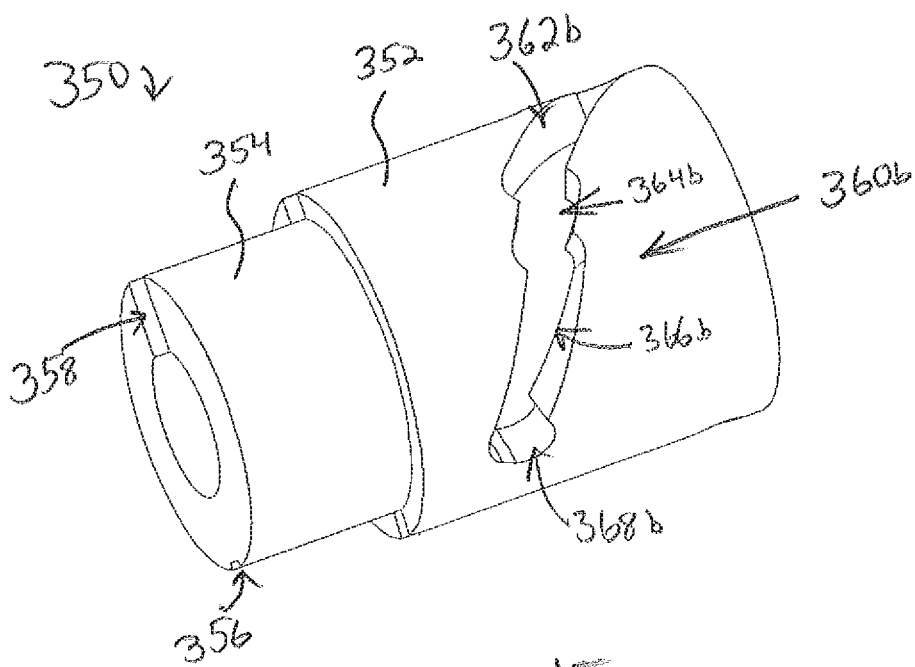
FIG. 15 depicts another perspective view of the cam barrel of FIG. 12.

The configuration of cam slot (360b) complements the configuration of cam slot (360a). Thus, as shown in FIGS. 14-15, cam slot (360b) is bounded by ends (361b, 368b) and includes a first section (362b), a second section (364b), and a third section (366b).

Figure 18:
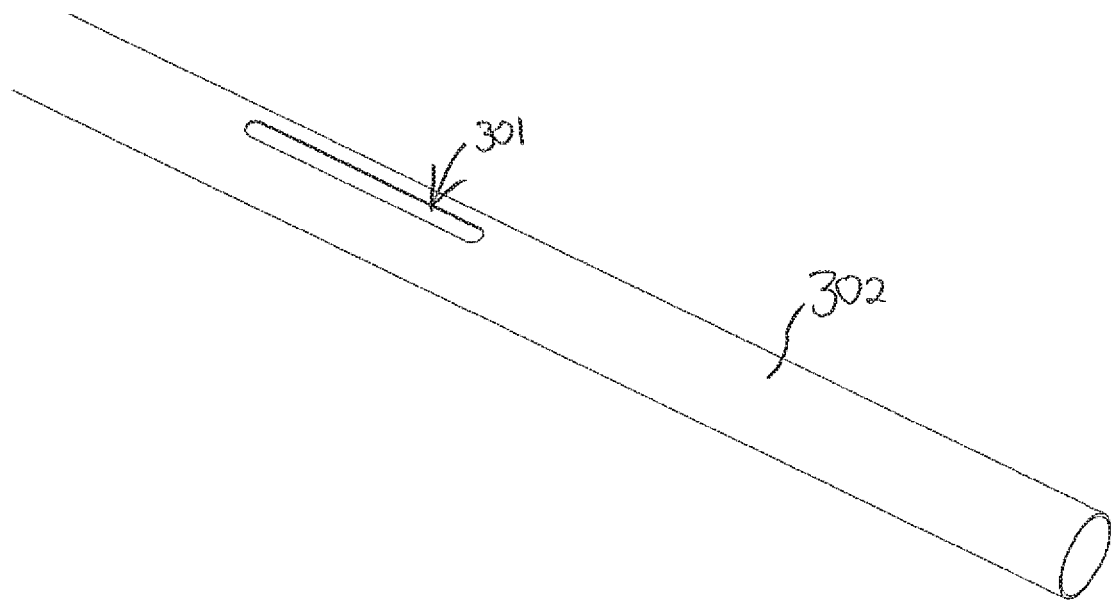
FIG. 18 depicts a perspective view of a proximal portion of a rigid shaft member of the shaft assembly of FIG. 11.
Figure 19:
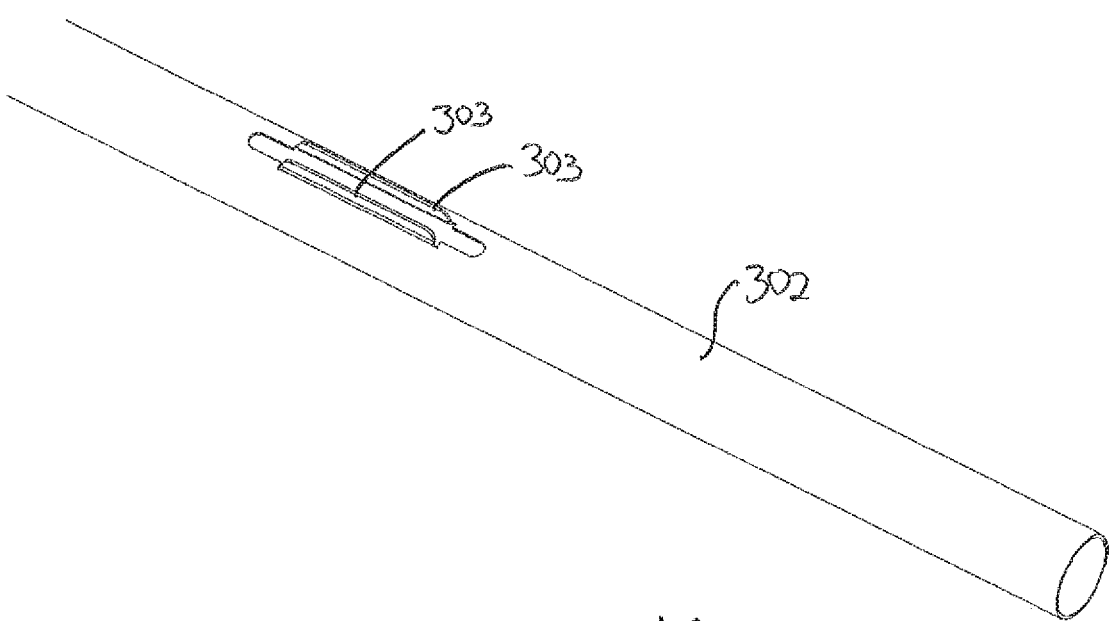
FIG. 19 depicts another perspective view of the proximal portion of the rigid shaft member of FIG. 18.

Cam barrel (350) is coupled with rigid shaft member (302) such that cam barrel (350) is allowed to slide longitudinally along rigid shaft member (302); yet cam barrel (350) is prevented from rotating about rigid shaft member (302). As shown in FIG. 18, one side of the proximal portion of rigid shaft member (302) includes an elongate slot (301). Slot (301) is configured to enable push-pull wire (330) to pass transversely through rigid shaft member (302). Slot (301) is also configured to enable the transversely-extending portion of push-pull wire (330) to translate relative to rigid shaft member (302) during the operational sequence shown in FIGS. 20A-20D and described further below. As shown in FIG. 19, the other side of the proximal portion of rigid shaft member (302) includes a pair of transversely extending, rigid fins (303). Fins (303) are disposed in lateral channel (358) of cam barrel (350). Due to the relationship between fins (303) and lateral channel (358), cam barrel (350) is allowed to slide longitudinally along rigid shaft member (302); yet cam barrel (350) is prevented from rotating about rigid shaft member (302). Alternatively, any other suitable kinds of features may provide such a relationship between cam barrel (350) and rigid shaft member (302).

Figure 17:
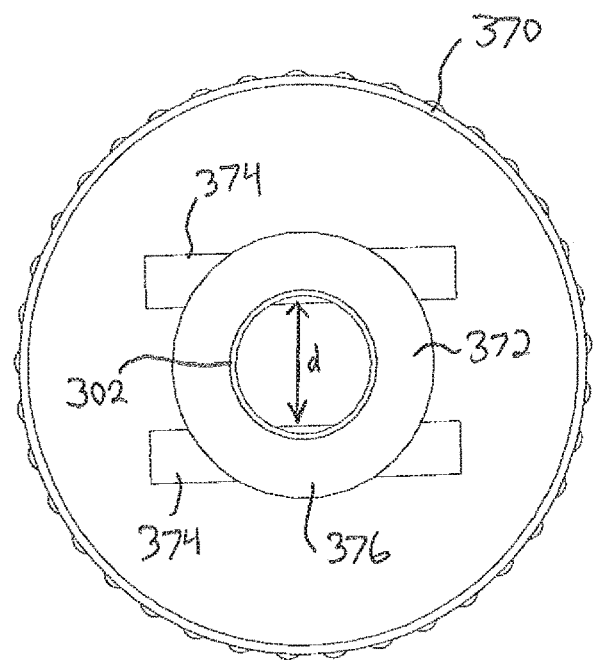
FIG. 17 depicts an end view of a rotary control knob of the shaft assembly of FIG. 11.

As shown in FIGS. 17 and 20A-20D, rotary control knob (370) includes a pair of transversely extending pins (374) that are rigidly secured to a distal cylindraceous portion (372) of rotary control knob (370). Pins (374) cooperate with an annular flange (321) of deflection control knob (320) to longitudinally restrain deflection control knob (320) relative to rotary control knob (370); while allowing deflection control knob (320) to rotate relative to rotary control knob (370). As best seen in FIG. 17, pins (374) are spaced apart from each other by a distance (d). This distance (d) is less than the outer diameter of rigid shaft member (302). Thus, pins (374) provide an interference with rigid shaft member (302), thereby providing a unitary coupling between rotary control knob (370) and rigid shaft member (302). In other words, rotary control knob (370) may be manipulated to rotate the entire shaft assembly (300) about the longitudinal axis of shaft assembly (300). This may be done to re-orient the distal end of shaft assembly to promote access to a particular anatomical passageway, particularly when flex section (310) is in a bent configuration.

Figure 20A:
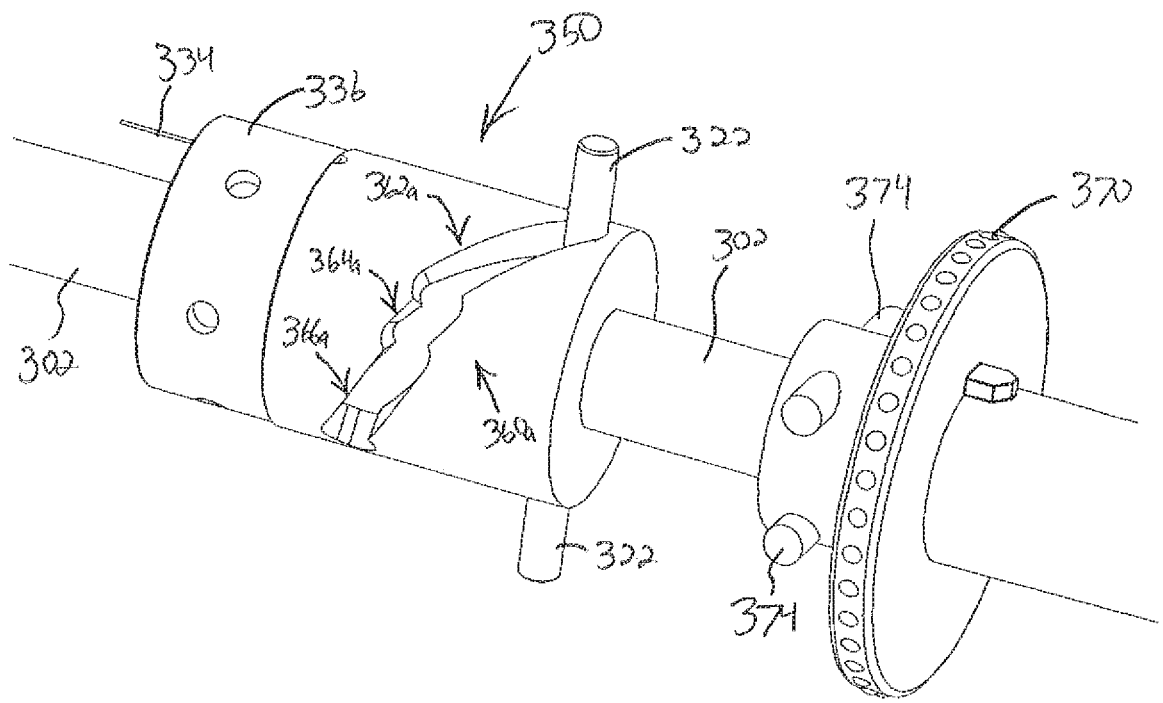
FIG. 20A depicts a perspective view of components of the shaft assembly of FIG. 11, with drive pins of the shaft assembly at a first angular position and with the cam barrel and a drive cable of the shaft assembly at a first longitudinal position.

FIGS. 20A-20D show pins (322) travelling along cam slots (360a, 360b) during an exemplary sequence of operation. While deflection control knob (320) is omitted from FIGS. 20A-20D, it should be understood that pins (322) are rigidly secured within deflection control knob (320). Thus, the angular motion of pins (322) about the longitudinal axis of shaft assembly (300) is provided by rotating deflection control knob (320) about the longitudinal axis of shaft assembly (300). FIG. 20A shows pins (322) at respective ends (361a, 361b). In this state, cam barrel (350) and push-pull wire (330) are at distal-most positions, such that flex section (310) is in a straight configuration. When flex section (310) is in this straight configuration, shaft assembly (300) will easily guide guidewire (260) and dilation catheter (400) into a first particular anatomical passageway such as the sphenoid sinus ostium.

Figure 20B:
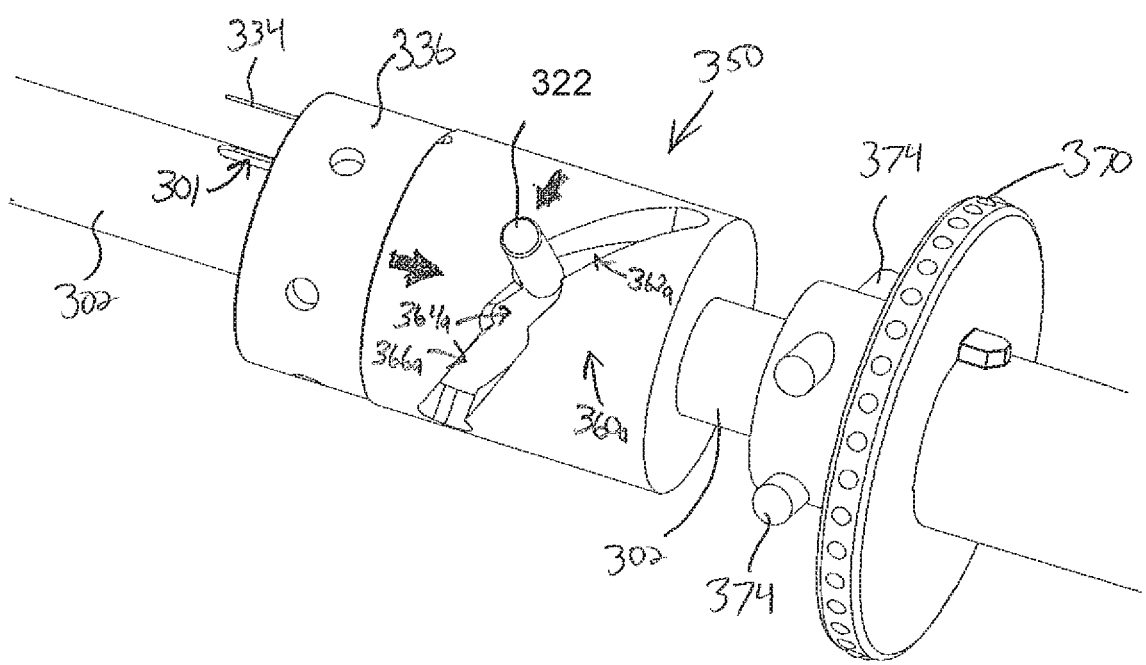
FIG. 20B depicts a perspective view of components of the shaft assembly of FIG. 11, with the drive pins at a second angular position and with the cam barrel and drive cable at a second longitudinal position.

FIG. 20B shows pins (322) having fully traversed first sections (362a, 362b). This motion is accomplished by rotation of deflection control knob (320). While cam barrel (350) remains angularly stationary during this rotation of deflection control knob (320), cam barrel (350) and push-pull wire (330) translate proximally during this rotation of deflection control knob (320). This proximal movement of push-pull wire (330) causes partial deflection of flex section (310), such that flex section (310) is no longer in a straight configuration. Upon traversal of first sections (362a, 362b), pins (322) reach ends (363a, 363b). The step provided by ends (363a, 363b) provides resistance to further motion of pins (322), thereby providing tactile feedback to the operator indicating that flex section (310) has achieved a first deflected state. This first deflected state may be associated with an angle that facilitates access to a second particular anatomical passageway, such as the Eustachian tube. Thus, when flex section (310) is in this first deflected state, shaft assembly (300) will easily guide guidewire (260) and dilation catheter (400) into that second particular anatomical passageway. By way of example only, the angle of the first deflected state may be between approximately 50 degrees and approximately 60 degrees, or more particularly at approximately 55 degrees.

Figure 20C:
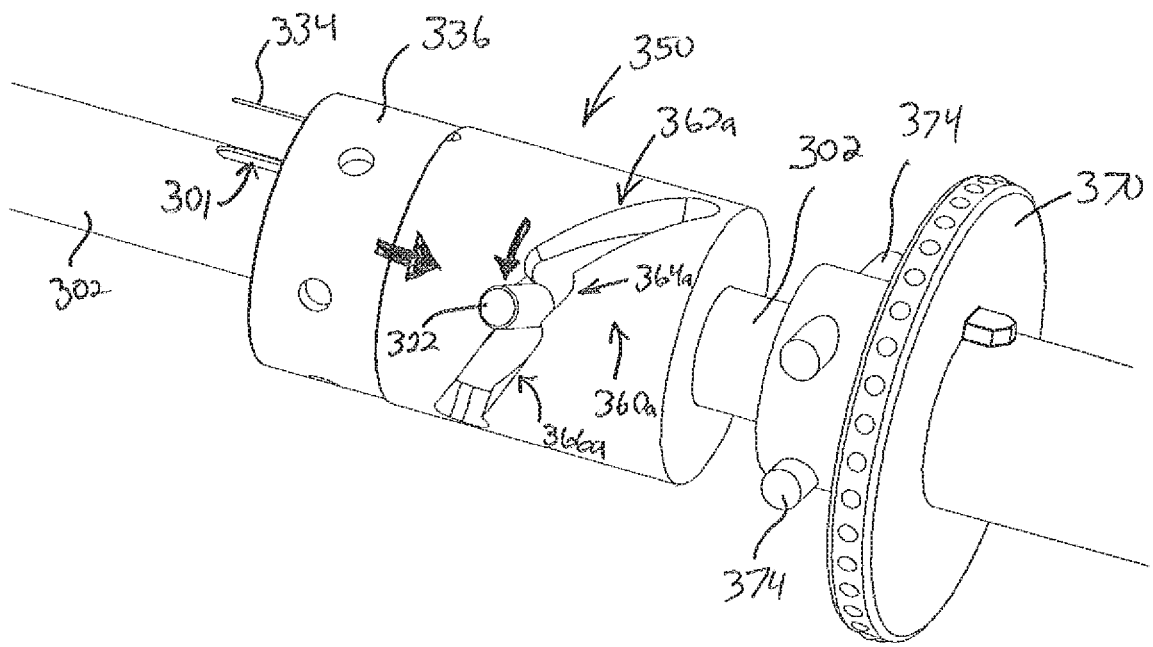
FIG. 20C depicts a perspective view of components of the shaft assembly of FIG. 11, with the drive pins at a third angular position and with the cam barrel and drive cable at a third longitudinal position.

FIG. 20C shows pins (322) having fully traversed second sections (364a, 364b). This motion is accomplished by rotation of deflection control knob (320). As noted above, while cam barrel (350) remains angularly stationary during this rotation of deflection control knob (320), cam barrel (350) and push-pull wire (330) translate proximally during this rotation of deflection control knob (320). This proximal movement of push-pull wire (330) causes further partial deflection of flex section (310). Upon traversal of second sections (364a, 364b), pins (322) reach ends (365a, 365b). The step provided by ends (365a, 365b) provides resistance to further motion of pins (322), thereby providing tactile feedback to the operator indicating that flex section (310) has achieved a second deflected state. This second deflected state may be associated with an angle that facilitates access to a third particular anatomical passageway, such as the frontal recess or frontal sinus ostium. Thus, when flex section (310) is in this second deflected state, shaft assembly (300) will easily guide guidewire (260) and dilation catheter (400) into that third particular anatomical passageway. By way of example only, the angle of the second deflected state may be between approximately 65 degrees and approximately 75 degrees, or more particularly at approximately 70 degrees.

Figure 20D:
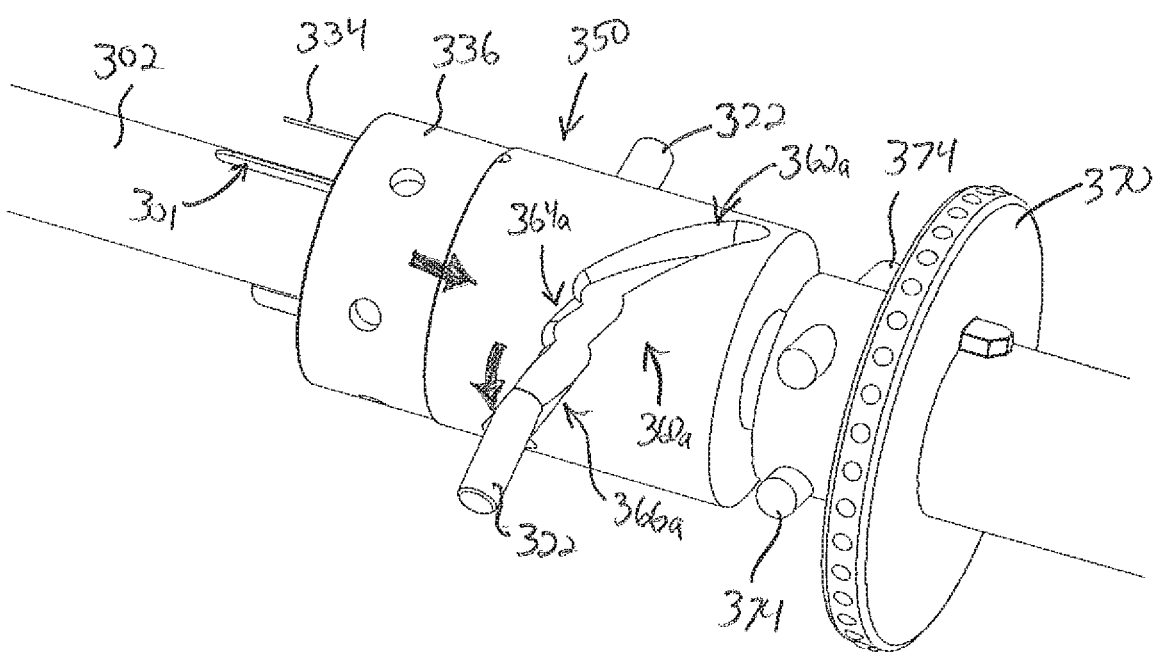
FIG. 20D depicts a perspective view of components of the shaft assembly of FIG. 11, with the drive pins at a fourth angular position and with the cam barrel and drive cable at a fourth longitudinal position.

FIG. 20D shows pins (322) having fully traversed third sections (366a, 366b). This motion is accomplished by rotation of deflection control knob (320). As noted above, while cam barrel (350) remains angularly stationary during this rotation of deflection control knob (320), cam barrel (350) and push-pull wire (330) translate proximally during this rotation of deflection control knob (320). This proximal movement of push-pull wire (330) causes further partial deflection of flex section (310). Upon traversal of third sections (366a, 366b), pins (322) reach ends (368a, 368b). Ends (368a, 368b) prevent further motion of pins (322), thereby providing tactile feedback to the operator indicating that flex section (310) has achieved a third deflected state. This third deflected state may be associated with an angle that facilitates access to a fourth particular anatomical passageway, such as the maxillary sinus ostium. Thus, when flex section (310) is in this second deflected state, shaft assembly (300) will easily guide guidewire (260) and dilation catheter (400) into that fourth particular anatomical passageway. By way of example only, the angle of the third deflected state may be between approximately 105 degrees and approximately 115 degrees, or more particularly at approximately 110 degrees.

In view of the foregoing, an operator may readily achieve various exit angles for guidewire (260) and dilation catheter (400) by rotating deflection control knob (320). Thus, the operator may readily dilate various anatomical passageways without having to exchange instruments; and without having to replace pieces of instrument (200). In some versions, deflection control knob (320) and/or other components of instrument (200) includes/include markings indicating a particular passageway associated with different angular positions of deflection control knob (320). Thus, when the operator wishes to dilate a particular anatomical passageway, the operator may observe such markings while rotating deflection control knob (320), until the markings indicate that deflection control knob (320) has reached an angular position providing a deflection angle of flex section (260) associated with the targeted anatomical passageway.

C. Exemplary Guide Proximal End Deflection Assembly

Figure 21A:
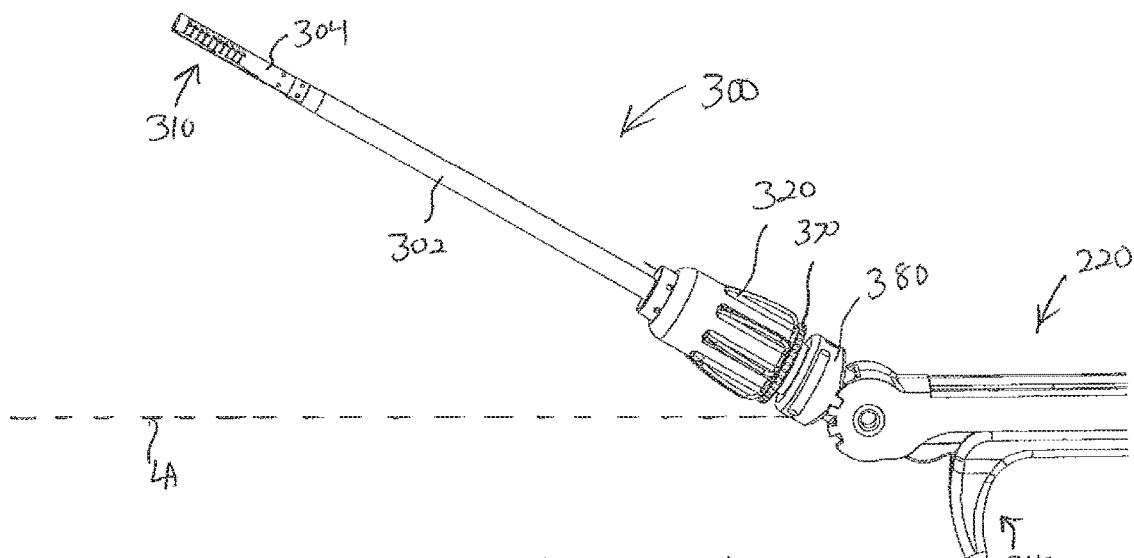
FIG. 21A depicts a perspective view of a distal portion of the instrument of FIG. 8, with the shaft assembly at a first angular orientation.
Figure 21B:
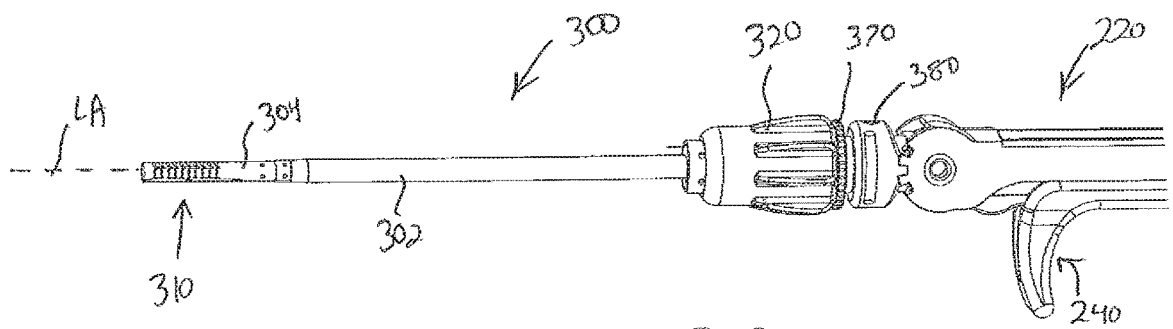
FIG. 21B depicts a perspective view of a distal portion of the instrument of FIG. 8, with the shaft assembly at a second angular orientation.
Figure 21C:
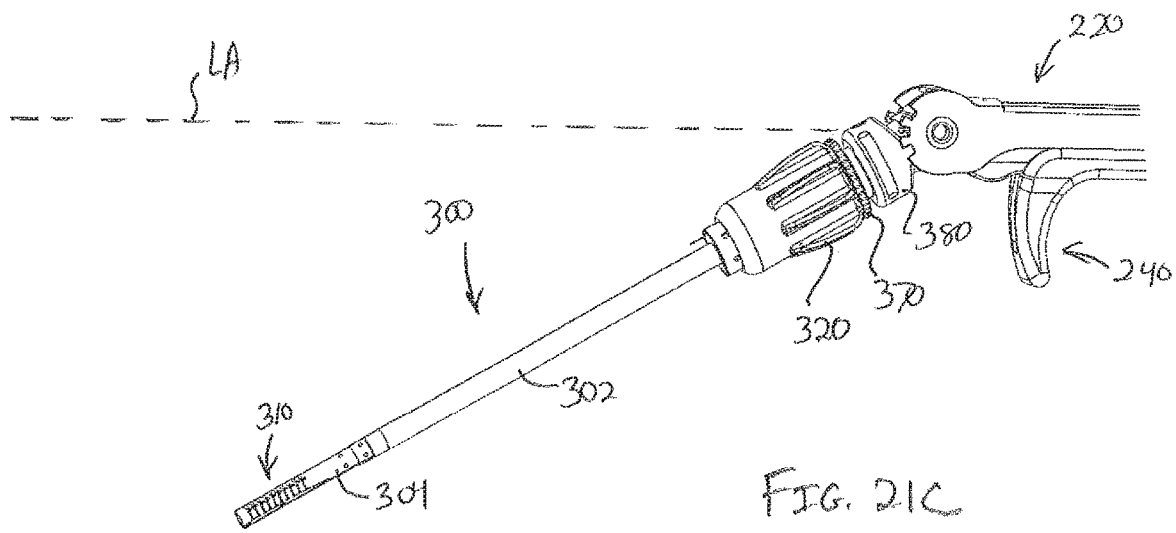
FIG. 21C depicts a perspective view of a distal portion of the instrument of FIG. 8, with the shaft assembly at a third angular orientation.

As noted above, it may be desirable to facilitate use of a single dilation instrument to perform procedures on a patient regardless of whether the patient is in a sitting position or supine position. For instance, when the patient is in a sitting or otherwise upright position, it may be desirable to adjust instrument (200) to reorient shaft assembly (300) at an oblique upward angle relative to the longitudinal axis (LA) of handle assembly (210), as shown in FIG. 21A. When the patient is in a supine position, it may be desirable to have shaft assembly (300) oriented coaxially or otherwise parallel with the longitudinal axis (LA) of handle assembly (210), as shown in FIG. 21B. Regardless of whether the patient is in an upright or supine position, an operator may wish to adjust instrument (200) to reorient shaft assembly (300) at an oblique downward angle relative to the longitudinal axis (LA) of handle assembly (210), as shown in FIG. 21C. By way of example only, the operator may wish to make such an adjustment to facilitate simultaneous co-positioning of shaft assembly (300) and a straight endoscope in the patient's nasal cavity through the same nostril. To enable adjustment of the pivotal position of shaft assembly (300) relative to handle assembly (210), instrument (200) of the present example includes a translating lock collar (380), which is longitudinally interposed between handle assembly (210) and rotary control knob (370).

As shown in FIGS. 22A-22D, lock collar (380) includes a proximally projecting tooth (382). Body (220) of handle assembly (210) includes an angularly spaced array of notches (222) that are configured to receive tooth (382). Lock collar (380) is resiliently biased toward a proximal position. By way of example only, lock collar may be biased by a coil spring, a wave spring, a leaf spring, and/or any other suitable kind of resilient member.

Figure 22A:
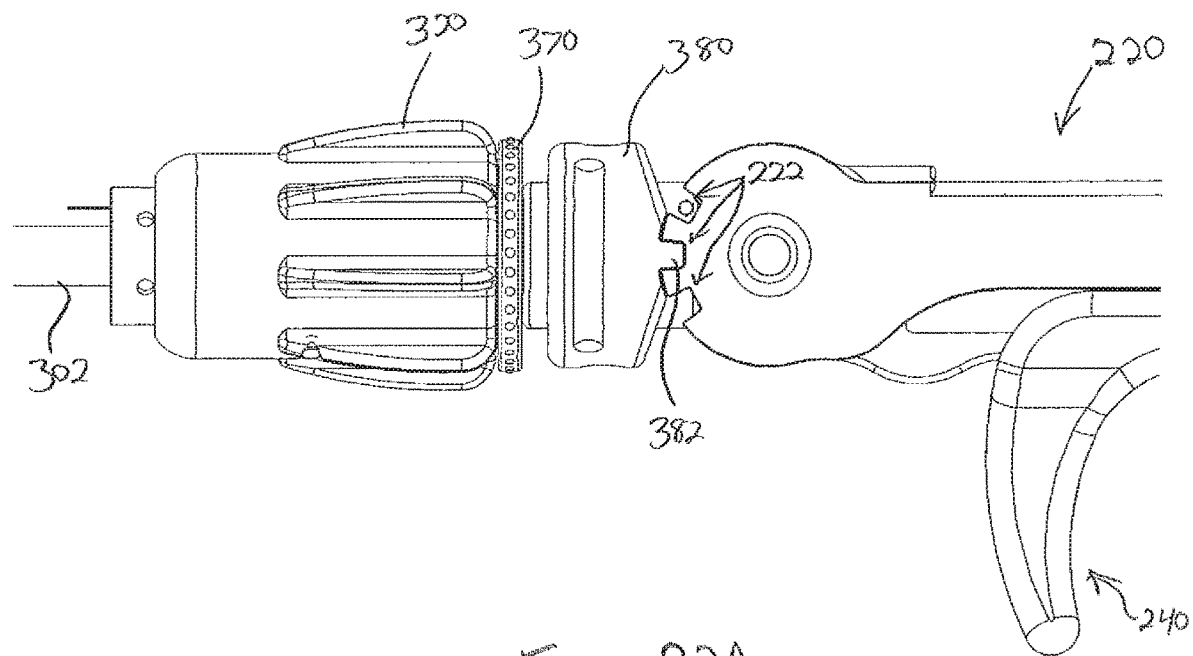
FIG. 22A depicts a side elevational view of a shaft pivot control region of the instrument of FIG. 8, with the shaft assembly at the second angular orientation, and with a shaft pivot lock in a proximal position.
Figure 22B:
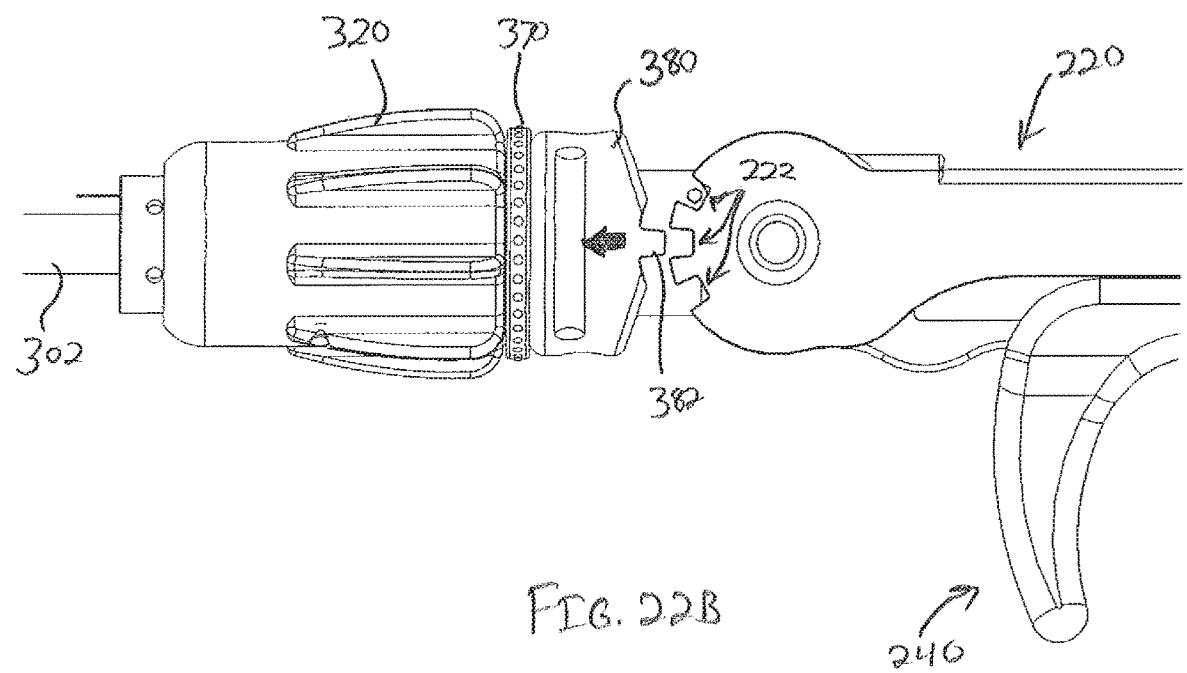
FIG. 22B depicts a side elevational view of the shaft pivot control region of FIG. 22A, with the shaft assembly at the second angular orientation, and with the shaft pivot lock in a distal position.
Figure 22C:
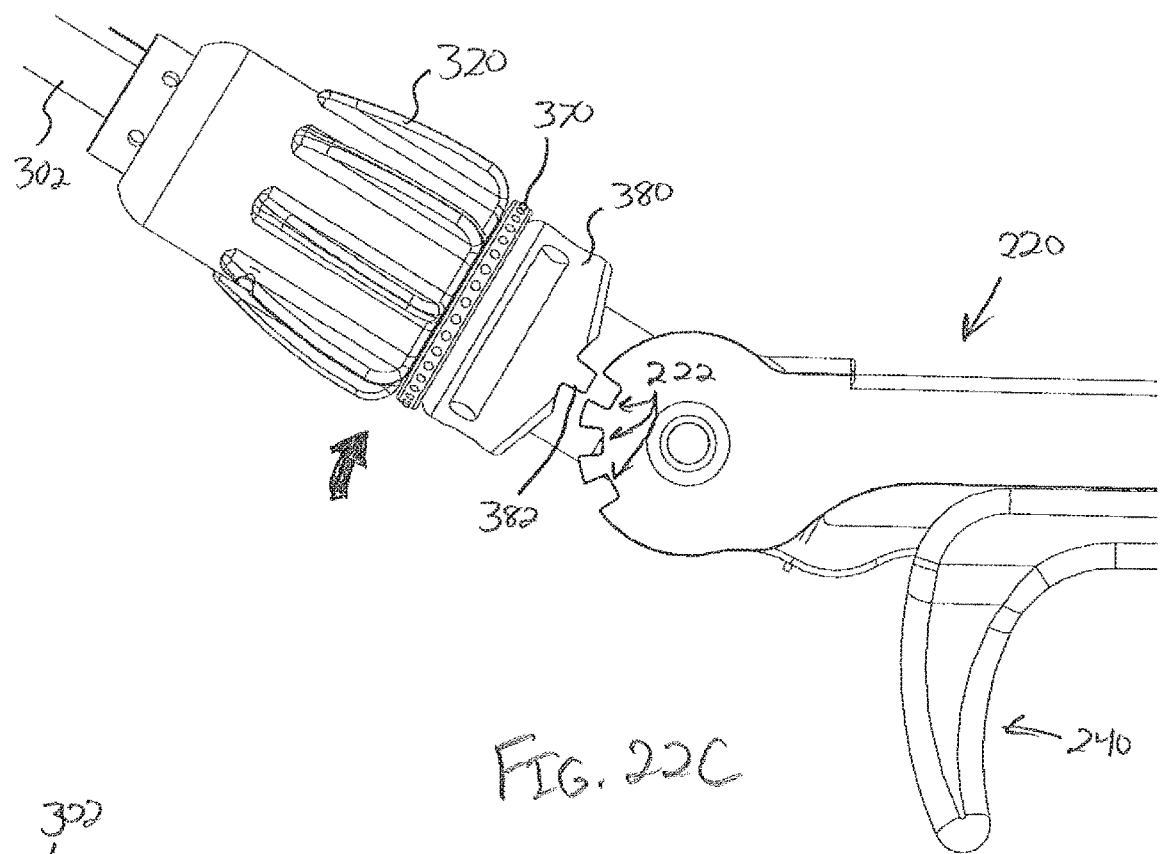
FIG. 22C depicts a side elevational view of the shaft pivot control region of FIG. 22A, with the shaft assembly at the first angular orientation, and with the shaft pivot lock in the distal position.
Figure 22D:
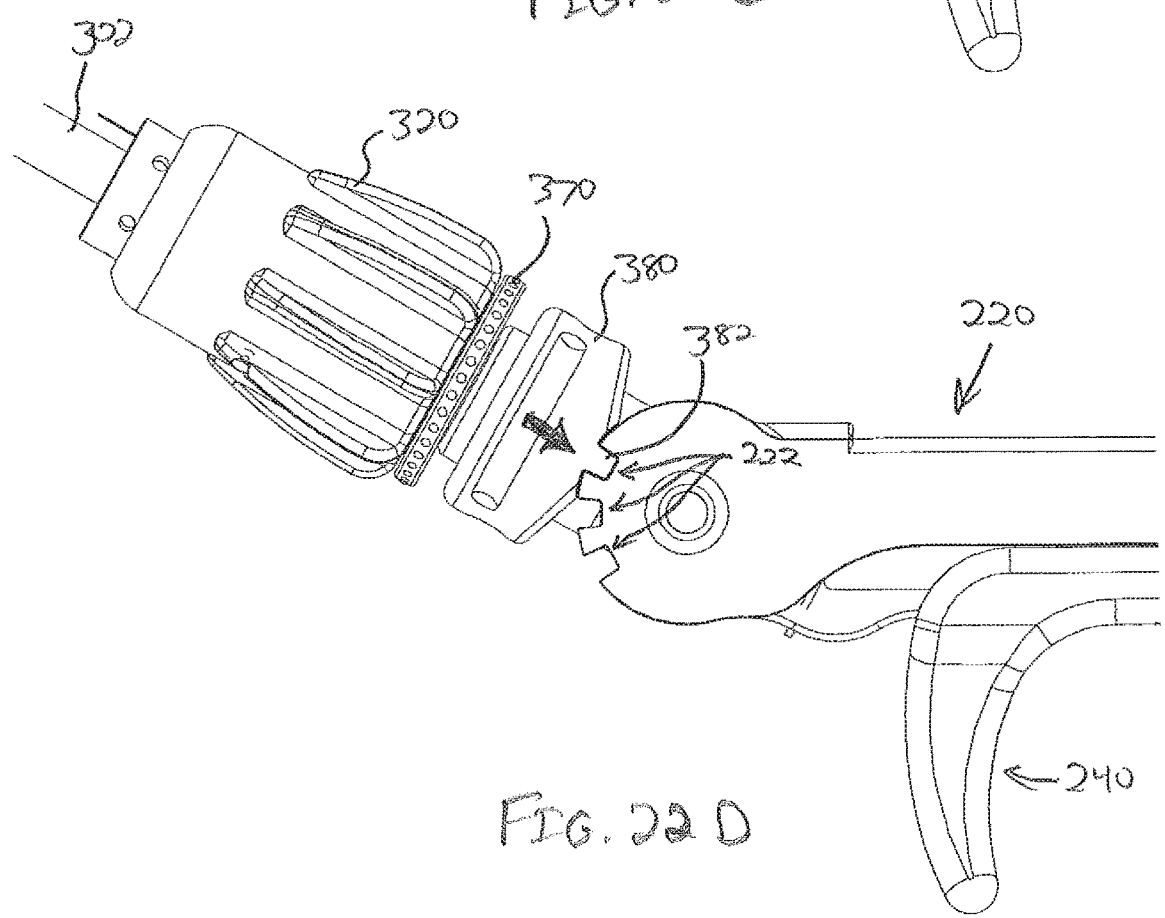
FIG. 22D depicts a side elevational view of the shaft pivot control region of FIG. 22A, with the shaft assembly at the first angular orientation, and with the shaft pivot lock in the proximal position.

In order to adjust the angular orientation of shaft assembly (300) relative to the longitudinal axis (LA), the operator may urge lock collar (380) distally from the position shown in FIG. 22A to the position shown in FIG. 22B. This distal positioning of lock collar (380) will disengage tooth (382) from notch (222). While holding lock collar (380) in a distal position, the operator may then pivot shaft assembly (300) about an axis that is perpendicular to the longitudinal axis (LA), reaching the obliquely oriented configuration shown in FIG. 22C. After reaching the appropriate oblique angle, the operator may then release lock collar (380), allowing lock collar (380) to return to a proximal position as shown in FIG. 22D. This proximal positioning of lock collar (380) will position tooth (382) in notch (222), thereby locking shaft assembly (300) at the oblique orientation.

As described above, deflection control knob (320) and flex section (310) enable an operator to adjust the orientation of the distal end of shaft assembly (300) relative to the remainder of shaft assembly (300), rotary control knob (370) enables the operator to adjust the angular orientation of the entire shaft assembly (300) about the longitudinal axis of shaft assembly (300), and lock collar (380) enables the operator to adjust the orientation of the entire shaft assembly (300) relative to the longitudinal axis (LA) of handle assembly (210). Taken together, all of these adjustment features enable an operator to access various anatomical passageways via either nostril of a patient, regardless of whether the patient is in a supine position or in a sitting or otherwise upright position, and regardless of whether the operator is left-handed or right-handed, without requiring the operator to replace instrument (200) or a portion of instrument (200).

D. Exemplary Dilation Catheter and Multi-Purpose Actuator

1. Overview

As noted above, it may me desirable to provide an instrument with actuation features that enable translation of a dilation catheter, translation of a guidewire, and spinning of a guidewire, all with a single hand. Actuator (500) of the present example provides all this functionality. As shown in FIGS. 23 and 25-27, the proximal end of dilation catheter (400) is secured to actuator (500). Actuator (500) is operable to slide longitudinally relative to body (220) to thereby translate dilation catheter (400) relative to body (220). Actuator (500) comprises a pair of body portions (502a, 502b) that are coupled together to support a set of drive wheels (510, 520a, 520b), a spool (530), a pair of manifold body portions (550a, 550b), and a guidewire spin control assembly (600). Drive wheels (510, 520a, 520b) and a spool (530) are operable to translate guidewire (260) longitudinally, as will be described in greater detail below. Guidewire spin control assembly (600) is operable to spin guidewire (260) about the longitudinal axis of guidewire (260), as will also be described in greater detail below.

Manifold body portions (550a, 550b) are configured to cooperate with each other to provide pathways for fluid communication between dilation catheter (400) and conduits (270, 280). Manifold body portions (550a, 550b) thereby enable dilation catheter (400) to receive irrigation fluid from irrigation conduit (280); and inflation fluid from inflation conduit (270). By way of example only, dilation catheter (400) may provide irrigation functionality in accordance with at least some of the teachings of U.S. Pub. No. 2008/0183128, entitled "Methods, Devices and Systems for Treatment and/or Diagnosis of Disorders of the Ear, Nose and Throat," published Jul. 31, 2008, the disclosure of which is incorporated by reference herein; and/or U.S. Pat. No. 9,095,646, entitled "Devices and Methods for Transnasal Dilation and Irrigation of the Sinuses," issued Aug. 4, 2015, the disclosure of which is incorporated by reference herein. In some alternative versions, irrigation is provided through a different catheter. Thus, irrigation conduit (280) may be omitted in some versions. Manifold body portions (550a, 550b) also cooperate with each other to provide a pathway for guidewire (260) to pass into the proximal end of dilation catheter (400). While guidewire (260) is omitted from FIG. 27, FIGS. 32A-32D show guidewire (260) being diverted by manifold body portion (550b) to enter dilation catheter (400).

A seal (540) is provided to prevent fluids from escaping at the region where guidewire (260) enters manifold body portions (550a, 550b). While seal (540) prevents egress of fluid from manifold body portions (550a, 550b) where guidewire (260) enters manifold body portions (550a, 550b), seal (540) enables guidewire (260) to translate freely relative to manifold body portions (550a, 550b).

Figure 24A:
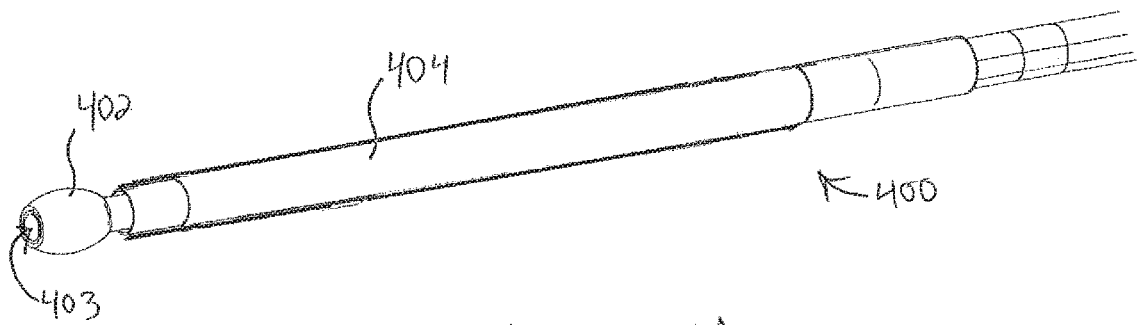
FIG. 24A depicts a perspective view of a distal portion of the dilation catheter of FIG. 23, with a distal tip in an expanded state, and with the dilator in the non-expanded state.
Figure 24B:
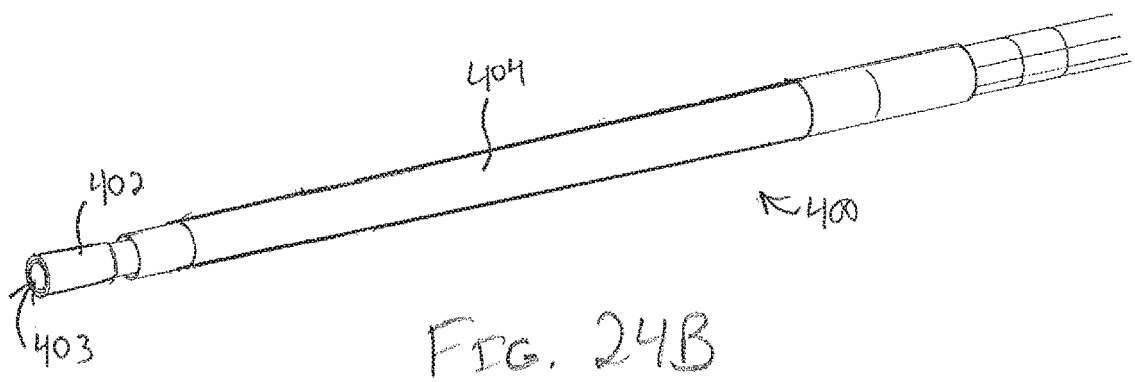
FIG. 24B depicts a perspective view of the distal portion of FIG. 24A, with the distal tip in a non-expanded state, and with the dilator in the non-expanded state.
Figure 24C:
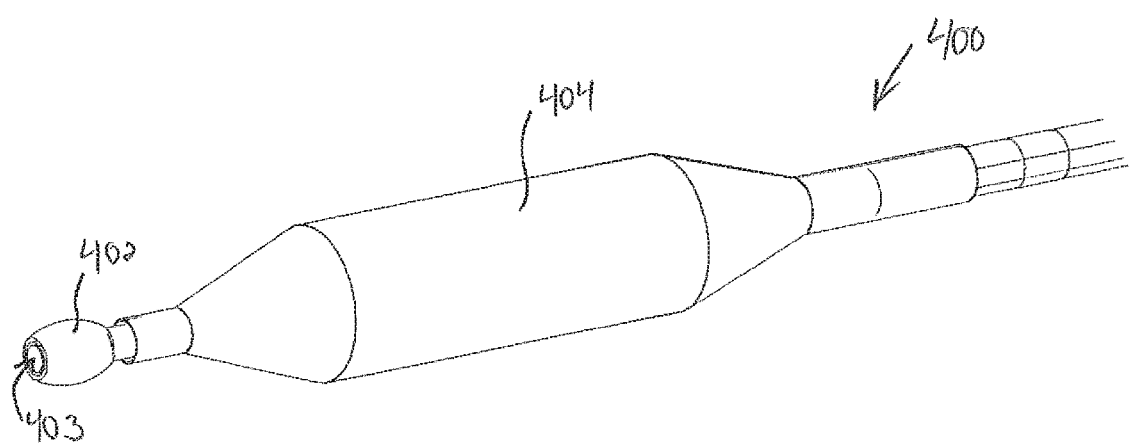
FIG. 24C depicts a perspective view of the distal portion of FIG. 24A, with the distal tip in the expanded state, and with the dilator in the expanded state.
Figure 25:
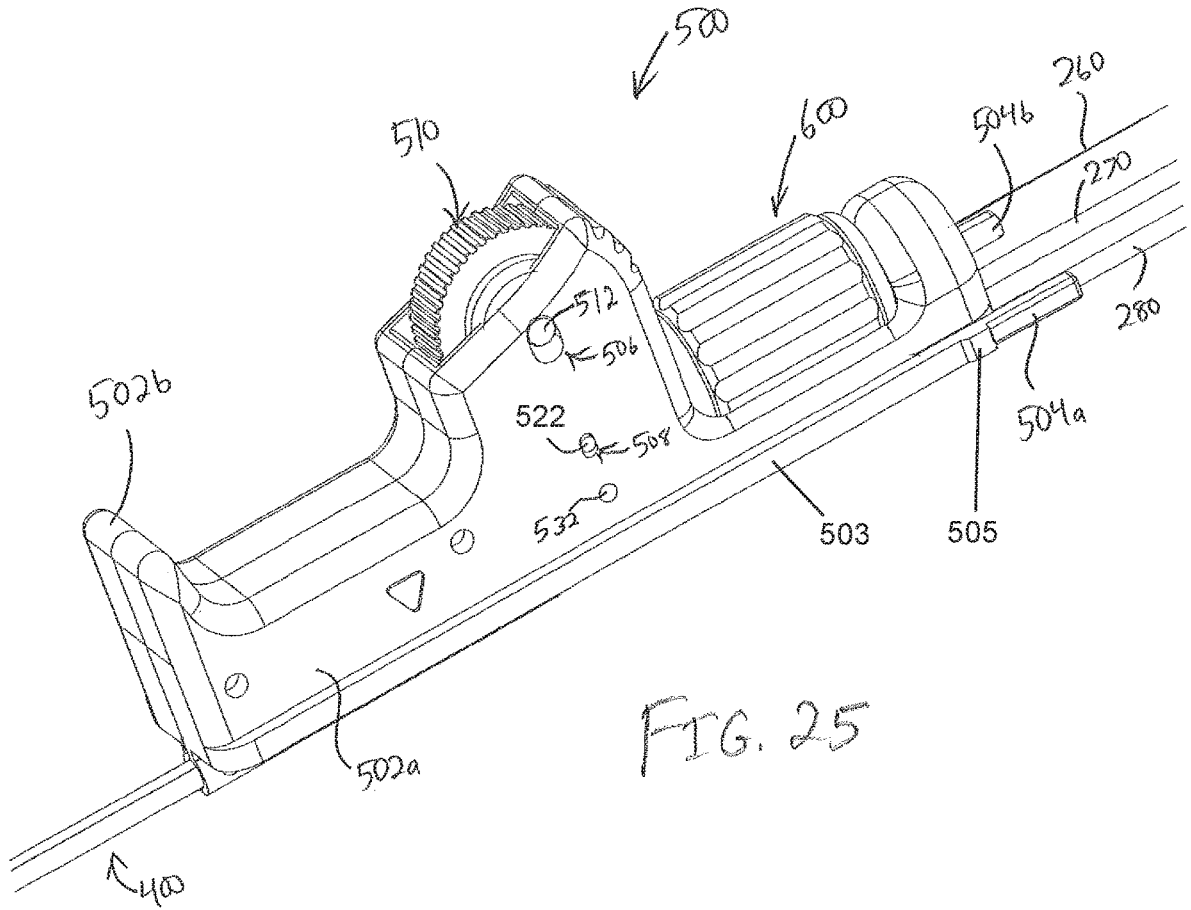
FIG. 25 depicts a perspective view of the actuator of FIG. 23.
Figure 26:
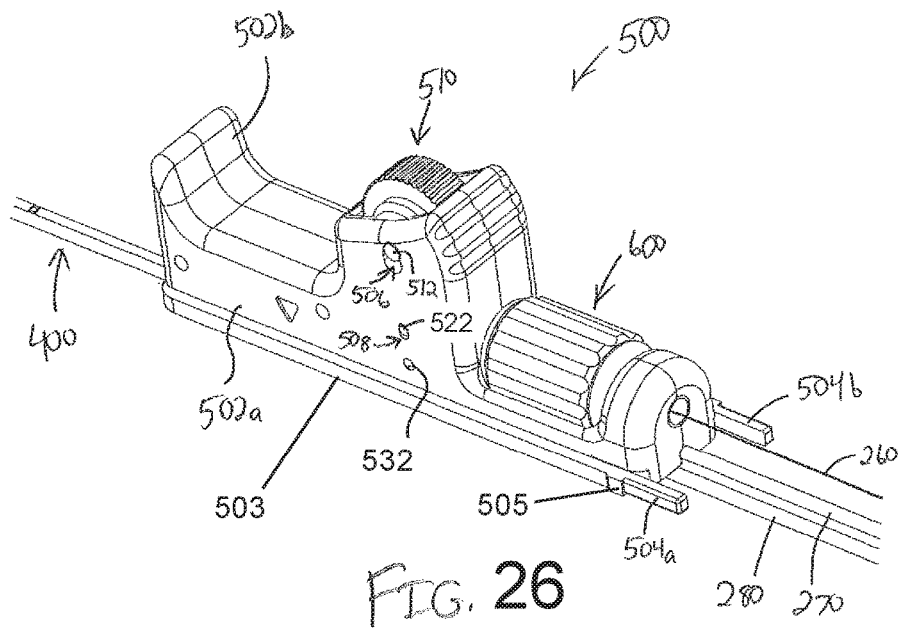
FIG. 26 depicts another perspective view of the actuator of FIG. 23.
Figure 27:
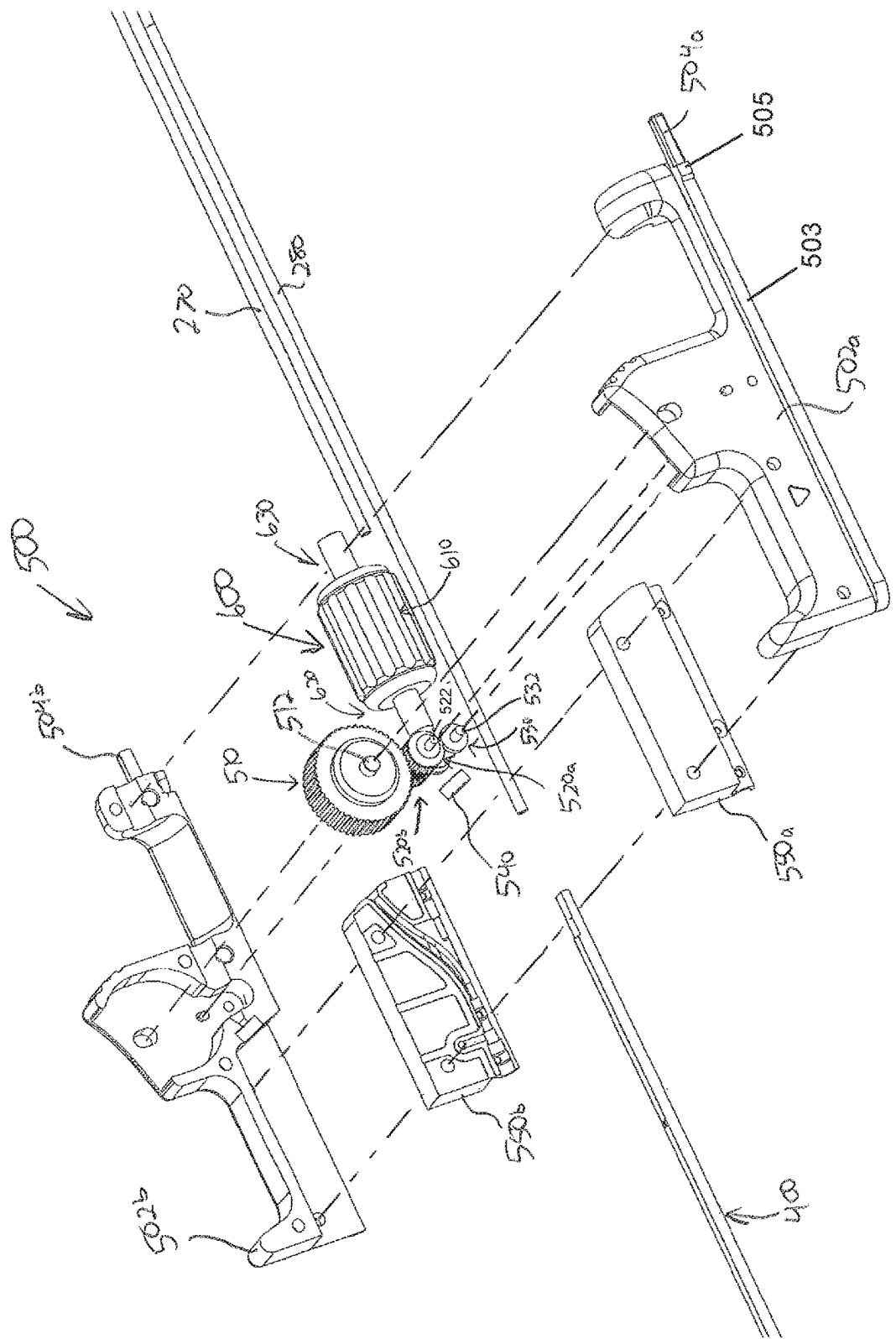
FIG. 27 depicts an exploded perspective view of the actuator of FIG. 23.

FIGS. 24A-24C show the distal end of dilation catheter (400) in greater detail. As shown, dilation catheter (400) of this example comprises a distal tip (402) and an expandable dilator (404) located proximal to distal tip (402). Distal tip (402) defines an opening (403) that is sized to accommodate guidewire (260). Distal tip (402) is resiliently bias to assume the expanded configuration shown in FIGS. 24A and 24C. However, distal tip (402) is also configured to collapse to the non-expanded state shown in FIG. 24B, when sufficient inwardly-oriented forces act upon distal tip (402). Dilator (404) is configured to expand from the non-expanded state shown in FIGS. 24A-24B to the expanded state shown in FIG. 24C, based on the transfer of inflation fluid into and out of dilator (404) as described above.

During operation, dilation catheter (400) may be advanced into the targeted anatomical passageway while in the configuration shown in FIG. 24A. If the targeted anatomical passageway is the Eustachian tube, distal tip (402) will eventually encounter the bony isthmus near the middle ear. Distal tip (402) is larger than the isthmus of the Eustachian tube, such that the operator will feel resistance to further advancement of dilation catheter (400) once distal tip (402) reaches the isthmus of the Eustachian tube. Because it may be undesirable for distal tip (402) to reach the middle ear, the operator may immediately cease advancement of dilation catheter (400) and expand dilator (404) to reach the state shown in FIG. 24C, thereby dilating the Eustachian tube.

In scenarios where the targeted anatomical passageway is not a Eustachian tube, distal tip (402) may eventually encounter a passageway that is smaller than distal tip (402). For instance, distal tip (402) may encounter a paranasal sinus ostium. In such scenarios, the operator may continue to urge distal tip (402) through the passageway, which will cause distal tip (402) to collapse to the configuration shown in FIG. 24B. Eventually, distal tip (402) will clear the passageway and re-expand; and dilator (404) will be positioned in the passageway. At this point, the operator may expand dilator (404) to reach the state shown in FIG. 24C.

In some variations, distal tip (402) is selectively expandable and collapsible based on the introduction or evacuation of fluid to or from distal tip (402). By way of example only, such variations may be constructed and operable in accordance with at least some of the teachings of U.S. Pub. No. 2017/0056632, entitled "Dilation Catheter with Expandable Stop Element," published Mar. 2, 2017, the disclosure of which is incorporated by reference herein. In some other variations, distal tip (402) does not have a bulbous configuration and is simply narrow (e.g., like the configuration shown in FIG. 24B).

2. Exemplary Guidewire Translation Control Assembly

Figure 28:
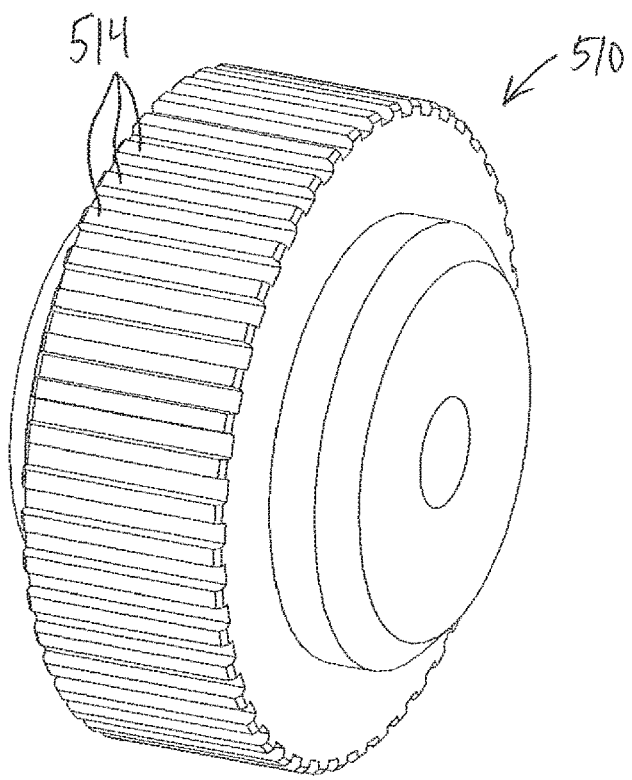
FIG. 28 depicts a perspective view of a first drive wheel of the actuator of FIG. 23.
Figure 29:
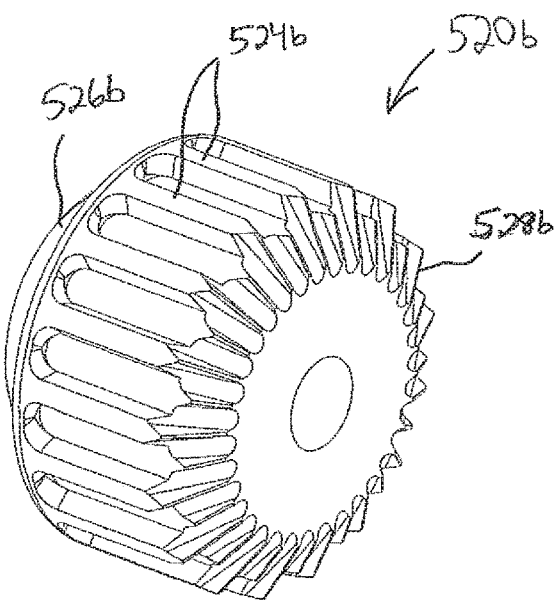
FIG. 29 depicts a perspective view of a second drive wheel of the actuator of FIG. 23.
Figure 30:
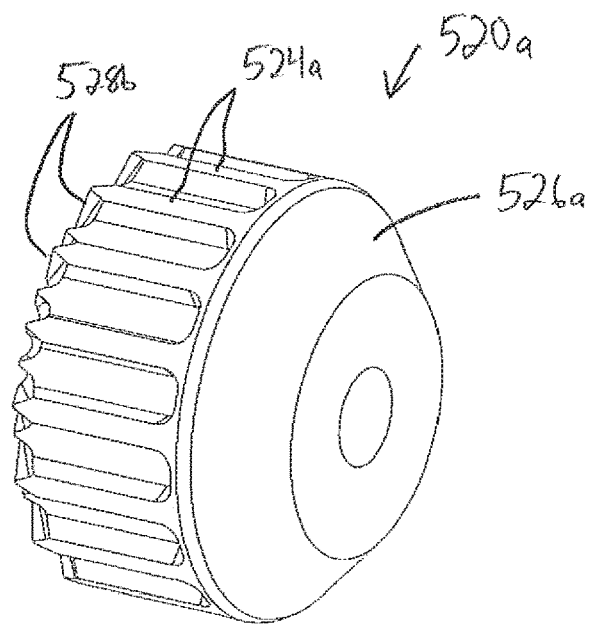
FIG. 30 depicts a perspective view of a third drive wheel of the actuator of FIG. 23.
Figure 31:
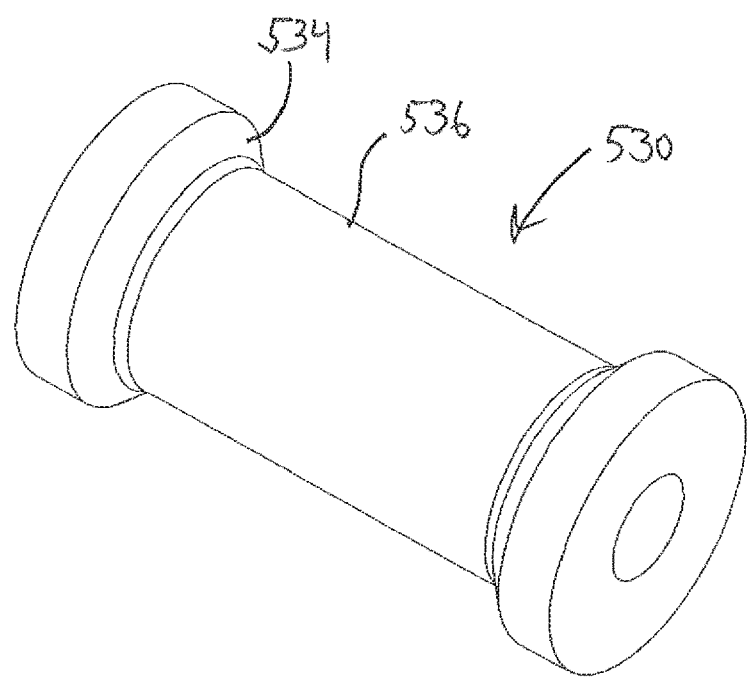
FIG. 31 depicts a perspective view of a spool of the actuator of FIG. 23.

FIGS. 27-34 show the components of actuator (500) that are used to translate guidewire (260) longitudinally. These components include drive wheels (510, 520a, 520b) and spool (530). As best seen in FIG. 28, drive wheel (510) includes an angularly spaced array of teeth (514). As best seen in FIGS. 29-30, each drive wheel (520a, 520b) includes a respective angularly spaced array of teeth (524a, 524b), an outer annular chamfer (526a, 526b), and an inner set of gripping teeth (528a, 528b). As best seen in FIG. 31, spool (530) includes a pair of inner annular chamfers (534) and a smooth guidewire rolling surface (536). As shown in FIGS. 27, 32A-32D, and 33A-34, drive wheels (510, 520a, 520b) and spool (530) are rotatably supported by respective axles (512, 522, 532). In particular, drive wheel (510) is rotatably supported by a dedicated axle (512), drive wheels (520a, 520b) are supported by a shared axle (522), and spool (530) is rotatably supported by a dedicated axle (532). Drive wheels (510, 520a, 520b) and spool (530) are operable to rotate about respective axles (512, 522, 532). In addition, drive wheels (520a, 520b) are operable to translate along shared axle (522).

As best seen in FIGS. 33A-33B, axle (512) is disposed in an elongate opening (506) of body portions (502a, 502b). Axle (522) is also disposed in an elongate opening (508) of body portions (502a, 502b). Axle (532) is disposed in a circular opening (509) of body portions (502a, 502b). Elongate opening (506) enables axle (512) and drive wheel (510) to translate vertically, along a restricted range of motion, relative to body portions (502a, 502b). Elongate opening (508) enables axle (522) and drive wheels (520a, 520b) to translate vertically, along a restricted range of motion, relative to body portions (502a, 502b). Circular opening (509) prevents axle (522) and spool (530) from translating vertically relative to body portions (502a, 502b).

Drive wheels (520a, 520b) are operable to selectively engage guidewire (260). In particular, when drive wheels (520a, 520b) are in an upper position as shown in FIGS. 32A-32B, 33A, and 34, drive wheels (520a, 520b) are substantially disengaged from guidewire (260). In this state, actuator (500) may translate freely along body portion (220) without translating guidewire (260). As described elsewhere herein, this translation of actuator (500) may be desired when positioning dilator (400) relative to a targeted anatomical passageway, after guidewire (260) has been suitably positioned relative to the targeted anatomical passageway.

Figure 34:
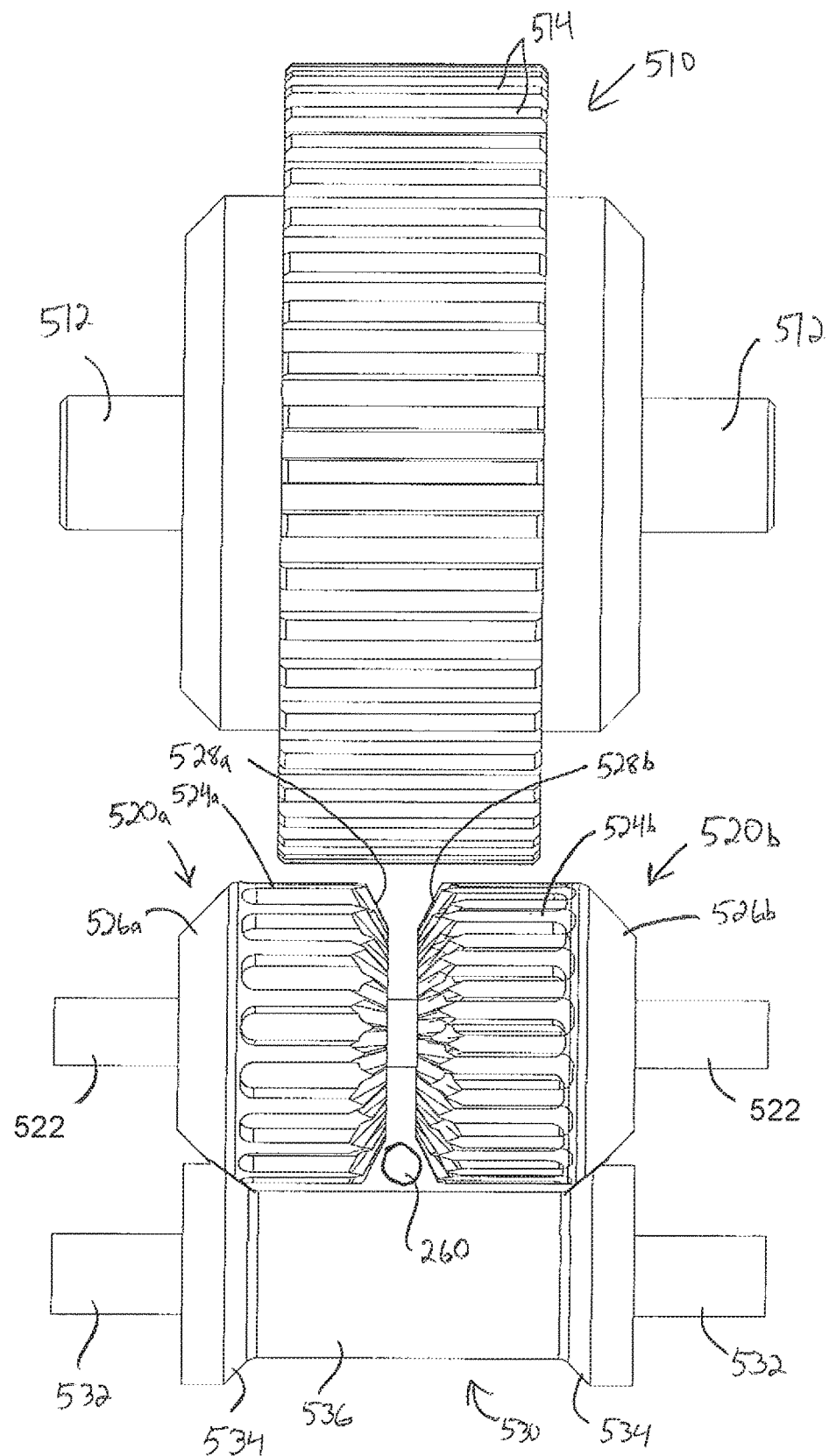
FIG. 34 depicts an end view of the drive wheels and spools of FIGS. 28-31 positioned in relation to the guidewire of the instrument of FIG. 8.

In order to urge drive wheels (520a, 520b) into engagement with guidewire (260), the operator may urge drive wheel (510) downwardly. As shown in the transition from FIG. 32A to FIG. 32B, drive wheel (510) will travel downwardly through a first range of motion where drive wheel (510) eventually contacts drive wheels (520a, 520b). At the stage shown in FIG. 32B, drive wheels (520a, 520b) are not yet substantially engaged with guidewire (260). As the operator continues to urge drive wheel (510) downwardly, drive wheel (510) urges drive wheels (520a, 520b) downwardly, as shown in the transition from FIG. 32B to FIG. 32C. As shown in FIG. 34, outer annular chamfers (526a, 526b) of drive wheels (520a, 520b) are engaged with inner annular chamfers (534) of spool (530). As drive wheels (520a, 520b) move downwardly from the position shown in FIG. 32B to the position shown in FIG. 32C, camming cooperation between chamfers (526a, 526b, 534) urges drive wheels (520a, 520b) inwardly toward each other along axle (522). Thus, drive wheels (520a, 520b) travel inwardly and downwardly during the transition from the state shown in FIG. 32B to the state shown in FIG. 32C.

Figure 32C:
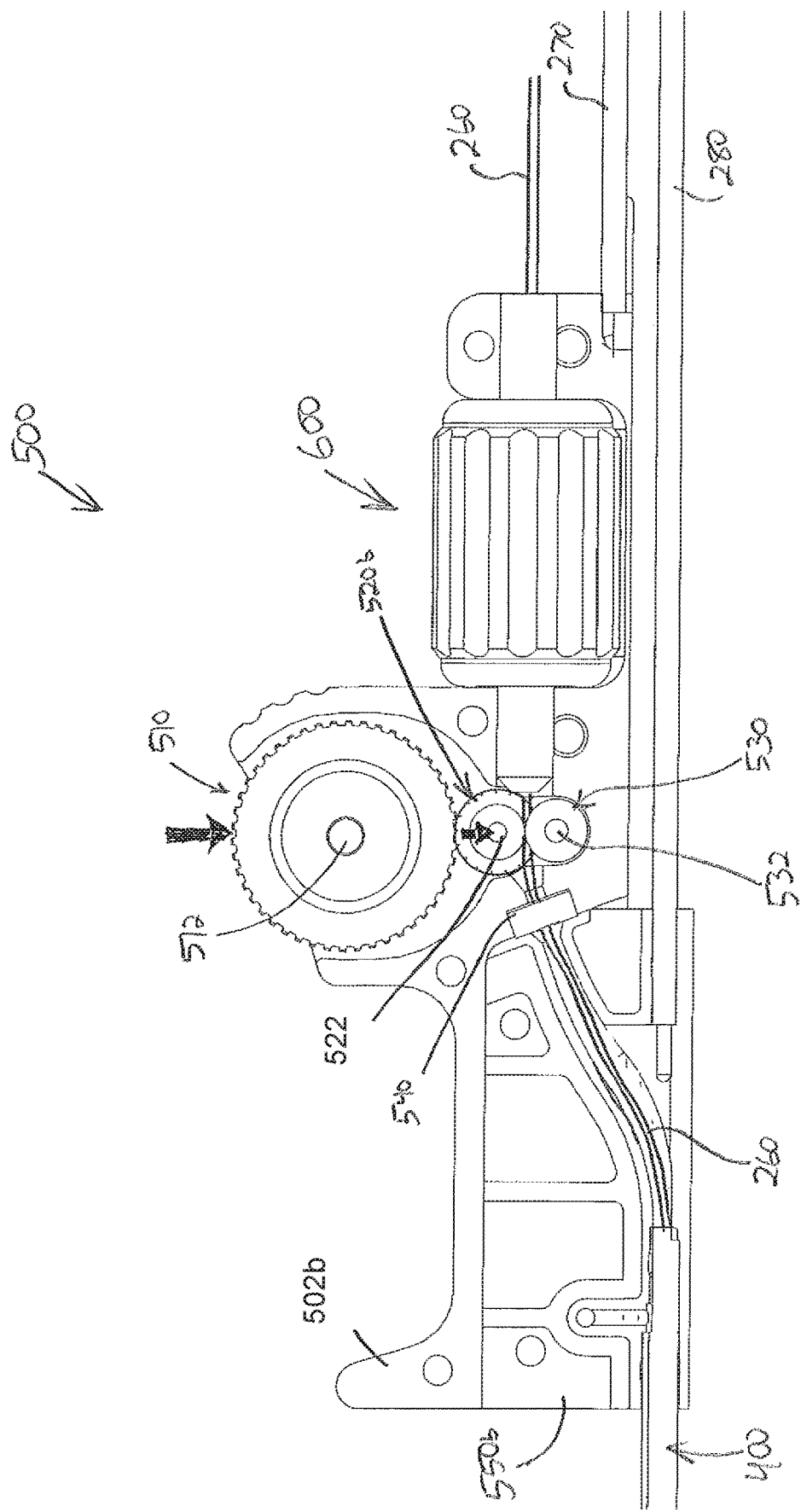
FIG. 32C depicts a side elevational view of the actuator of FIG. 23, with a housing half omitted, with the first drive wheel in a third vertical position, and with the second drive wheel in a second vertical position.

With drive wheels (520a, 520b) moved downwardly and inwardly to the state shown in FIG. 32C, gripping teeth (528a, 528b) are engaged with guidewire (260). Moreover, gripping teeth (528a, 528b) urge guidewire (260) against guidewire rolling surface (536) of spool (530). Thus, as drive wheels (520a, 520b) rotate in this state, drive wheels (520a, 520b) and spool (530) cooperate to drive guidewire (260) longitudinally. To provide such rotation of drive wheels (520a, 520b), teeth (514) of drive wheel (510) mesh with teeth (524a, 524b) of drive wheels (520a, 520b). Teeth (514) of drive wheel (510) also provide a gripping surface for the operator's thumb or finger as the operator rotates drive wheel (510). As shown in FIG. 32D, guidewire (260) will translate distally when the operator rotates drive wheel (510) distally. Guidewire (260) will translate proximally when the operator rotates drive wheel (510) proximally. Thus, the translation control provided by drive wheel (510) is intuitive, providing a direction of longitudinal guidewire (260) motion that directly corresponds with the direction of angular motion of driver wheel (510).

It should be understood from the foregoing that, when the operator wishes to translate guidewire (260) distally or proximally, the operator may urge drive wheel (510) downwardly to the position shown in FIGS. 32D and 32D, to thereby engage guidewire (260) with drive wheels (520a, 520b). When the operator no longer wishes to translate guidewire (260), the operator may release drive wheel (510) to substantially disengage drive wheels (520a, 520b) from guidewire (260). In some versions, one or more resilient members may be used to resiliently bias drive wheels (520a, 520b) apart from each other, to resiliently bias drive wheels (520a, 520b) upwardly, and/or to resiliently bias drive wheel (510) upwardly. When drive wheels (520a, 520b) are substantially disengaged from drive wheels (520a, 520b), actuator (500) may be translated distally relative to body portion (220) (i.e., to translate dilator (400) relative to handle assembly (210)) without translating guidewire (260) relative to body portion (220).

3. Exemplary Guidewire Spin Control Assembly

Figure 35:
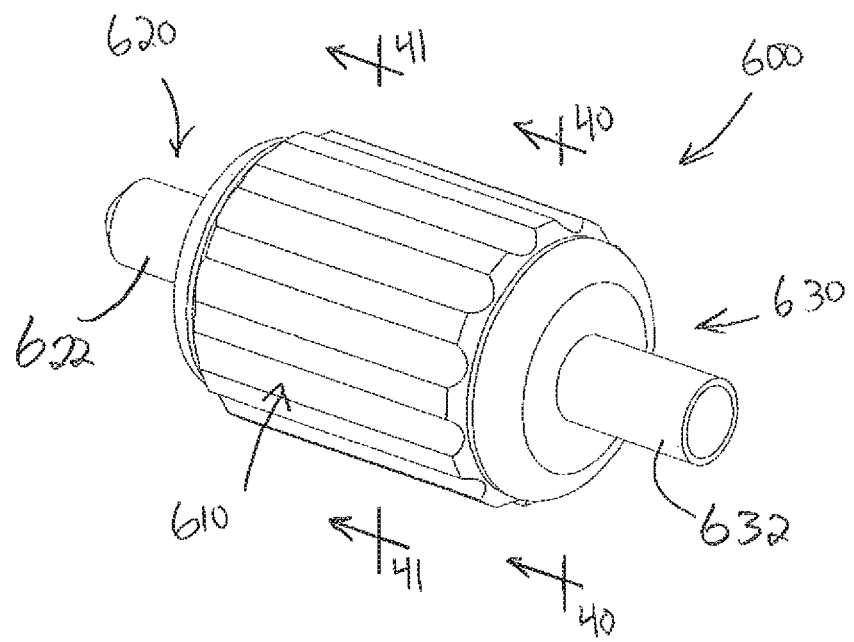
FIG. 35 depicts a perspective view of a guidewire spin control assembly of the actuator of FIG. 23.
Figure 36:
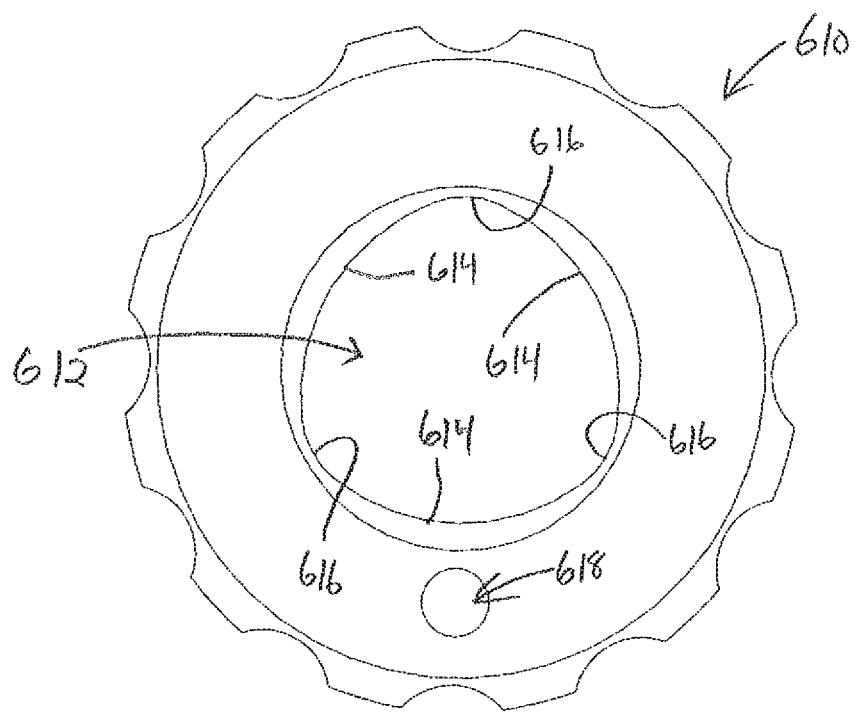
FIG. 36 depicts an end view of a barrel member of the guidewire spin control assembly of FIG. 35.
Figure 37:
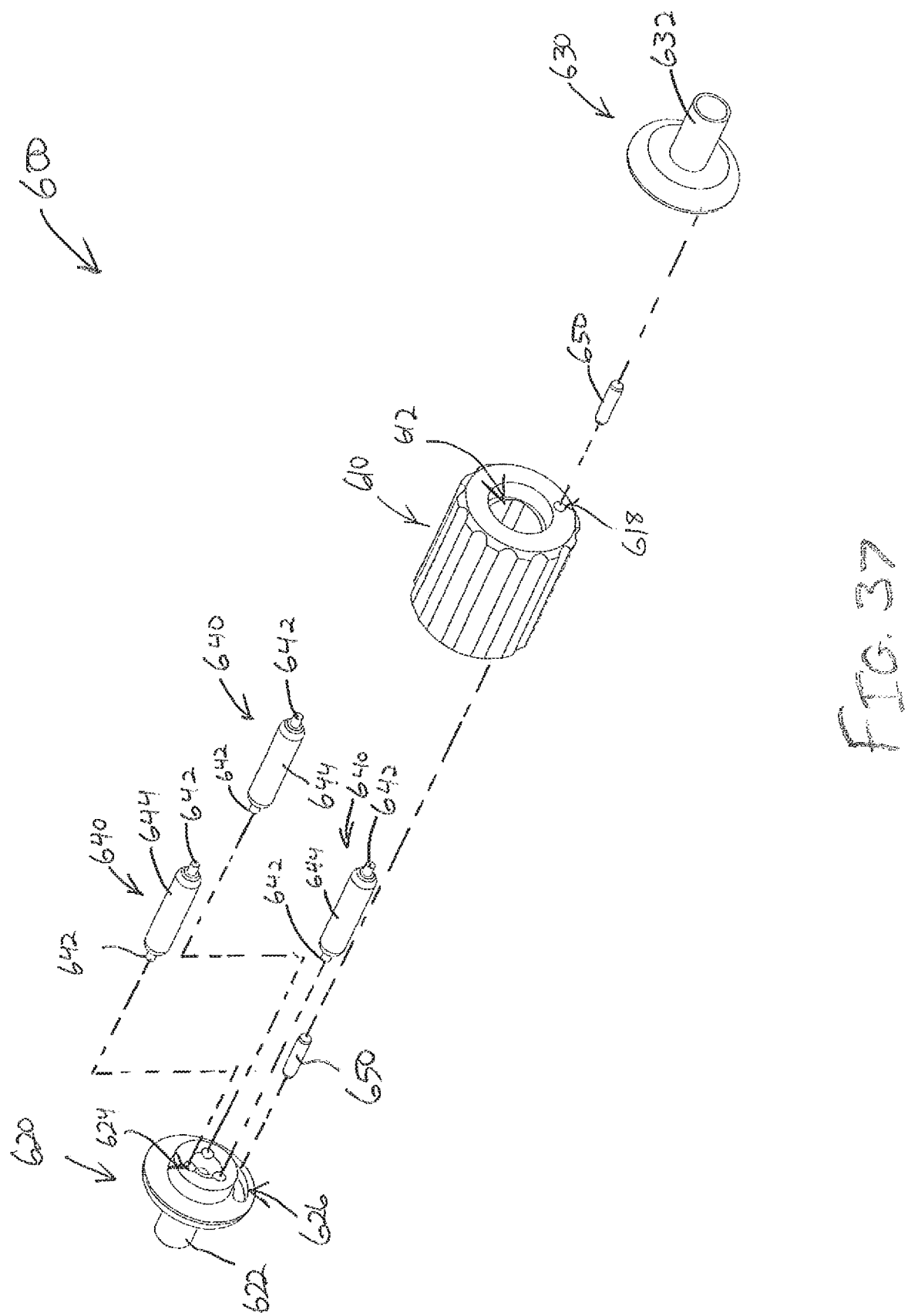
FIG. 37 depicts an exploded perspective view of the guidewire spin control assembly of FIG. 35.

In some instances, it may be desirable to enable the operator to spin guidewire (260) about the longitudinal axis of guidewire (260). Such spinning capabilities may be particularly desirable when the distal end of guidewire (260) has a bent configuration, as spinning guidewire (260) may assist in orienting the bent distal end toward a targeted anatomical passageway. In the present example, guidewire spin control assembly (600) provides this spinning capability. FIGS. 35-41C show guidewire spin control assembly (600) in further detail. As best seen in FIGS. 35 and 37, guidewire spin control assembly (600) comprises a barrel member (610), a pair of end caps (620, 630), a set of rollers (640), and a set of pins (650). As best seen in FIG. 36, barrel member (610) defines a bore (612) having a profile like a Reulaux triangle, with arcuate segments (614) joined by rounded corners (616). Barrel member (610) further includes a circular recess (618) at each end. Circular recesses (618) are configured to receive corresponding pins (650).

Figure 38:
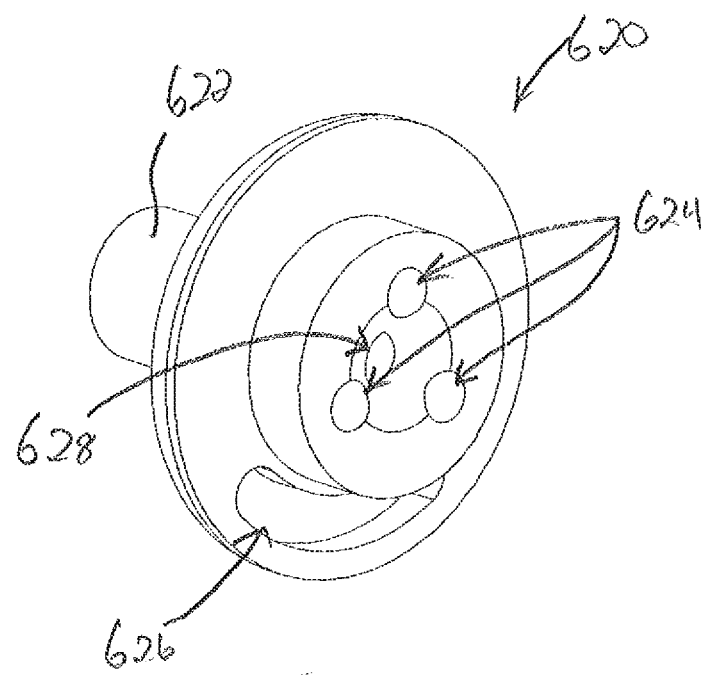
FIG. 38 depicts a perspective view of a first end cap of the guidewire spin control assembly of FIG. 35.
Figure 39:
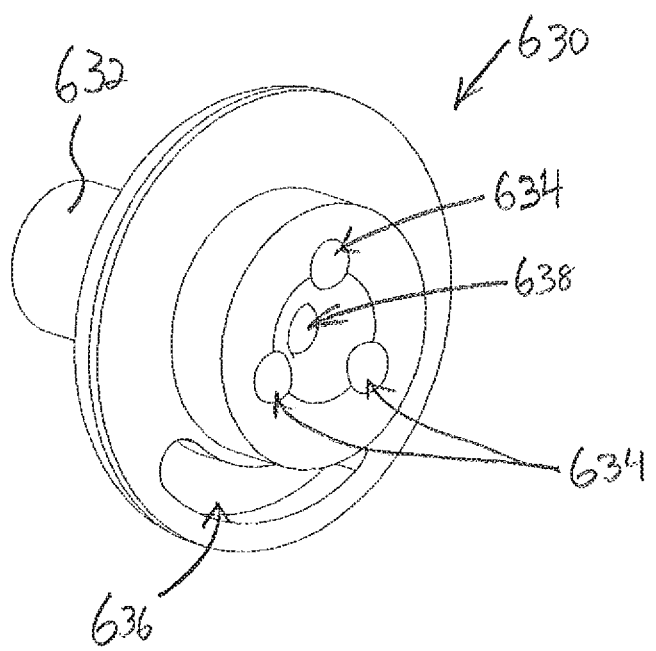
FIG. 39 depicts a perspective view of a second end cap of the guidewire spin control assembly of FIG. 35.

As shown in FIG. 38, end cap (620) includes a guidewire exit post (622), an array of circular recesses (624), an arcuate recess (626), and a guidewire passageway (628). As shown in FIG. 39, end cap (630) includes a guidewire exit post (632), an array of circular recesses (634), an arcuate recess (636), and a guidewire passageway (638). Guidewire spin control assembly (600) is rotatably supported in actuator (500) via posts (622, 632). Circular recesses (624, 634) are configured to receive corresponding end pins (642) of rollers (640). Arcuate recesses (626, 636) are configured to receive corresponding pins (650). End caps (620, 630) are rotatably secured to barrel member (610), such that barrel member (610) is rotatable relative to end caps (620, 630) along a certain range of angular movement. This range of angular movement is based on the angular extent of arcuate recesses (626, 636). As described in greater detail below, once pins (650) engage the ends of arcuate recesses (626, 636), end caps (620, 630) will rotate with barrel member (610).

Each roller (640) of the present example further includes a deformable body (644) extending between end pins (642). Deformable bodies (644) are resiliently biased to assume a straight configuration, where deformable bodies (644) are coaxially aligned with respective pins (642). Deformable bodies (644) are configured to cooperate with arcuate segments (614) in bore (612) of barrel member (610) to selectively engage guidewire (260). As will be described below with reference to FIGS. 40A and 41A, when barrel member (610) is in a first angular position relative to end caps (620, 630), deformable bodies (644) will be substantially straight, such that deformable bodies (644) are coaxially aligned with their respective end pins (642) and circular recesses (624, 634). In this non-deformed state, deformable bodies (644) are spaced away from guidewire (260), such that guidewire (260) may slide freely through guidewire spin control assembly (600). As will be described below with reference to FIGS. 40B-40C and 41B-41C, when barrel member (610) is in a second angular position relative to end caps (620, 630), deformable bodies (644) are deformed inwardly. In this deformed state, deformable bodies (644) are engaged with guidewire (260) and thereby grip guidewire (260), such that rotation of guidewire spin control assembly (600) will rotate guidewire (260).

Figure 40A:
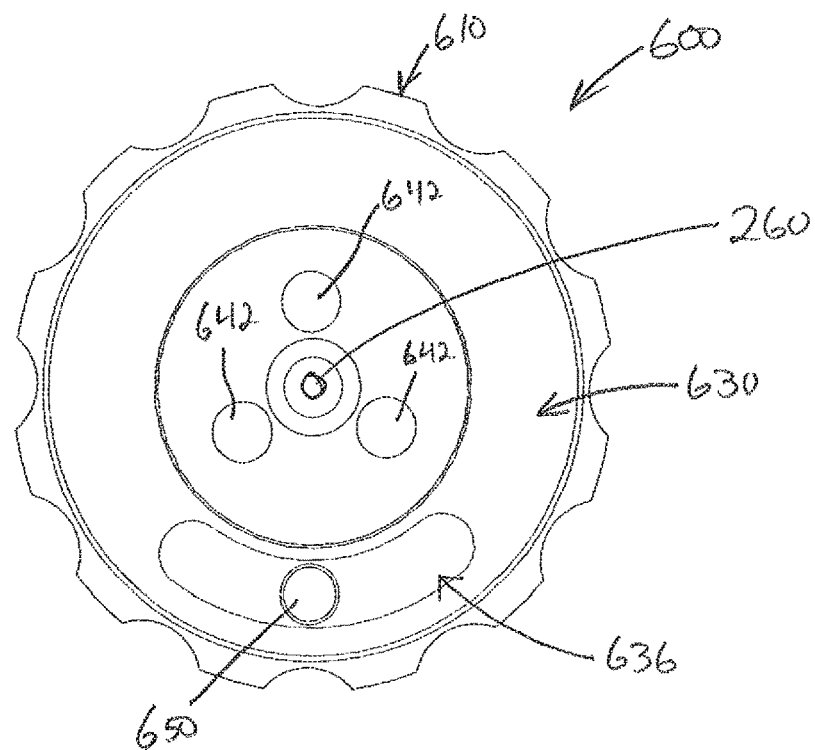
FIG. 40A depicts a cross-sectional view of the guidewire spin control assembly of FIG. 35, taken along line 40-40 of FIG. 35, with the barrel member at a first angular position and the second end cap at a first angular position.
Figure 41A:
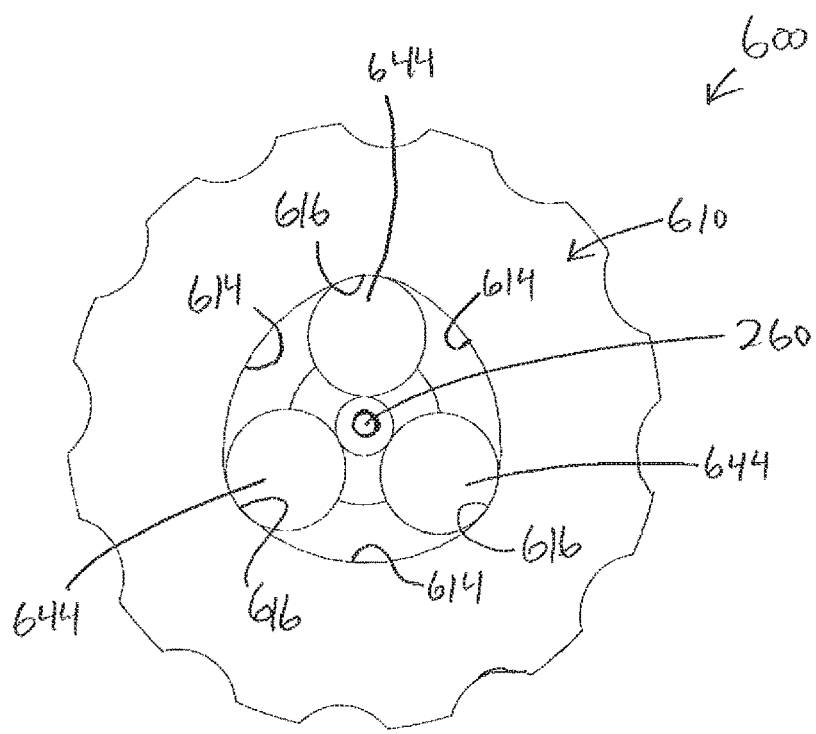
FIG. 41A depicts a cross-sectional view of the guidewire spin control assembly of FIG. 35, taken along line 41-41 of FIG. 35, with the barrel member at the first angular position and the second end cap at the first angular position.

FIGS. 40A and 41A show guidewire spin control assembly (600) in a non-actuated state. In this state, the operator has not rotated barrel member (610), deformable bodies (644) are spaced away from guidewire (260). Deformable bodies (644) are positioned in respective rounded corners (616) within bore (612) of barrel member (610). With deformable bodies (644) being spaced away from guidewire (260), when the operator actuates drive wheel (510), guidewire (260) will slide freely through guidewire spin control assembly (600). Also, when the longitudinal position of guidewire (260) is fixed by guidewire locking assembly (800) as described below, actuator (500) may slide freely relative to guidewire (260) with deformable bodies (644) in the state shown in FIGS. 40A and 41A. As also shown in FIGS. 40A and 41A, pins (650) are disposed in the center of each arcuate recess (626, 636) when guidewire spin control assembly (600) is in the non-actuated state.

Figure 40B:
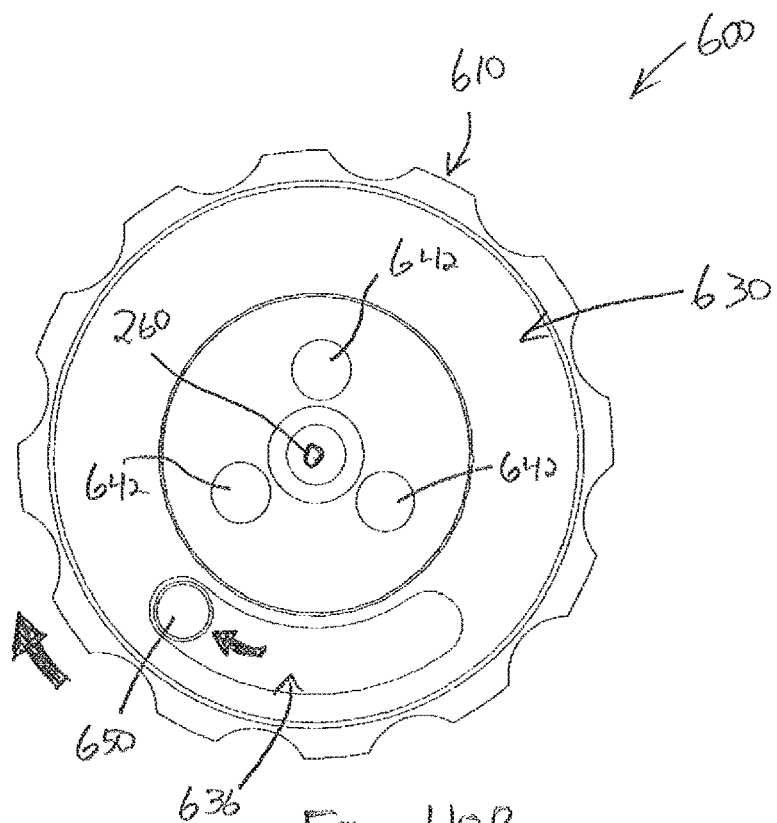
FIG. 40B depicts a cross-sectional view of the guidewire spin control assembly of FIG. 35, taken along line 40-40 of FIG. 35, with the barrel member at a second angular position and the second end cap at the first angular position.
Figure 41B:
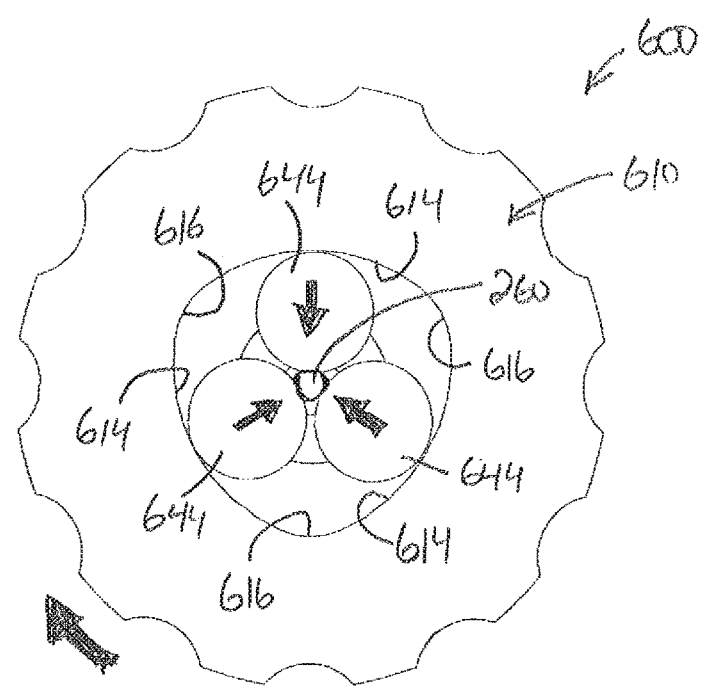
FIG. 41B depicts a cross-sectional view of the guidewire spin control assembly of FIG. 35, taken along line 41-41 of FIG. 35, with the barrel member at the second angular position and the second end cap at the first angular position.
Figure 40C:
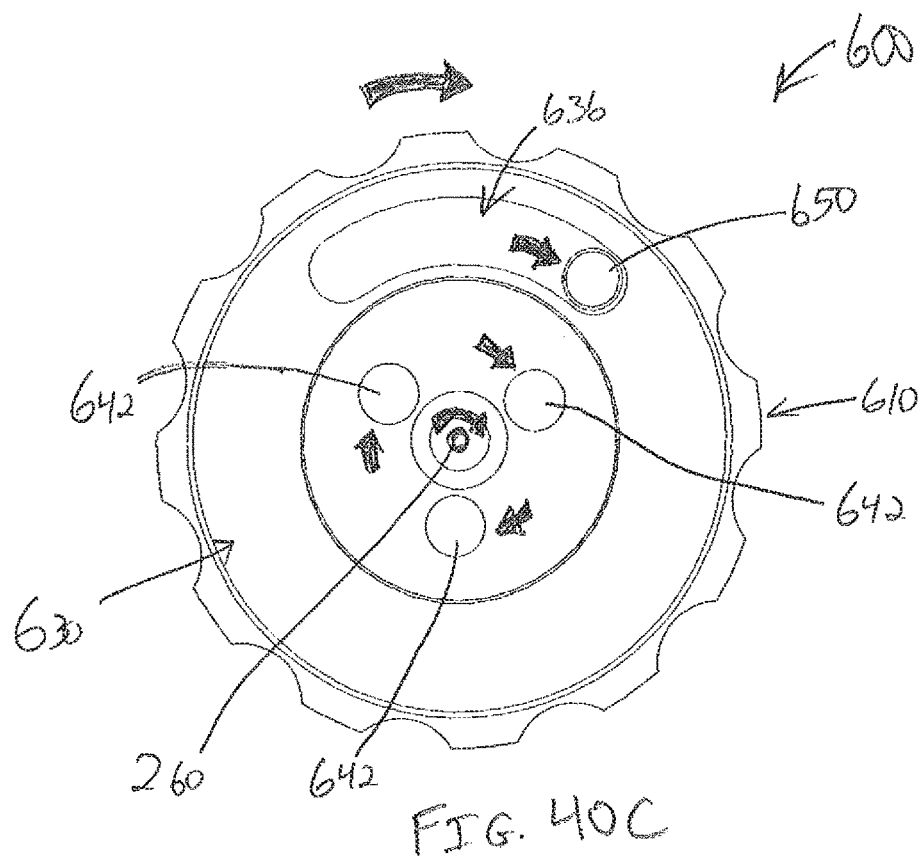
FIG. 40C depicts a cross-sectional view of the guidewire spin control assembly of FIG. 35, taken along line 40-40 of FIG. 35, with the barrel member at a third angular position and the second end cap at a second angular position.
Figure 41C:
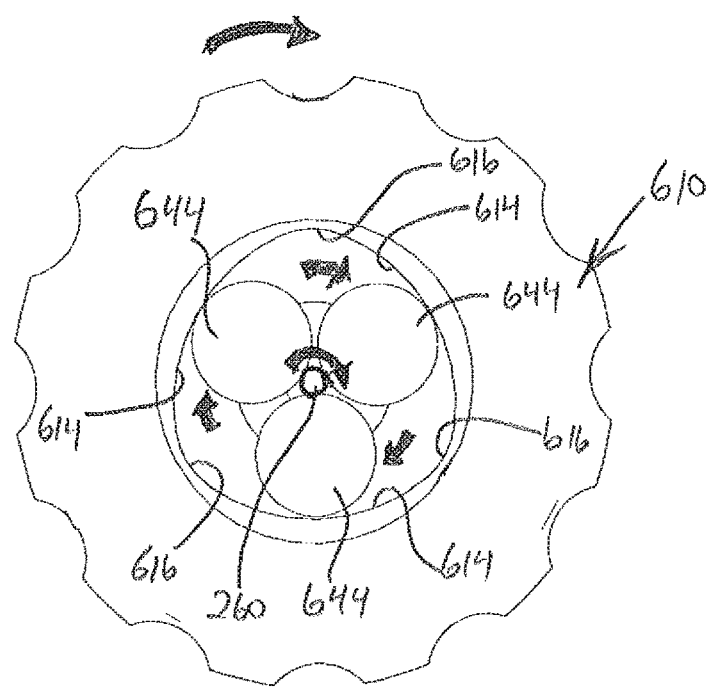
FIG. 41C depicts a cross-sectional view of the guidewire spin control assembly of FIG. 35, taken along line 41-41 of FIG. 35, with the barrel member at the third angular position and the second end cap at the second angular position.

FIGS. 40B and 41B show guidewire spin control assembly (600) after the operator has rotated barrel member (610) through a first range of angular motion. End caps (620, 630) and rollers (640) remain rotationally stationary through this first range of angular motion. As barrel member (610) rotates relative to end caps (620, 630) and rollers (640), arcuate segments (614) within bore (612) urge deformable bodies (644) inwardly into engagement with guidewire (260) as shown in FIG. 41B, such that deformable bodies (644) cooperate to grip guidewire (260). In some versions, deformable bodies (644) comprise an elastomeric material that enhances the grip of guidewire (260) when deformable bodies (644) are in the inwardly-deformed state. Barrel member (610) reaches the end of the first range of angular motion when pins (650) reaches the ends of respective arcuate recesses (626, 636), as shown in FIG. 40B.

As the operator continues to rotate barrel member (610) through a second range of angular motion after completing the first range of angular motion, pins (650) begin to drive end caps (620, 630), such that end caps (620, 630) rotate with barrel member (610). This rotation of end caps (620, 630) also provides rotation of rollers (640) about the longitudinal axis of guidewire spin control assembly (600). Deformable bodies (644) remain engaged with guidewire (260), such that rotation of guidewire spin control assembly (600) through a second range of angular motion after completing the first range of angular motion will cause guidewire (260) to rotate about the longitudinal axis of guidewire (260).

After the operator has rotated guidewire (260) to a desired angular position, the operator may disengage their thumb or finger from barrel member (610). When barrel member (610) is released, the resilience of deformable bodies (644) may urge deformable bodies (644) back into rounded corners (616). The resilience of deformable bodies (644) may thus urge barrel (610) to rotate relative to end caps (620, 630) back to a relationship like that shown in FIGS. 40A and 41A, such that deformable bodies (644) are again disengaged from guidewire (260). Guidewire (260) is thereby again free to translate relative to guidewire spin control assembly (600).

E. Exemplary Guidewire Locking Assembly

In some instances, after the operator has translated guidewire (260) to a desired longitudinal position where the distal end of guidewire (260) has passed through a targeted anatomical passageway, the operator may wish to keep guidewire (260) in a stationary longitudinal position as the operator translates dilation catheter (400) distally to position dilator (404) in the targeted anatomical passageway. This may be particularly desirable in contexts where guidewire (260) has no position sensing capabilities, such as when guidewire (260) is in the form of guidewire (50) or when guidewire (260) otherwise lacks a position sensor. While guidewire (260) should remain longitudinally stationary when an operator translates actuator (500) longitudinally, assuming that the operator is not simultaneously pressing drive wheel (510) or partially rotating guidewire spin control assembly (600) while translating actuator (500) longitudinally, it may be desirable to provide a locking mechanism to ensure that guidewire (260) will not translate as dilation catheter (400) is being translated. To that end, guidewire locking assembly (800) is operable to lock the longitudinal position of guidewire (260) relative to handle assembly (210) and shaft assembly (300) when actuator (500) is anywhere distal to a proximal-most position.

Figure 42:
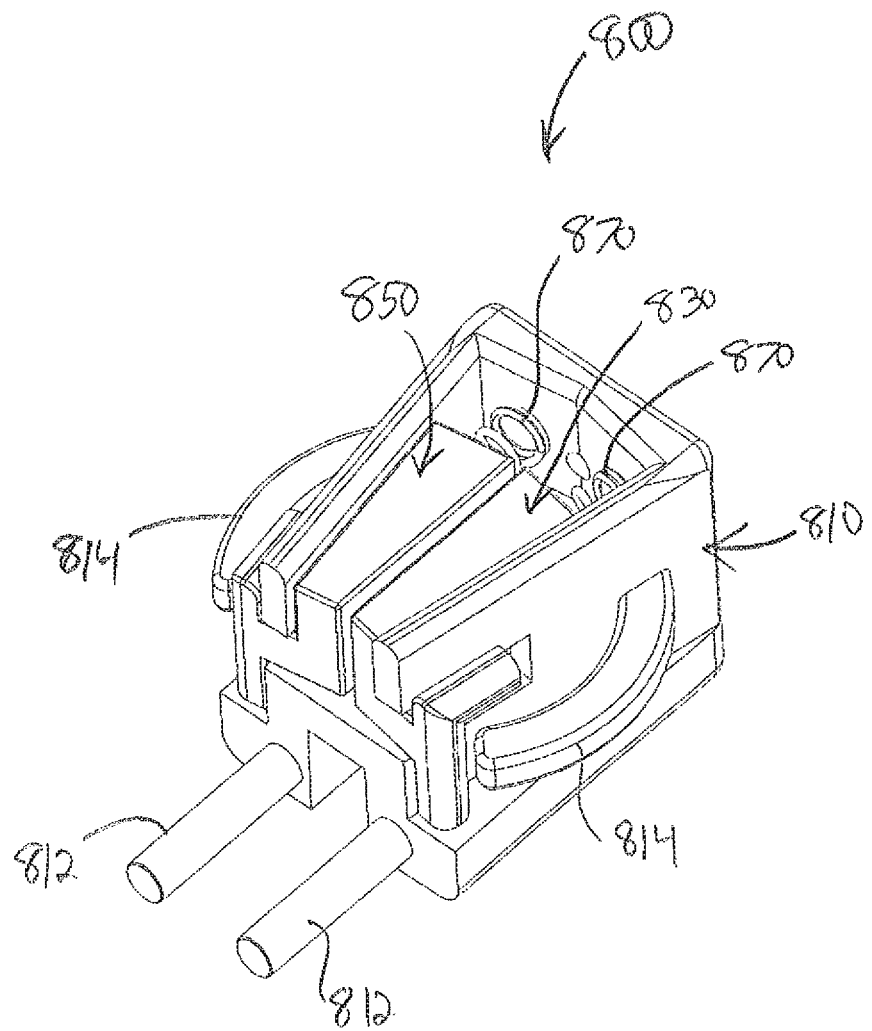
FIG. 42 depicts a perspective view of a guidewire locking assembly of the instrument of FIG. 8.
Figure 43:
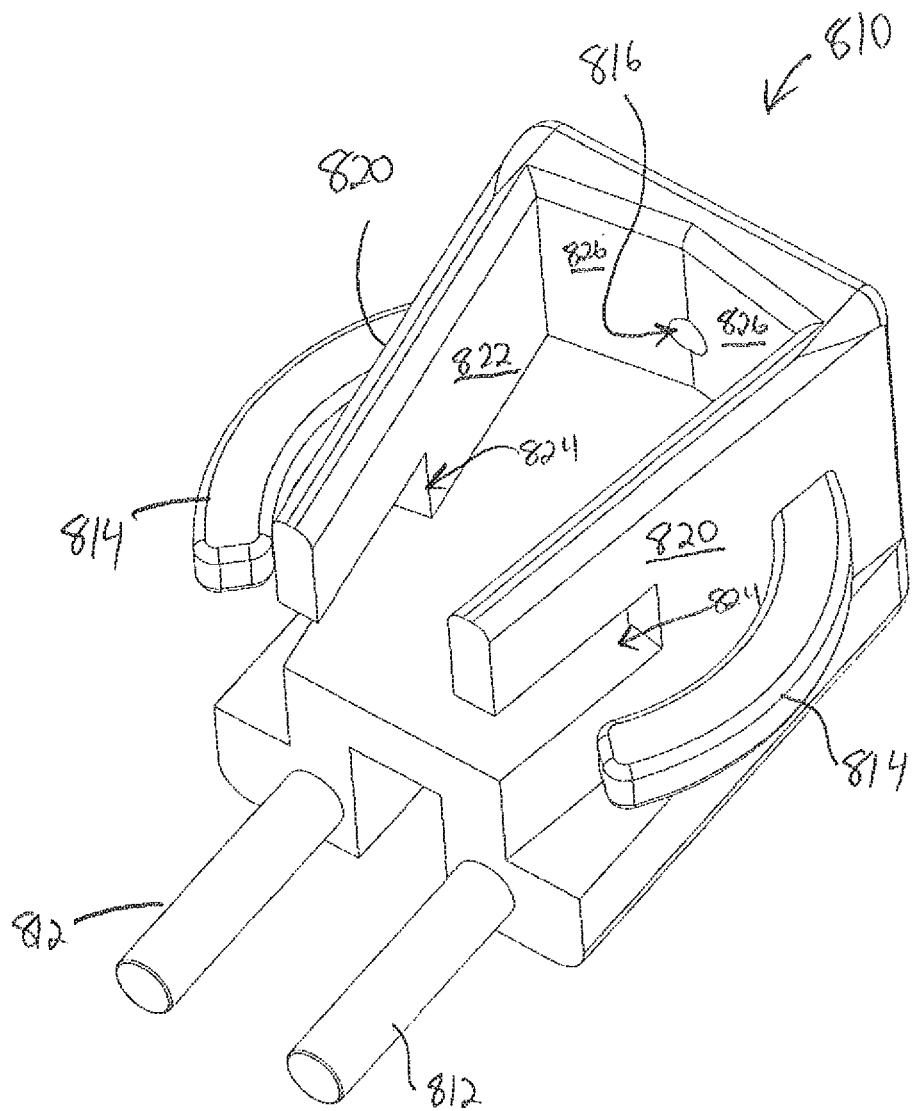
FIG. 43 depicts a perspective view of a frame of the guidewire locking assembly of FIG. 42.
Figure 44:
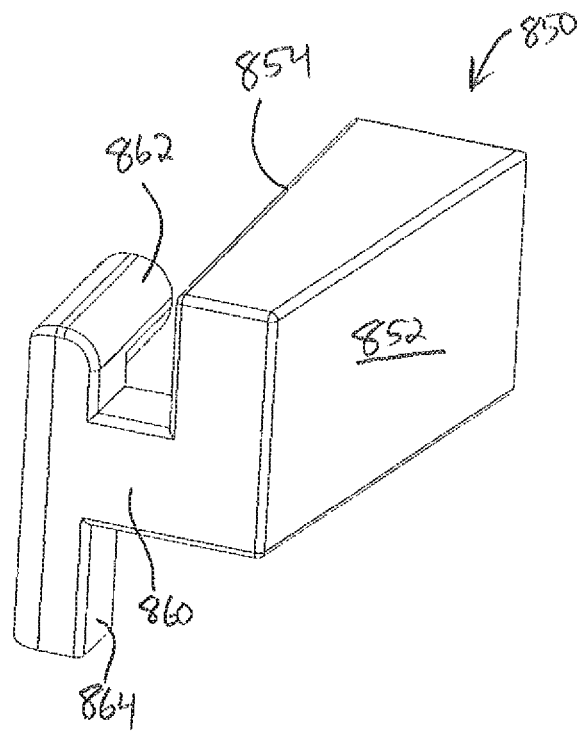
FIG. 44 depicts a perspective view of a first lock shoe of the guidewire locking assembly of FIG. 42.
Figure 45:
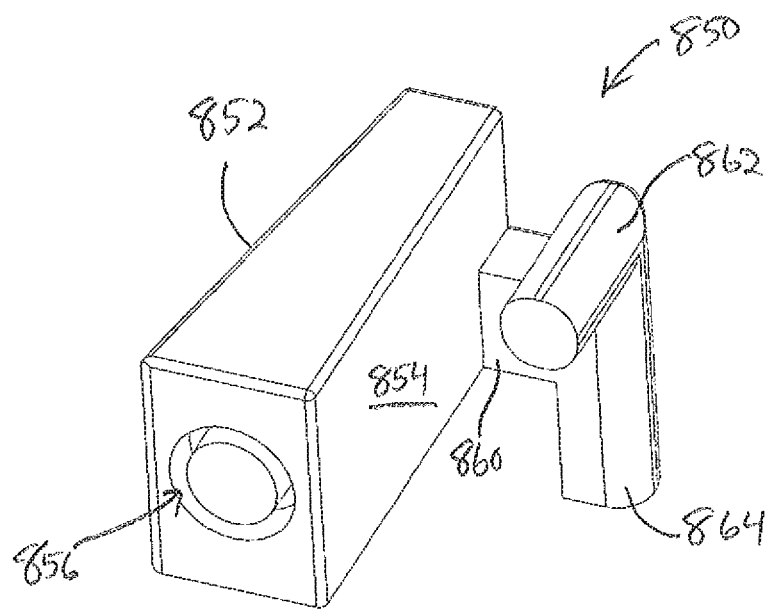
FIG. 45 depicts another perspective view of the lock shoe of FIG. 44.

As shown in FIG. 42, guidewire locking assembly (800) of the present example comprises a frame (810), a pair of lock shoes (830, 850), and a pair of coil springs (870). As shown in FIG. 43, frame (810) comprises a pair of coupling prongs (812), a pair of guard members (814), a guidewire passageway (816), outer sidewall surfaces (820), inner sidewall surfaces (822), a pair of lateral notches (824), and rear sidewall surfaces (826). Coupling prongs (812) are disposed in body (220) of handle assembly (210) to thereby fixedly secure frame (810) to body (220). As shown in FIGS. 44-45, lock shoe (850) comprises an inner sidewall surface (852), an outer sidewall surface (854), spring recess (856), a lateral projection (860), a proximally projecting prong (862), and a downwardly projecting prong (864). Lock shoe (830) is configured as a mirror image of lock shoe (850).

Figure 46A:
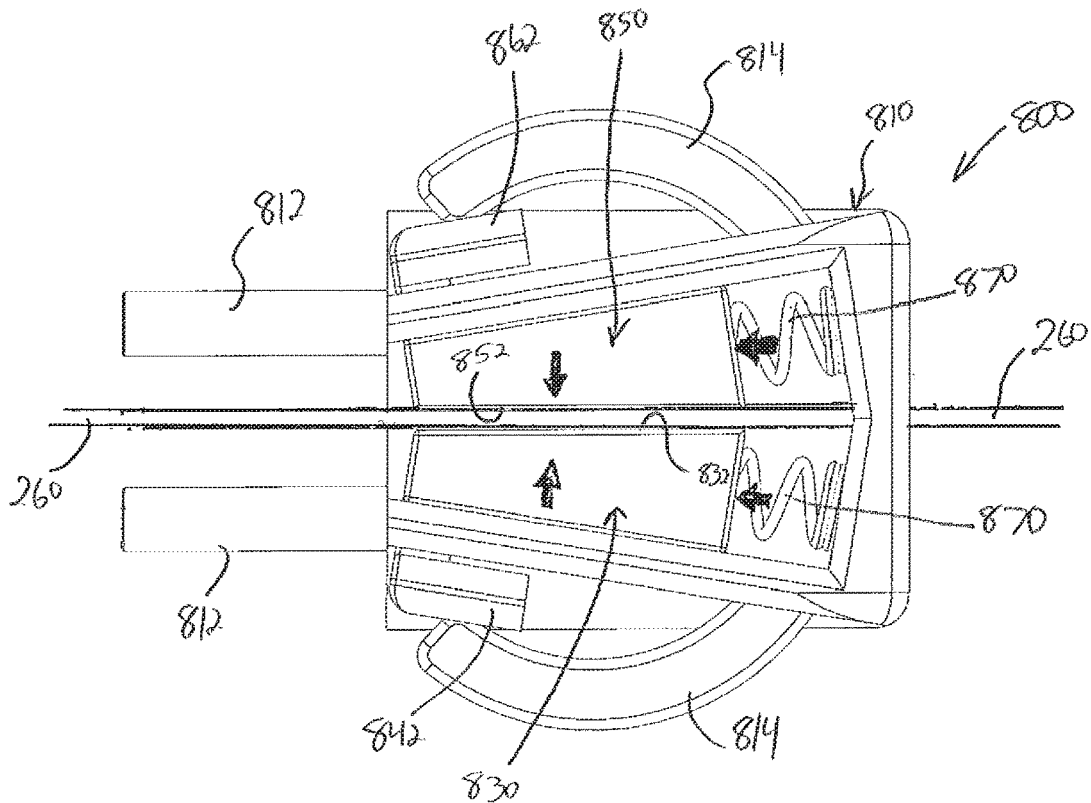
FIG. 46A depicts a top plan view of the guidewire locking assembly of FIG. 42, with guidewire locking assembly in a locked state.
Figure 46B:
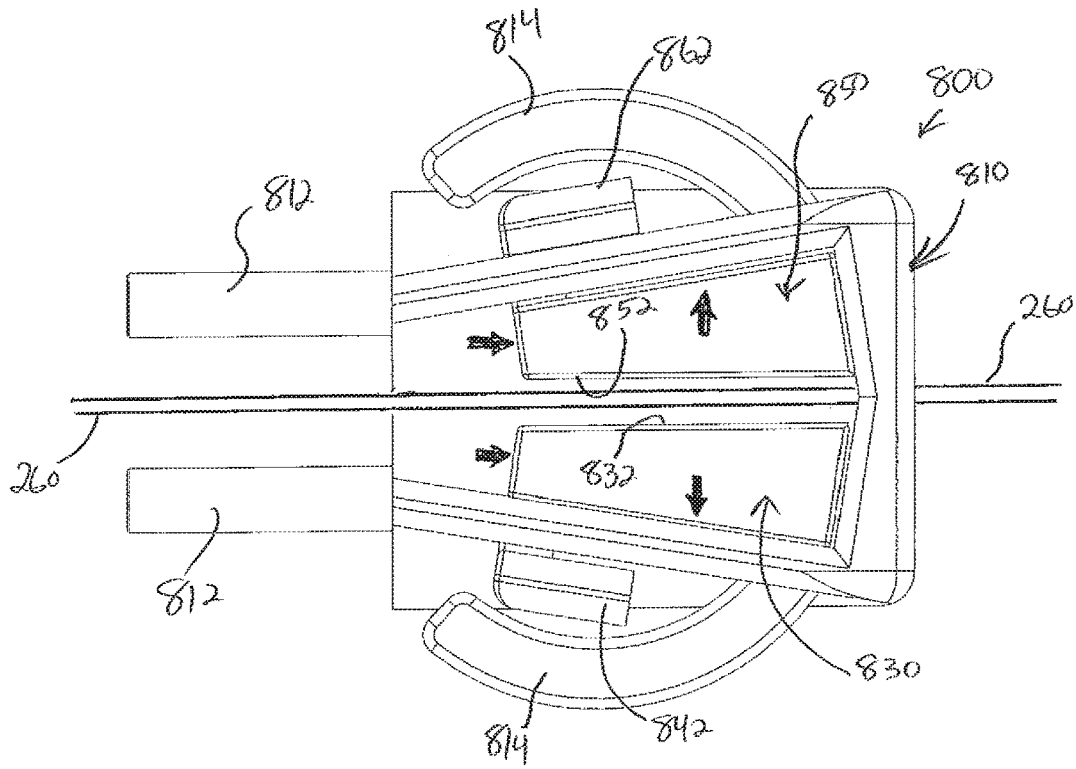
FIG. 46B depicts a top plan view of the guidewire locking assembly of FIG. 42, with guidewire locking assembly in an unlocked state.

As shown in FIGS. 42 and 46A-46B, lock shoes (830, 850) are configured to fit within frame (810) such that outer sidewall surfaces (854) of lock shoes (830, 850) are adjacent to inner sidewall surfaces (822) of frame (810), such that lateral projections (860) of lock shoes (830, 850) are disposed in lateral notches (824) of frame (810), and such that proximally projecting prongs (862) of lock shoes (830, 850) are adjacent to outer sidewall surfaces (826) of frame (810). Coil springs (870) are seated in spring recesses (856) of lock shoes (830, 850) and bear against rear sidewall surfaces (826) of frame (810). Coil springs (870) resiliently bias lock shoes (830, 850) to the distal position shown in FIGS. 42 and 46A. While coil springs (870) are used in the present example, any other kind of resilient member may be used.

Sidewall surfaces (822, 854) are angled such that lock shoes (830, 850) are urged toward each other when lock shoes (830, 850) are in the distal position. When lock shoes (830, 850) are in the distal position as shown in FIG. 46A, inner sidewall surfaces (852) of lock shoes (830, 850) cooperate to grip guidewire (260). Lock shoes (830, 850) thus lock the longitudinal position of guidewire (260) when lock shoes (830, 850) are in the distal position. Since coil springs (870) urge lock shoes (830, 850) distally, coil springs (870) resiliently bias guidewire locking assembly (800) to a locked state.

Outer sidewall surfaces (820) and proximally projecting prongs (842, 862) are angled such that lock shoes (830, 850) are urged away from each other when lock shoes (830, 850) are in the proximal position. When lock shoes (830, 850) are in the proximal position as shown in FIG. 46B, inner sidewall surfaces (852) of lock shoes (830, 850) are spaced apart from guidewire (260) such that that lock shoes (830, 850) are disengaged from guidewire (260). Guidewire (260) is thus free to translate relative to guidewire locking assembly (800) when guidewire locking assembly (800) is in the unlocked state shown in FIG. 46B.

Figure 47A:
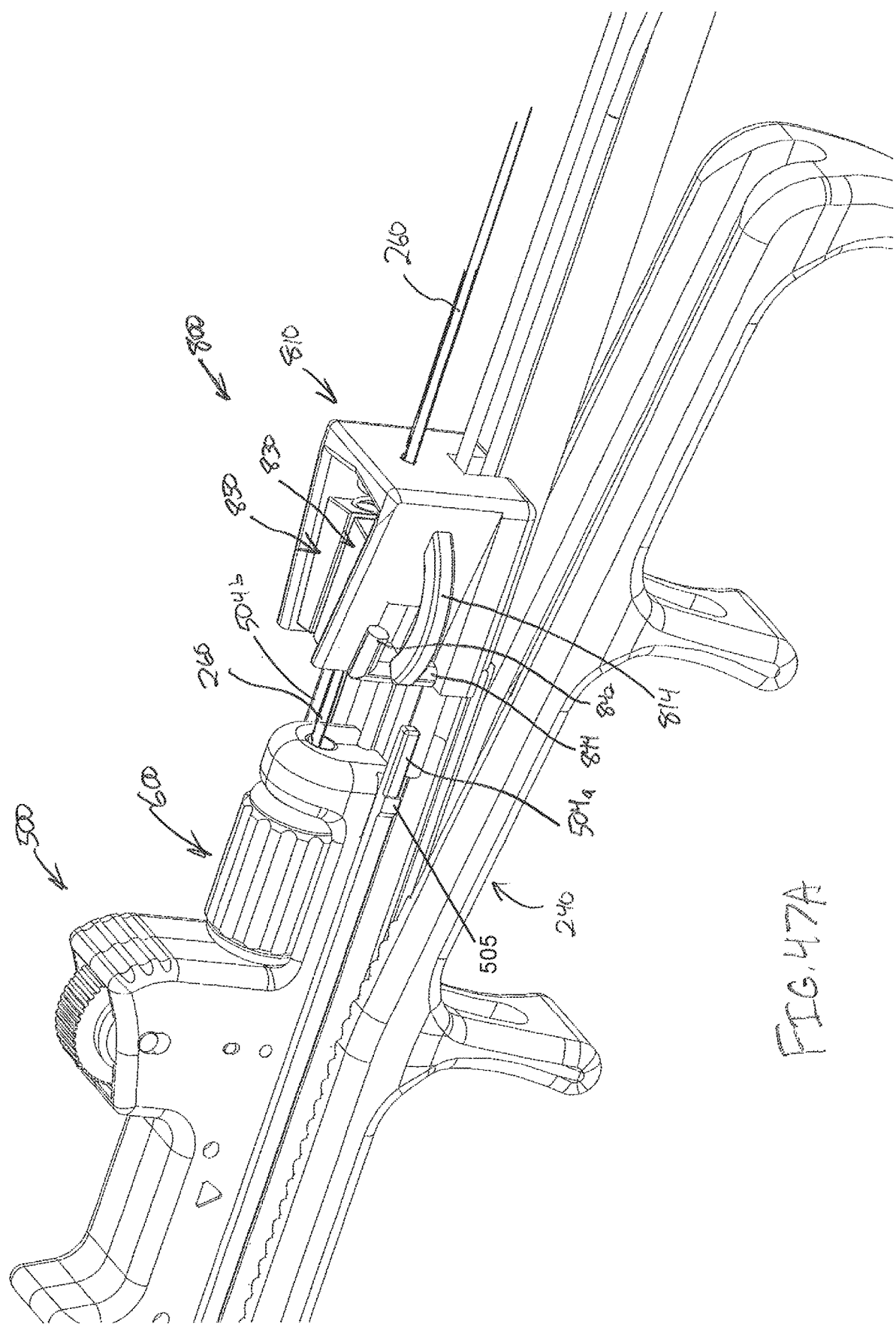
FIG. 47A depicts a perspective view of a proximal portion of the instrument of FIG. 8, with the actuator in a distal position and the guidewire locking assembly in the locked state.
Figure 47B:
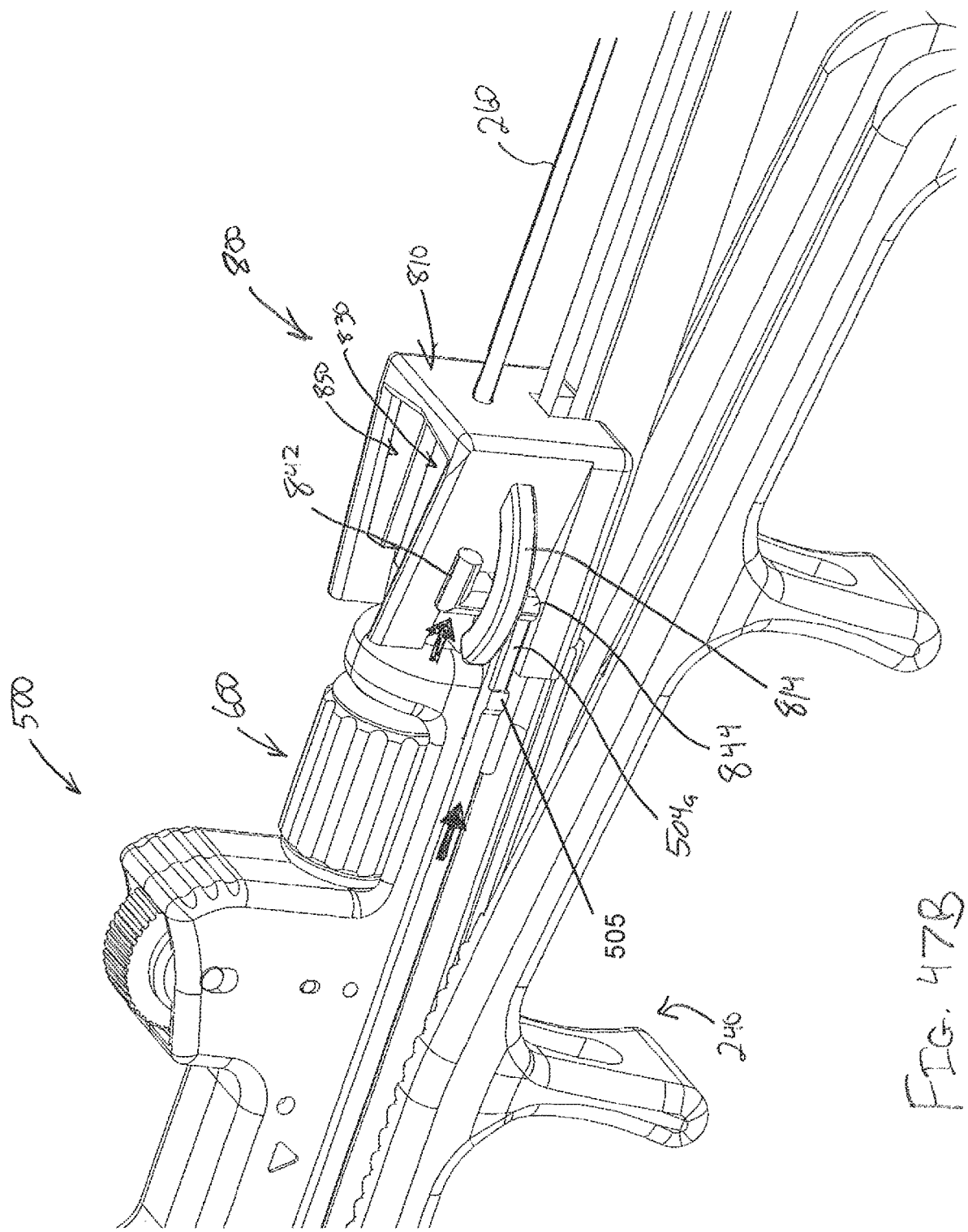
FIG. 47B depicts a perspective view of a proximal portion of the instrument of FIG. 8, with the actuator in a proximal position and the guidewire locking assembly in the unlocked state.

FIGS. 47A-47B show how actuator (500) transitions guidewire locking assembly (800) between the locked state of FIG. 46A and the unlocked state of FIG. 46B. Half of body (220) is omitted from FIGS. 47A-47B for clarity. As shown in FIGS. 47A-47B, and as further shown in FIGS. 25-26, actuator (500) comprises a pair of proximally projecting prongs (504a, 504b). Prongs (504a, 504b) of actuator (500) are positioned to engage downwardly projecting prongs (844, 864) of lock shoes (830, 850). As shown in FIG. 47A, when actuator (500) is positioned distal to a proximal-most position, prongs (504a, 504b) of actuator (500) are spaced away from downwardly projecting prongs (844, 864) of lock shoes (830, 850), such that prongs (504a, 504b) of actuator (500) disengaged from downwardly projecting prongs (844, 864) of lock shoes (830, 850). In this state, lock shoes (830, 850) are distally positioned within frame (810), such that lock shoes (830, 850) secure the longitudinal position of guidewire (260). As shown in FIG. 47B, when actuator (500) is positioned in the proximal-most position, prongs (504a, 504b) of actuator (500) engage downwardly projecting prongs (844, 864) of lock shoes (830, 850) and thereby urge lock shoes (830, 850) to the proximal position. In this state lock shoes (830, 850) are proximally positioned within frame (810), such that lock shoes (830, 850) disengage guidewire (260) and thereby allow guidewire (260) to translate and rotate freely.

In view of the foregoing, when dilatation catheter (400) is fully retracted within shaft assembly (300), guidewire locking assembly (800) is in an unlocked state such that guidewire (260) is free to translate and rotate. However, when dilation catheter (400) is advanced anywhere distal to a proximal-most position, guidewire locking assembly (800) is in a locked state such that guidewire (260) is no longer free to translate and rotate. In the present example, actuator (500) further includes lateral projections (505) extending outwardly near prongs (504a, 504b). These projections (505) are configured to cooperate with corresponding notches (not shown) formed in body (220) of handle assembly (210) to provide a detent assembly that releasably retains actuator (500) and dilation catheter (400) in the proximal-most position. In some variations, a clip, clasp, latch, or other feature is used to selectively secure actuator (500) and dilation catheter (400) in the proximal-most position.

In some other instances, the operator may wish to translate guidewire (260) and dilation catheter (400) simultaneously, as if guidewire (260) and dilation catheter (400) were a unitary structure. This simultaneous translation may be desirable in contexts where guidewire (260) has position sensing capabilities, such as when guidewire is in the form of guidewire (130). In such instances, it may be desirable to maintain guidewire locking assembly (800) in an unlocked state, even as actuator (500) is located distal to the proximal-most position. By way of example only, guard members (814) may be configured to deflect inwardly and maintain an inwardly-deflected configuration to engage prongs (844, 864) of lock shoes (830, 850) and thereby hold lock shoes (830, 850) in the proximal position. Guard members (814) may thus maintain guidewire locking assembly (800) in the unlocked state even when actuator (500) is positioned distal to the proximal-most position. As another merely illustrative example, a clamp, clip, or other feature may be applied to or incorporated with guidewire locking assembly (800) to selectively maintain guidewire locking assembly (800) in the unlocked state even when actuator (500) is positioned distal to the proximal-most position. Various suitable components and configurations that may be used to provide such functionality will be apparent to those of ordinary skill in the art in view of the teachings herein.

Regardless of the structures and methods used to maintain guidewire locking assembly (800) in an unlocked state, even as actuator (500) is located distal to the proximal-most position, it would be necessary to secure the longitudinal position of guidewire (260) relative to actuator (500) in order to have actuator (500) drive guidewire (260) longitudinally as actuator (500) is driven longitudinally. To that end, the operator may depress drive wheel (510) to urge drive wheels (520a, 520b) into engagement with guidewire (260) as actuator (500) is driven longitudinally. Drive wheels (520a, 520b) and spool (530) will cooperate to maintain a grip on guidewire (260). Thus, even if drive wheel (510) is not being rotated as actuator (500) is driven longitudinally, the downwardly urged drive wheels (510, 520a, 520b) will provide translation of guidewire (260) with actuator (500) as actuator (500) is driven longitudinally to translate dilation catheter (400).

In addition to having detent features that cooperate with lateral projections (505) of actuator (500) to selectively maintain actuator (500) in the proximal position, body (220) of handle assembly (210) may also have detent features that cooperate with lateral projections (505) of actuator (500) to selectively maintain actuator (500) in one or more distal positions. For instance, a first set of distal detent features may cooperate with lateral projections (505) of actuator (500) to selectively maintain actuator (500) (and, hence, dilation catheter (400)) in a first distal position that is associated with dilation of a Eustachian tube, a maxillary sinus ostium, and a sphenoid sinus ostium. A second set of distal detent features may cooperate with lateral projections (505) of actuator (500) to selectively maintain actuator (500) (and, hence, dilation catheter (400)) in a second distal position that is associated with dilation of a frontal recess or frontal sinus ostium. By way of further example only, the second distal position may be approximately 20 mm distal to the first distal position. In addition to selectively maintaining actuator (500) in these distal positions, the distal detent features may provide the operator with tactile feedback indicating the advancement distance of dilator (400) within the nasal cavity.

F. Exemplary Handle Assembly Components

Depending on the position of the patient and the personal preference of the operator, an operator may wish to manipulate an instrument using various kinds of grasping techniques. For instance, some operators in some scenarios may wish to grasp an instrument using a power grip. Alternatively, some operators in some scenarios may wish to grasp an instrument using a pencil grip. In addition, even within the same category of grip (e.g., power grip), the hand size or general preference of an operator may warrant selectability in the structural configuration of the structure that the operator will be grasping. To that end, handle assembly (210) of the present example includes features that allow the operator to change the structural configuration of handle assembly (210) to accommodate or otherwise facilitate different grasping configurations and techniques. In particular, handle assembly (210) of the present example comprises a body portion (220) and a grip portion (240), which are removably coupled together.

Figure 48:
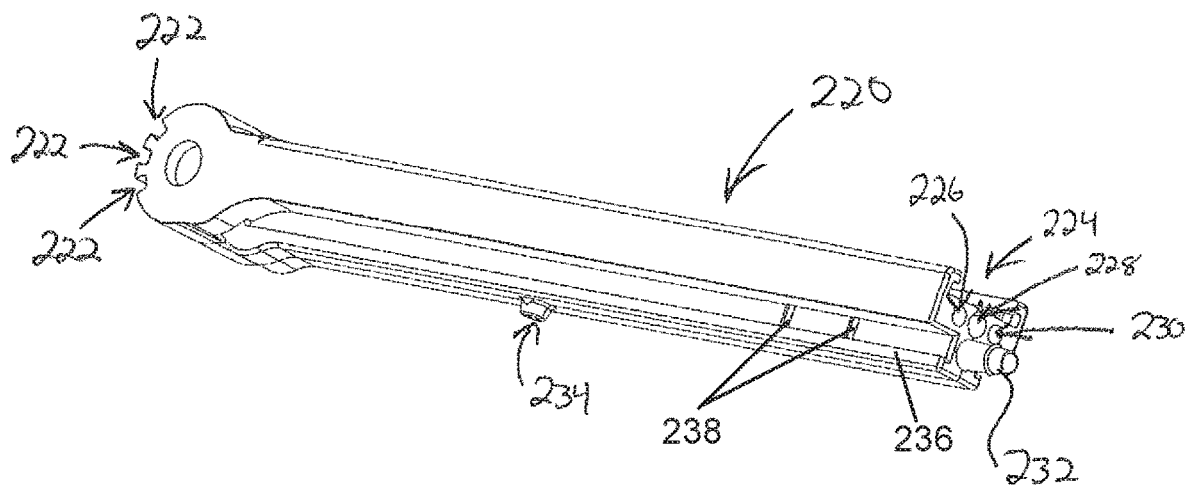
FIG. 48 depicts a perspective view of a body portion of a handle assembly of the instrument of FIG. 8.

As shown in FIG. 48, body portion (220) of the present example comprises an upper "T" channel (224), a pair of outer openings (226, 230), an inner passageway (228), a suction tube fitting (232), a vent port (234), a lower "T" rail (236), and a pair of detent ribs (238). "T" channel (224) is configured to receive a corresponding "T" rail (505) of actuator (500) to provide a slidable coupling between actuator (500) and body portion (220). Outer openings (226, 230) are configured to receive coupling prongs (812) of guidewire locking assembly (800) to thereby provide a rigid coupling between body portion (220) and guidewire locking assembly (800). Inner passageway (228) is configured to slidably receive inflation conduit (270). Suction tube fitting (232) is configured to couple with suction conduit (290).

Body portion (220) further defines a suction lumen (not shown) that is in fluid communication with suction tube fitting (232), vent port (234), and shaft assembly (300). These features thereby enable the operator to apply suction to a target site via shaft assembly (300). In scenarios where suction is not desired, the operator may simply leave vent port (234) uncovered. When vent port (234) is uncovered, suction that is drawn via suction conduit (290) and suction tube fitting (232) will simply be applied to atmosphere via uncovered vent port (234). In scenarios where suction is desired, the operator may cover vent port (234) with a finger of the hand grasping handle assembly (210). When vent port (234) is covered, suction that is drawn via suction conduit (290) and suction tube fitting (232) will simply be applied to the target site via shaft assembly (300). In some variations, these suction features are simply omitted.

Figure 49:
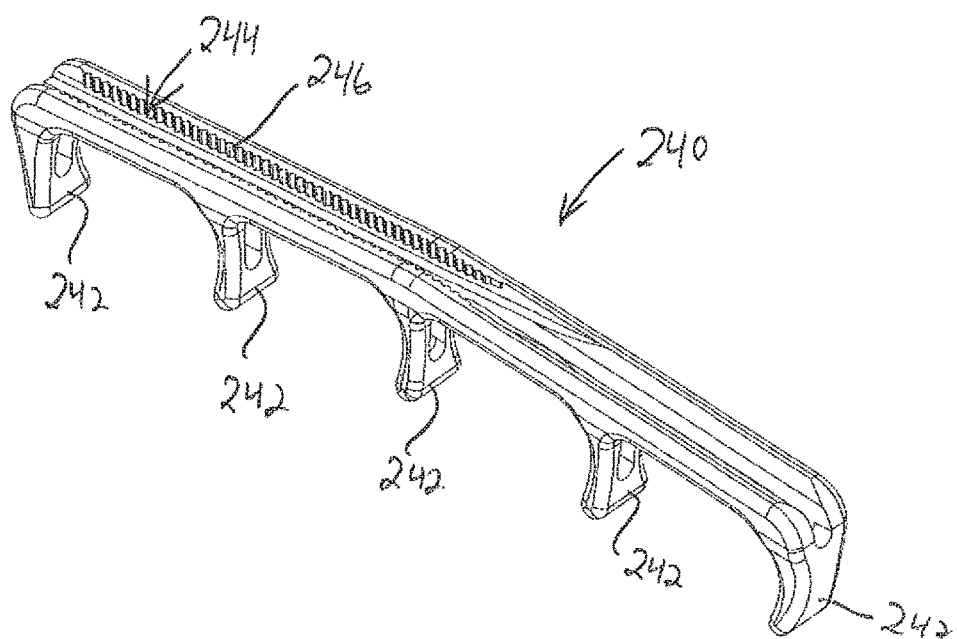
FIG. 49 depicts a perspective view of a grip portion of the handle assembly of the instrument of FIG. 8.

As shown in FIG. 49, grip portion (240) of the present example comprises an array of downwardly projecting finger grips (242), a "T" channel (244), and an array of ratchet teeth (246). While not shown, the underside of grip portion (240) also includes an opening or other feature that enables the operator to access vent port (234) when grip portion (240) is coupled with body portion (220). "T" channel (244) of grip portion (240) is configured to receive "T" rail (236) of body portion (220) to thereby provide a slidable coupling between grip portion (240) and body portion (220). Detent ribs (238) are configured to ratchet along ratchet teeth (246) as grip portion (240) is slid along body portion (220). Detent ribs (238) and ratchet teeth (246) thus cooperate to selectively secure the longitudinal position of grip portion (240) relative to body portion (220). This may facilitate removal of grip portion (240) from body portion (220) in instances where the operator wishes to grasp body portion (220) without grip portion (240). Moreover, the selective nature of the coupling between grip portion (240) and body portion may promote use of modular forms of grip portion (240). In other words, the operator may be presented with various kinds of grip portions (240) that accommodate different hand sizes and/or gripping techniques, and the operator may choose from this selection and secure the selected grip portion (240) to body portion (220) as desired. Other suitable ways in which grip portion (240) may be selectively coupled with body portion (220) will be apparent to those of ordinary skill in the art in view of the teachings herein.

V. Second Exemplary Alternative Dilation Catheter Instrument

A. Overview

FIG. 52 shows another exemplary alternative instrument (1000) that may be used to dilate an anatomical structure, such as a paranasal sinus ostium or other drainage passageway within a head of a patient. Except as otherwise described below, instrument (1000) may be configured and operable like instrument (200) described above. Instrument (1000) of this example includes a shaft assembly (1010), a grip body (1002), guidewire (1020), a dilation catheter (1030), a guidewire actuator assembly (1040), and a dilation catheter slider (1100). In the present example, guidewire actuator assembly (1040) is positioned proximal to dilation catheter slider (1100). Guidewire (1020) may be constructed and operable just like any other guidewire (50, 130, 260) described herein. Similarly, dilation catheter (1030) may be constructed and operable just like any other dilation catheter (20, 400) described herein.

Figure 53A:
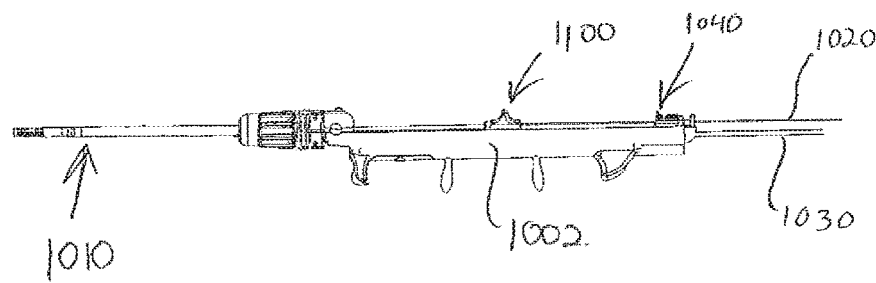
FIG. 53A depicts a side elevational view of the instrument of FIG. 52, with a guidewire and a dilation catheter both in respective proximal positions.
Figure 53B:
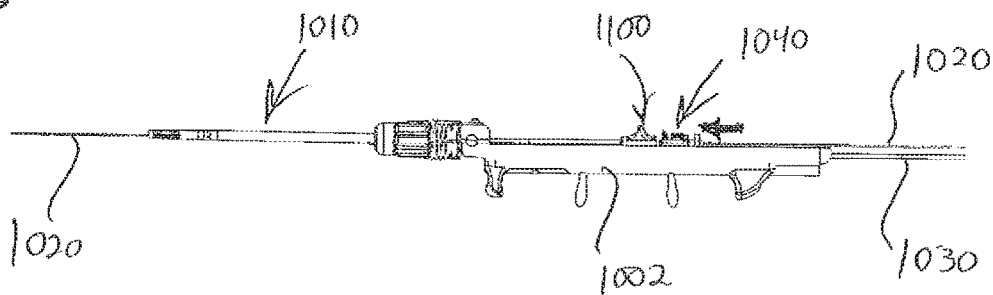
FIG. 53B depicts a side elevational view of the instrument of FIG. 52 with the guidewire in a first distal position and the dilation catheter in the proximal position.
Figure 53C:
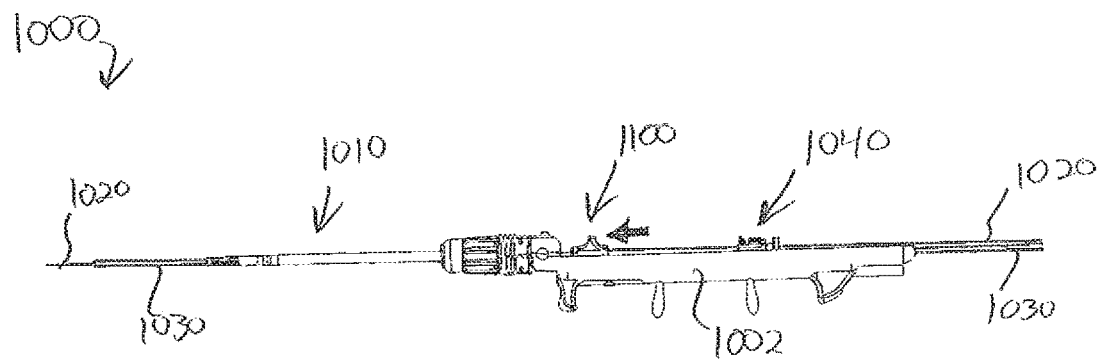
FIG. 53C depicts a side elevational view of the instrument of FIG. 52 with the guidewire in the first distal position and the dilation catheter in a second distal position.
Figure 53C:
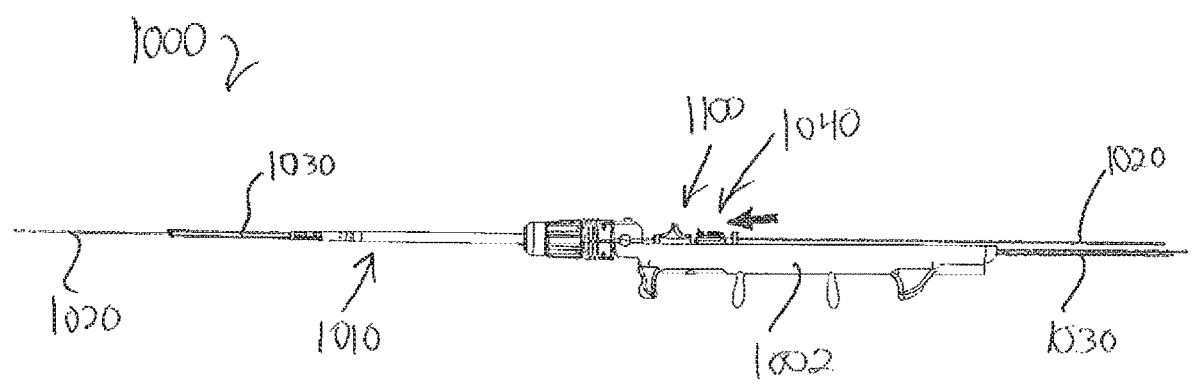

As shown in FIGS. 53A-53C, guidewire actuator assembly (1040) and dilation catheter slider (1100) are operable to translate guidewire (1020) and dilation catheter (1030), respectively, relative to grip body (1002) and relative to shaft assembly (1010). Components that are used to couple guidewire actuator assembly (1040) with guidewire (1020) are described in greater detail below. Similarly, components that are used to couple dilation catheter (1030) with dilation catheter slider (1100) are described in greater detail below.

While shaft assembly (1010) is shown in a straight configuration in FIGS. 53A-53C, shaft assembly (1010) is configured to bend to thereby direct guidewire (1020) and dilation catheter (1030) away from a longitudinal axis, similar to the bending of shaft assembly (300) described above. Components that are used to achieve such bending of shaft assembly (1010) will be described in greater detail below.

As shown in the transition from FIG. 53A to FIG. 53B, guidewire actuator assembly (1040) is translatable from a proximal position to a first distal position. As guidewire actuator assembly (1040) translates from the proximal position to the first distal position, guidewire actuator assembly (1040) correspondingly drives guidewire (1020) from a proximal position to a first distal position, such that the distal end of guidewire (1020) exits the distal end of shaft assembly (1010) and is thereby positioned distally relative to the distal end of shaft assembly. As described above, the operator may advance guidewire actuator assembly (1040) and guidewire (1020) distally to the position shown in FIG. 53B in order to position the distal end of guidewire (1020) through a paranasal sinus ostium (or other drainage passageway) and into a paranasal sinus cavity, to thereby assist in guiding a distal portion of dilation catheter (1030) into the paranasal sinus ostium (or other drainage passageway).

As shown in the transition from FIG. 53B to FIG. 53C, dilation catheter slider (1100) is translatable from a proximal position to a second distal position. As dilation catheter slider (1100) translates from the proximal position to the first distal position, dilation catheter slider (1100) correspondingly drives dilation catheter (1030) from a proximal position to a second distal position, such that an expandable dilator (not shown) near the distal end of dilation catheter (1030) exits the distal end of shaft assembly (1010) and is thereby positioned distally relative to the distal end of shaft assembly. As described above, the operator may advance dilation catheter slider (1100) and dilation catheter (1030) distally to the position shown in FIG. 53C in order to position the expandable dilator of dilation catheter (1030) in a paranasal sinus ostium (or other drainage passageway), to thereby position the expandable dilator to dilate the paranasal sinus ostium (or other drainage passageway).

In the example shown in FIG. 53C, dilation catheter slider (1100) and dilation catheter (1030) are translated distally while guidewire actuator assembly (1040) and guidewire (1020) remain longitudinally stationary. In some scenarios, the operator may wish to translate dilation catheter (1030) and guidewire (1020) together as a unit. By way of example only, such operability may be desirable when guidewire (1020) includes a navigation coil or other navigation feature, similar to guidewire (130) described above. As shown in FIG. 53C', dilation catheter slider (1100) and guidewire actuator assembly (1040) may be translated distally together as a unit, from the respective positions shown in FIG. 53B to the positions shown in FIG. 53C'. This may be accomplished simply by pushing guidewire actuator assembly (1040) distally from the position shown in FIG. 53B to the position shown in FIG. 53C', such that guidewire actuator assembly (1040) engages dilation catheter slider (1100) and thereby urges dilation catheter slider (1100) distally. When dilation catheter slider (1100) and guidewire actuator assembly (1040) are translated distally together as a unit, dilation catheter (1030) and guidewire (1020) are also translated distally together as a unit.

In the present example, as will be described in greater detail below, complementary structural features provide a removable coupling between dilation catheter slider (1100) and guidewire actuator assembly (1040), such that dilation catheter slider (1100) and guidewire actuator assembly (1040) may translate back proximally from the position shown in FIG. 53C' to the position shown in FIG. 53B (e.g., simply by urging guidewire actuator assembly (1040)), to thereby retract dilation catheter (1030) and guidewire (1020) proximally together as a unit. These complementary structural features that provide a removable coupling between dilation catheter slider (1100) and guidewire actuator assembly (1040) are further configured to disengage upon return to the state shown in FIG. 53B, to allow guidewire actuator assembly (1040) and guidewire (1020) to retract further proximally to the position shown in FIG. 53A. These complementary structural features that provide a removable coupling between dilation catheter slider (1100) and guidewire actuator assembly (1040) are further configured to disengage when the operator wishes to translate dilation catheter slider (1100) and dilation catheter (1030) independently of guidewire actuator assembly (1040) and guidewire (1020), to transition from the state shown in FIG. 53B to the state shown in FIG. 53C.

B. Exemplary Guidewire Actuator Assembly and Dilation Catheter Slider

Figure 54:
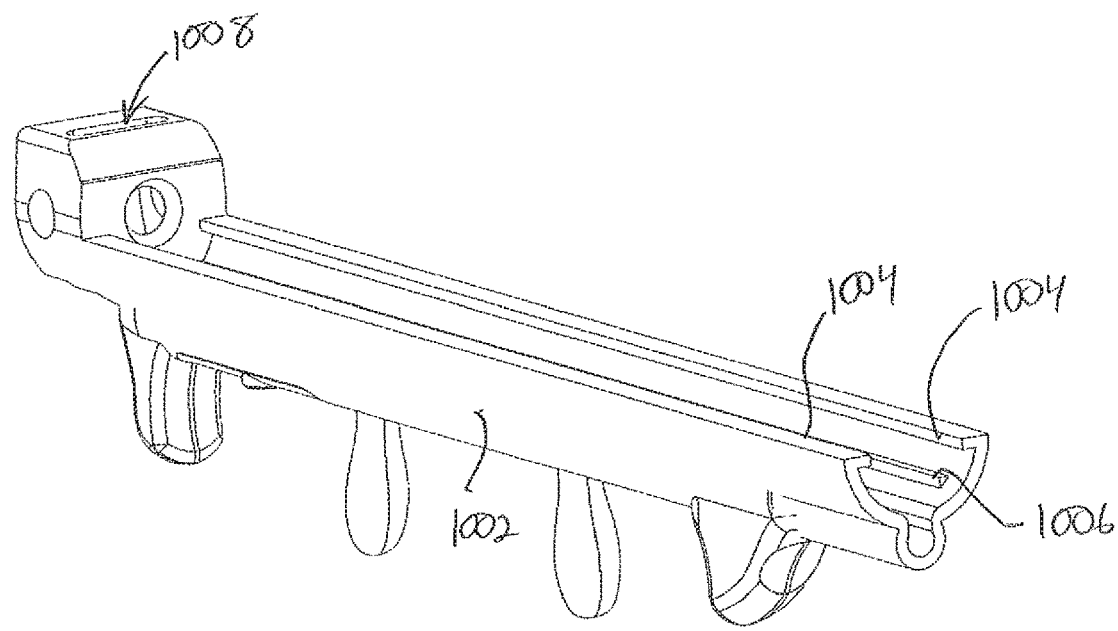
FIG. 54 depicts a perspective view of a grip body of the instrument if FIG. 52.
Figure 55:
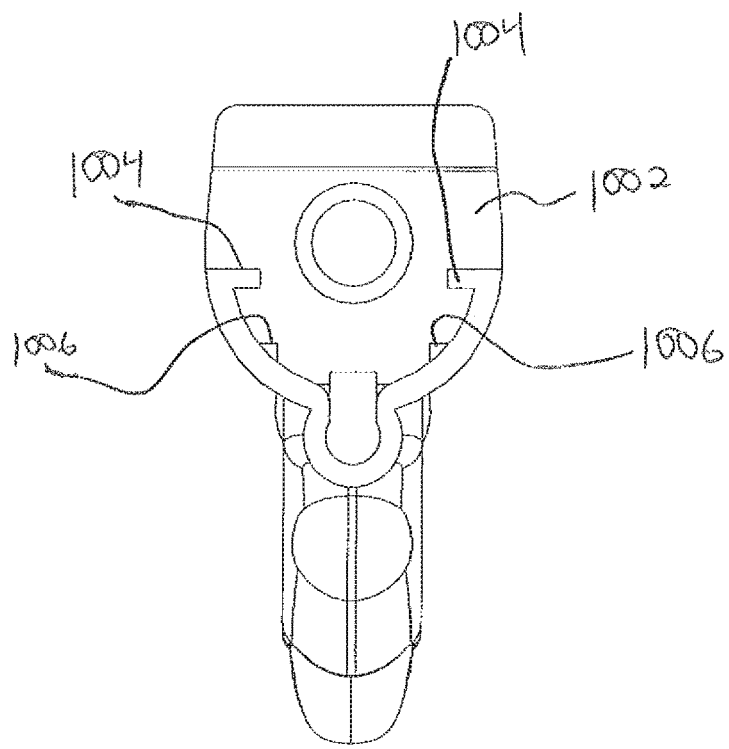
FIG. 55 depicts a proximal end view of the grip body of FIG. 54.

As sown in FIGS. 54-55, grip body (1002) defines a pair of inwardly extending rails (1004) that extend along a substantial portion of the length of grip body (1002). The interior region of grip body (1002) also includes a pair of longitudinally extending shelves (1006). Rails (1004) and shelves (1004) together provide slidable support to guidewire actuator assembly (1040) and dilation catheter slider (1100) relative to grip body (1002). The distal portion of grip body (1002) also includes a transverse slot (1008), which will be described in greater detail below.

Figure 57:
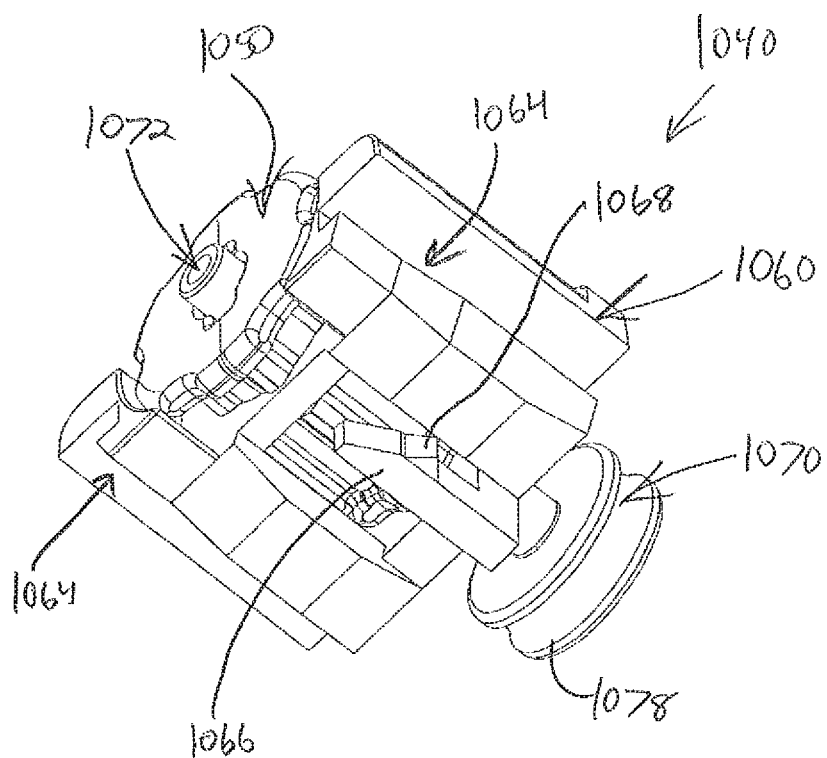
FIG. 57 depicts another perspective view of the guidewire actuator assembly of FIG. 56.
Figure 58:
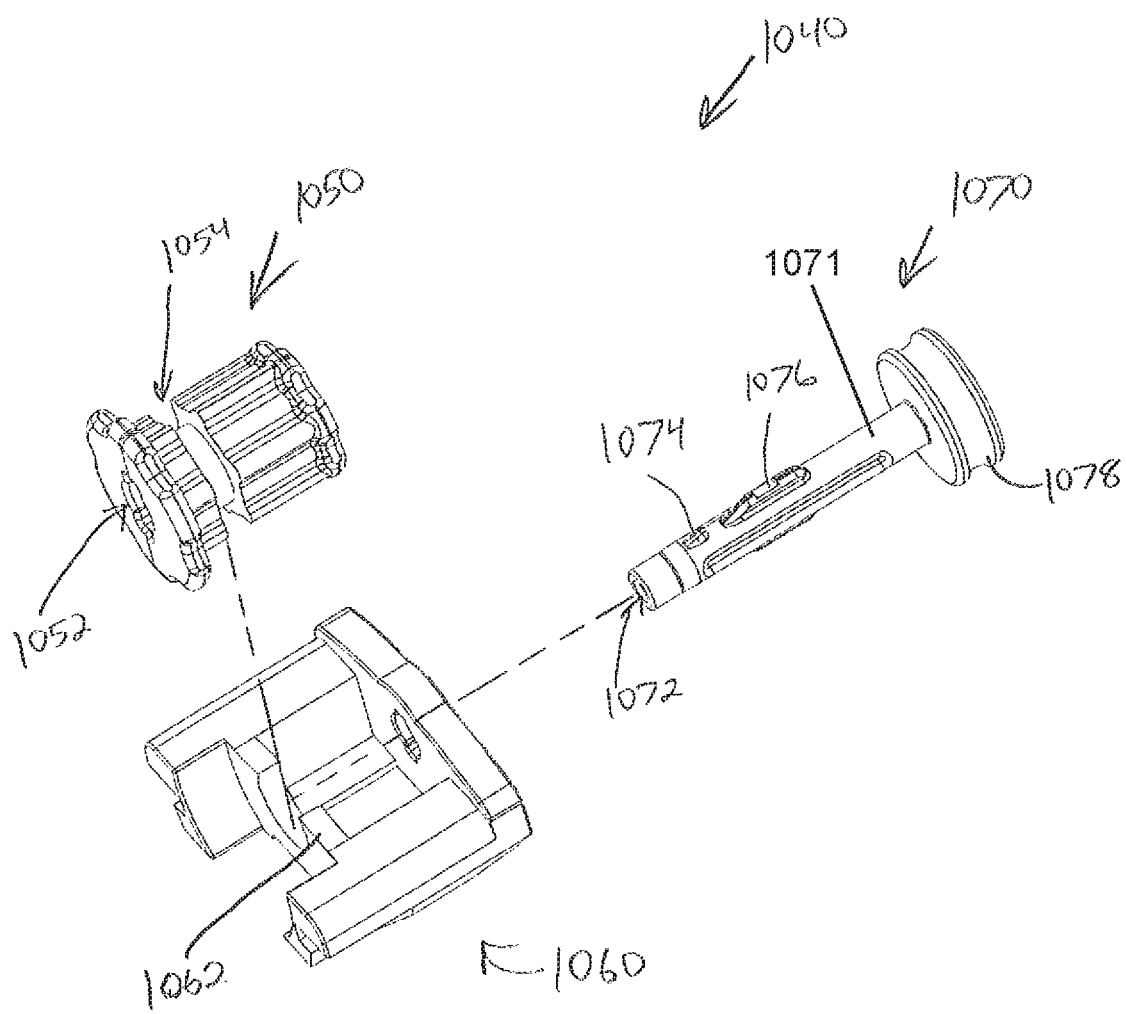
FIG. 58 depicts an exploded perspective view of the guidewire actuator assembly of FIG. 56.
Figure 59:
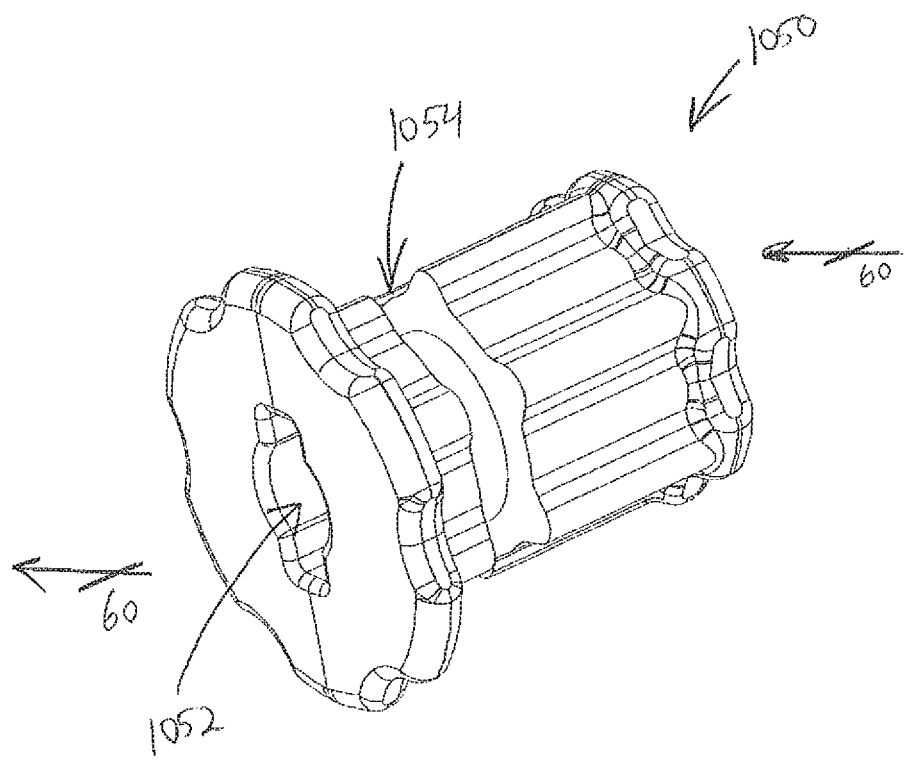
FIG. 59 depicts a perspective view of a guidewire spin actuator of the guidewire actuator assembly of FIG. 56.
Figure 60:
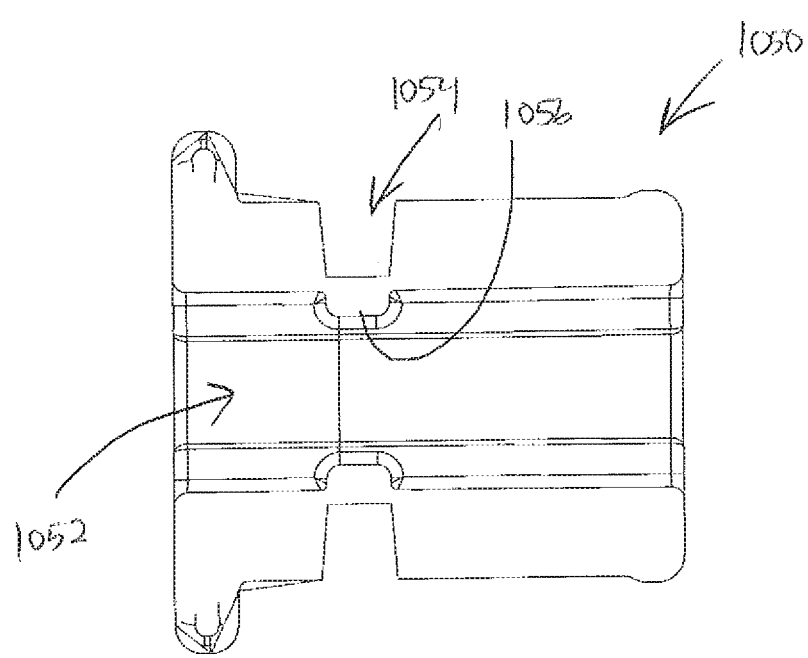
FIG. 60 depicts a cross-sectional view of the guidewire spin actuator of FIG. 59, taken along line 60-60 of FIG. 59.
Figure 61:
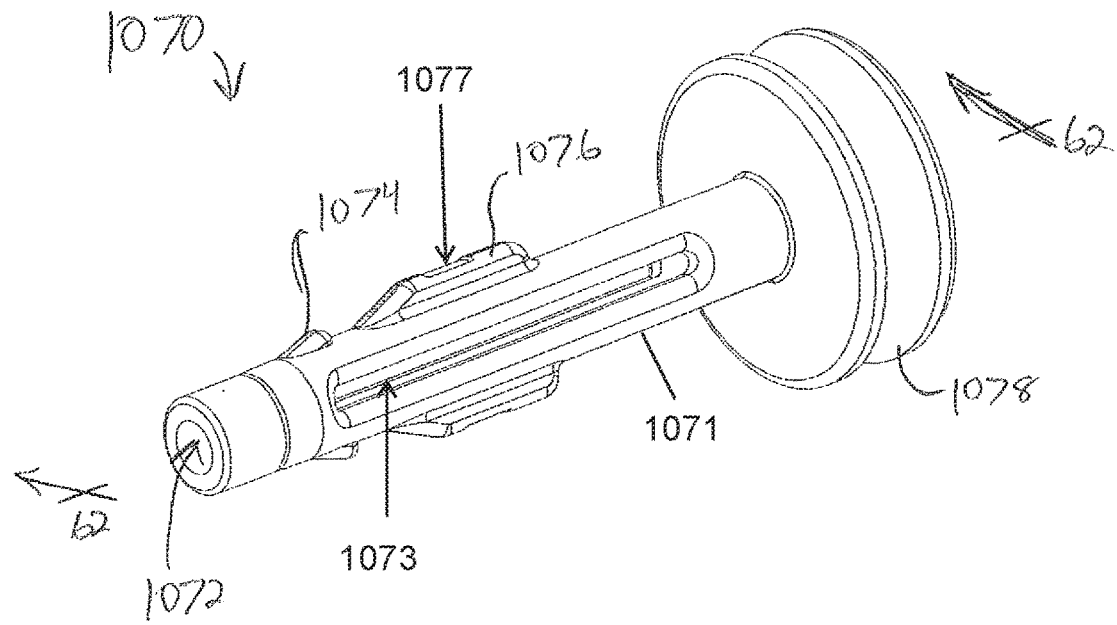
FIG. 61 depicts a perspective view of a collet member of the guidewire actuator assembly of FIG. 56.
Figure 62:
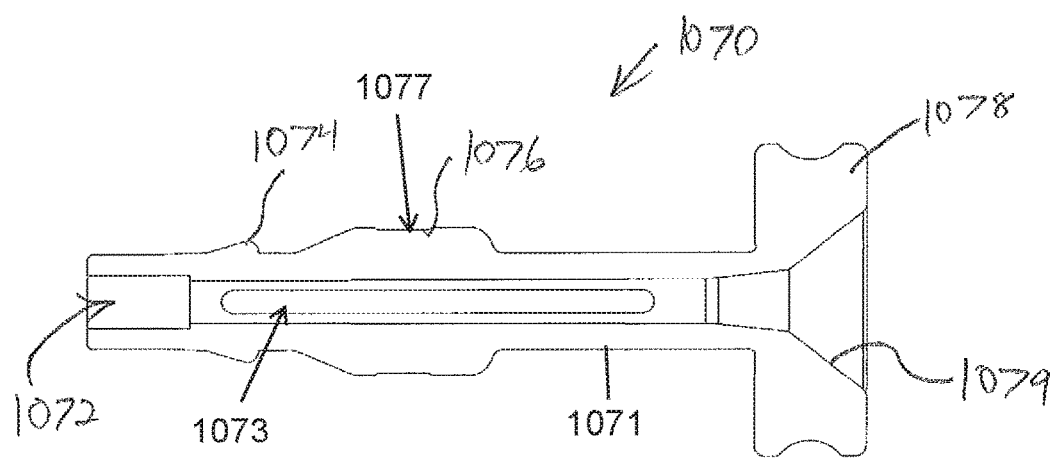
FIG. 62 depicts a cross-sectional view of the collet member of FIG. 61, taken along line 62-62 of FIG. 61.
Figure 63:
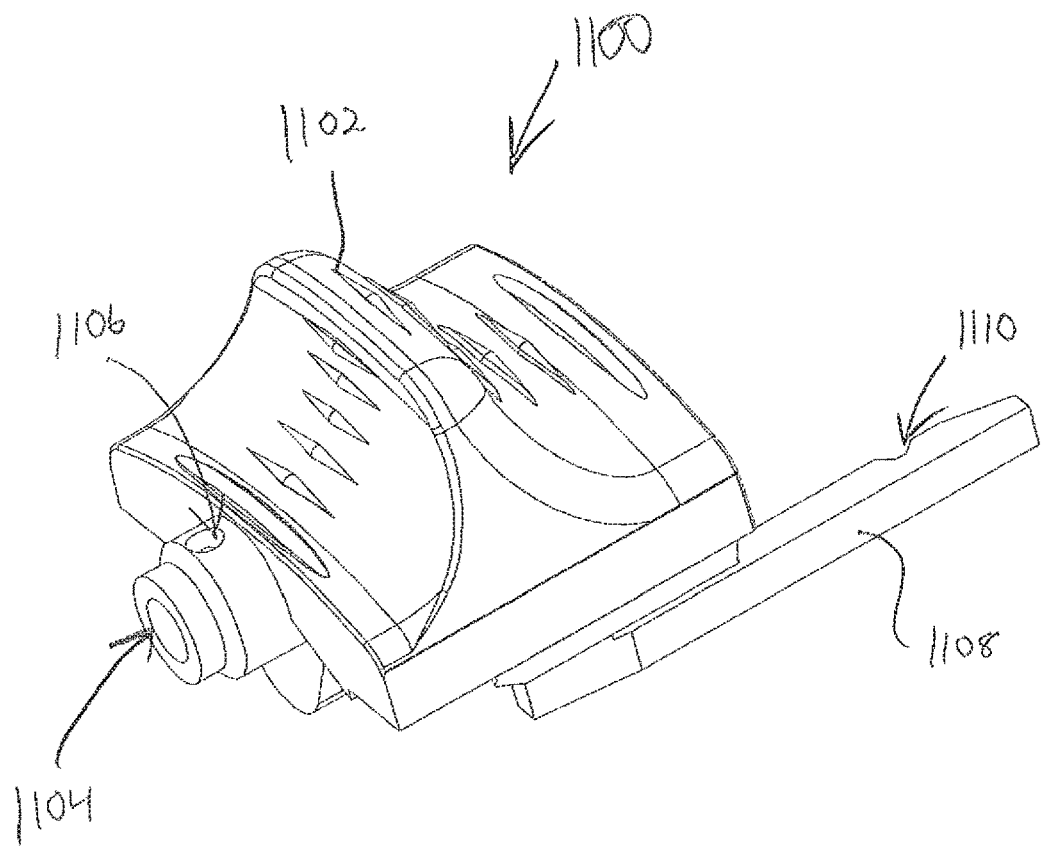
FIG. 63 depicts a perspective view of a dilation catheter slider of the instrument of FIG. 52.
Figure 64:
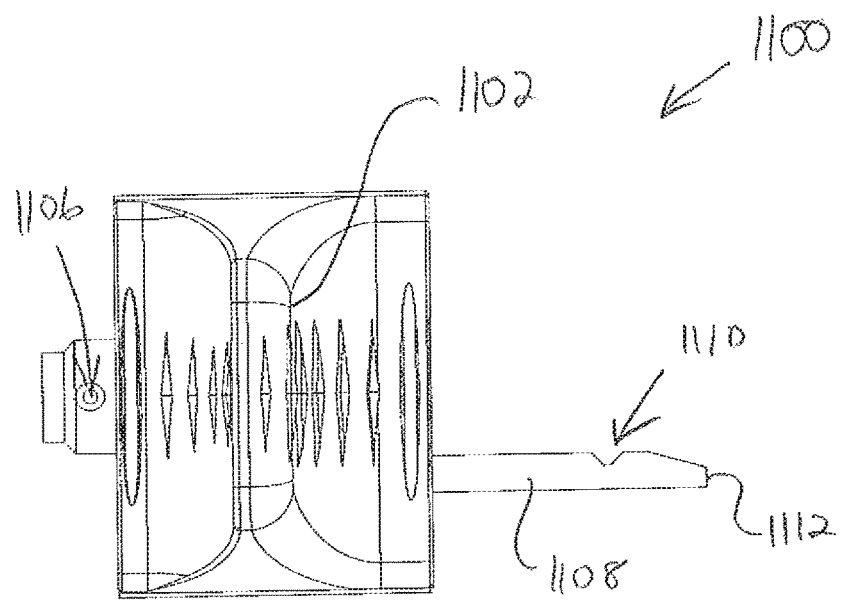
FIG. 64 depicts a top plan view of the dilation catheter slider of FIG. 63.
Figure 65:
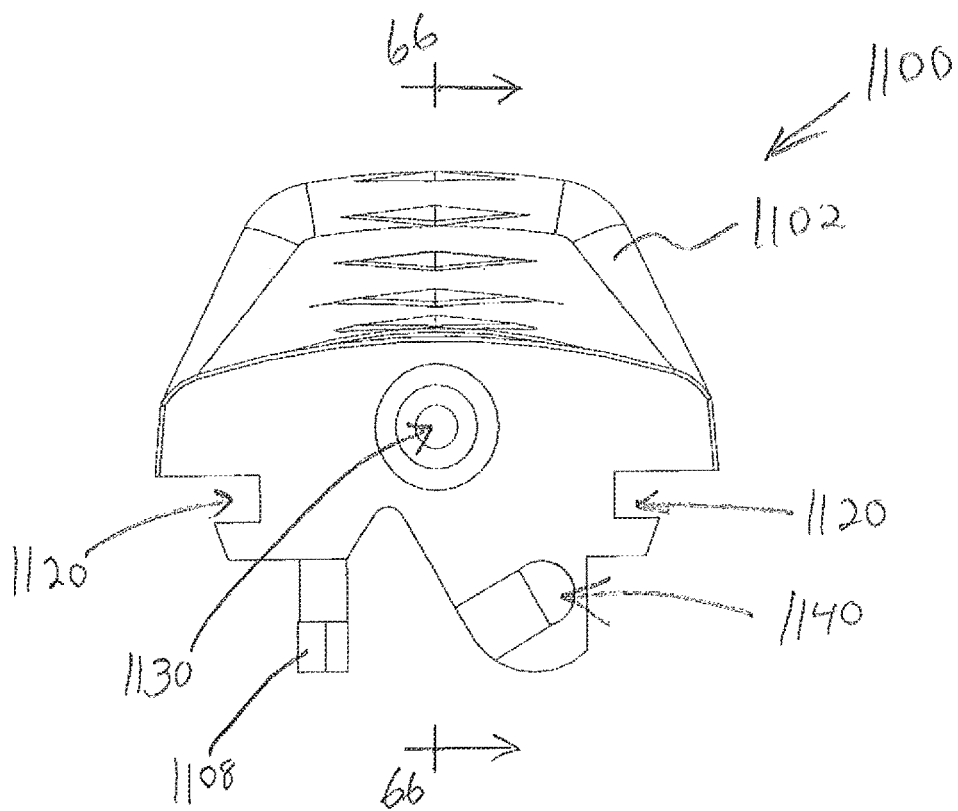
FIG. 65 depicts a proximal end view of the dilation catheter slider of FIG. 63.
Figure 66:
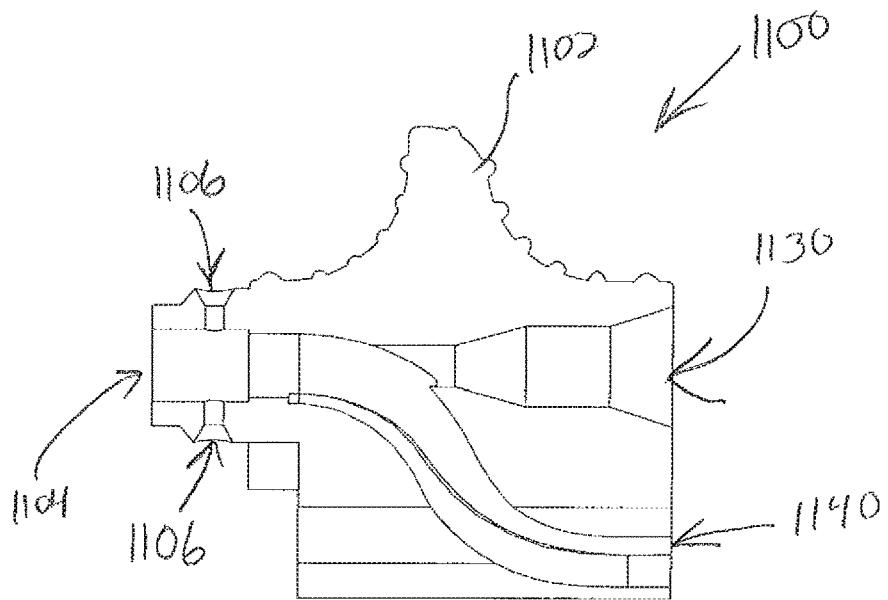
FIG. 66 depicts a cross-sectional view of the dilation catheter slider of FIG. 63, taken along line 66-66 of FIG. 65.

FIGS. 56-62 show the components of guidewire actuator assembly (1040) in greater detail. These components include a spin actuator (1050), a frame (1060), and a collet member (1070). As best seen in FIGS. 59-60, spin actuator (1050) defines a central bore (1052) and an annular recess (1054). An annular rib (1056) is defined within central bore (1052). As best seen in FIGS. 61-62, collet member (1070) includes an elongate shaft (1071) defining a central bore (1072). Central bore (1072) is sized to receive guidewire (1020). Collet member (1070) further includes a distal pair of fins (1074) extending radially outwardly from elongate shaft (1071), a proximal pair of fins (1076) extending radially outwardly from elongate shaft (1071), and a proximal flange (1078). As shown in FIG. 62, the interior of flange (1078) defines a sloped lead-in (1079) to central bore (1072). Such a lead-in (1079) may facilitate insertion of the distal end of guidewire (1020) into bore (1072).

Figure 56:
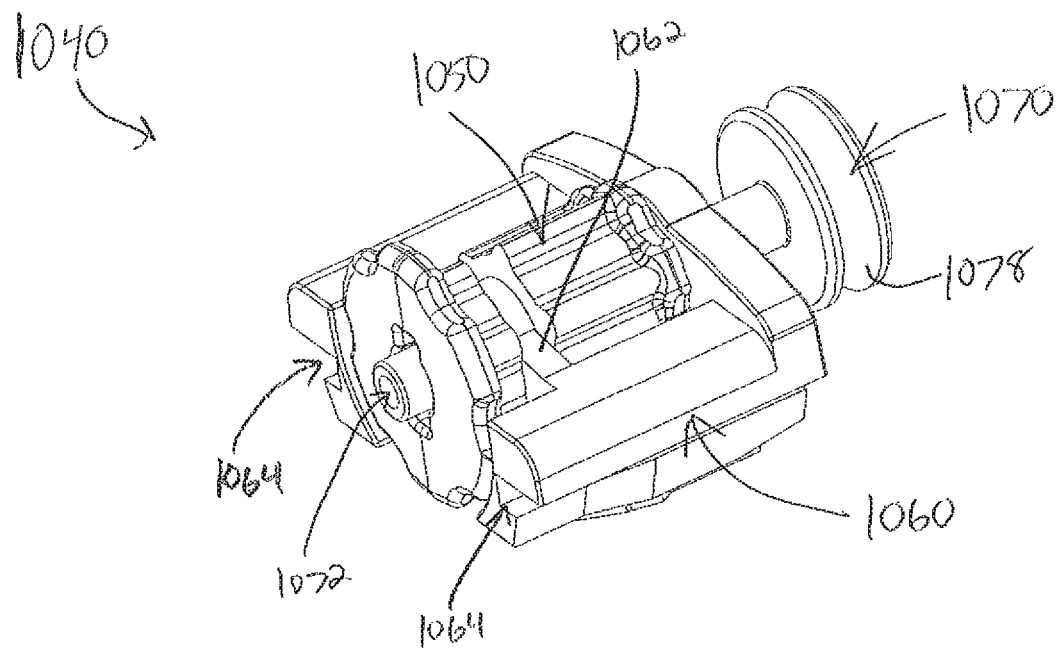
FIG. 56 depicts a perspective view of a guidewire actuator assembly of the instrument of FIG. 52.

As shown in FIGS. 56-57, elongate shaft (1071) is configured for insertion into central bore (1052) of spin actuator (1050). When collet member (1070) is initially in central bore (1052), annular rib (1056) is captured between distal pair of fins (1074) and proximal pair of fins (1076), such that rib (1056) and fins (1074) cooperate to prevent collet member (1070) from being pulled proximally out of spin actuator (1050). In the present example, elongate shaft (1071) defines a pair of longitudinally extending slots (1073) that are configured to promote inward deformation of elongate shaft (1071). Such inward deformation occurs when collet member (1070) is pressed further distally into central bore (1052) to a point where fins (1076) engage rib (1056). As collet member (1070) is pressed further into central bore (1052) to a point where fins (1076) engage rib (1056), rib (1056) and fins (1076) cooperate to provide a camming action that deforms the central region of elongate shaft (1071) inwardly.

Central bore (1072) of elongate shaft (1071) is configured such that the inner diameter of central bore (1072) is slightly larger than the outer diameter of guidewire (1020) when elongate shaft (1071) is in a non-deformed state. Central bore (1072) of elongate shaft (1071) is further configured such that the inner diameter of central bore (1072) is less than the outer diameter of guidewire (1020) when elongate shaft (1071) is in an inwardly-deformed state. Thus, when rib (1056) and fins (1076) cooperate to deform the central region of elongate shaft (1071) inwardly, elongate shaft (1071) will grip guidewire (1020). Detent recesses (1077) in fins (1076) will receive rib (1056) and thereby substantially maintain the longitudinal position of elongate shaft (1071) in central bore (1072). The frictional engagement between elongate shaft (1071) and guidewire (1020), as well as the frictional engagement between elongate shaft (1071) and spin actuator (1050), will effectively secure guidewire (1020) to spin actuator (1050) such that guidewire (1020) will translate along a longitudinal axis with spin actuator (1050) and rotate about the longitudinal axis with spin actuator (1050).

The above-described relationship between spin actuator (1050) and collet member (1070) enables an operator to switch between using different kinds of guidewire (1020) in instrument (1000). In some scenarios, the operator may wish to use a guidewire (1020) that is configured and operable like illuminating guidewire (50). In some other scenarios, the operator may wish to use a guidewire (1020) that is configured and operable like navigation guidewire (130). To secure a first guidewire (1020) relative to guidewire actuator assembly (1040), the operator may slide the first guidewire (1020) into central bore (1072) while collet member (1070) is in a proximal position relative to spin actuator (1050). In this example, the "proximal position" means that rib (1056) is longitudinally interposed between distal pair of ribs (1074) and proximal pair of ribs (1077), such that elongate shaft (1071) is in a non-deformed state. Once the first guidewire (1020) has been suitably inserted through central more (1072), the operator may urge collet member (1070) distally relative to spin actuator (1050), to thereby drive proximal pair of fins (1076) into engagement with rib (1056), to thereby deform elongate shaft (1071) inwardly to grip the first guidewire (1020).

To remove the first guidewire (1020) from guidewire actuator assembly (1040), the operator may pull collet member (1070) proximally relative to spin actuator (1050), eventually disengaging fins (1076) from rib (1056) to allow elongate shaft (1071) to return to the non-deformed state. The operator may then slide the first guidewire (1020) proximally from guidewire actuator assembly (1040). When the operator pulls collet member (1070) proximally relative to spin actuator (1050) to release the grip on the first guidewire (1020), distal pair of fins (1074) will eventually engage rib (1056) to arrest the proximal motion of collet member (1070) relative to spin actuator (1050), thereby preventing collet member (1070) from inadvertently being pulled completely out of spin actuator. If the operator wishes to replace the first guidewire (1020) with a second guidewire (1020), the operator may simply repeat the same process described above.

As shown in FIGS. 56-58, frame (1060) of guidewire actuator assembly (1040) comprises a support web (1062), a pair of rail recesses (1064), a detent arm (1066), and a detent protrusion (1068). Support web (1062) is configured for insertion in annular recess (1054) of spin actuator (1050). With support web (1062) disposed in annular recess (1054) of spin actuator (1050), frame (1060) and spin actuator (1050) will translate together longitudinally, though spin actuator (1050) is enabled to rotate relative to frame (1060) about a longitudinal axis. Rail recesses (1064) are configured to slidably receive rails (1004) of grip body (1002), such that rails (1004) and rail recesses (1064) cooperate to allow grip body (1002) to provide sliding support to guidewire actuator assembly (1040). Shelves (1006) of grip body are also configured to engage an underside of frame (1060), thereby providing additional sliding support to guidewire actuator assembly (1040). Detent arm (1066) extends distally from a proximal portion of frame (1060) and is configured to slightly deflect laterally as described below. Detent protrusion (1068) is in the form of a triangular tooth that extends laterally from the distal end of detent arm (1066).

In view of the foregoing, it should be understood that guidewire actuator assembly (1040) is operable to releasably retain guidewire (1020), to drive guidewire (1020) longitudinally relative to grip body (1002), and to rotate guidewire (1020) about a longitudinal axis.

FIGS. 63-66 show dilation catheter slider (1100) in greater detail. As shown, dilation catheter slider (1100) of this example comprises a crest feature (1102), a distal bore (1104), a pair of transverse bores (1106), a detent arm (1108), a pair of rail recesses (1120), a first proximal bore (1130), and a second proximal bore (1140). Crest feature (1102) is configured to promote sliding of dilation catheter slider (1100) by an operator's thumb or other finger. Rail recesses (1120) are configured to slidably receive rails (1004) of grip body (1002), such that rails (1004) and rail recesses (1120) cooperate to allow grip body (1002) to provide sliding support to dilation catheter slider (1100). Shelves (1006) of grip body are also configured to engage an underside of dilation catheter slider (1100), thereby providing additional sliding support to dilation catheter slider (1100).

Bores (1104, 1130, 1140) are all in communication with each other. Distal bore (1104) is coaxially aligned with first proximal bore (1130). Bores (1104, 1130) are also coaxially aligned with bores (1052, 1072). Second proximal bore (1140) is offset from bores (1104, 1130) laterally and downwardly, but curves upwardly and inwardly to reach distal bore (1104). Bores (1104, 1140) are sized to receive dilation catheter (1030). Bore (1130) is sized to receive guidewire (1020). Bores (1104, 1130, 1140) and dilation catheter (1030) are configured such that guidewire (1020) enters dilation catheter (1030) within dilation catheter slider (1100). For instance, guidewire (1020) may enter dilation catheter (1030) via a transverse slit formed in dilation catheter (1030), with the transverse slit leading to a guidewire lumen (not shown) formed in dilation catheter (1030). In the present example, this guidewire lumen extends along the central axis of dilation catheter (1030), all the way through the length of dilation catheter (1030), to the open distal end of dilation catheter (1030). A separate inflation lumen (not shown) of dilation catheter (1030) is laterally offset from the guidewire lumen of dilation catheter (1030) and is used to communicate fluid to the expandable dilator at the distal end of dilation catheter (1030) to thereby inflate the expandable dilator.

In some versions, a seal (not shown), like seal (540) described above, is provided in bore (1130) to prevent fluids from escaping through bore (1130). In versions where such a seal is used, such a seal may nevertheless permit guidewire (1020) to rotate and translate relative to dilation catheter slider (1100).

As noted above, dilation catheter (1030) passes through bores (1104, 1140). In the present example, set screws (not shown) are disposed in transverse bores (1106) and fixedly secure dilation catheter (1030) to dilation catheter slider (1100). Dilation catheter (1030) thus translates with dilation catheter slider (1100) relative to grip body (1002). Other suitable ways in which dilation catheter (1030) may be secured to dilation catheter slider (1100) will be apparent to those of ordinary skill in the art in view of the teachings herein.

Figure 67C:
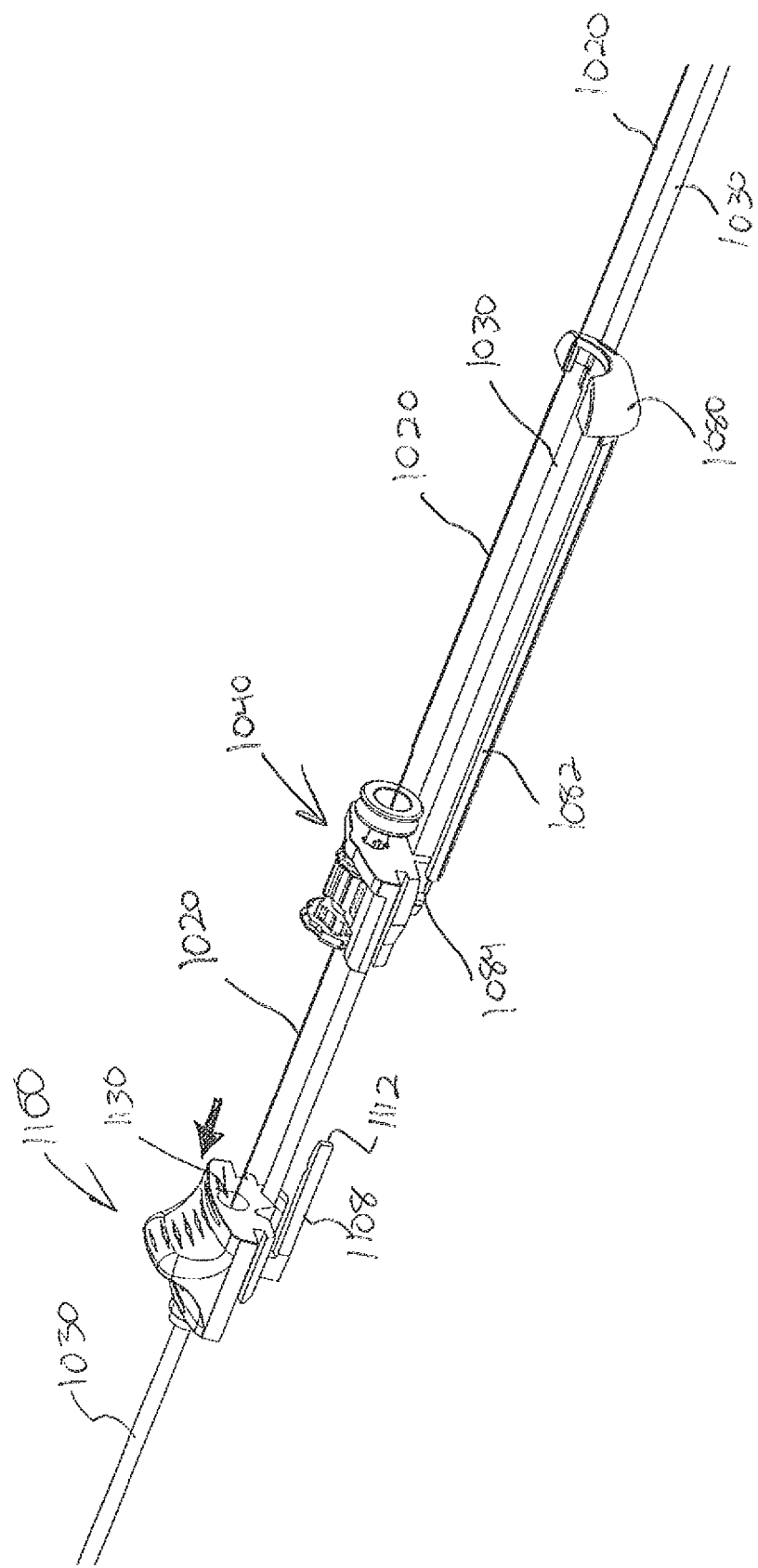
FIG. 67C depicts a perspective view of the dilation catheter and guidewire actuation components of FIG. 67A, with the guidewire in the first distal position and the dilation catheter in the second distal position of FIG. 53C.

FIGS. 67A-67C show interaction between guidewire actuator assembly (1040), dilation catheter slider (1100), and a proximal stop member (1080). As shown in FIG. 52, proximal stop member (1080) is fixedly secured to the proximal end of grip body (1002). As shown in FIGS. 67A-67C, proximal stop member (1080) comprises a distally projecting arm (1082) that distally terminates at a distal end (1084). Arm (1082) of stop member (1080) is configured to engage detent arm (1108) of dilation catheter slider (1100). In particular, distal end (1084) is configured to engage proximal end (1112) of detent arm (1108) when dilation catheter slider (1100) is in the proximal position. Arm (1082) thus restricts proximal movement of dilation catheter slider (1100). However, as shown in FIGS. 67A-67C, arm (1082) does not restrict distal movement of dilation catheter slider (1100); nor does arm restrict translation of guidewire actuator assembly (1040).

Figure 68:
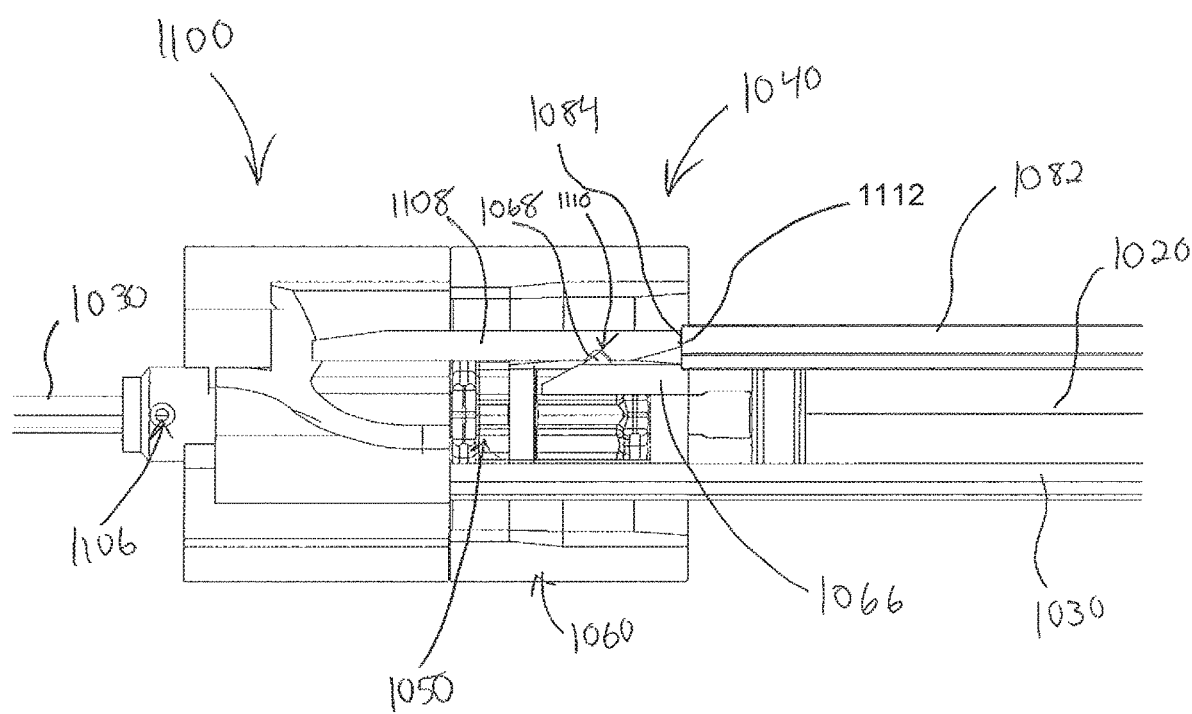
FIG. 68 depicts a bottom plan view of a portion of the dilation catheter and guidewire actuation components of FIG. 67A, with the guidewire in the first distal position and the dilation catheter in the proximal position of FIG. 53B.

As shown in FIG. 68, detent arms (1108, 1066) are configured to engage each other when dilation catheter slider (1100) and guidewire actuator assembly (1040) are in the state shown in FIG. 67B. In particular, detent protrusion (1068) of detent arm (1066) is configured to enter detent recess (1110) of detent arm (1108). As shown in FIG. 67C, if the operator wishes to advance dilation catheter slider (1100) and dilation catheter (1030) distally relative to guidewire actuator assembly (1040) and guidewire (1020), the operator may simply urge dilation catheter slider (1100) while holding guidewire actuator assembly (1040) stationary. This will result in disengagement of detent arm (1108) from detent arm (1066), allowing dilation catheter slider (1100) to translate distally independent of guidewire actuator assembly (1040).

However, if the operator wishes to advance dilation catheter slider (1100) and dilation catheter (1030) distally with guidewire actuator assembly (1040) and guidewire (1020), the operator may continue urging guidewire actuator assembly (1040) distally to push dilation catheter slider (1100), dilation catheter (1030), guidewire actuator assembly (1040), and guidewire (1020) distally. This will eventually result in an arrangement like that shown in FIG. 53C' and described above. When the operator wishes to retract dilation catheter slider (1100), dilation catheter (1030), guidewire actuator assembly (1040), and guidewire (1020) together proximally, the operator may engage dilation catheter slider (1100) and urge dilation catheter slider (1100) proximally to thereby drive dilation catheter slider (1100), dilation catheter (1030), guidewire actuator assembly (1040), and guidewire (1020) together proximally. Alternatively, the operator my engage guidewire actuator assembly (1040) and urge guidewire actuator assembly (1040) proximally to thereby drive dilation catheter slider (1100), dilation catheter (1030), guidewire actuator assembly (1040), and guidewire (1020) together proximally. The engagement between detent arms (1108, 1066) may be strong enough to enable guidewire actuator assembly (1040) to effectively pull dilation catheter slider (1100) and dilation catheter (1030) proximally. When proximal end (1112) of detent arm (1108) engages distal end (1084) of arm (1082), and the operator continues urging guidewire actuator assembly (1040) proximally, arm (1082) will arrest further proximal motion of dilation catheter slider (1100), detent arms (1108, 1066) will disengage each other, and guidewire actuator assembly (1040) may eventually return to the position shown in FIG. 67A.

C. Exemplary Guide Distal End Deflection Assembly

Figure 69:
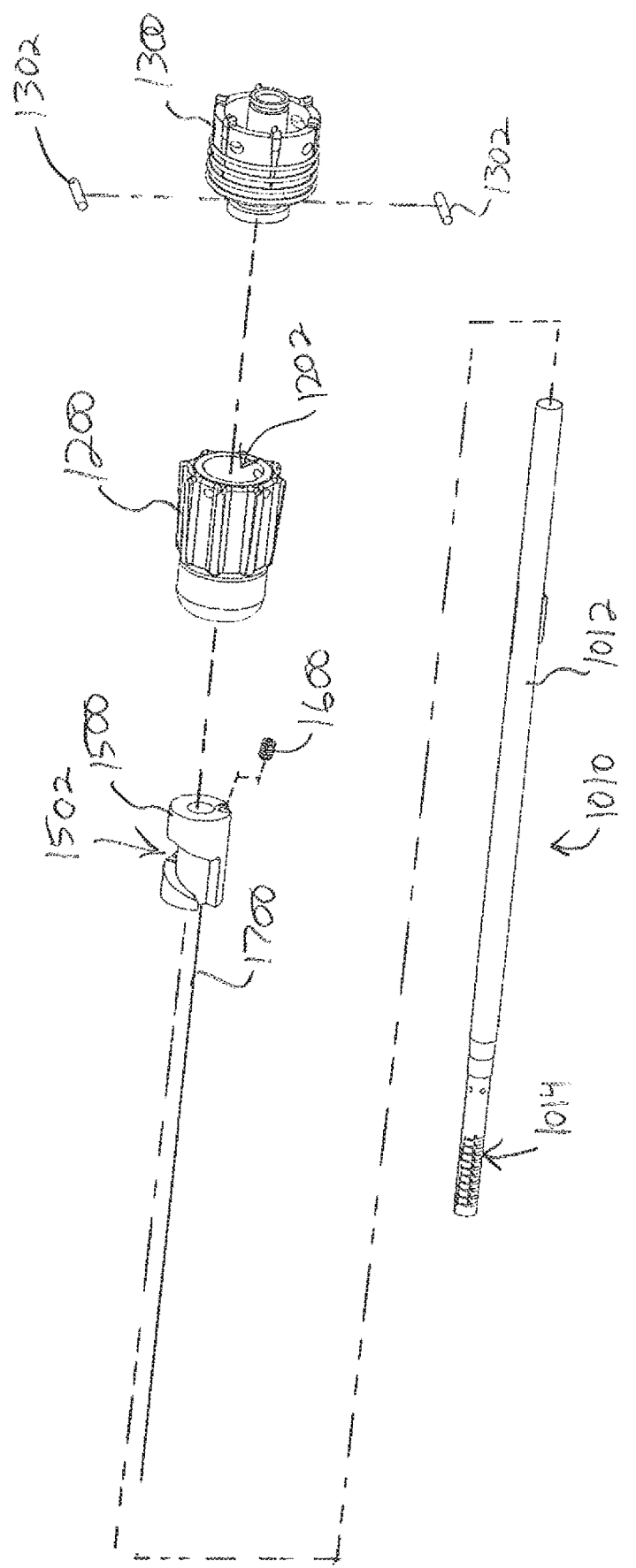
FIG. 69 depicts an exploded perspective view of a shaft assembly of the instrument of FIG. 52.
Figure 70:
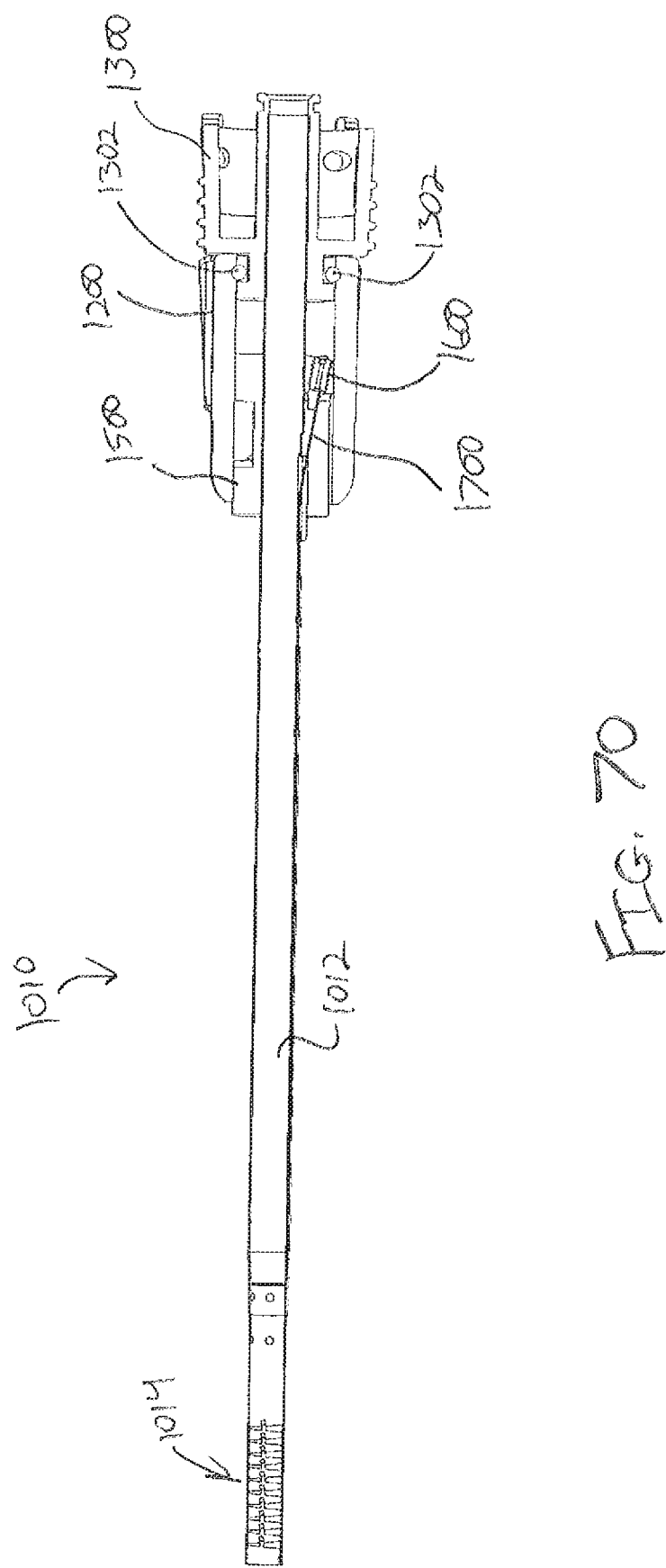
FIG. 70 depicts a cross-sectional side view of the shaft assembly of FIG. 69.

FIGS. 69-70 show shaft assembly (1010) in greater detail. Shaft assembly (1010) of the present example comprises a rigid shaft member (1012) and a flexible shaft member (1014). Flexible shaft member (1014) is configured and operable just like flexible shaft member (304) described above, such that additional details will not be repeated here. As shown, a push-pull wire (1700) extends distally from a cam barrel (1500) and is secured to the distal end of flexible shaft member (1014), such that push-pull wire (1700) is operable to bend flexible shaft member (1014) when push-pull wire (1700) is pulled proximally by cam barrel (1500). A screw (1600) is threadably secured in a screw bore (1504) of cam barrel (1500) and thereby secures push-pull wire (1700) to cam barrel (1500), such that push-pull wire (1700) will translate longitudinally with cam barrel (1500).

Figure 71:
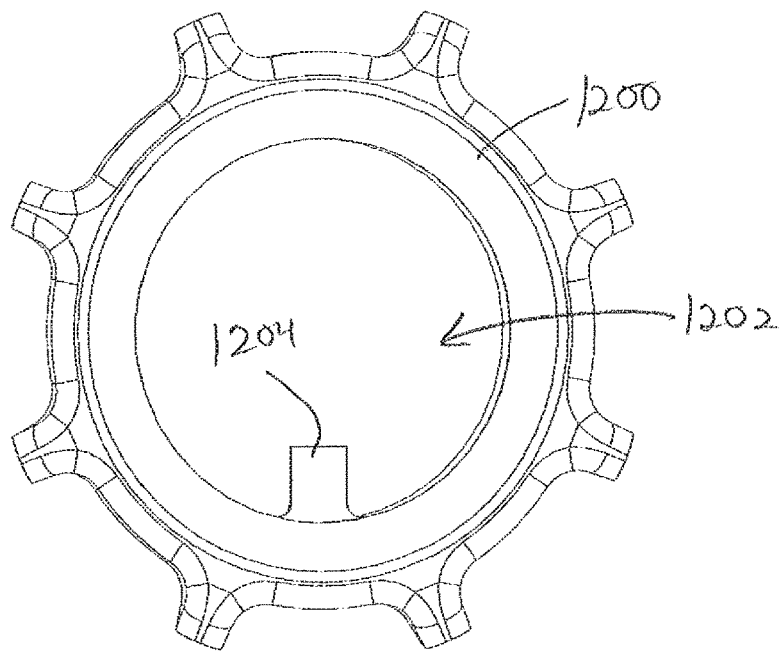
FIG. 71 depicts a proximal end view of a deflection control knob of the shaft assembly of FIG. 69.
Figure 72:
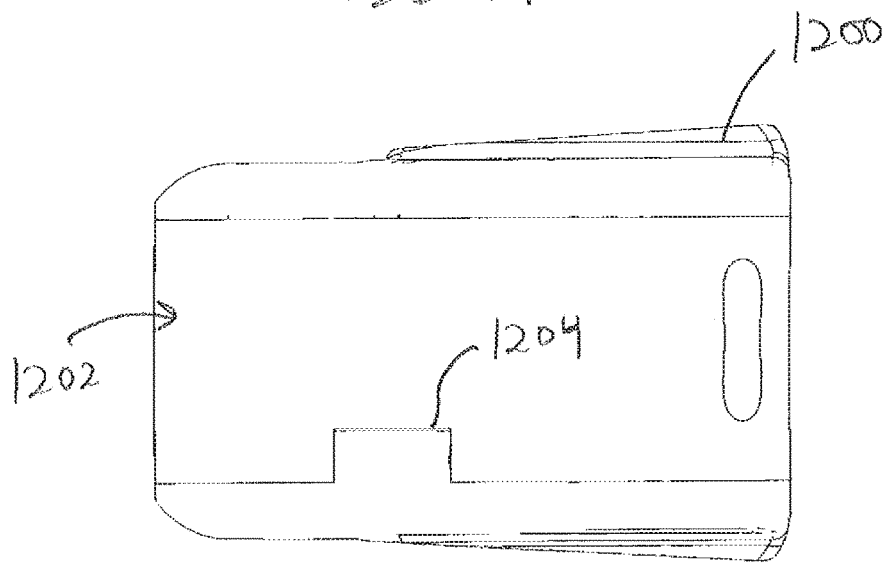
FIG. 72 depicts a cross-sectional view of the deflection control knob of FIG. 71, taken along line 72-72 of FIG. 71.

A deflection control knob (1200) is coaxially positioned about cam barrel (1500) at the proximal end of shaft assembly (1010). As shown in FIGS. 71-72, deflection control knob (1200) defines a central bore (1200) with an inwardly extending cam fin (1204). A rotary control knob (1300) is longitudinally secured to deflection control knob (1200) via a pair of pins (1302), such that rotary control knob (1300) and deflection control knob (1200) translate together along a common longitudinal axis; yet such that deflection control knob (1200) is rotatable relative to rotary control knob (1300) about the longitudinal axis.

Figure 73:
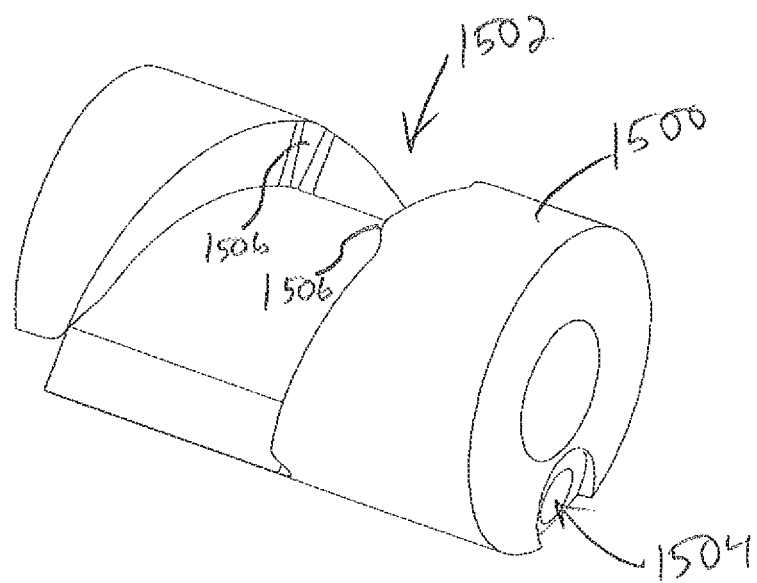
FIG. 73 depicts a perspective view of a cam barrel of the shaft assembly of FIG. 69.
Figure 74:
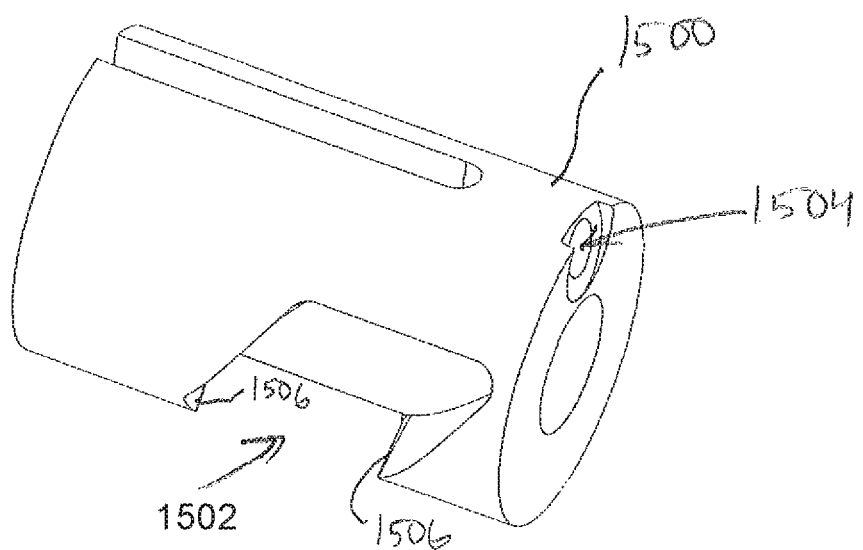
FIG. 74 depicts another perspective view of the cam barrel of FIG. 73.

As best seen in FIGS. 73-74, cam barrel (1500) defines a generally helical cam slot (1502) that is configured to slidably receive cam fin (1204) of deflection control knob (1200). Cam slot (1502) includes steps (1506) that are configured to provide stepped transitions similar to those described above with respect to cam slots (360a, 360b). Cam barrel (1500) is configured to rotate with shaft assembly (1010) yet translate relative to shaft assembly (1010), just like the relationship between cam barrel (350) and shaft assembly (300) described above. Similarly, deflection control knob (1200) is configured to translate with shaft assembly (1010) yet rotate relative to shaft assembly (1010), just like the relationship between deflection control knob (320) and shaft assembly (300) described above.

As deflection control knob (1200) is rotated relative to shaft assembly (1010), cam fin (1204) slidably travels along helical cam slot (1502) and thereby causes cam barrel (1500) to translate relative to shaft assembly (1010). This translation of cam barrel (1500) causes push-pull wire (1700) to translate relative to shaft assembly (1010), which in turn causes flexible shaft member (1014) to deflect toward or away from the longitudinal axis of shaft assembly (1010). The operator may this adjust the angle of deflection of flexible shaft member (1014) by rotating deflection control knob (1200) relative to shaft assembly (1010). Once the operator achieves a desired angle of deflection, cam fin (1204) and helical cam slot (1502) may provide self-locking functionality such that flexible shaft member (1014) may maintain the selected angle of deflection during subsequent normal use of instrument (1000), until the operator again rotates deflection control knob (1200) relative to shaft assembly (1010) to further adjust the angle of deflection. Since guidewire (1020) and dilation catheter (1030) are slidably positioned within shaft assembly (1010), guidewire (1020) and dilation catheter (1030) will exit the distal end of shaft assembly (1010) at whatever deflection angle the operator has selected.

D. Exemplary Guide Rotation Assembly

Like shaft assembly (300) described above, shaft assembly (1010) of the present example is rotatable relative to grip body (1002) about the longitudinal axis of shaft assembly (1010). FIGS. 75A-75D show features of shaft assembly (1010) providing such operability. As noted above, a rotary control knob (1300) is positioned proximal to deflection control knob (1200). As shown in FIGS. 75A-75D, the proximal end of rotary control knob (1300) includes an angularly spaced array of proximally oriented projections (1304). Projections (1304) are sized and configured to mate with complementary recesses (1802) that are formed in a shaft deflection body (1800). As described below, shaft deflection body (1800) is configured to pivot relative to grip body (1002) about an axis that is transverse to the longitudinal axis of shaft assembly (1010). However, shaft deflection body (1800) is secured to grip body (1002) such that shaft deflection body (1800) is not capable of translating relative to grip body along the longitudinal axis of shaft assembly (1010); and such that deflection body (1800) is not capable of rotating relative to grip body about the longitudinal axis of shaft assembly (1010).

A coil spring or other resilient member (not shown) is longitudinally interposed between a distal flange (1840) of shaft deflection body (1800) and a proximal flange of rotary control knob (1300), such that the coil spring or other resilient member is located within a hollow interior of rotary control knob (1300). This coil spring or other resilient member imparts a resilient bias to rotary control knob (1300), urging rotary control knob (1300) to the proximal position shown in FIG. 75A. When rotary control knob (1300) is in this proximal position, projections (1304) are seated in corresponding recesses (1802), and this engagement between projections (1304) and recesses (1802) locks the angular orientation of shaft assembly (1010) about the longitudinal axis of shaft assembly (1010).

Figure 75A:
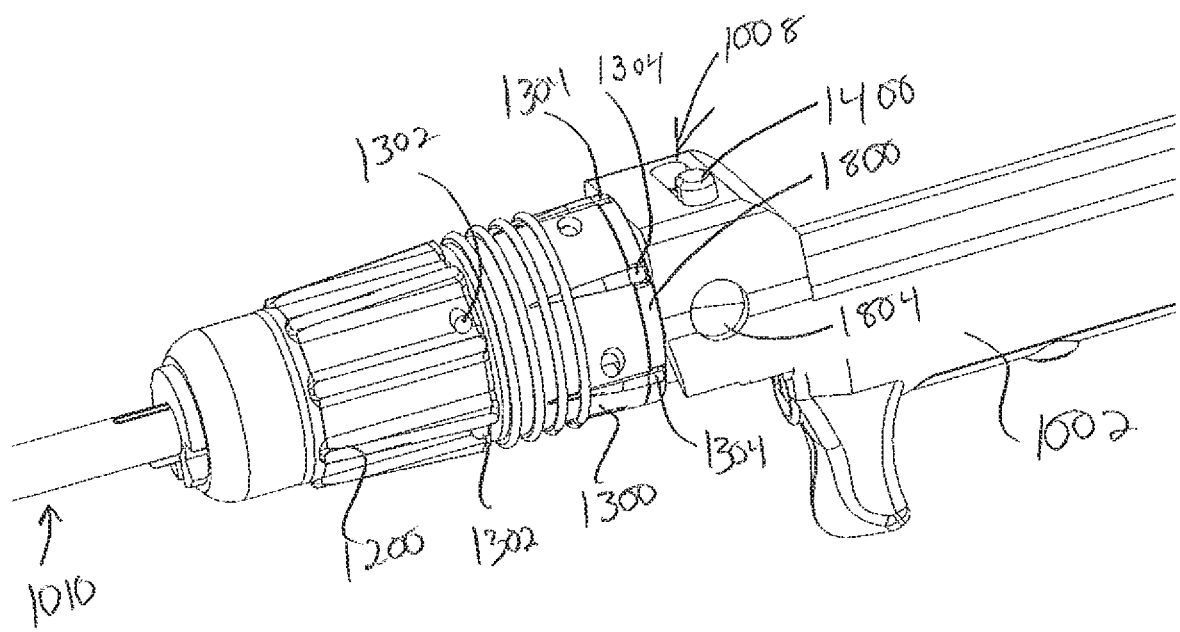
FIG. 75A depicts a perspective view of shaft rotation components of the instrument of FIG. 52, with a shaft rotation knob in a proximal position and the shaft assembly at a first angular orientation about a longitudinal axis.
Figure 75B:
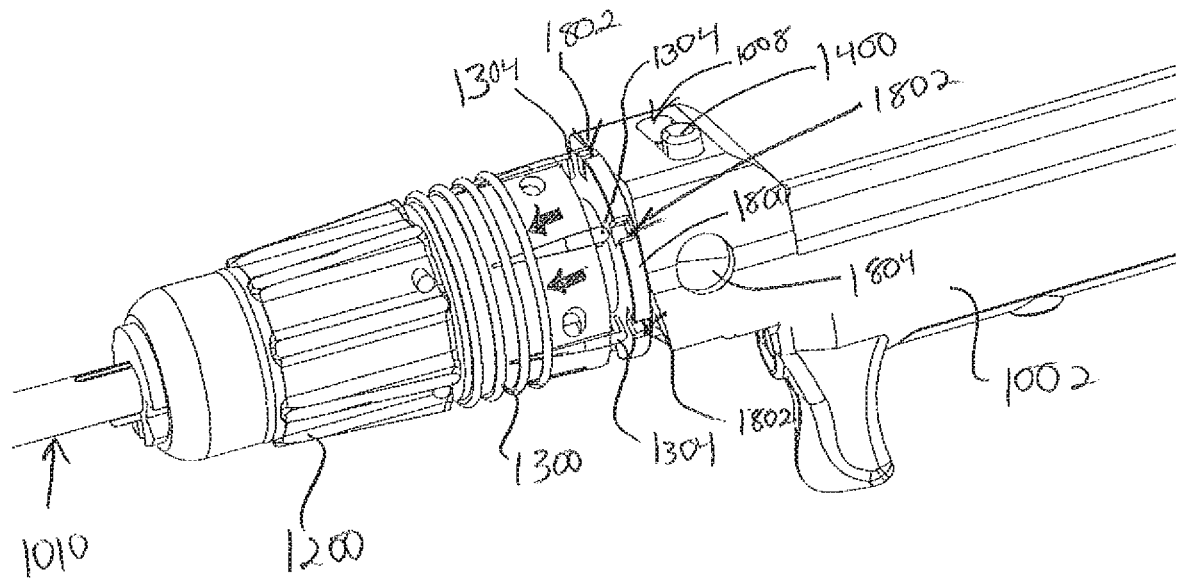
FIG. 75B depicts a perspective view of the shaft rotation components of FIG. 75A, with the shaft rotation knob in a distal position and the shaft assembly at the first angular orientation about the longitudinal axis.
Figure 75C:
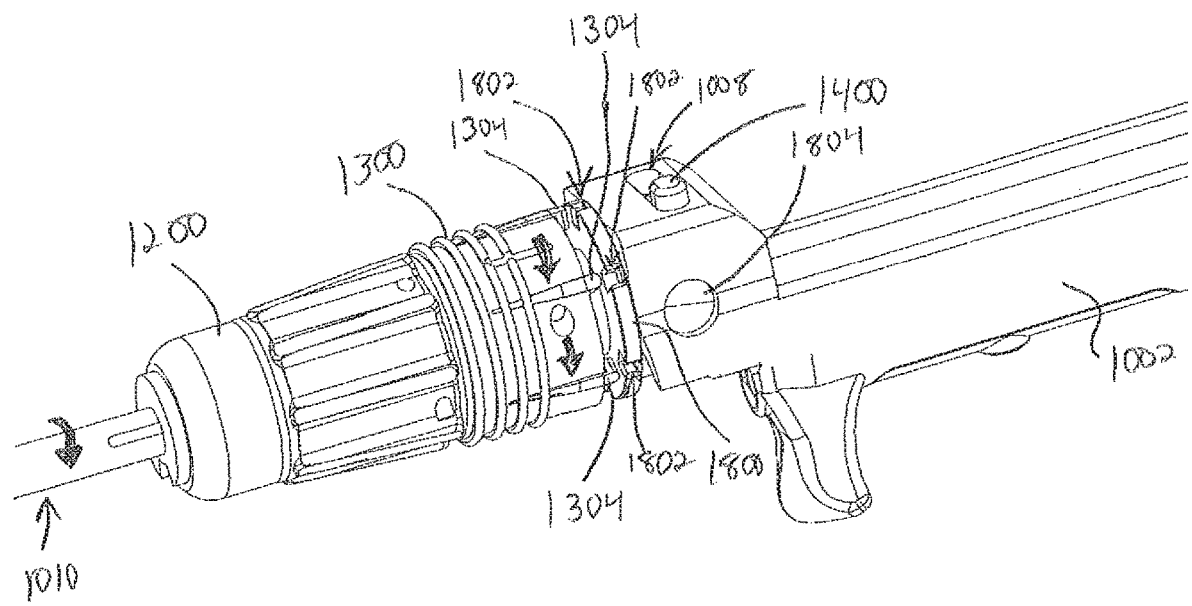
FIG. 75C depicts a perspective view of the shaft rotation components of FIG. 75A, with the shaft rotation knob in a distal position and the shaft assembly at a second angular orientation about the longitudinal axis.
Figure 75D:
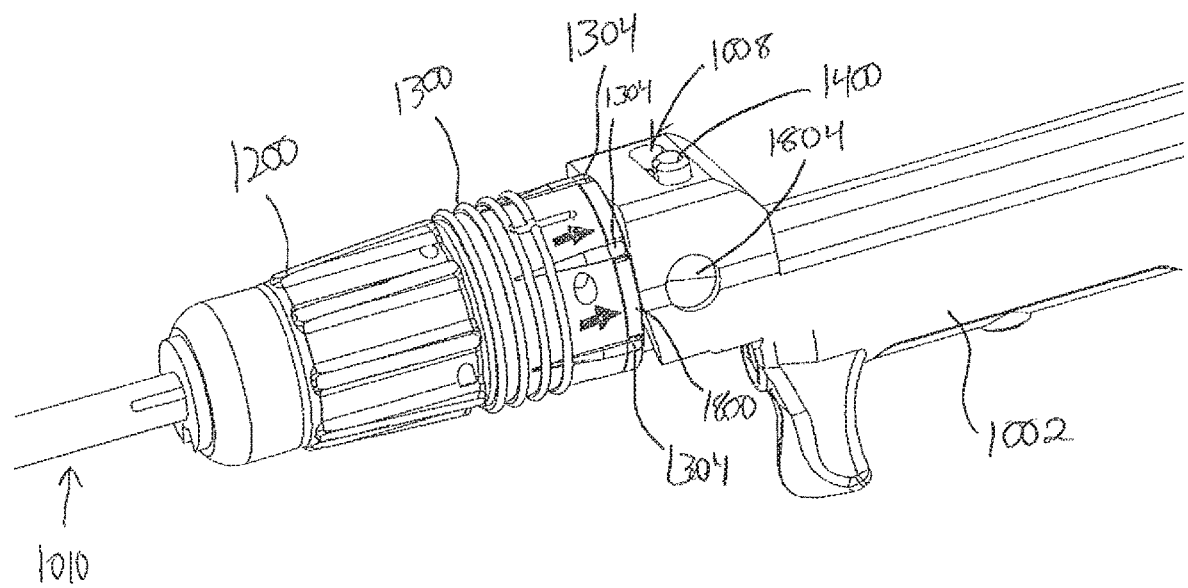
FIG. 75D depicts a perspective view of the shaft rotation components of FIG. 75A, with the shaft rotation knob in the proximal position and the shaft assembly at the second angular orientation about the longitudinal axis.

When the operator wishes to re-orient shaft assembly (1010) at a different angular orientation about the longitudinal axis of shaft assembly (1010), the operator may grasp rotary control knob (1300) and urge rotary control knob (1300) distally, thereby unseating projections (1304) from recesses (1802) as shown in FIG. 75B. With projections (1304) unseated from recesses (1802), rotary control knob (1300) is now free to rotate to a different angular orientation about the longitudinal axis of shaft assembly (1010), as shown in FIG. 75C. When the operator rotates rotary control knob (1300) in this fashion, the entire shaft assembly (1010) rotates with rotary control knob (1300). Once the operator has achieved the desired angular orientation of shaft assembly (1010) about the longitudinal axis of shaft assembly (1010), the operator may release rotary control knob (1300). The coil spring or other resilient member will then drive rotary control knob (1300) proximally to re-seat projections (1304) in corresponding recesses (1802) as shown in FIG. 75D, thereby locking the angular position of shaft assembly (1010) at the adjusted angular orientation.

In the present example, there are a total of six projections (1304) and six recesses (1802), providing a total of six predefined angular orientations. Of course, any other suitable number of projections (1304) and recesses (1802) may be used to provide any other suitable number of predefined angular orientations. In some other variations, projections (1304) and recesses (1802) are replaced with frictionally engaging features that provide a virtually infinite number of angular orientations. Other suitable configurations and operabilities will be apparent to those of ordinary skill in the art in view of the teachings herein.

E. Exemplary Guide Proximal End Deflection Assembly

Figure 76A:
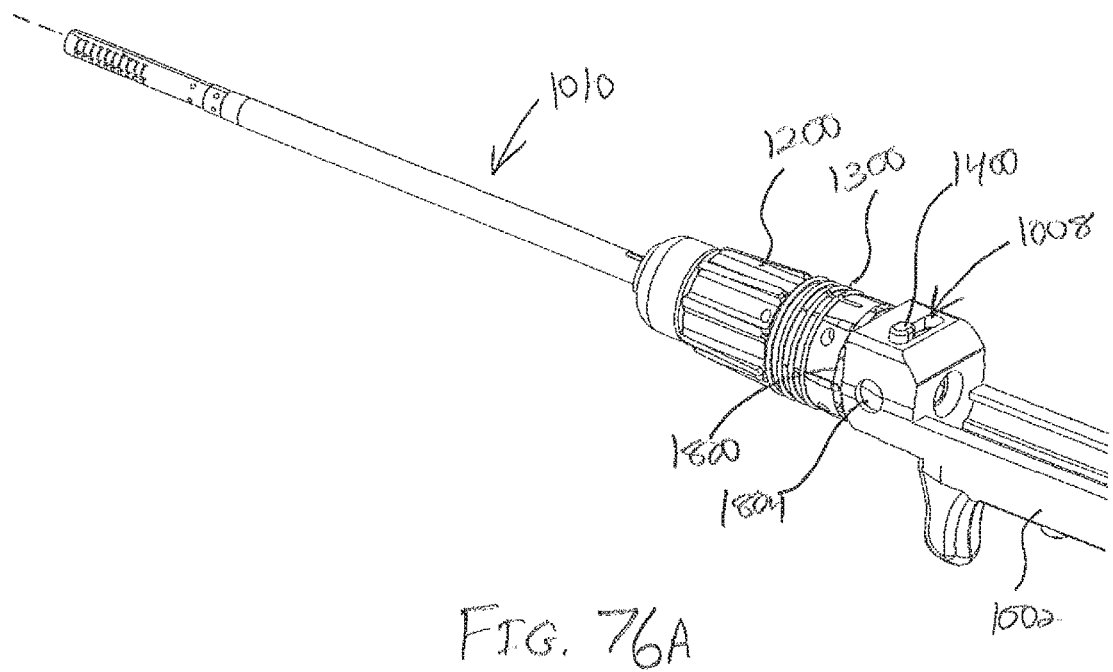
FIG. 76A depicts a perspective view of a distal portion of the instrument of FIG. 52, with the shaft assembly coaxially aligned with the longitudinal axis.
Figure 76B:
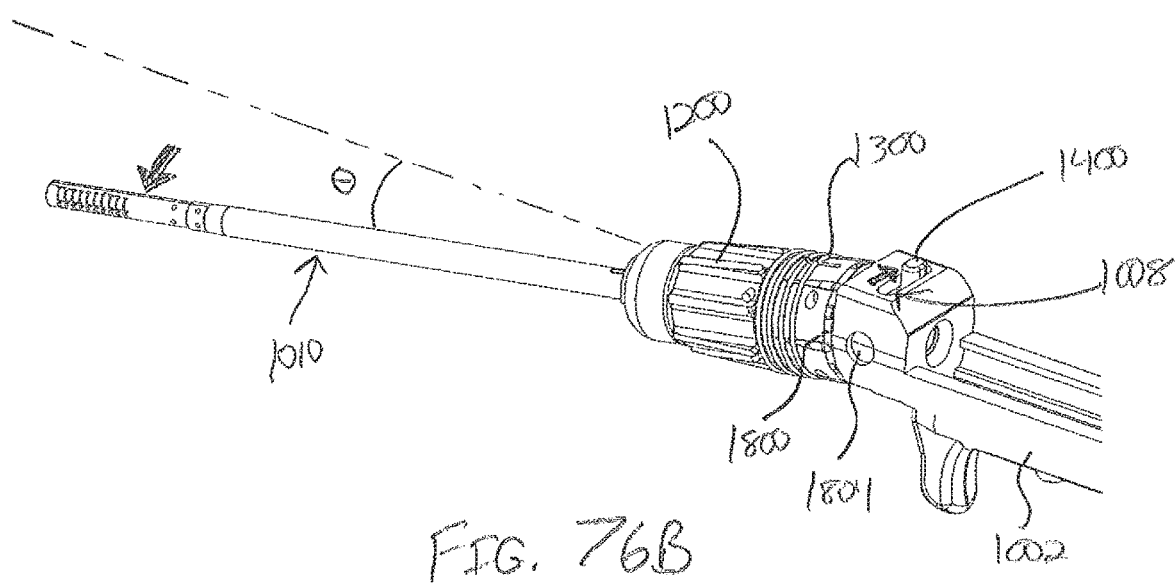
FIG. 76B depicts a perspective view of a distal portion of the instrument of FIG. 52, with the shaft assembly deflected from the longitudinal axis by an angle ($\Theta$)

Like shaft assembly (300) described above, shaft assembly (1010) of the present example is configured to pivot relative to grip body (1002) about an axis that is transverse to a central longitudinal axis. As noted above, such pivotal motion may facilitate switching between use of instrument (1000) on a patient in a sitting or otherwise upright position and on a patient in a supine position. FIGS. 76A-76B show shaft assembly (1010) being deflected from a first position (FIG. 76A), in which shaft assembly (1010) is aligned with the central longitudinal axis (shown in phantom line), to a second position (FIG. 76B), in which shaft assembly (1010) is deflected from the central longitudinal axis by a deflection angle (Θ). Flexible shaft member (1014) may still bend away from and toward the longitudinal axis of shaft assembly (1010), and shaft assembly (1010) may still be rotated about the longitudinal axis of shaft assembly (1010), regardless of whether shaft assembly (1010) is in an aligned orientation (FIG. 76A) or a deflected orientation (76B).

Figure 77:
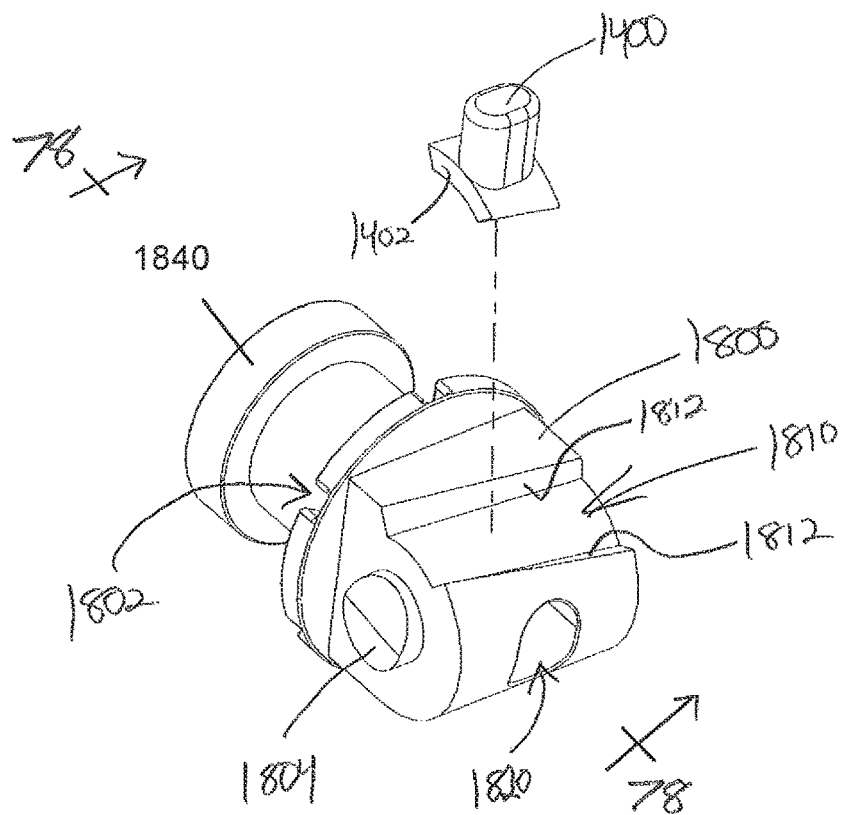
FIG. 77 depicts a perspective view of shaft deflection slider of the instrument of FIG. 52 separated from a shaft deflection body of the instrument of FIG. 52.

As shown in FIGS. 76A-76B, a shaft deflection slider (1400) is slidably disposed in transverse slot (1008) of grip body (1002). Shaft deflection slider (1400) is operable to drive deflection of shaft assembly (1010) by being slid laterally from a first position (FIG. 76A) to a second position (FIG. 76B). As shown in FIG. 77, shaft deflection slider (1400) includes a cam flange (1402) that is configured for receipt in a cam channel (1800) that is formed in shaft deflection body (1800). Cam channel (1800) extends transversely along shaft deflection body (1800) and is defined in part by an opposing pair of cam surfaces (1812). Cam surfaces (1812) are obliquely oriented relative to the central longitudinal axis in this example. This oblique orientation provides pivotal movement of shaft deflection body (1800) in response to transverse movement of shaft deflection slider (1400), due to camming interaction between cam flange (1402) and cam surfaces (1812).

Figure 78:
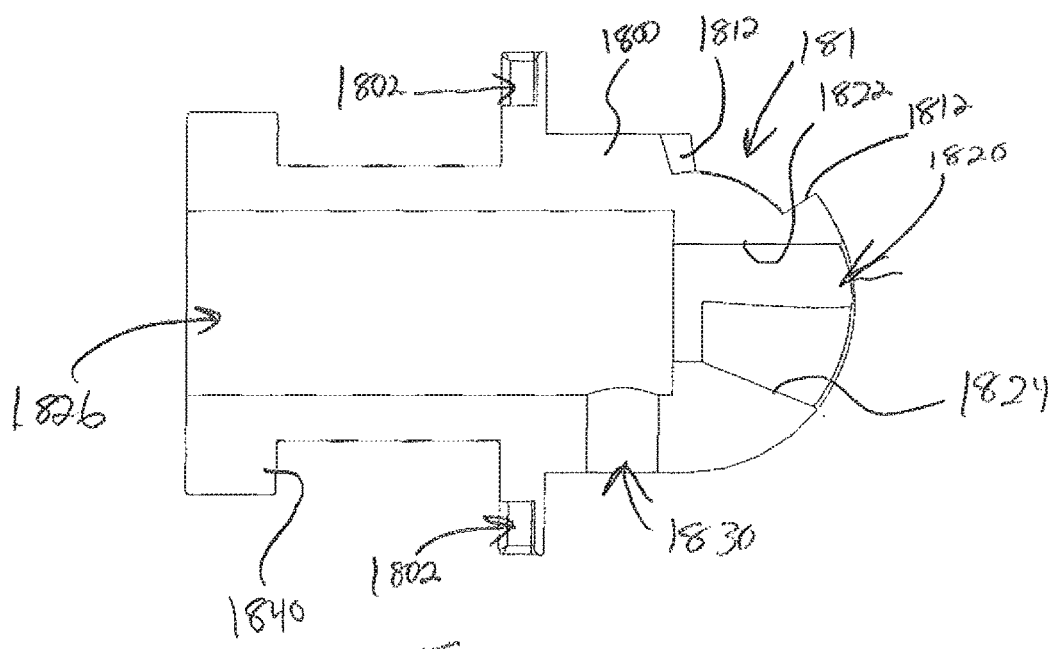
FIG. 78 depicts a cross-sectional view of the shaft deflection body of FIG. 77, taken along line 78-78 of FIG. 77.

As also shown in FIG. 77-78, shaft deflection body (1800) includes a pair of integral transversely extending pins (1804), a proximal bore (1820), a distal bore (1826), and a transverse bore (1830). Pins (1804) provide a pivotal coupling between shaft deflection body (1800) and grip body (1002). Distal bore (1826) is configured to receive the proximal end of rigid shaft member (1012). Transverse bore (1030) is configured to receive a screw (not shown) to fixedly secure rigid shaft member (1012) in transverse bore (1030). Of course, shaft assembly (1010) may be secured to shaft deflection body (1800) in any other suitable fashion. Proximal bore (1820) is configured to provide a path for dilation catheter (1030) to enter the proximal end of shaft assembly (1010). Proximal bore (1820) includes an upper surface (1822) and a lower surface (1824). In the present example, upper surface (1822) is substantially parallel to the longitudinal axis of distal bore (1826) while lower surface (1824) is obliquely oriented relative to the longitudinal axis of distal bore (1826). This configuration of proximal bore (1820) will accommodate dilation catheter (1030), allowing dilation catheter to translate freely through proximal bore (1820), regardless of whether shaft assembly (1010) is in an aligned orientation (FIG. 76A) or a deflected orientation (76B).

In the present example, shaft deflection body (1800) and shaft assembly (1010) are only configured to pivot downwardly to deflect away from the central longitudinal axis. In some other variations, shaft deflection body (1800) and shaft assembly (1010) are also configured to pivot upwardly to deflect away from the central longitudinal axis. Also in the present example, the maximum angle of deflection (Θ) for shaft deflection body (1800) and shaft assembly (1010) is approximately 10°. However, any other suitable maximum angle of deflection (Θ) may be provided.

VI. Third Exemplary Alternative Dilation Catheter Instrument

FIGS. 79A-80B show another exemplary alternative instrument (1900) that may be used to dilate an anatomical structure, such as a paranasal sinus ostium or other drainage passageway within a head of a patient. Except as otherwise described below, instrument (1900) may be configured and operable like instrument (200, 1000) described above. Instrument (1900) of this example includes a handle assembly (1910), a shaft assembly (1920), a guidewire (not shown), a dilation catheter (not shown), a guidewire actuator assembly (1914), and a dilation catheter slider (1912). In the present example, dilation catheter slider (1912) is configured and operable substantially identically to dilation catheter slider (1100). Likewise, guidewire actuator assembly (1040) of the present example is configured and operable substantially identically to guidewire actuator assembly (1914) described above. The guidewire of instrument (1900) may be constructed and operable just like any other guidewire (50, 130, 260) described herein. Similarly, the dilation catheter of instrument (1900) may be constructed and operable just like any other dilation catheter (20, 400) described herein.

Shaft assembly (1920) of the present example includes a rigid shaft member (1922) and a flexible shaft member (1924). Flexible shaft member (1924) includes a flex section (1926) that is configured and operable just like flex section (310). A deflection control knob (1930) is coaxially positioned about rigid shaft member (1922) is and is operable to controllably deflect flex section (1926) just like deflection control knob (320). A rotary control knob (1940) is also coaxially positioned about rigid shaft member (1922), proximal to deflection control knob (1920). Rotary control knob (1940) is operable to rotate shaft assembly (1920) about the central longitudinal axis of shaft assembly (1920), like rotary control knob (370).

Figure 79A:
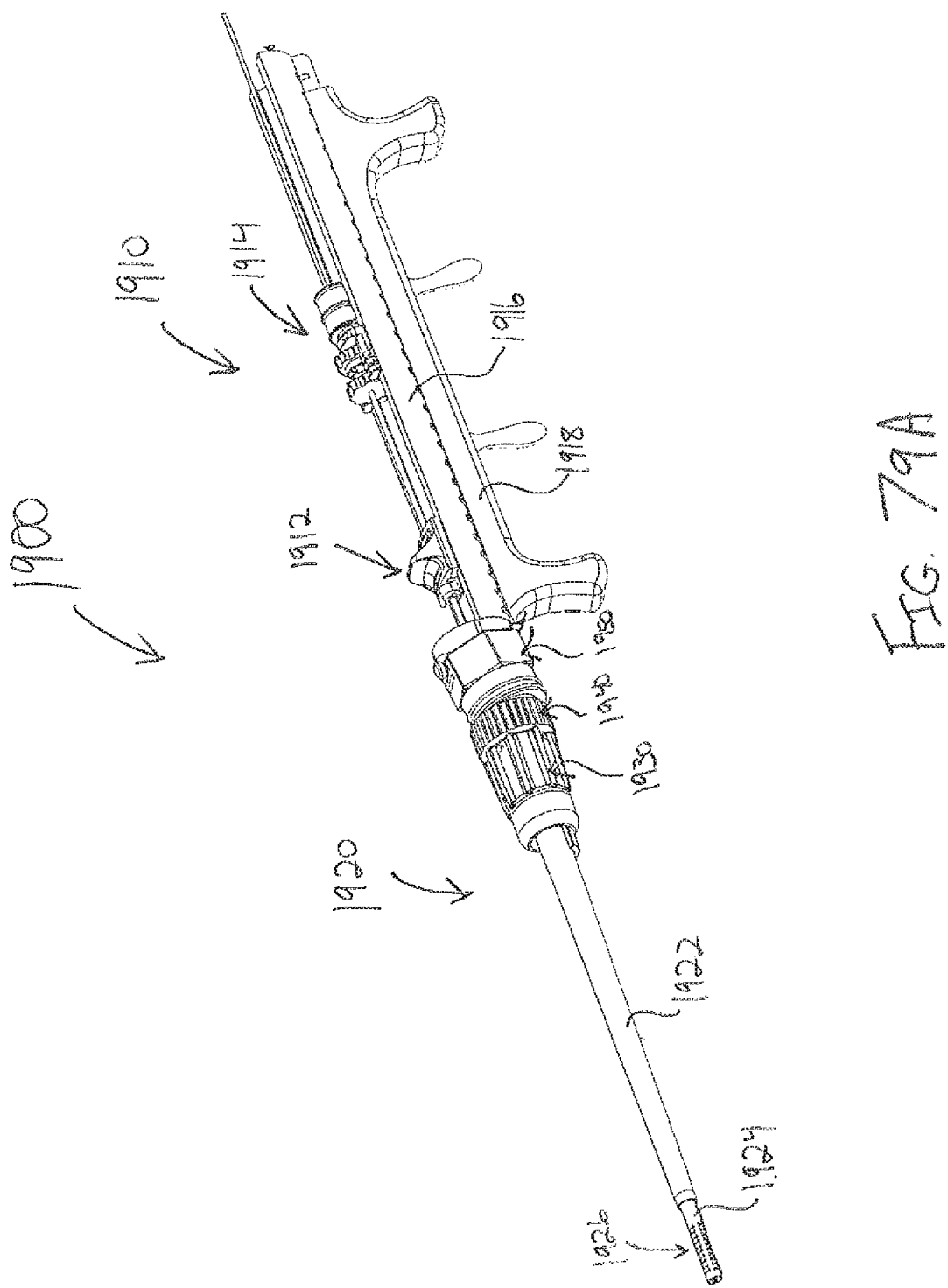
FIG. 79A depicts a perspective view of another exemplary alternative dilation catheter instrument, with a shaft assembly oriented parallel to the longitudinal axis of a handle assembly.
Figure 76B:
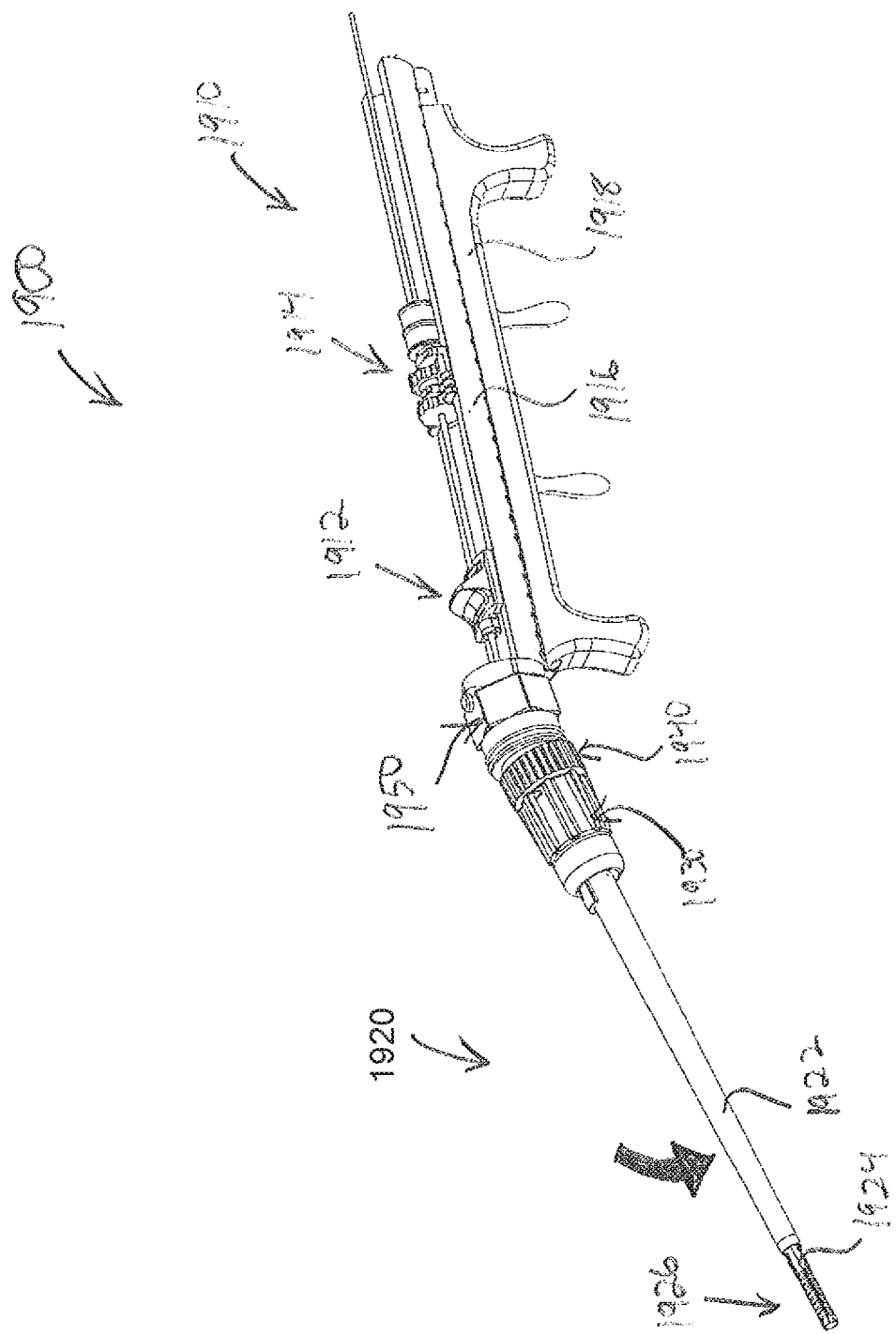
Figure 80A:
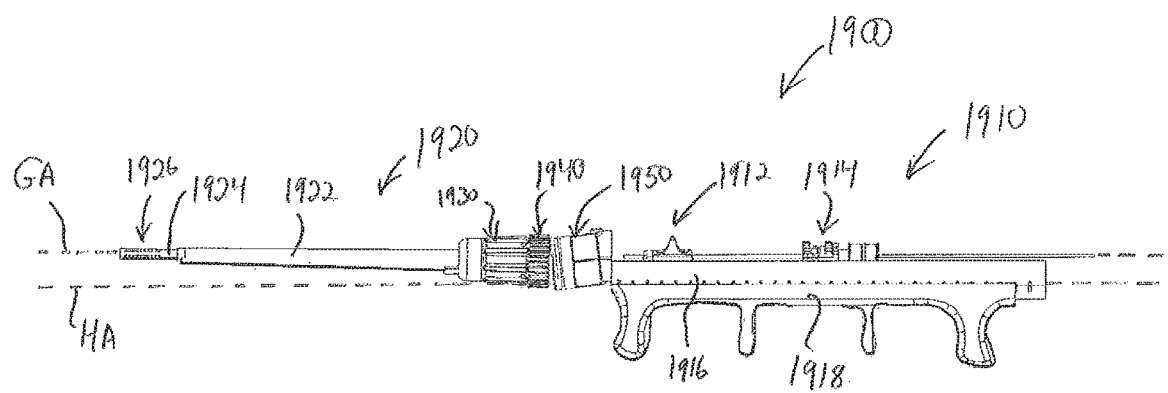
Figure 80B:
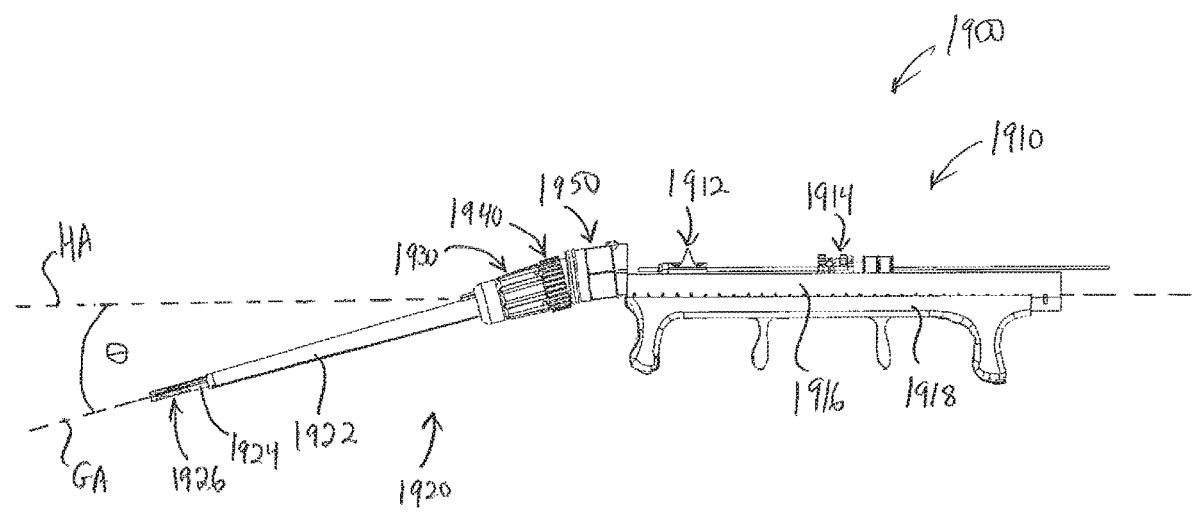

Instrument (1900) further includes a deflection adjustment knob (1950), positioned proximal to rotary control knob (1940). As shown in FIG. 81, deflection adjustment knob (1950) is longitudinally interposed between rotary control knob (1940) and a distal nose portion (1960) of handle assembly (1910). Deflection adjustment knob (1950) is operable to rotate relative to handle assembly (1910) to thereby transition shaft assembly (1920) between a first orientation (FIGS. 79A and 80A) and a second orientation (FIGS. 79B and 80B). In the first orientation as shown in FIGS. 79A and 80A, the guide axis (GA) defined by shaft assembly (1920) is parallel with the handle axis (HA) defined by handle assembly (1910). In the second orientation as shown in FIGS. 79B and 80B, the guide axis (GA) defined by shaft assembly (1920) is oblique to the handle axis (HA) defined by handle assembly (1910).

Figure 82:
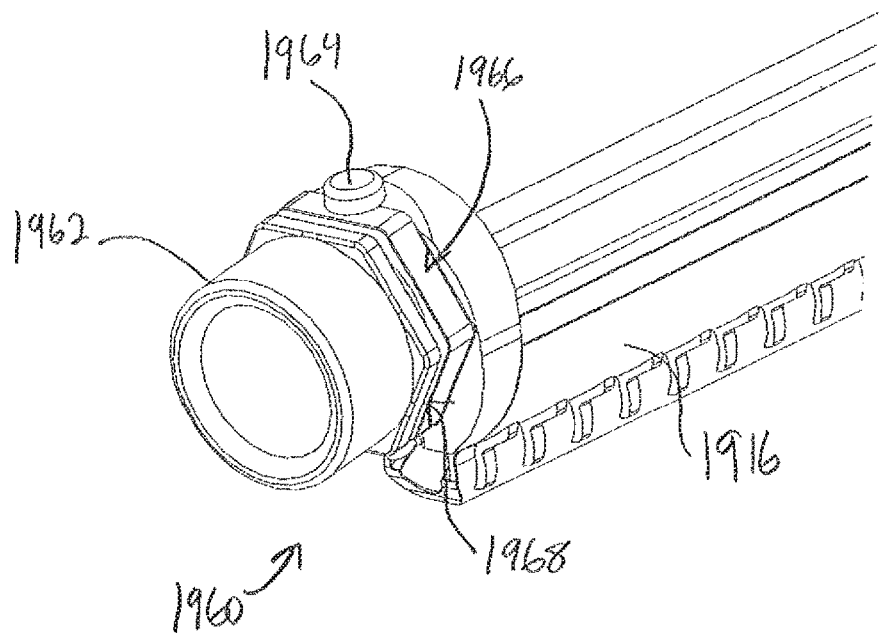
Figure 83:
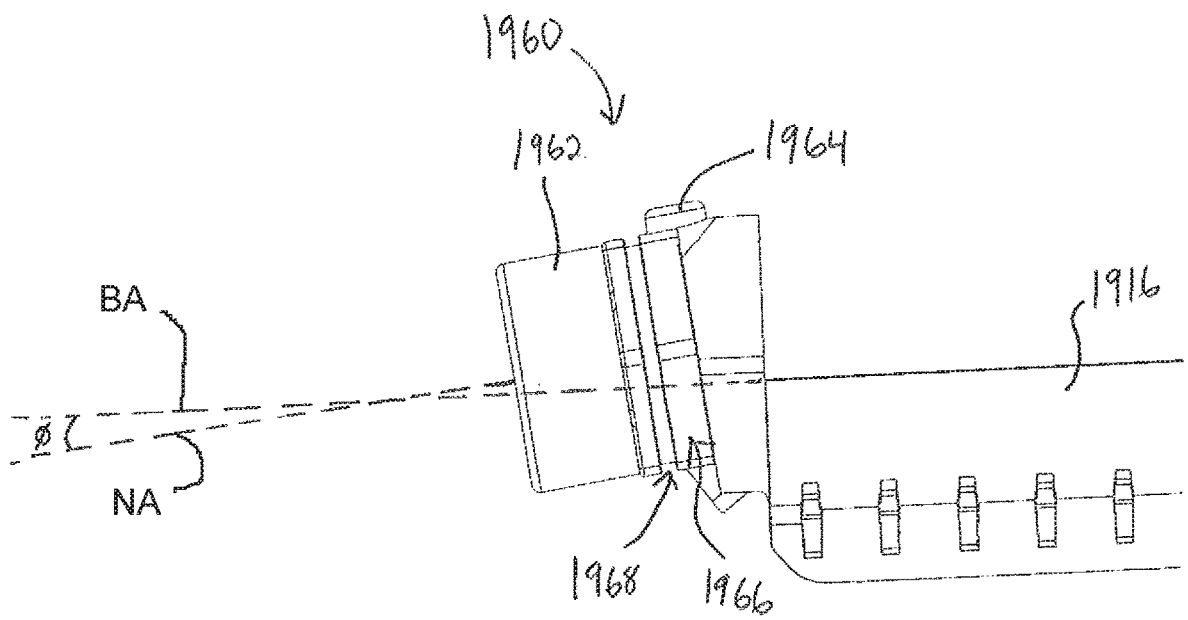

As shown in FIGS. 82-83, distal nose portion (1960) of handle assembly (1910) is an integral feature of body (1916) of handle assembly (1910). Distal nose portion (1960) includes a distally extending cylindraceous feature (1962), an upwardly extending peg (1964), a hexagonal interface feature (1966), and an annular recess (1968). As best seen in FIG. 83, distal nose portion (1960) is oriented such that the central longitudinal axis or nose axis (NA) of cylindraceous feature (1962) deviates from the central body axis (BA) of body (1916) by a deflection angle ($\varphi$). By way of example only, this deflection angle ($\varphi$) may be approximately 7.5°. Alternatively, any other suitable deflection angle may be provided.

Figure 84:
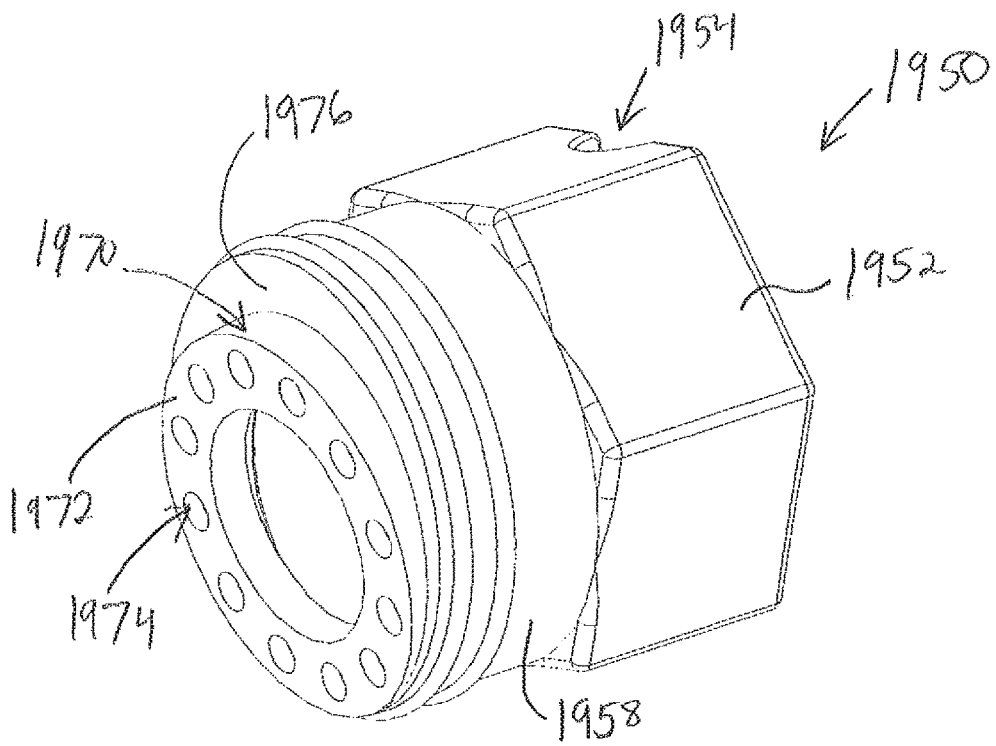
Figure 85:
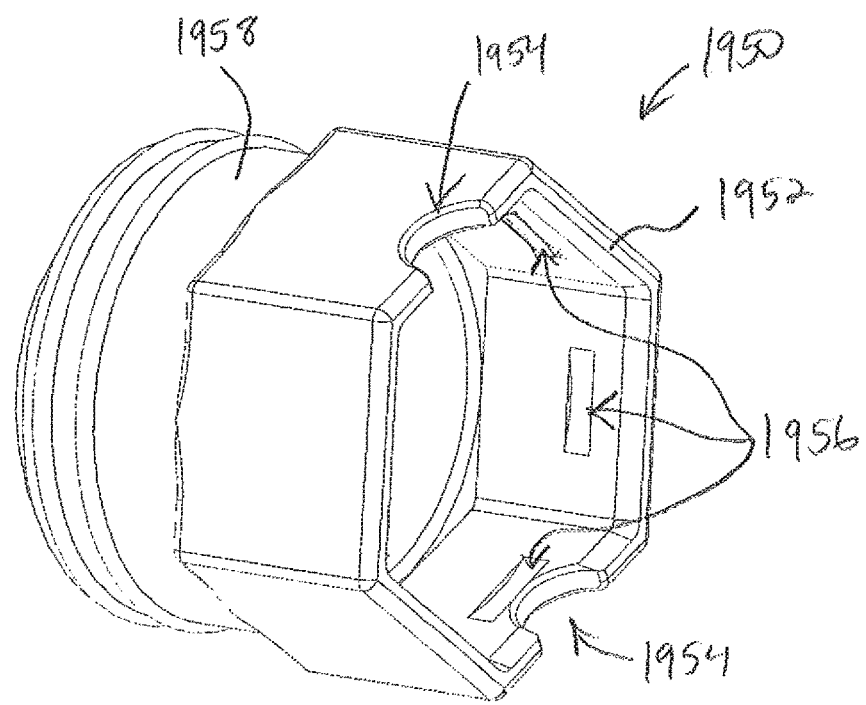
Figure 86:
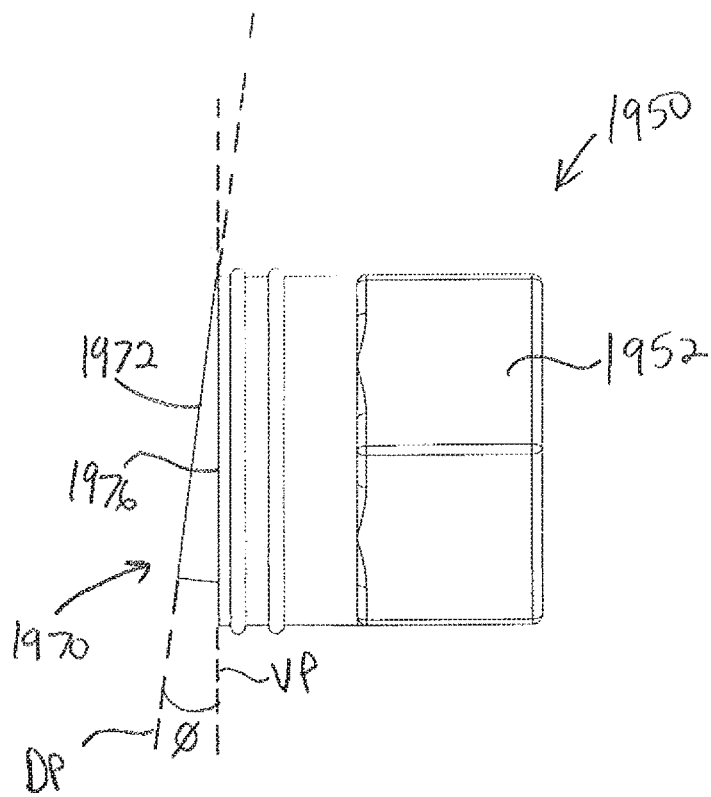

As shown in FIGS. 84-86, deflection adjustment knob (1950) includes a hexagonal body portion (1952) defining a pair of proximal arcuate notches (1954). As shown in FIG. 85, a set of internal notches (1956) are formed in the interior of hexagonal body portion (1952). A cylindraceous feature (1958) extends distally from hexagonal body portion (1952). Cylindraceous feature (1958) includes a first distal face (1976) with an oblique feature (1970) projecting distally from distal face (1976). Oblique feature (1970) includes a distal face (1972) with an annular array of openings (1974) spaced equiangularly from each other. As shown in FIG. 86, distal face (1972) of oblique feature (1970) extends along a distal plane (DP) that is obliquely oriented relative to a vertical plane (VP) along which distal face (1976) of cylindraceous feature (1958) extends. In the present example, the vertical plane (VP) is perpendicular to the nose axis (NA) when deflection adjustment knob (1950) is seated on nose portion (1960), regardless of the angular orientation of deflection adjustment knob (1950) about the nose axis (NA). Distal plane (DP) is oriented at a deflection angle ($\varphi$) relative to vertical plane (VP). By way of example only, this deflection angle ($\varphi$) may be approximately 7.5°. Alternatively, any other suitable deflection angle may be provided. Deflection angle ($\varphi$) shown in FIG. 83 and deflection angle ($\varphi$) shown in FIG. 86 are the same angle in the present example.

Deflection adjustment knob (1950) is configured to rotate about nose axis (NA) between two angular positions that are spaced 180° apart from each other. Notches (1954) and peg (1964) are configured to cooperate to allow deflection instrument knob (1950) to properly seat on distal nose portion (1960) only when deflection adjustment knob (1950) is at one of these two predetermined angular positions. When deflection adjustment knob (1950) is at one of the two predetermined angular positions, distal face (1972) of oblique feature (1970) is oriented such that the angle of distal plane (DP) effectively cancels out the angle of nose axis (NA). In other words, the central longitudinal axis of oblique feature (1970) is parallel with the central body axis (BA) of body (1916) when deflection adjustment knob (1950) is at the first of two predetermined angular positions. This results in the configuration shown in FIGS. 79A and 80A, in which the guide axis (GA) defined by shaft assembly (1920) is parallel with the handle axis (HA) defined by handle assembly (1910). This is due to the deflection angle ($\varphi$) shown in FIG. 83 being equal to the deflection angle ($\varphi$) shown in FIG. 86.

When deflection adjustment knob (1950) is at a second of the two predetermined angular positions, distal face (1972) of oblique feature (1970) is oriented such that the angle of distal plane (DP) cooperates with the angle of nose axis (NA) to provide an augmented deflection angle for shaft assembly (1920). This results in the configuration shown in FIGS. 79B and 80B, in which the guide axis (GA) defined by shaft assembly (1920) is oblique to the handle axis (HA) defined by handle assembly (1910). In the present example where each deflection angle ($\varphi$) is be approximately 7.5°, the deflection angle ($\Theta$) shown in FIG. 80B is approximately 15°. Alternatively, any other suitable deflection angles ($\varphi$, $\Theta$) may be provided.

The operator may wish to manipulate deflection adjustment knob (1950) to thereby selectively provide shaft assembly (1920) in either the orientation shown in FIGS. 79A and 80A or the orientation shown in FIGS. 79B and 80B, based on whether the patient is in an upright seated position or in a supine position; or based on other considerations. In some versions, a resilient member or other feature resiliently biases reflection adjustment knob (1950) proximally along nose portion (1960), thereby urging notch (1954) to receive peg (1964). In addition, an o-ring (not shown) may be positioned in annular recess (1968) of nose portion (1960) and may be received in internal notches (1956) of deflection adjustment knob (1950) to selectively retain the longitudinal position of deflection adjustment knob (1950) along nose portion (1960). Other suitable components and configurations that may be used to provide various relationships between deflection adjustment knob (1950) and nose portion (1960) will be apparent to those skilled in the art in view of the teachings herein.

Figure 87:
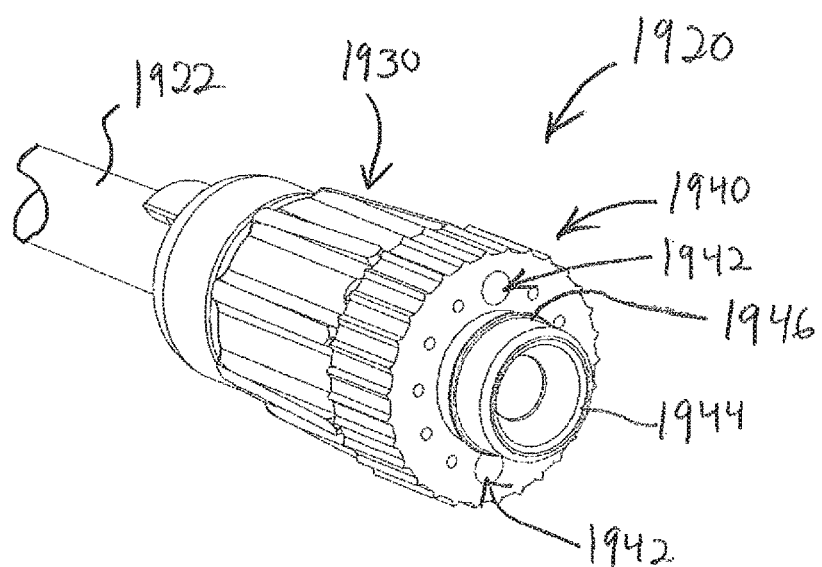

As shown in FIG. 87, the proximal end of rotary control knob (1940) includes a pair of bearing sockets (1942), a proximally extending cylindraceous feature (1944), and an annular flange (1946) on cylindraceous feature (1944). Bearing sockets (1942) are configured to receive respective ball bearings (not shown). These bearings are positioned to be interposed between sockets (1942) and openings (1974) to thereby provide detents as rotary control knob (1940) is rotated relative to deflection adjustment knob (1950) to rotate shaft assembly (1920) about the longitudinal axis of shaft assembly (1920). Flange (1946) of rotary control knob (1940) may cooperate with oblique feature (1970) of deflection adjustment knob (1950) to restrict longitudinal movement of shaft assembly (1920) relative to deflection adjustment knob (1950).

VII. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a body; (b) a shaft assembly extending distally from the body, wherein the shaft assembly comprises: (i) a rigid proximal portion, and (ii) a flexible distal portion; (c) an deflection actuation assembly comprising: (i) a rotary actuator, (ii) first translatable actuation member at least partially disposed within the rotary actuator, and (iii) a second translatable actuation member extending through the shaft assembly, wherein the second translatable actuation member couples the first translatable actuation member with the flexible distal portion of the shaft assembly, wherein the rotary actuator is rotatable about a longitudinal axis to thereby drive the first and second translatable actuation members longitudinally, wherein the flexible distal portion is configured to deflect away from the longitudinal axis in response to translation of the first and second translatable actuation members longitudinally; and (d) a dilation catheter, wherein the dilation catheter is slidable relative to the shaft assembly, wherein the dilation catheter comprises an expandable dilator.

Example 2

The apparatus of Example 1, wherein the deflection actuation assembly further comprises a pin fixedly secured to the rotary actuator, wherein the first translatable actuation member comprises a cam channel, wherein the pin is disposed in the cam channel.

Example 3

The apparatus of Example 2, wherein the cam channel has a helical configuration.

Example 4

The apparatus of any one or more of Examples 2 through 3, wherein the cam channel has a plurality of channel portions, wherein the channel portions are in communication with each other, wherein the cam channel further includes step features providing transitions between the channel portions.

Example 5

The apparatus of any one or more of Examples 1 through 4, wherein the first translatable actuation member is coaxially and slidably disposed about a proximal end of the rigid proximal portion of the shaft assembly.

Example 6

The apparatus of Example 5, wherein the first translatable actuation member and the rigid proximal portion of the shaft assembly comprise complementary features permitting the translatable actuation member to slide along the rigid proximal portion while preventing the translatable actuation member from rotating about the rigid proximal portion.

Example 7

The apparatus of any one or more of Examples 1 through 6, wherein the shaft assembly is coupled with the body by a pivotal coupling, wherein the pivotal coupling is configured to enable the entire shaft assembly to pivot relative to the body, about an axis that is transverse to the longitudinal axis, to thereby deflect the entire shaft assembly away from the longitudinal axis.

Example 8

The apparatus of Example 7, further comprising a shaft pivot lock member, wherein the shaft pivot lock member is configured to selectively lock a pivotal position of the entire shaft assembly relative to the longitudinal axis.

Example 9

The apparatus of Example 8, wherein the shaft pivot lock member comprises a translatable member, wherein the translatable member is operable to translate relative to the body to thereby selectively engage one or more complementary locking features of the body.

Example 10

The apparatus of Example 9, wherein the complementary locking features are configured to provide selective locking of the pivotal position of the entire shaft assembly at two or more discretely predefined angles relative to the longitudinal axis.

Example 11

The apparatus of any one or more of Examples 1 through 10, wherein the dilation catheter further comprises: (i) a shaft having an outer diameter, and (ii) a bulbous tip feature, wherein the bulbous tip feature is located distal to the dilator, wherein the bulbous tip feature has a width greater than the outer diameter of the shaft.

Example 12

The apparatus of Example 11, wherein the bulbous tip is deformable to reduce the width of the bulbous tip feature in response to inwardly directed forces exerted on the bulbous tip feature.

Example 13

The apparatus of any one or more of Examples 1 through 12, further comprising a guidewire, wherein the guidewire is slidably disposed in the dilation catheter.

Example 14

The apparatus of any one or more of Examples 1 through 13, wherein the body comprises a body portion and a grip portion, wherein the grip portion is selectively removable from the body portion.

Example 15

An apparatus comprising: (a) an instrument body; (b) a shaft assembly extending distally from the instrument body; (c) a dilation catheter, wherein the dilation catheter is slidable relative to the shaft assembly, wherein the dilation catheter comprises an expandable dilator; (d) a guidewire, wherein the guidewire is slidable relative to the shaft assembly; and (e) an actuator assembly, wherein the actuator assembly comprises (i) an actuator body, wherein the actuator body is translatable relative to instrument body to thereby translate the dilation catheter relative to the shaft assembly, and (ii) a first drive wheel, wherein the first drive wheel is rotatably supported by the actuator body, wherein the first drive wheel is operable to drive the guidewire longitudinally relative to the shaft assembly.

Example 16

The apparatus of Example 15, wherein the actuator assembly further comprises a second drive wheel, wherein the second drive wheel is coupled with the first drive wheel such that the second drive wheel is configured to rotate in a second direction in response to rotation of the first drive wheel in a first direction, wherein the second drive wheel is operable to drive the guidewire longitudinally relative to the shaft assembly in response to rotation of the first and second drive wheels.

Example 17

The apparatus of Example 16, wherein the second drive wheel is configured to translate relative to the actuator body between a first position and a second position along a path that is transverse to a longitudinal axis of the guidewire, wherein the second drive wheel is configured to contact the guidewire in the first position, wherein the second drive wheel is configured to be spaced away from the guidewire in the second position.

Example 18

The apparatus of Example 17, wherein the first drive wheel is configured to translate relative to the actuator body along a path that is transverse to a longitudinal axis of the guidewire to thereby drive the second drive wheel from the second position to the first position.

Example 19

The apparatus of Example 18, wherein the first drive wheel is configured to translate relative to the actuator body through a first range of motion without contacting the second drive wheel, wherein the first drive wheel is further configured to translate relative to the actuator body through a second range of motion to thereby drive the second drive wheel from the second position to the first position.

Example 20

The apparatus of any one or more of Examples 15 through 19, further comprising a manifold assembly coupled with the actuator body, wherein the manifold assembly is configured to translate with the actuator body relative to the instrument body.

Example 21

The apparatus of Example 20, wherein the manifold assembly is configured to couple the dilation catheter with at least two fluid inputs.

Example 22

The apparatus of any one or more of Examples 15 through 21, wherein the actuator assembly further comprises a guidewire rotation drive assembly, wherein the guidewire rotation drive assembly is configured to translate with the actuator body relative to the instrument body.

Example 23

The apparatus of Example 22, wherein the guidewire rotation drive assembly is configured to selectively grip the guidewire and thereby rotate the guidewire about a longitudinal axis of the guidewire, wherein the guidewire rotation drive assembly is further configured to selectively release the guidewire and thereby enable the guidewire to translate longitudinally through the guidewire rotation drive assembly.

Example 24

The apparatus of any one or more of Examples 15 through 23 further comprising a dilation catheter actuator, wherein the dilation catheter actuator is operable to translate relative to the instrument body, wherein the dilation catheter actuator is operable to translate the dilation catheter longitudinally relative to the shaft assembly, wherein the guidewire rotation drive assembly is coupled with the dilation catheter actuator such that the guidewire rotation drive assembly is configured to translate with the dilation catheter actuator relative to the instrument body.

Example 25

The apparatus of Example 15, further comprising a guidewire locking assembly fixedly secured to the instrument body, wherein the guidewire locking assembly is further configured to selectively lock the longitudinal position of the guidewire relative to the instrument body.

Example 26

The apparatus of Example 25, wherein the guidewire locking assembly is configured to lock the longitudinal position of the guidewire relative to the instrument body when the dilation catheter actuator is distal to a proximal-most position relative to the body.

Example 27

The apparatus of Example 26, wherein the guidewire locking assembly is further configured to unlock the longitudinal position of the guidewire relative to the instrument body when the dilation catheter actuator is at the proximal-most position relative to the body.

Example 28

An apparatus comprising: (a) an instrument body; (b) a shaft assembly extending distally from the instrument body; (c) a dilation catheter, wherein the dilation catheter is slidable relative to the shaft assembly, wherein the dilation catheter comprises an expandable dilator; (d) a guidewire, wherein the guidewire is slidable relative to the shaft assembly; (e) a guidewire rotation drive assembly, wherein the guidewire rotation drive assembly is configured to selectively grip the guidewire and thereby rotate the guidewire about a longitudinal axis of the guidewire, wherein the guidewire rotation drive assembly is further configured to selectively release the guidewire and thereby enable the guidewire to translate longitudinally through the guidewire rotation drive assembly.

Example 29

The apparatus of Example 28, wherein the guidewire rotation drive assembly comprises: (i) a barrel member, (ii) a first end cap, (iii) a second end cap, and (iv) a plurality of rollers, wherein the guidewire is disposed within the barrel member and the end caps, wherein the rollers are configured to selectively grip the guidewire based on an angular position of the barrel member relative to the first and second end caps.

Example 30

The apparatus of Example 29, wherein the rollers are deformable, wherein the barrel member comprises a bore having internal surfaces configured to deform the rollers inwardly to thereby grip the guidewire based on an angular position of the barrel member relative to the first and second end caps.

Example 31

The apparatus of Example 30, wherein the bore has a set of arcuate surfaces joined by rounded corners, wherein the arcuate surfaces are configured to deform the rollers inwardly.

Example 32

The apparatus of any one or more of Examples 29 through 31, further comprising at least one pin, wherein the at least one pin couples the barrel member with at least one of the end caps via an arcuate recess, wherein the arcuate recess and the pin cooperate to provide relative angular movement between the barrel member and the at least one of the end caps as the barrel member is rotated through a first range of angular motion, wherein the arcuate recess and the pin further cooperate to provide concomitant angular movement of the barrel member and the at least one of the end caps as the barrel member is rotated through a second range of angular motion.

Example 33

The apparatus of any one or more of Examples 28 through 32, wherein the guidewire further comprises: (i) a distal portion, (ii) a proximal portion, and (iii) a slip coupling joining the distal portion with the proximal portion, wherein the distal portion is disposed in the guidewire rotation drive assembly, wherein the slip coupling is configured to enable the distal portion to rotate relative to the proximal portion.

Example 34

An apparatus comprising: (a) an instrument body; (b) a shaft assembly extending distally from the instrument body; (c) a dilation catheter, wherein the dilation catheter is slidable relative to the shaft assembly, wherein the dilation catheter comprises an expandable dilator; (d) a guidewire, wherein the guidewire is slidable relative to the shaft assembly; (e) an actuator assembly, wherein the actuator assembly is operable to translate the dilation catheter relative to the shaft assembly; and (f) a guidewire locking assembly fixedly secured to the instrument body, wherein the guidewire locking assembly is further configured to selectively lock the longitudinal position of the guidewire relative to the instrument body.

Example 35

The apparatus of Example 34, wherein the guidewire locking assembly is configured to lock the longitudinal position of the guidewire relative to the instrument body when the actuator assembly is distal to a proximal-most position relative to the body.

Example 36

The apparatus of any one or more of Examples 34 through 35, wherein the guidewire locking assembly is further configured to unlock the longitudinal position of the guidewire relative to the instrument body when the actuator assembly is at the proximal-most position relative to the body.

Example 37

The apparatus of Example 36, wherein the actuator assembly is configured to engage the guidewire locking assembly when the actuator assembly is at the proximal-most position relative to the body, to thereby transition the guidewire locking assembly to an unlocked state.

Example 38

The apparatus of any one or more of Examples 34 through 37, wherein the guidewire locking assembly comprises (i) a frame, (ii) a first shoe, and (iii) a second shoe, wherein the frame is configured to urge the first and second shoes toward each other to thereby grip the guidewire.

Example 39

The apparatus of Example 38, wherein the guidewire locking assembly further comprises at least one resilient member configured to cooperate with the frame member to thereby urge the first and second shoes toward each other to thereby grip the guidewire.

VIII. Miscellaneous

In addition to the foregoing, any of the instruments described herein may be modified in accordance with at least some of the teachings of U.S. Pat. App. No. 16/032,471, entitled "Adjustable Instrument for Dilation of Anatomical Passageway," filed on Jul. 11, 2018, issued as U.S. Pat. No. 10,874,839 Dec. 29, 2020, the disclosure of which is incorporated by reference herein.

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) an instrument body, wherein the instrument body defines a longitudinal axis;
   (b) a shaft assembly extending distally from the instrument body, wherein the shaft assembly has a proximal end and a distal end, with a length defined between the proximal and distal ends, wherein the shaft assembly further defines a longitudinal axis along the length;
   (c) a dilation catheter, wherein the dilation catheter comprises an expandable dilator, wherein the dilation catheter is slidable relative to the shaft assembly to thereby position the dilator distally relative to the distal end of the shaft assembly; and
   (d) a guidewire, wherein the guidewire is slidable relative to the dilation catheter,
   wherein at least a portion of the length of the shaft assembly is operable to be selectively deflected relative to the longitudinal axis of the instrument body to thereby deflect the longitudinal axis of the shaft assembly away from the longitudinal axis of the instrument body.

2. The apparatus of claim 1, further comprising a lock collar, wherein the lock collar is configured to translate to thereby transition between a locking position and an unlocking position, wherein the lock collar in the locking position is configured to maintain an angle defined between the longitudinal axis of the shaft assembly and the longitudinal axis of the instrument body, wherein the lock collar in the unlocking position is configured to enable adjustment of the angle defined between the longitudinal axis of the shaft assembly away from the longitudinal axis of the instrument body.

3. The apparatus of claim 1, further comprising a deflection slider, wherein the deflection slider is operable to translate laterally relative to the longitudinal axis of the instrument body to thereby deflect the length of the shaft assembly relative to the longitudinal axis of the instrument body.

4. The apparatus of claim 1, wherein the shaft assembly is operable to pivot relative to the instrument body about a pivot axis that is perpendicular to the longitudinal axis of the instrument body.

5. The apparatus of claim 1, further comprising a deflection adjustment knob, wherein the deflection adjustment knob is operable to rotate about the longitudinal axis of the shaft assembly to thereby deflect the length of the shaft assembly relative to the longitudinal axis of the instrument body.

6. The apparatus of claim 5, wherein the instrument body includes a distal portion defining a deflection adjustment knob engagement feature that is oriented obliquely relative to the longitudinal axis of the instrument body, wherein the deflection adjustment knob defines an engagement feature that is oriented obliquely relative to the longitudinal axis of the shaft assembly, wherein the deflection adjustment knob engagement feature and the engagement feature of the deflection adjustment knob are configured to cooperate with each other to transition the length of the shaft assembly between a deflected orientation and a non-deflected orientation.

7. The apparatus of claim 1, wherein the shaft assembly includes a flexible distal portion, the apparatus further comprising a distal deflection actuation assembly, the distal deflection actuation assembly comprising:
   (i) a rotary actuator,
   (ii) a first translatable actuation member at least partially disposed within the rotary actuator, and
   (iii) a second translatable actuation member extending through the shaft assembly, wherein the second translatable actuation member couples the first translatable actuation member with the flexible distal portion of the shaft assembly, wherein the rotary actuator is rotatable about a longitudinal axis to thereby drive the first and second translatable actuation members longitudinally, wherein the flexible distal portion is configured to deflect away from the longitudinal axis of the shaft assembly in response to translation of the first and second translatable actuation members longitudinally.

8. The apparatus of claim 1, wherein the dilation catheter further comprises:
  (i) a shaft having an outer diameter, and
  (ii) a bulbous tip feature, wherein the bulbous tip feature is located distal to the dilator, wherein the bulbous tip feature has a width greater than the outer diameter of the shaft, wherein the bulbous tip is deformable to reduce the width of the bulbous tip feature in response to inwardly directed forces exerted on the bulbous tip feature.

9. The apparatus of claim 1, further comprising an actuator assembly, wherein the actuator assembly comprises:
  (i) an actuator body, wherein the actuator body is translatable relative to instrument body to thereby translate the dilation catheter relative to the shaft assembly, and
  (ii) a first drive wheel, wherein the first drive wheel is rotatably supported by the actuator body, wherein the first drive wheel is operable to drive the guidewire longitudinally relative to the shaft assembly.

10. The apparatus of claim 9, wherein the actuator assembly further comprises a second drive wheel, wherein the second drive wheel is coupled with the first drive wheel such that the second drive wheel is configured to rotate in a second direction in response to rotation of the first drive wheel in a first direction, wherein the second drive wheel is operable to drive the guidewire longitudinally relative to the shaft assembly in response to rotation of the first and second drive wheels.

11. The apparatus of claim 10, wherein the second drive wheel is configured to translate relative to the actuator body between a first position and a second position along a path that is transverse to a longitudinal axis of the guidewire, wherein the second drive wheel is configured to contact the guidewire in the first position, wherein the second drive wheel is configured to be spaced away from the guidewire in the second position.

12. The apparatus of claim 11, wherein the first drive wheel is configured to translate relative to the actuator body along a path that is transverse to a longitudinal axis of the guidewire to thereby drive the second drive wheel from the second position to the first position.

13. The apparatus of claim 9, further comprising a manifold assembly coupled with the actuator body, wherein the manifold assembly is configured to translate with the actuator body relative to the instrument body, wherein the manifold assembly is configured to couple the dilation catheter with at least two fluid inputs.

14. An apparatus comprising:
  (a) an instrument body;
  (b) a shaft assembly extending distally from the instrument body;
  (c) a dilation catheter, wherein the dilation catheter is slidable relative to the shaft assembly, wherein the dilation catheter comprises an expandable dilator;
  (d) a guidewire, wherein the guidewire is slidable relative to the shaft assembly;
  (e) a guidewire rotation drive assembly, wherein the guidewire rotation drive assembly comprises:
    (i) a barrel member,
    (ii) a first end cap,
    (iii) a second end cap, and
    (iv) a plurality of rollers, wherein the guidewire is disposed within the barrel member and the end caps, wherein the rollers are configured to selectively grip the guidewire based on an angular position of the barrel member relative to the first and second end caps.

15. The apparatus of claim 14, wherein the rollers are deformable, wherein the barrel member comprises a bore having internal surfaces configured to deform the rollers inwardly to thereby grip the guidewire based on an angular position of the barrel member relative to the first and second end caps.

16. The apparatus of claim 15, wherein the bore has a set of arcuate surfaces joined by rounded corners, wherein the arcuate surfaces are configured to deform the rollers inwardly.

17. The apparatus of claim 14, further comprising at least one pin, wherein the at least one pin couples the barrel member with at least one of the end caps via an arcuate recess, wherein the arcuate recess and the pin cooperate to provide relative angular movement between the barrel member and the at least one of the end caps as the barrel member is rotated through a first range of angular motion, wherein the arcuate recess and the pin further cooperate to provide concomitant angular movement of the barrel member and the at least one of the end caps as the barrel member is rotated through a second range of angular motion.

18. An apparatus comprising:
  (a) an instrument body;
  (b) a shaft assembly extending distally from the instrument body;
  (c) a dilation catheter, wherein the dilation catheter is slidable relative to the shaft assembly, wherein the dilation catheter comprises an expandable dilator;
  (d) a guidewire, wherein the guidewire is slidable relative to the shaft assembly;
  (e) an actuator assembly, wherein the actuator assembly is operable to translate the dilation catheter relative to the shaft assembly; and
  (f) a guidewire locking assembly fixedly secured to the instrument body, wherein the guidewire locking assembly is further configured to selectively lock the longitudinal position of the guidewire relative to the instrument body.

19. The apparatus of claim 18, wherein the guidewire locking assembly comprises:
  (i) a frame,
  (ii) a first shoe, and
  (iii) a second shoe, wherein the frame is configured to urge the first and second shoes toward each other to thereby grip the guidewire.

20. The apparatus of claim 19, wherein the guidewire locking assembly further comprises at least one resilient member configured to cooperate with the frame member to thereby urge the first and second shoes toward each other to thereby grip the guidewire.

* * * * *